US011555058B2

(12) United States Patent
Lancaster et al.

(10) Patent No.: US 11,555,058 B2
(45) Date of Patent: Jan. 17, 2023

(54) CELLS ENGINEERED TO EXPRESS ULTRA-LONG ACTING INSULIN-FC FUSION PROTEINS

(71) Applicant: Akston Biosciences Corporation, Beverly, MA (US)

(72) Inventors: Thomas M. Lancaster, Wenham, MA (US); Todd C. Zion, Marblehead, MA (US)

(73) Assignee: Akston Biosciences Corporation, Beverly, MA (US)

( * ) Notice: Subject to any disclaimer, the term of this patent is extended or adjusted under 35 U.S.C. 154(b) by 0 days.

(21) Appl. No.: 17/531,033

(22) Filed: Nov. 19, 2021

(65) Prior Publication Data

US 2022/0064251 A1 Mar. 3, 2022

Related U.S. Application Data

(63) Continuation of application No. 17/114,395, filed on Dec. 7, 2020, now Pat. No. 11,352,407.

(60) Provisional application No. 62/988,441, filed on Mar. 12, 2020, provisional application No. 62/950,803, filed on Dec. 19, 2019.

(51) Int. Cl.

| | |
|---|---|
| ***C07K 14/62*** | (2006.01) |
| ***A61P 3/10*** | (2006.01) |
| ***A61K 9/00*** | (2006.01) |
| ***C12N 15/62*** | (2006.01) |

(52) U.S. Cl.

CPC ............ *C07K 14/62* (2013.01); *A61K 9/0019* (2013.01); *A61P 3/10* (2018.01); *C12N 15/62* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 8,188,231 | B2 | 5/2012 | Lazar et al. |
| 8,933,207 | B2 | 1/2015 | Chen et al. |
| 9,074,015 | B2 | 7/2015 | Lancaster et al. |
| 9,855,318 | B2 | 1/2018 | Baldwin et al. |
| 10,597,435 | B2 | 3/2020 | Lancaster et al. |
| 10,709,766 | B2 | 7/2020 | Baldwin et al. |
| 10,822,386 | B2 | 11/2020 | Weiss |
| 10,851,147 | B2 | 12/2020 | Lancaster et al. |
| 10,870,686 | B2 | 12/2020 | Lancaster et al. |
| 10,894,089 | B2 | 1/2021 | Heo et al. |
| 10,947,292 | B2 | 3/2021 | Lancaster et al. |
| 10,961,294 | B2 | 3/2021 | Lancaster et al. |
| 2003/0040601 | A1 | 2/2003 | Diers et al. |
| 2012/0093814 | A1 | 4/2012 | Canada et al. |
| 2013/0142795 | A1 | 6/2013 | Bai et al. |
| 2013/0190475 | A1 | 7/2013 | Chen et al. |
| 2013/0190476 | A1 | 7/2013 | Lancaster et al. |
| 2014/0037699 | A1 | 2/2014 | Zion et al. |
| 2014/0302028 | A1 | 10/2014 | Zha |
| 2016/0289290 | A1 | 10/2016 | Meehl et al. |
| 2016/0324932 | A1 | 11/2016 | Baldwin et al. |
| 2018/0009869 | A1 | 1/2018 | Lu et al. |
| 2018/0161448 | A1 | 6/2018 | Heo et al. |
| 2018/0177851 | A1 | 6/2018 | Baldwin et al. |
| 2019/0315828 | A1 | 10/2019 | Lancaster et al. |
| 2019/0382439 | A1 | 12/2019 | Kim et al. |
| 2020/0131243 | A1 | 4/2020 | Lancaster et al. |
| 2020/0140516 | A1 | 5/2020 | Weiss |
| 2020/0140517 | A1 | 5/2020 | Weiss |
| 2020/0157169 | A1 | 5/2020 | Lancaster et al. |
| 2020/0157170 | A1 | 5/2020 | Lancaster et al. |
| 2020/0157171 | A1 | 5/2020 | Lancaster et al. |
| 2020/0231646 | A1 | 7/2020 | Lancaster et al. |
| 2020/0299343 | A1 | 9/2020 | Doerner et al. |
| 2020/0407413 | A1 | 12/2020 | Lancaster et al. |
| 2020/0407414 | A1 | 12/2020 | Lancaster et al. |
| 2021/0300983 | A1 | 9/2021 | Lancaster et al. |
| 2021/0309709 | A1 | 10/2021 | Lancaster et al. |
| 2021/0324033 | A1 | 10/2021 | Lancaster et al. |
| 2021/0340212 | A1 | 10/2021 | Lancaster et al. |

FOREIGN PATENT DOCUMENTS

| | | |
|---|---|---|
| EP | 3517544 | 7/2019 |
| WO | 2010117760 | 10/2010 |
| WO | 2016044676 | 3/2016 |
| WO | 2016119023 | 8/2016 |
| WO | 2016177771 | 11/2016 |

(Continued)

OTHER PUBLICATIONS

Alleva, et al., "Immunological characterization and therapeutic activity of an altered-peptide ligand, NBI-6024, based on the immunodominant type 1 diabetes autoantigen insulin B-chain (9-23) peptide", Diabetes, 2002, 51(7) pp. 2126-2134.

Baeshen, et al., "Cell factories for insulin production", Microbial Cell Factories, 2014,13(141).

Brüggemann, et al., "The immunogenicity of chimeric antibodies", Journal of Experimental Medicine, 1989, 170(6) pp. 2153-2157.

Hua, et al., "Design of an Active Ultrastable Single-chain Insulin Analog", Journal of Biological Chemistry, 2008, 283(21) pp. 14703-14716.

Strietzel, et al., "In Vitro functional characterization of feline IgGs", Veterinary Immunology and Immunopathology, 2014, 158(3-4) pp. 214-223 (abstract attached).

(Continued)

*Primary Examiner* — G. R. Ewoldt

(74) *Attorney, Agent, or Firm* — Hovey Williams LLP

(57) ABSTRACT

The present disclosure provides cells engineered to express recombinantly manufactured ultra-long acting insulin-Fc fusion proteins for use in treating diabetes. The insulin-Fc fusion proteins comprise an insulin polypeptide linked via a peptide linker to an Fc-fragment of human origin. Exemplary ultra-long acting insulin-Fc fusion proteins, cells engineered to express the fusion proteins, polynucleotides encoding these insulin-Fc fusion proteins, and pharmaceutical formulations of exemplary insulin-Fc fusion proteins are provided, in addition to methods of use and preparation.

23 Claims, 30 Drawing Sheets

Specification includes a Sequence Listing.

(56) References Cited

FOREIGN PATENT DOCUMENTS

| | | |
|---|---|---|
| WO | 2016178905 | 11/2016 |
| WO | 2018009921 | 1/2018 |
| WO | 2018073185 | 4/2018 |
| WO | 2018107117 | 6/2018 |
| WO | 2019035010 | 2/2019 |
| WO | 2020006529 | 1/2020 |
| WO | 2020070276 | 4/2020 |
| WO | 2020106748 | 5/2020 |
| WO | 2020236762 | 11/2020 |
| WO | 2021011827 | 1/2021 |
| WO | 2021022149 | 2/2021 |
| WO | 2021126584 | 6/2021 |

OTHER PUBLICATIONS

Wang, et al., "Proinsulin-Transferrin Fusion Protein as a Novel Long-Acting Insulin Analog for the Inhibition of Hepatic Glucose Production", Diabetes, 2014, 63 pp. 1779-1788.

yourgenome.org, "What does DNA do?", 2016, https://www.yourgenome.org/facts/what-does-dna-do.

Yang, et al., "IgG Fc engineering to modulate antibody effector functions", Protein Cell, Jan. 2018, 9(1), pp. 63-73.

Kim, et al., "Mammalian cell transfection: the present and the future", Analytical and Bioanalytical Chemistry, 2010, 397(8), pp. 3173-3178.

Fan, et al., "Improving the efficiency of CHO cell line generation using glutamine synthetase gene knockout cells", Biotechnology and Bioengineering, 2012, 109(4), pp. 1007-1015 (abstract attached).

Lodish, et al.,Molecular Cell Biology, Molecular Cell Biology, 4th edition, 2000, www.ncbi.nlm.gov/ books/NBK21654 (abstract attached).

Horvath, et al., "An automated DNA synthesizer employing deoxynucleoside 3'-phosphoramidites", Methods in Enzymology, Academic Press, 1987, 154, pp. 314-326 (abstract attached).

Dumont, et al., "Human cell lines for biopharmaceutical manufacturing: history, status, and future perspectives", Critical Reviews in Biotechnology, 2016, 36(6), pp. 1110-1122.

Singh, et al., "Combined blockade of HER2 and VEGF exerts greater growth inhibition of HER2-overexpressing gastric cancer xenografts than individual blockade", Experimental and Molecular Medicine, 2013, 45, 11 pages.

Huang, et al., "Production of recombinant murine-human chimeric IgM and IgG anti-Jsb for use in the clinical laboratory", Transfusion, 2003, 43(6), pp. 758-764 (abstract attached).

```
SEQ ID NO: 32      FVNQHLCGSDLVEALALVCGERGFFYTDPTGGGPRRGIVEQCCHSICSLYQLENYCNGGG 60
SEQ ID NO: 33      FVNQHLCGSDLVEALALVCGERGFFYTDPTGGGPRRGIVEQCCHSICSLYQLENYCNGGG 60
SEQ ID NO: 34      FVNQHLCGSDLVEALALVCGERGFFYTDPTGGGPRRGIVEQCCHSICSLYQLENYCNGGG 60
SEQ ID NO: 31      FVNQHLCGSDLVEALALVCGERGFFYTDPTGGGPRRGIVEQCCHSICSLYQLENYCNGGG 60
SEQ ID NO: 35      FVNQHLCGSDLVEALALVCGERGFFYTDPTGGGPRRGIVEQCCHSICSLYQLENYCNGGG 60
                   ************************************************************

SEQ ID NO: 32      GAGGGGRCTDTPPCPVPEPLGGPSVLIFPPKPKDILRITRTPEVTCVVLDLGREDPEVQI 120
SEQ ID NO: 33      GAGGGGRCTDTPPCPVPEPLGGPSVLIFPPKPKDILRITRTPEVTCVVLDLGREDPEVQI 120
SEQ ID NO: 34      GAGGGGRCTDTPPCPVPEPLGGPSVLIFPPKPKDILRITRTPEVTCVVLDLGREDPEVQI 120
SEQ ID NO: 31      GAGGGGRCTDTPPCPVPEPLGGPSVLIFPPKPKDILRITRTPEVTCVVLDLGREDPEVQI 120
SEQ ID NO: 35      GAGGGGRCTDTPPCPVPEPLGGPSVLIFPPKPKDILRITRTPEVTCVVLDLGREDPEVQI 120
                   ************************************************************

SEQ ID NO: 32      SWFVDGKEVHTAKTQSREQQFNGTYRVVSVLPIEHQDWLTGKEFKCRVNHIDLPSPIERT 180
SEQ ID NO: 33      SWFVDGKEVHTAKTQSREQQFNGTYRVVSVLPIEHQDWLTGKEFKCRVNHIDLPSPIERT 180
SEQ ID NO: 34      SWFVDGKEVHTAKTQSREQQFNGTYRVVSVLPIEHQDWLTGKEFKCRVNHIDLPSPIERT 180
SEQ ID NO: 31      SWFVDGKEVHTAKTQSREQQFNGTYRVVSVLPIEHQDWLTGKEFKCRVNHIDLPSPIERT 180
SEQ ID NO: 35      SWFVDGKEVHTAKTQSREQQFNGTYRVVSVLPIEHQDWLTGKEFKCRVNHIDLPSPIERT 180
                   ************************************************************

SEQ ID NO: 32      ISKARGRAHKPSVYVLPPSPKELSSSDTVSITCLIKDFYPPDIDVEWQSNGQQEPERKHR 240
SEQ ID NO: 33      ISKARGRAHKPSVYVLPPSPKELSSSDTVSITCLIKDFYPPDIDVEWQSNGQQEPERKHR 240
SEQ ID NO: 34      ISKARGRAHKPSVYVLPPSPKELSSSDTVSITCLIKDFYPPDIDVEWQSNGQQEPERKHR 240
SEQ ID NO: 31      ISKARGRAHKPSVYVLPPSPKELSSSDTVSITCLIKDFYPPDIDVEWQSNGQQEPERKHR 240
SEQ ID NO: 35      ISKARGRAHKPSVYVLPPSPKELSSSDTVSITCLIKDFYPPDIDVEWQSNGQQEPERKHR 240
                   ************************************************************

SEQ ID NO: 32      MTPPQLDEDGSYFLYSKLSVDKSRWQQGDPFTCAVLHEALHSHYTQKSLSLSPG 294
SEQ ID NO: 33      MTPPQLDEDGSYFLYSKLSVDKSRWQQGDPFTCAVLHETLQSHYTDLSLSHSPG 294
SEQ ID NO: 34      MTPPQLDEDGSYFLYSKLSVDKSRWQQGDPFTCAVMHETLQSHYTDLSLSHSPG 294
SEQ ID NO: 31      MTPPQLDEDGSYFLYSKLSVDKSRWQQGDPFTCAVMHETLQNHYTDLSLSHSPG 294
SEQ ID NO: 35      MTPPQLDEDGSYFLYSKLSVDKSRWQQGDPFTCAVLHETLQNHYTDLSLSHSPG 294
                   ***********************************:**:*:.***: *** ***
```

FIG. 3

```
SEQ ID NO: 31     FVNQHLCGSDLVEALALVCGERGFFYTDPTGGGPRRGIVEQCCHSICSLYQLENYCNGGG 60
SEQ ID NO: 38     FVNQHLCGSDLVEALALVCGERGFFYTDPTGGGPRRGIVEQCCHSICSLYQLENYCNGGG 60
SEQ ID NO: 36     FVNQHLCGSDLVEALALVCGERGFFYTDPTGGGPRRGIVEQCCHSICSLYQLENYCNGGG 60
SEQ ID NO: 37     FVNQHLCGSDLVEALALVCGERGFFYTDPTGGGPRRGIVEQCCHSICSLYQLENYCNGGG 60
                  ************************************************************

SEQ ID NO: 31     GAGGGGRCTDTPPCPVPEPLGGPSVLIFPPKPKDILRITRTPEVTCVVLDLGREDPEVQI 120
SEQ ID NO: 38     GAGGGGC---ISPCPVPESLGGPSVFIFPPKPKDILRITRTPEITCVVLDLGREDPEVQI 117
SEQ ID NO: 36     GAGGGGDCPK---CPAPEMLGGPSVFIFPPKPKDTLLIARTPEVTCVVVDLDPEDPEVQI 117
SEQ ID NO: 37     GAGGGG-CNN-CPCPGCGLLGGPSVFIFPPKPKDILVTARTPTVTCVVVDLDPENPEVQI 118
                  ******       **    ******:******** *  :*** :****:**. *:*****

SEQ ID NO: 31     SWFVDGKEVHTAKTQSREQQFNGTYRVVSVLPIEHQDWLTGKEFKCRVNHIDLPSPIERT 180
SEQ ID NO: 38     SWFVDGKEVHTAKTQPREQQFNSTYRVVSVLPIEHQDWLTGKEFKCRVNHIGLPSPIERT 177
SEQ ID NO: 36     SWFVDGKQMQTAKTQPREEQFNGTYRVVSVLPIGHQDWLKGKQFTCKVNNKALPSPIERT 177
SEQ ID NO: 37     SWFVDSKQVQTANTQPREEQSNGTYRVVSVLPIGHQDWLSGKQFKCKVNNKALPSPIEEI 178
                  *****.*:::**:** **:* *.********** *****.**:*.*:**:  ******.

SEQ ID NO: 31     ISKARGRAHKPSVYVLPPSPKELSSSDTVSITCLIKDFYPPDIDVEWQSNGQQEPERKHR 240
SEQ ID NO: 38     ISKARGQAHQPSVYVLPPSPKELSSSDTVTLTCLIKDFFPPEIDVEWQSNGQPEPESKYH 237
SEQ ID NO: 36     ISKARGQAHQPSVYVLPPSREELS-KNTVSLTCLIKDFFPPDIDVEWQSNGQQEPESKYR 236
SEQ ID NO: 37     ISKTPGQAHQPNVYVLPPSRDEMS-KNTVTLTCLVKDFFPPEIDVEWQSNGQQEPESKYR 237
                  ***: *:**:*.******* .*:* .:**::***:***:**:********** *** *::

SEQ ID NO: 31     MTPPQLDEDGSYFLYSKLSVDKSRWQQGDPFTCAVMHETLQNHYTDLSLSHSPG 294
SEQ ID NO: 38     TTAPQLDEDGSYFLYSKLSVDKSRWQQGDTFTCAVMHEALQNHYTDLSLSHSPG 291
SEQ ID NO: 36     TTPPQLDEDGSYFLYSKLSVDKSRWQRGDTFICAVMHEALHNHYTQESLSHSPG 290
SEQ ID NO: 37     MTPPQLDEDGSYFLYSKLSVDKSRWQRGDTFICAVMHEALHNHYTQISLSHSPG 291
                  * ***********************:** * ******:*:****: *******
```

FIG. 4

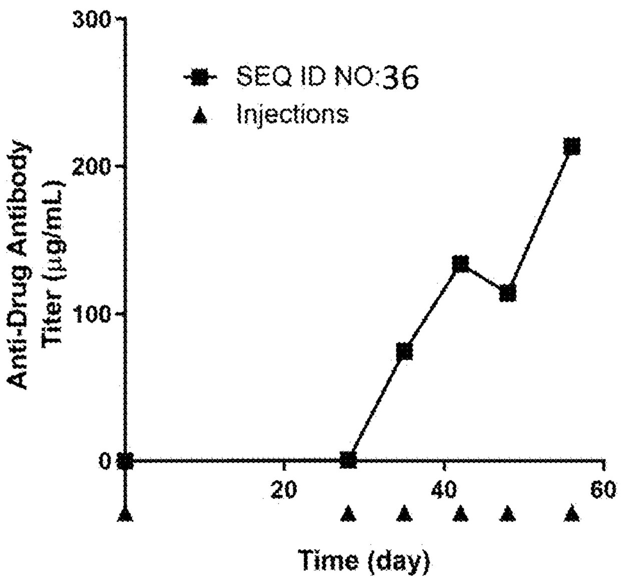

FIG. 7

```
SEQ ID NO: 39    FVNQHLCGSDLVEALALVCGERGFFYTDPTGGGPRRGIVEQCCHSICSLYQLENYCNGGG    60
SEQ ID NO: 40    FVNQHLCGSDLVEALALVCGERGFFYTDPTGGGPRRGIVEQCCHSICSLYQLENYCNGGG    60
SEQ ID NO: 41    FVNQHLCGSDLVEALALVCGERGFFYTDPTGGGPRRGIVEQCCHSICSLYQLENYCNGGG    60
SEQ ID NO: 42    FVNQHLCGSDLVEALALVCGERGFFYTDPTGGGPRRGIVEQCCHSICSLYQLENYCNGGG    60
                 ************************************************************

SEQ ID NO: 39    GAGGGGDCPKCPAPEMLGGPSVFIFPPKPKDTLLIARTPEVTCVVVDLDPEDPEVQISWF    120
SEQ ID NO: 40    GAGGGGDCPKCPAPEMLGGPSVFIFPPKPKDTLLIARTPEVTCVVVDLDPEDPEVQISWF    120
SEQ ID NO: 41    GAGGGGDCPKCPAPEMLGGPSVFIFPPKPKDTLLIARTPEVTCVVVDLDPEDPEVQISWF    120
SEQ ID NO: 42    GAGGGGDCPKCPAPEMLGGPSVFIFPPKPKDTLLIARTPEVTCVVVDLDPEDPEVQISWF    120
                 ************************************************************

SEQ ID NO: 39    VDGKQMQTAKTQPREEQFQGTYRVVSVLPIGHQDWLKGKQFTCKVNNKALPSPIERTISK    180
SEQ ID NO: 40    VDGKQMQTAKTQPREEQFSGTYRVVSVLPIGHQDWLKGKQFTCKVNNKALPSPIERTISK    180
SEQ ID NO: 41    VDGKQMQTAKTQPREEQFDGTYRVVSVLPIGHQDWLKGKQFTCKVNNKALPSPIERTISK    180
SEQ ID NO: 42    VDGKQMQTAKTQPREEQFKGTYRVVSVLPIGHQDWLKGKQFTCKVNNKALPSPIERTISK    180
                 ******************.*****************************************

SEQ ID NO: 39    ARGQAHQPSVYVLPPSREELSKNTVSLTCLIKDFFPPDIDVEWQSNGQQEPESKYRTTPP    240
SEQ ID NO: 40    ARGQAHQPSVYVLPPSREELSKNTVSLTCLIKDFFPPDIDVEWQSNGQQEPESKYRTTPP    240
SEQ ID NO: 41    ARGQAHQPSVYVLPPSREELSKNTVSLTCLIKDFFPPDIDVEWQSNGQQEPESKYRTTPP    240
SEQ ID NO: 42    ARGQAHQPSVYVLPPSREELSKNTVSLTCLIKDFFPPDIDVEWQSNGQQEPESKYRTTPP    240
                 ************************************************************

SEQ ID NO: 39    QLDEDGSYFLYSKLSVDKSRWQRGDTFICAVMHEALHNHYTQESLSHSPG    290
SEQ ID NO: 40    QLDEDGSYFLYSKLSVDKSRWQRGDTFICAVMHEALHNHYTQESLSHSPG    290
SEQ ID NO: 41    QLDEDGSYFLYSKLSVDKSRWQRGDTFICAVMHEALHNHYTQESLSHSPG    290
SEQ ID NO: 42    QLDEDGSYFLYSKLSVDKSRWQRGDTFICAVMHEALHNHYTQESLSHSPG    290
                 **************************************************
```

FIG. 8

```
SEQ ID NO: 43      FVNQHLCGSHLVEALALVCGERGFFYTDPTGGGPRRGIVEQCCTSICSLYQLENYCNGGG 60
SEQ ID NO: 44      FVNQHLCGSHLVQALYLVCGERGFFYTDPTGGGPRRGIVEQCCTSICSLYQLENYCGG-G 59
SEQ ID NO: 45      FVNQHLCGSELVEALALVCGERGFFYTDPTGGGPRRGIVEQCCTSICSLYQLENYCGG-G 59
SEQ ID NO: 46      FVNQHLCGSHLVEALALVCGEAGFFYTDPTGGGPRRGIVEQCCTSICSLYQLENYCGG-G 59
SEQ ID NO: 47      FVNQHLCGSHLVEALALVCGERGFYYTDPTGGGPRRGIVEQCCTSICSLYQLENYCGG-G 59
SEQ ID NO: 48      FVNQHLCGSHLVEALALVCGERGFFYTDPTGGGPRRGIVEQCCTSICSLYQLENYCGG-G 59
                   *********.**:** ***** **:*******************************.* *

SEQ ID NO: 43      GAGGGGDCPKCPAPEMLGGPSVFIFPPKPKDTLLIARTPEVTCVVVDLDPEDPEVQISWF 120
SEQ ID NO: 44      GAGGGGDCPKCPAPEMLGGPSVFIFPPKPKDTLLIARTPEVTCVVVDLDPEDPEVQISWF 119
SEQ ID NO: 45      GAGGGGDCPKCPAPEMLGGPSVFIFPPKPKDTLLIARTPEVTCVVVDLDPEDPEVQISWF 119
SEQ ID NO: 46      GAGGGGDCPKCPAPEMLGGPSVFIFPPKPKDTLLIARTPEVTCVVVDLDPEDPEVQISWF 119
SEQ ID NO: 47      GAGGGGDCPKCPAPEMLGGPSVFIFPPKPKDTLLIARTPEVTCVVVDLDPEDPEVQISWF 119
SEQ ID NO: 48      GAGGGGDCPKCPAPEMLGGPSVFIFPPKPKDTLLIARTPEVTCVVVDLDPEDPEVQISWF 119
                   ************************************************************

SEQ ID NO: 43      VDGKQMQTAKTQPREEQFQGTYRVVSVLPIGHQDWLKGKQFTCKVNNKALPSPIERTISK 180
SEQ ID NO: 44      VDGKQMQTAKTQPREEQFSGTYRVVSVLPIGHQDWLKGKQFTCKVNNKALPSPIERTISK 179
SEQ ID NO: 45      VDGKQMQTAKTQPREEQFSGTYRVVSVLPIGHQDWLKGKQFTCKVNNKALPSPIERTISK 179
SEQ ID NO: 46      VDGKQMQTAKTQPREEQFSGTYRVVSVLPIGHQDWLKGKQFTCKVNNKALPSPIERTISK 179
SEQ ID NO: 47      VDGKQMQTAKTQPREEQFSGTYRVVSVLPIGHQDWLKGKQFTCKVNNKALPSPIERTISK 179
SEQ ID NO: 48      VDGKQMQTAKTQPREEQFSGTYRVVSVLPIGHQDWLKGKQFTCKVNNKALPSPIERTISK 179
                   ******************.*****************************************

SEQ ID NO: 43      ARGQAHQPSVYVLPPSREELSKNTVSLTCLIKDFFPPDIDVEWQSNGQQEPESKYRTTPP 240
SEQ ID NO: 44      ARGQAHQPSVYVLPPSREELSKNTVSLTCLIKDFFPPDIDVEWQSNGQQEPESKYRTTPP 239
SEQ ID NO: 45      ARGQAHQPSVYVLPPSREELSKNTVSLTCLIKDFFPPDIDVEWQSNGQQEPESKYRTTPP 239
SEQ ID NO: 46      ARGQAHQPSVYVLPPSREELSKNTVSLTCLIKDFFPPDIDVEWQSNGQQEPESKYRTTPP 239
SEQ ID NO: 47      ARGQAHQPSVYVLPPSREELSKNTVSLTCLIKDFFPPDIDVEWQSNGQQEPESKYRTTPP 239
SEQ ID NO: 48      ARGQAHQPSVYVLPPSREELSKNTVSLTCLIKDFFPPDIDVEWQSNGQQEPESKYRTTPP 239
                   ************************************************************

SEQ ID NO: 43      QLDEDGSYFLYSKLSVDKSRWQRGDTFICAVMHEALHNHYTQESLSHSPG     290
SEQ ID NO: 44      QLDEDGSYFLYSKLSVDKSRWQRGDTFICAVMHEALHNHYTQESLSHSPG     289
SEQ ID NO: 45      QLDEDGSYFLYSKLSVDKSRWQRGDTFICAVMHEALHNHYTQESLSHSPG     289
SEQ ID NO: 46      QLDEDGSYFLYSKLSVDKSRWQRGDTFICAVMHEALHNHYTQESLSHSPG     289
SEQ ID NO: 47      QLDEDGSYFLYSKLSVDKSRWQRGDTFICAVMHEALHNHYTQESLSHSPG     289
SEQ ID NO: 48      QLDEDGSYFLYSKLSVDKSRWQRGDTFICAVMHEALHNHYTQESLSHSPG     289
                   **************************************************
```

FIG. 12

```
SEQ ID NO: 43      FVNQHLCGSHLVEALALVCGERGFFYTDPTGG------GPRRGIVEQCCTSICSLYQLENY      55
SEQ ID NO: 49      FVNQHLCGSHLVQALYLVCGERGFFYTDPTQRGGG--GGQRGIVEQCCTSICSLYQLENY      58
SEQ ID NO: 50      FVNQHLCGSHLVEALALVCGERGFFYTDPTGGGGGGSGGGGGIVEQCCTSICSLYQLENY      60
SEQ ID NO: 51      FVNQHLCGSHLVEALALVCGERGFFYTDPGGGG----GGGGGIVEQCCTSICSLYQLENY      56
SEQ ID NO: 52      FVNQHLCGSHLVEALALVCGERGFFYT-PGGGG-----GGGGGIVEQCCTSICSLYQLENY     55
                   ************:** *********** *         *   *******************

SEQ ID NO: 43      CNGGGGAGGGGDCPKCPAPEMLGGPSVFIFPPKPKDTLLIARTPEVTCVVVDLDPEDPEV     115
SEQ ID NO: 49      CGG-GGAGGGGDCPKCPAPEMLGGPSVFIFPPKPKDTLLIARTPEVTCVVVDLDPEDPEV     117
SEQ ID NO: 50      CGG-GGAGGGGDCPKCPAPEMLGGPSVFIFPPKPKDTLLIARTPEVTCVVVDLDPEDPEV     119
SEQ ID NO: 51      CGG-GGAGGGGDCPKCPAPEMLGGPSVFIFPPKPKDTLLIARTPEVTCVVVDLDPEDPEV     115
SEQ ID NO: 52      CGG-GGAGGGGDCPKCPAPEMLGGPSVFIFPPKPKDTLLIARTPEVTCVVVDLDPEDPEV     114
                   *.* ********************************************************

SEQ ID NO: 43      QISWFVDGKQMQTAKTQPREEQFQGTYRVVSVLPIGHQDWLKGKQFTCKVNNKALPSPIE     175
SEQ ID NO: 49      QISWFVDGKQMQTAKTQPREEQFSGTYRVVSVLPIGHQDWLKGKQFTCKVNNKALPSPIE     177
SEQ ID NO: 50      QISWFVDGKQMQTAKTQPREEQFSGTYRVVSVLPIGHQDWLKGKQFTCKVNNKALPSPIE     179
SEQ ID NO: 51      QISWFVDGKQMQTAKTQPREEQFSGTYRVVSVLPIGHQDWLKGKQFTCKVNNKALPSPIE     175
SEQ ID NO: 52      QISWFVDGKQMQTAKTQPREEQFSGTYRVVSVLPIGHQDWLKGKQFTCKVNNKALPSPIE     174
                   ***********************.************************************

SEQ ID NO: 43      RTISKARGQAHQPSVYVLPPSREELSKNTVSLTCLIKDFFPPDIDVEWQSNGQQEPESKY     235
SEQ ID NO: 49      RTISKARGQAHQPSVYVLPPSREELSKNTVSLTCLIKDFFPPDIDVEWQSNGQQEPESKY     237
SEQ ID NO: 50      RTISKARGQAHQPSVYVLPPSREELSKNTVSLTCLIKDFFPPDIDVEWQSNGQQEPESKY     239
SEQ ID NO: 51      RTISKARGQAHQPSVYVLPPSREELSKNTVSLTCLIKDFFPPDIDVEWQSNGQQEPESKY     235
SEQ ID NO: 52      RTISKARGQAHQPSVYVLPPSREELSKNTVSLTCLIKDFFPPDIDVEWQSNGQQEPESKY     234
                   ************************************************************

SEQ ID NO: 43      RTTPPQLDEDGSYFLYSKLSVDKSRWQRGDTFICAVMHEALHNHYTQESLSHSPG     290
SEQ ID NO: 49      RTTPPQLDEDGSYFLYSKLSVDKSRWQRGDTFICAVMHEALHNHYTQESLSHSPG     292
SEQ ID NO: 50      RTTPPQLDEDGSYFLYSKLSVDKSRWQRGDTFICAVMHEALHNHYTQESLSHSPG     294
SEQ ID NO: 51      RTTPPQLDEDGSYFLYSKLSVDKSRWQRGDTFICAVMHEALHNHYTQESLSHSPG     290
SEQ ID NO: 52      RTTPPQLDEDGSYFLYSKLSVDKSRWQRGDTFICAVMHEALHNHYTQESLSHSPG     289
                   *******************************************************
```

FIG. 13

```
SEQ ID NO: 43      FVNQHLCGSHLVEALALVCGERGFFYTDPTGGGPRRGIVEQCCTSICSLYQLENYCNGGG      60
SEQ ID NO: 53      FVNQHLCGSHLVEALALVCGERGFFYTDPTGGGPRRGIVEQCCTSICSLYQLENYCGGGG      60
SEQ ID NO: 48      FVNQHLCGSHLVEALALVCGERGFFYTDPTGGGPRRGIVEQCCTSICSLYQLENYCGGGG      60
                   ********************************************************.***

SEQ ID NO: 43      GA-----------GGGGDCPKCPAPEMLGGPSVFIFPPKPKDTLLIARTPEVTCVVVDLD      109
SEQ ID NO: 53      GQGGGGQGGGGQGGGGGDCPKCPAPEMLGGPSVFIFPPKPKDTLLIARTPEVTCVVVDLD      120
SEQ ID NO: 48      A------------GGGGDCPKCPAPEMLGGPSVFIFPPKPKDTLLIARTPEVTCVVVDLD      108
                   .            ***********************************************

SEQ ID NO: 43      PEDPEVQISWFVDGKQMQTAKTQPREEQFQGTYRVVSVLPIGHQDWLKGKQFTCKVNNKA      169
SEQ ID NO: 53      PEDPEVQISWFVDGKQMQTAKTQPREEQFSGTYRVVSVLPIGHQDWLKGKQFTCKVNNKA      180
SEQ ID NO: 48      PEDPEVQISWFVDGKQMQTAKTQPREEQFSGTYRVVSVLPIGHQDWLKGKQFTCKVNNKA      168
                   *****************************.******************************

SEQ ID NO: 43      LPSPIERTISKARGQAHQPSVYVLPPSREELSKNTVSLTCLIKDFFPPDIDVEWQSNGQQ      229
SEQ ID NO: 53      LPSPIERTISKARGQAHQPSVYVLPPSREELSKNTVSLTCLIKDFFPPDIDVEWQSNGQQ      240
SEQ ID NO: 48      LPSPIERTISKARGQAHQPSVYVLPPSREELSKNTVSLTCLIKDFFPPDIDVEWQSNGQQ      228
                   ************************************************************

SEQ ID NO: 43      EPESKYRTTPPQLDEDGSYFLYSKLSVDKSRWQRGDTFICAVMHEALHNHYTQESLSHSP      289
SEQ ID NO: 53      EPESKYRTTPPQLDEDGSYFLYSKLSVDKSRWQRGDTFICAVMHEALHNHYTQESLSHSP      300
SEQ ID NO: 48      EPESKYRTTPPQLDEDGSYFLYSKLSVDKSRWQRGDTFICAVMHEALHNHYTQESLSHSP      288
                   ************************************************************

SEQ ID NO: 43      G   290
SEQ ID NO: 53      G   301
SEQ ID NO: 48      G   289
                   *
```

FIG. 14

```
SEQ ID NO: 43    FVNQHLCGSHLVEALALVCGERGFFYTDPTGGG~PRRGIVEQCCTSICSLYQLENYCNGG    59
SEQ ID NO: 51    FVNQHLCGSHLVEALALVCGERGFFYTDPGGGGGGGGIVEQCCTSICSLYQLENYCGG~    59
SEQ ID NO: 54    FVNQHLCGSHLVEALALVCGERGFFYTQG~GGGGGGGGIVEQCCTSICSLYQLENYCGG~    58
SEQ ID NO: 52    FVNQHLCGSHLVEALALVCGERGFFYTPG~GGGGGGGGIVEQCCTSICSLYQLENYCGG~    58
                 ***************************   ***    ********************.*

SEQ ID NO: 43    GGAGGGGDCPKCPAPEMLGGPSVFIFPPKPKDTLLIARTPEVTCVVVDLDPEDPEVQISW    119
SEQ ID NO: 51    GGAGGGGDCPKCPAPEMLGGPSVFIFPPKPKDTLLIARTPEVTCVVVDLDPEDPEVQISW    119
SEQ ID NO: 54    GGAGGGGDCPKCPAPEMLGGPSVFIFPPKPKDTLLIARTPEVTCVVVDLDPEDPEVQISW    118
SEQ ID NO: 52    GGAGGGGDCPKCPAPEMLGGPSVFIFPPKPKDTLLIARTPEVTCVVVDLDPEDPEVQISW    118
                 ************************************************************

SEQ ID NO: 43    FVDGKQMQTAKTQPREEQFQGTYRVVSVLPIGHQDWLKGKQFTCKVNNKALPSPIERTIS    179
SEQ ID NO: 51    FVDGKQMQTAKTQPREEQFSGTYRVVSVLPIGHQDWLKGKQFTCKVNNKALPSPIERTIS    179
SEQ ID NO: 54    FVDGKQMQTAKTQPREEQFSGTYRVVSVLPIGHQDWLKGKQFTCKVNNKALPSPIERTIS    178
SEQ ID NO: 52    FVDGKQMQTAKTQPREEQFSGTYRVVSVLPIGHQDWLKGKQFTCKVNNKALPSPIERTIS    178
                 *******************.****************************************

SEQ ID NO: 43    KARGQAHQPSVYVLPPSREELSKNTVSLTCLIKDFFPPDIDVEWQSNGQQEPESKYRTTP    239
SEQ ID NO: 51    KARGQAHQPSVYVLPPSREELSKNTVSLTCLIKDFFPPDIDVEWQSNGQQEPESKYRTTP    239
SEQ ID NO: 54    KARGQAHQPSVYVLPPSREELSKNTVSLTCLIKDFFPPDIDVEWQSNGQQEPESKYRTTP    238
SEQ ID NO: 52    KARGQAHQPSVYVLPPSREELSKNTVSLTCLIKDFFPPDIDVEWQSNGQQEPESKYRTTP    238
                 ************************************************************

SEQ ID NO: 43    PQLDEDGSYFLYSKLSVDKSRWQRGDTFICAVMHEALHNHYTQESLSHSPG    290
SEQ ID NO: 51    PQLDEDGSYFLYSKLSVDKSRWQRGDTFICAVMHEALHNHYTQESLSHSPG    290
SEQ ID NO: 54    PQLDEDGSYFLYSKLSVDKSRWQRGDTFICAVMHEALHNHYTQESLSHSPG    289
SEQ ID NO: 52    PQLDEDGSYFLYSKLSVDKSRWQRGDTFICAVMHEALHNHYTQESLSHSPG    289
                 ***************************************************
```

FIG. 15

```
SEQ ID NO: 43     FVNQHLCGSHLVEALALVCGERGFFYTDPTGG~GPRRGIVEQCCTSICSLYQLENYCNGG     59
SEQ ID NO: 55     FVNQHLCGSHLVEALELVCGERGFFYTPKTGGSGGGGGIVEQCCTSTCSLDQLENYCGG~     59
SEQ ID NO: 56     FVNQHLCGSHLVEALELVCGERGFHYGGGGGGSGGGGGIVEQCCTSTCSLDQLENYCNHG     60
SEQ ID NO: 28     FVNQHLCGSHLVEALELVCGERGFHYGGGGGGSGGGGGIVEQCCTSTCSLDQLENYCNGG     60
SEQ ID NO: 26     FVNQHLCGSHLVEALELVCGERGFHYGGGGGGSGGGGGIVEQCCTSTCSLDQLENYCGG~     59
SEQ ID NO: 57     FVNQHLCGSHLVEALELVCGERGFFYGGGGGGSGGGGGIVEQCCTSTCSLDQLENYCGG~     59
                  *************** ********.*     ** *    ********* *** ******.

SEQ ID NO: 43     GG~~~~~~~~~~~~AGGGGDCPKCPAPEMLGGPSVFIFPPKPKDTLLIARTPEVTCVVVD     107
SEQ ID NO: 55     GGGQGGGGQGGGGQGGGGGDCPKCPAPEMLGGPSVFIFPPKPKDTLLIARTPEVTCVVVD     119
SEQ ID NO: 56     GGGQGGGGQGGGGQGGGGGDCPKCPAPEMLGGPSVFIFPPKPKDTLLIARTPEVTCVVVD     120
SEQ ID NO: 28     GGGQGGGGQGGGGQGGGGGDCPKCPAPEMLGGPSVFIFPPKPKDTLLIARTPEVTCVVVD     120
SEQ ID NO: 26     GGGQGGGGQGGGGQGGGGGDCPKCPAPEMLGGPSVFIFPPKPKDTLLIARTPEVTCVVVD     119
SEQ ID NO: 57     GGGQGGGGQGGGGQGGGGGDCPKCPAPEMLGGPSVFIFPPKPKDTLLIARTPEVTCVVVD     119
                  **            .*********************************************

SEQ ID NO: 43     LDPEDPEVQISWFVDGKQMQTAKTQPREEQFQGTYRVVSVLPIGHQDWLKGKQFTCKVNN     167
SEQ ID NO: 55     LDPEDPEVQISWFVDGKQMQTAKTQPREEQFNGTYRVVSVLPIGHQDWLKGKQFTCKVNN     179
SEQ ID NO: 56     LDPEDPEVQISWFVDGKQMQTAKTQPREEQFNGTYRVVSVLPIGHQDWLKGKQFTCKVNN     180
SEQ ID NO: 28     LDPEDPEVQISWFVDGKQMQTAKTQPREEQFNGTYRVVSVLPIGHQDWLKGKQFTCKVNN     180
SEQ ID NO: 26     LDPEDPEVQISWFVDGKQMQTAKTQPREEQFNGTYRVVSVLPIGHQDWLKGKQFTCKVNN     179
SEQ ID NO: 57     LDPEDPEVQISWFVDGKQMQTAKTQPREEQFNGTYRVVSVLPIGHQDWLKGKQFTCKVNN     179
                  *******************************:****************************

SEQ ID NO: 43     KALPSPIERTISKARGQAHQPSVYVLPPSREELSKNTVSLTCLIKDFFPPDIDVEWQSNG     227
SEQ ID NO: 55     KALPSPIERTISKARGQAHQPSVYVLPPSREELSKNTVSLTCLIKDFFPPDIDVEWQSNG     239
SEQ ID NO: 56     KALPSPIERTISKARGQAHQPSVYVLPPSREELSKNTVSLTCLIKDFFPPDIDVEWQSNG     240
SEQ ID NO: 28     KALPSPIERTISKARGQAHQPSVYVLPPSREELSKNTVSLTCLIKDFFPPDIDVEWQSNG     240
SEQ ID NO: 26     KALPSPIERTISKARGQAHQPSVYVLPPSREELSKNTVSLTCLIKDFFPPDIDVEWQSNG     239
SEQ ID NO: 57     KALPSPIERTISKARGQAHQPSVYVLPPSREELSKNTVSLTCLIKDFFPPDIDVEWQSNG     239
                  ************************************************************

SEQ ID NO: 43     QQEPESKYRTTPPQLDEDGSYFLYSKLSVDKSRWQRGDTFICAVMHEALHNHYTQESLSH     287
SEQ ID NO: 55     QQEPESKYRTTPPQLDEDGSYFLYSKLSVDKSRWQRGDTFICAVMHEALHNHYTQESLSH     299
SEQ ID NO: 56     QQEPESKYRTTPPQLDEDGSYFLYSKLSVDKSRWQRGDTFICAVMHEALHNHYTQESLSH     300
SEQ ID NO: 28     QQEPESKYRTTPPQLDEDGSYFLYSKLSVDKSRWQRGDTFICAVMHEALHNHYTQESLSH     300
SEQ ID NO: 26     QQEPESKYRTTPPQLDEDGSYFLYSKLSVDKSRWQRGDTFICAVMHEALHNHYTQESLSH     299
SEQ ID NO: 57     QQEPESKYRTTPPQLDEDGSYFLYSKLSVDKSRWQRGDTFICAVMHEALHNHYTQESLSH     299
                  ************************************************************

SEQ ID NO: 43     SPG 290
SEQ ID NO: 55     SPG 302
SEQ ID NO: 56     SPG 303
SEQ ID NO: 28     SPG 303
SEQ ID NO: 26     SPG 302
SEQ ID NO: 57     SPG 302
                  ***
```

FIG. 16

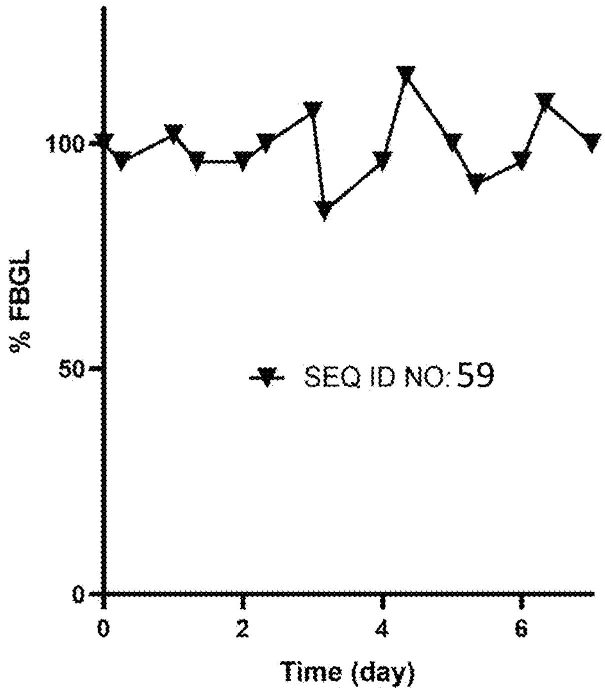

FIG. 23

```
SEQ ID NO: 61      FVNQHLCGSHLVEALELVCGERGFHYGGGGGGSGGGGGIVEQCCTSTCSLDQLENYCGGG     60
SEQ ID NO: 62      FVNQHLCGSHLVEALELVCGERGFHYGGGGGGSGGGGGIVEQCCTSTCSLDQLENYCGGG     60
                   ************************************************************

SEQ ID NO: 61      GGQGGGGQGGGGQGGGGGDCPKCPAPEMLGGPSVFIFPPKPKDTLLIARTPEVTCVVVAL     120
SEQ ID NO: 62      GGQGGGGQGGGGQGGGGGDCPKCPAPEMLGGPSVFIFPPKPKDTLLIARTPEVTCVVVDL     120
                   ********************************************************** *

SEQ ID NO: 61      DPEDPEVQISWFVDGKQMQTAKTQPREEQFSGTYRVVSVLPIGHQDWLKGKQFTCKVNNK     180
SEQ ID NO: 62      DPEDPEVQISWFVDGKQMQTAKTQPREEQFSGTYRVVSVLPIGHQDWLKGKQFTCKVNNK     180
                   ************************************************************

SEQ ID NO: 61      ALPSPIERTISKARGQAHQPSVYVLPPSREELSKNTVSLTCLIKDFFPPDIDVEWQSNGQ     240
SEQ ID NO: 62      ALPSPIERTISKARGQAHQPSVYVLPPSREELSKNTVSLTCLIKDFFPPDIDVEWQSNGQ     240
                   ************************************************************

SEQ ID NO: 61      QEPESKYRTTPPQLDEDGSYFLYSKLSVDKSRWQRGDTFICAVMHEALHNHYTQESLSHS     300
SEQ ID NO: 62      QEPESKYRTTPPQLDEDGSYFLYSKLSVDKSRWQRGDTFICAVMHEALHNHYTQESLSHS     300
                   ************************************************************

SEQ ID NO: 61      PG  302
SEQ ID NO: 62      PG  302
                   **
```

FIG. 24

```
SEQ ID NO: 76     FVNQHLCGSHLVEALELVCGERGFHYGGGGGGSGGGGGIVEQCCTSTCSLDQLENYCGGG     60
SEQ ID NO: 91     FVNQHLCGSHLVEALELVCGERGFHYGGGGGGSGGGGGIVEQCCTSTCSLDQLENYCGGG     60
SEQ ID NO: 78     FVNQHLCGSHLVEALALVCGERGFHYGGGGGGSGGGGGIVEQCCTSTCSLDQLENYCGGG     60
                  *************** ********************************************

SEQ ID NO: 76     GGQGGGGQGGGGQGGGGGDKTHTCPPCPAPELLGGPSVFLFPPKPKDTLMISRTPEVTCV     120
SEQ ID NO: 91     GGQGGGGQGGGGQGGGGGDKTHTCPPCPAPELLGGPSVFLFPPKPKDTLMISRTPEVTCV     120
SEQ ID NO: 78     GGQGGGGQGGGGQGGGGGDKTHTCPPCPAPELLGGPSVFLFPPKPKDTLMISRTPEVTCV     120
                  ************************************************************

SEQ ID NO: 76     VVDVSHEDPEVKFNWYVDGVEVHNAKTKPREEQYNSTYRVVSVLTVLHQDWLNGKEYKCK     180
SEQ ID NO: 91     VVDVSHEDPEVKFNWYVDGVEVHNAKTKPREEQYSSTYRVVSVLTVLHQDWLNGKEYKCK     180
SEQ ID NO: 78     VVDVSHEDPEVKFNWYVDGVEVHNAKTKPREEQYSSTYRVVSVLTVLHQDWLNGKEYKCK     180
                  **********************************.*************************

SEQ ID NO: 76     VSNKALPAPIEKTISKAKGQPREPQVYTLPPSRDELTKNQVSLTCLVKGFYPSDIAVEWE     240
SEQ ID NO: 91     VSNKALPAPIEKTISKAKGQPREPQVYTLPPSRDELTKNQVSLTCLVKGFYPSDIAVEWE     240
SEQ ID NO: 78     VSNKALPAPIEKTISKAKGQPREPQVYTLPPSRDELTKNQVSLTCLVKGFYPSDIAVEWE     240
                  ************************************************************

SEQ ID NO: 76     SNGQPENNYKTTPPVLDSDGSFFLYSKLTVDKSRWQQGNVFSCSVMHEALHNHYTQKSLS     300
SEQ ID NO: 91     SNGQPENNYKTTPPVLDSDGSFFLYSKLTVDKSRWQQGNVFSCSVMHEALHNHYTQKSLS     300
SEQ ID NO: 78     SNGQPENNYKTTPPVLDSDGSFFLYSKLTVDKSRWQQGNVFSCSVMHEALHNHYTQKSLS     300
                  ************************************************************

SEQ ID NO: 76     LSPG     304
SEQ ID NO: 91     LSPG     304
SEQ ID NO: 78     LSPG     304
                  ****
```

FIG. 27

```
SEQ ID NO: 75    FVNQHLCGSHLVEALELVCGERGFHYGGGGGGSGGGGGIVEQCCTSTCSLDQLENYCGGG    60
SEQ ID NO: 76    FVNQHLCGSHLVEALELVCGERGFHYGGGGGGSGGGGGIVEQCCTSTCSLDQLENYCGGG    60
SEQ ID NO: 91    FVNQHLCGSHLVEALELVCGERGFHYGGGGGGSGGGGGIVEQCCTSTCSLDQLENYCGGG    60
SEQ ID NO: 92    FVNQHLCGSHLVEALELVCGERGFHYGGGGGGSGGGGGIVEQCCTSTCSLDQLENYCGGG    60
SEQ ID NO: 93    FVNQHLCGSHLVEALELVCGERGFHYGGGGGGSGGGGGIVEQCCTSTCSLDQLENYCGGG    60
SEQ ID NO: 94    FVNQHLCGSHLVEALELVCGERGFHYGGGGGGSGGGGGIVEQCCTSTCSLDQLENYCGGG    60
SEQ ID NO: 95    FVNQHLCGSHLVEALELVCGERGFHYGGGGGGSGGGGGIVEQCCTSTCSLDQLENYCGGG    60
                 ************************************************************

SEQ ID NO: 75    GGQGGGGQGGGGQGGGGG----ECPPCPAPPV-AGPSVFLFPPKPKDTLMISRTPEVTCV    115
SEQ ID NO: 76    GGQGGGGQGGGGQGGGGGDKTHTCPPCPAPELLGGPSVFLFPPKPKDTLMISRTPEVTCV    120
SEQ ID NO: 91    GGQGGGGQGGGGQGGGGGDKTHTCPPCPAPELLGGPSVFLFPPKPKDTLMISRTPEVTCV    120
SEQ ID NO: 92    GGQGGGGQGGGGQGGGGGDKTHTCPPCPAPELLGGPSVFLFPPKPKDTLMISRTPEVTCV    120
SEQ ID NO: 93    GGQGGGGQGGGGQGGGGGDKTHTCPPCPAPELLGGPSVFLFPPKPKDTLMISRTPEVTCV    120
SEQ ID NO: 94    GGQGGGGQGGGGQGGGGGDKTHTCPPCPAPELLGGPSVFLFPPKPKDTLMISRTPEVTCV    120
SEQ ID NO: 95    GGQGGGGQGGGGQGGGGGDKTHTCPPCPAPELLGGPSVFLFPPKPKDTLMISRTPEVTCV    120
                 ******************     ******* : .**************************

SEQ ID NO: 75    VVDVSHEDPEVQFNWYVDGVEVHNAKTKPREEQFNSTFRVVSVLTVVHQDWLNGKEYKCK    175
SEQ ID NO: 76    VVDVSHEDPEVKFNWYVDGVEVHNAKTKPREEQYNSTYRVVSVLTVLHQDWLNGKEYKCK    180
SEQ ID NO: 91    VVDVSHEDPEVKFNWYVDGVEVHNAKTKPREEQYSSTYRVVSVLTVLHQDWLNGKEYKCK    180
SEQ ID NO: 92    VVDVSHEDPEVKFNWYVDGVEVHNAKTKPREEQYDSTYRVVSVLTVLHQDWLNGKEYKCK    180
SEQ ID NO: 93    VVDVSHEDPEVKFNWYVDGVEVHNAKTKPREEQYASTYRVVSVLTVLHQDWLNGKEYKCK    180
SEQ ID NO: 94    VVDVSHEDPEVKFNWYVDGVEVHNAKTKPREEQYRSTYRVVSVLTVLHQDWLNGKEYKCK    180
SEQ ID NO: 95    VVDVSHEDPEVKFNWYVDGVEVHNAKTKPREEQYQSTYRVVSVLTVLHQDWLNGKEYKCK    180
                 ***********:*********************: **:********:*************

SEQ ID NO: 75    VSNKGLPAPIEKTISKTKGQPREPQVYTLPPSREEMTKNQVSLTCLVKGFYPSDIAVEWE    235
SEQ ID NO: 76    VSNKALPAPIEKTISKAKGQPREPQVYTLPPSRDELTKNQVSLTCLVKGFYPSDIAVEWE    240
SEQ ID NO: 91    VSNKALPAPIEKTISKAKGQPREPQVYTLPPSRDELTKNQVSLTCLVKGFYPSDIAVEWE    240
SEQ ID NO: 92    VSNKALPAPIEKTISKAKGQPREPQVYTLPPSRDELTKNQVSLTCLVKGFYPSDIAVEWE    240
SEQ ID NO: 93    VSNKALPAPIEKTISKAKGQPREPQVYTLPPSRDELTKNQVSLTCLVKGFYPSDIAVEWE    240
SEQ ID NO: 94    VSNKALPAPIEKTISKAKGQPREPQVYTLPPSRDELTKNQVSLTCLVKGFYPSDIAVEWE    240
SEQ ID NO: 95    VSNKALPAPIEKTISKAKGQPREPQVYTLPPSRDELTKNQVSLTCLVKGFYPSDIAVEWE    240
                 ****.***********:****************:*:************************

SEQ ID NO: 75    SNGQPENNYKTTPPMLDSDGSFFLYSKLTVDKSRWQQGNVFSCSVMHEALHNHYTQKSLS    295
SEQ ID NO: 76    SNGQPENNYKTTPPVLDSDGSFFLYSKLTVDKSRWQQGNVFSCSVMHEALHNHYTQKSLS    300
SEQ ID NO: 91    SNGQPENNYKTTPPVLDSDGSFFLYSKLTVDKSRWQQGNVFSCSVMHEALHNHYTQKSLS    300
SEQ ID NO: 92    SNGQPENNYKTTPPVLDSDGSFFLYSKLTVDKSRWQQGNVFSCSVMHEALHNHYTQKSLS    300
SEQ ID NO: 93    SNGQPENNYKTTPPVLDSDGSFFLYSKLTVDKSRWQQGNVFSCSVMHEALHNHYTQKSLS    300
SEQ ID NO: 94    SNGQPENNYKTTPPVLDSDGSFFLYSKLTVDKSRWQQGNVFSCSVMHEALHNHYTQKSLS    300
SEQ ID NO: 95    SNGQPENNYKTTPPVLDSDGSFFLYSKLTVDKSRWQQGNVFSCSVMHEALHNHYTQKSLS    300
                 **************:*********************************************

SEQ ID NO: 75    LSPG  299
SEQ ID NO: 76    LSPG  304
SEQ ID NO: 91    LSPG  304
SEQ ID NO: 92    LSPG  304
SEQ ID NO: 93    LSPG  304
SEQ ID NO: 94    LSPG  304
SEQ ID NO: 95    LSPG  304
                 ****
```

FIG. 28

```
SEQ ID NO: 76    FVNQHLCGSHLVEALELVCGERGFHYGGGGGGSGGGGGIVEQCCTSTCSLDQLENYCGGG    60
SEQ ID NO: 78    FVNQHLCGSHLVEALALVCGERGFHYGGGGGGSGGGGGIVEQCCTSTCSLDQLENYCGGG    60
SEQ ID NO: 80    FVNQHLCGSHLVEALALVCGERGFHYGGGGGGSGGGGGIVEQCCTSTCSLDQLENYCGGG    60
SEQ ID NO: 82    FVNQHLCGSHLVEALALVCGERGFHYGGGGGGSGGGGGIVEQCCTSTCSLDQLENYCGGG    60
SEQ ID NO: 84    FVNQHLCGSHLVEALALVCGERGFHYGGGGGGSGGGGGIVEQCCTSTCSLDQLENYCGGG    60
SEQ ID NO: 86    FVNQHLCGSHLVEALALVCGERGFHYGGGGGGSGGGGGIVEQCCTSTCSLDQLENYCGGG    60
                 *************** ********************************************

SEQ ID NO: 76    GGQGGGGQGGGGQGGGGGDKTHTCPPCPAPELLGGPSVFLFPPKPKDTLMISRTPEVTCV    120
SEQ ID NO: 78    GGQGGGGQGGGGQGGGGGDKTHTCPPCPAPELLGGPSVFLFPPKPKDTLMISRTPEVTCV    120
SEQ ID NO: 80    GGQGGGGQGGGGQGGGGGDKTHTCPPCPAPELLGGPSVFLFPPKPKDTLMISRTPEVTCV    120
SEQ ID NO: 82    GGQGGGGQGGGGQGGGGGDKTHTCPPCPAPELLGGPSVFLFPPKPKDTLMISRTPEVTCV    120
SEQ ID NO: 84    GGQGGGGQGGGGQGGGGGDKTHTCPPCPAPELLGGPSVFLFPPKPKDTLMISRTPEVTCV    120
SEQ ID NO: 86    GGQGGGGQGGGGQGGGGGDKTHTCPPCPAPELLGGPSVFLFPPKPKDTLMISRTPEVTCV    120
                 ************************************************************

SEQ ID NO: 76    VVDVSHEDPEVKFNWYVDGVEVHNAKTKPREEQYNSTYRVVSVLTVLHQDWLNGKEYKCK    180
SEQ ID NO: 78    VVDVSHEDPEVKFNWYVDGVEVHNAKTKPREEQYSSTYRVVSVLTVLHQDWLNGKEYKCK    180
SEQ ID NO: 80    VVDVSHEDPEVKFNWYVDGVEVHNAKTKPREEQYDSTYRVVSVLTVLHQDWLNGKEYKCK    180
SEQ ID NO: 82    VVDVSHEDPEVKFNWYVDGVEVHNAKTKPREEQYASTYRVVSVLTVLHQDWLNGKEYKCK    180
SEQ ID NO: 84    VVDVSHEDPEVKFNWYVDGVEVHNAKTKPREEQYRSTYRVVSVLTVLHQDWLNGKEYKCK    180
SEQ ID NO: 86    VVDVSHEDPEVKFNWYVDGVEVHNAKTKPREEQYQSTYRVVSVLTVLHQDWLNGKEYKCK    180
                 ********************************** *************************

SEQ ID NO: 76    VSNKALPAPIEKTISKAKGQPREPQVYTLPPSRDELTKNQVSLTCLVKGFYPSDIAVEWE    240
SEQ ID NO: 78    VSNKALPAPIEKTISKAKGQPREPQVYTLPPSRDELTKNQVSLTCLVKGFYPSDIAVEWE    240
SEQ ID NO: 80    VSNKALPAPIEKTISKAKGQPREPQVYTLPPSRDELTKNQVSLTCLVKGFYPSDIAVEWE    240
SEQ ID NO: 82    VSNKALPAPIEKTISKAKGQPREPQVYTLPPSRDELTKNQVSLTCLVKGFYPSDIAVEWE    240
SEQ ID NO: 84    VSNKALPAPIEKTISKAKGQPREPQVYTLPPSRDELTKNQVSLTCLVKGFYPSDIAVEWE    240
SEQ ID NO: 86    VSNKALPAPIEKTISKAKGQPREPQVYTLPPSRDELTKNQVSLTCLVKGFYPSDIAVEWE    240
                 ************************************************************

SEQ ID NO: 76    SNGQPENNYKTTPPVLDSDGSFFLYSKLTVDKSRWQQGNVFSCSVMHEALHNHYTQKSLS    300
SEQ ID NO: 78    SNGQPENNYKTTPPVLDSDGSFFLYSKLTVDKSRWQQGNVFSCSVMHEALHNHYTQKSLS    300
SEQ ID NO: 80    SNGQPENNYKTTPPVLDSDGSFFLYSKLTVDKSRWQQGNVFSCSVMHEALHNHYTQKSLS    300
SEQ ID NO: 82    SNGQPENNYKTTPPVLDSDGSFFLYSKLTVDKSRWQQGNVFSCSVMHEALHNHYTQKSLS    300
SEQ ID NO: 84    SNGQPENNYKTTPPVLDSDGSFFLYSKLTVDKSRWQQGNVFSCSVMHEALHNHYTQKSLS    300
SEQ ID NO: 86    SNGQPENNYKTTPPVLDSDGSFFLYSKLTVDKSRWQQGNVFSCSVMHEALHNHYTQKSLS    300
                 ************************************************************

SEQ ID NO: 76    LSPG  304
SEQ ID NO: 78    LSPG  304
SEQ ID NO: 80    LSPG  304
SEQ ID NO: 82    LSPG  304
SEQ ID NO: 84    LSPG  304
SEQ ID NO: 86    LSPG  304
                 ****
```

FIG. 29

```
SEQ ID NO: 87    FVNQHLCGSHLVEALALVCGERGFHYGGGGGGSGGGGGIVEQCCTSTCSLDQLENYCGGG    60
SEQ ID NO: 96    FVNQHLCGSHLVEALALVCGERGFHYGGGGGGSGGGGGIVEQCCTSTCSLDQLENYCGGG    60
SEQ ID NO: 78    FVNQHLCGSHLVEALALVCGERGFHYGGGGGGSGGGGGIVEQCCTSTCSLDQLENYCGGG    60
SEQ ID NO: 97    FVNQHLCGSHLVEALALVCGERGFHYGGGGGGSGGGGGIVEQCCTSTCSLDQLENYCGGG    60
SEQ ID NO: 89    FVNQHLCGSHLVEALALVCGERGFHYGGGGGGSGGGGGIVEQCCTSTCSLDQLENYCGGG    60
SEQ ID NO: 98    FVNQHLCGSHLVEALALVCGERGFHYGGGGGGSGGGGGIVEQCCTSTCSLDQLENYCD--    58
                 *********************************************************.

SEQ ID NO: 87    GGAGGGGAGGGGA-----GGGGGDKTHTCPPCPAPELLGGPSVFLFPPKPKDTLMISRTP    115
SEQ ID NO: 96    GGQGGGGQGGGGQGGGGGQGGGGDKTHTCPPCPAPELLGGPSVFLFPPKPKDTLMISRTP    120
SEQ ID NO: 78    GGQGGGGQGGGGQGG-----GGGDKTHTCPPCPAPELLGGPSVFLFPPKPKDTLMISRTP    115
SEQ ID NO: 97    G-----------------QGGGGDKTHTCPPCPAPELLGGPSVFLFPPKPKDTLMISRTP    103
SEQ ID NO: 89    G-----------------AGGGGDKTHTCPPCPAPELLGGPSVFLFPPKPKDTLMISRTP    103
SEQ ID NO: 98    ------------------------KTHTCPPCPAPELLGGPSVFLFPPKPKDTLMISRTP    94
                                         ************************************

SEQ ID NO: 87    EVTCVVVDVSHEDPEVKFNWYVDGVEVHNAKTKPREEQYSSTYRVVSVLTVLHQDWLNGK    175
SEQ ID NO: 96    EVTCVVVDVSHEDPEVKFNWYVDGVEVHNAKTKPREEQYSSTYRVVSVLTVLHQDWLNGK    180
SEQ ID NO: 78    EVTCVVVDVSHEDPEVKFNWYVDGVEVHNAKTKPREEQYSSTYRVVSVLTVLHQDWLNGK    175
SEQ ID NO: 97    EVTCVVVDVSHEDPEVKFNWYVDGVEVHNAKTKPREEQYSSTYRVVSVLTVLHQDWLNGK    163
SEQ ID NO: 89    EVTCVVVDVSHEDPEVKFNWYVDGVEVHNAKTKPREEQYSSTYRVVSVLTVLHQDWLNGK    163
SEQ ID NO: 98    EVTCVVVDVSHEDPEVKFNWYVDGVEVHNAKTKPREEQYSSTYRVVSVLTVLHQDWLNGK    154
                 ************************************************************

SEQ ID NO: 87    EYKCKVSNKALPAPIEKTISKAKGQPREPQVYTLPPSRDELTKNQVSLTCLVKGFYPSDI    235
SEQ ID NO: 96    EYKCKVSNKALPAPIEKTISKAKGQPREPQVYTLPPSRDELTKNQVSLTCLVKGFYPSDI    240
SEQ ID NO: 78    EYKCKVSNKALPAPIEKTISKAKGQPREPQVYTLPPSRDELTKNQVSLTCLVKGFYPSDI    235
SEQ ID NO: 97    EYKCKVSNKALPAPIEKTISKAKGQPREPQVYTLPPSRDELTKNQVSLTCLVKGFYPSDI    223
SEQ ID NO: 89    EYKCKVSNKALPAPIEKTISKAKGQPREPQVYTLPPSRDELTKNQVSLTCLVKGFYPSDI    223
SEQ ID NO: 98    EYKCKVSNKALPAPIEKTISKAKGQPREPQVYTLPPSRDELTKNQVSLTCLVKGFYPSDI    214
                 ************************************************************

SEQ ID NO: 87    AVEWESNGQPENNYKTTPPVLDSDGSFFLYSKLTVDKSRWQQGNVFSCSVMHEALHNHYT    295
SEQ ID NO: 96    AVEWESNGQPENNYKTTPPVLDSDGSFFLYSKLTVDKSRWQQGNVFSCSVMHEALHNHYT    300
SEQ ID NO: 78    AVEWESNGQPENNYKTTPPVLDSDGSFFLYSKLTVDKSRWQQGNVFSCSVMHEALHNHYT    295
SEQ ID NO: 97    AVEWESNGQPENNYKTTPPVLDSDGSFFLYSKLTVDKSRWQQGNVFSCSVMHEALHNHYT    283
SEQ ID NO: 89    AVEWESNGQPENNYKTTPPVLDSDGSFFLYSKLTVDKSRWQQGNVFSCSVMHEALHNHYT    283
SEQ ID NO: 98    AVEWESNGQPENNYKTTPPVLDSDGSFFLYSKLTVDKSRWQQGNVFSCSVMHEALHNHYT    274
                 ************************************************************

SEQ ID NO: 87    QKSLSLSPG    304
SEQ ID NO: 96    QKSLSLSPG    309
SEQ ID NO: 78    QKSLSLSPG    304
SEQ ID NO: 97    QKSLSLSPG    292
SEQ ID NO: 89    QKSLSLSPG    292
SEQ ID NO: 98    QKSLSLSPG    283
                 *********
```

FIG. 30

```
SEQ ID NO: 79 atggaatggagctgggtctttctcttcttcctgtcagtaacgactggtgtccactccttc
SEQ ID NO: 78  M  E  W  S  W  V  F  L  F  F  L  S  V  T  T  G  V  H  S  F
              gtgaaccagcacctgtgcggctcccacctggtggaagctctggcactcgtgtgcggcgag
               V  N  Q  H  L  C  G  S  H  L  V  E  A  L  A  L  V  C  G  E
              cggggcttccactacgggggtggcggaggaggttctggtggcggcggaggcatcgtggaa
               R  G  F  H  Y  G  G  G  G  G  G  S  G  G  G  G  G  I  V  E
              cagtgctgcacctccacctgctccctggaccagctggaaaactactgcggtggcggaggt
               Q  C  C  T  S  T  C  S  L  D  Q  L  E  N  Y  C  G  G  G  G
              ggtcaaggaggcggtggacagggtggaggtggcagggaggaggcggggagacaaaact
               G  Q  G  G  G  G  Q  G  G  G  G  Q  G  G  G  G  G  D  K  T
              cacacatgcccaccgtgcccagcacctgaactcctggggggaccgtcagtcttcctcttc
               H  T  C  P  P  C  P  A  P  E  L  L  G  G  P  S  V  F  L  F
              cccccaaaacccaaggacaccctcatgatctcccggacccctgaggtcacatgcgtggtg
               P  P  K  P  K  D  T  L  M  I  S  R  T  P  E  V  T  C  V  V
              gtggacgtgagccacgaagaccctgaggtcaagttcaactggtacgtggacggcgtggag
               V  D  V  S  H  E  D  P  E  V  K  F  N  W  Y  V  D  G  V  E
              gtgcataatgccaagacaaagccgcgggaggagcagtacagcagcacgtaccgtgtggtc
               V  H  N  A  K  T  K  P  R  E  E  Q  Y  S  S  T  Y  R  V  V
              agcgtcctcaccgtcctgcaccaggactggctgaatggcaaggagtacaagtgcaaggtc
               S  V  L  T  V  L  H  Q  D  W  L  N  G  K  E  Y  K  C  K  V
              tccaacaaagccctcccagcccccatcgagaaaaccatctccaaagccaaagggcagccc
               S  N  K  A  L  P  A  P  I  E  K  T  I  S  K  A  K  G  Q  P
              cgagaaccacaggtgtacaccctgcccccatcccgggatgagctgaccaagaaccaggtc
               R  E  P  Q  V  Y  T  L  P  P  S  R  D  E  L  T  K  N  Q  V
              agcctgacctgcctggtcaaaggcttctatcccagcgacatcgccgtggagtgggagagc
               S  L  T  C  L  V  K  G  F  Y  P  S  D  I  A  V  E  W  E  S
              aatgggcagccggagaacaactacaagaccacgcctcccgtgctggactccgacggctcc
               N  G  Q  P  E  N  N  Y  K  T  T  P  P  V  L  D  S  D  G  S
              ttcttcctctacagcaagctcaccgtggacaagagcaggtggcagcaggggaacgtcttc
               F  F  L  Y  S  K  L  T  V  D  K  S  R  W  Q  Q  G  N  V  F
              tcatgctccgtgatgcatgaggctctgcacaaccactacacgcagaagagcctctccctg
               S  C  S  V  M  H  E  A  L  H  N  H  Y  T  Q  K  S  L  S  L
              tctccgggttag
               S  P  G  -
```

FIG. 31

SEQ ID NO: 81 atggaatggagctgggtctttctcttcttcctgtcagtaacgactggtgtccactccttc
SEQ ID NO: 80 M E W S W V F L F F L S V T T G V H S F
gtgaaccagcacctgtgcggctcccacctggtggaagctctggcactcgtgtgcggcgag
V N Q H L C G S H L V E A L A L V C G E
cggggcttccactacggggggtggcggaggaggttctggtggcggcggaggcatcgtggaa
R G F H Y G G G G G G S G G G G G I V E
cagtgctgcacctccacctgctccctggaccagctggaaaactactgcggtggcggaggt
Q C C T S T C S L D Q L E N Y C G G G G
ggtcaaggaggcggtggacagggtggaggtgggcagggaggaggcgggggagacaaaact
G Q G G G G Q G G G G Q G G G G G D K T
cacacatgcccaccgtgcccagcacctgaactcctggggggaccgtcagtcttcctcttc
H T C P P C P A P E L L G G P S V F L F
cccccaaaacccaaggacaccctcatgatctcccggacccctgaggtcacatgcgtggtg
P P K P K D T L M I S R T P E V T C V V
gtggacgtgagccacgaagaccctgaggtcaagttcaactggtacgtggacggcgtggag
V D V S H E D P E V K F N W Y V D G V E
gtgcataatgccaagacaaagccgcgggaggagcagtacgacagcacgtaccgtgtggtc
V H N A K T K P R E E Q Y D S T Y R V V
agcgtcctcaccgtcctgcaccaggactggctgaatggcaaggagtacaagtgcaaggtc
S V L T V L H Q D W L N G K E Y K C K V
tccaacaaagccctcccagcccccatcgagaaaaccatctccaaagccaaagggcagccc
S N K A L P A P I E K T I S K A K G Q P
cgagaaccacaggtgtacaccctgcccccatcccgggatgagctgaccaagaaccaggtc
R E P Q V Y T L P P S R D E L T K N Q V
agcctgacctgcctggtcaaaggcttctatcccagcgacatcgccgtggagtgggagagc
S L T C L V K G F Y P S D I A V E W E S
aatgggcagccggagaacaactacaagaccacgcctcccgtgctggactccgacggctcc
N G Q P E N N Y K T T P P V L D S D G S
ttcttcctctacagcaagctcaccgtggacaagagcaggtggcagcaggggaacgtcttc
F F L Y S K L T V D K S R W Q Q G N V F
tcatgctccgtgatgcatgaggctctgcacaaccactacacgcagaagagcctctccctg
S C S V M H E A L H N H Y T Q K S L S L
tctccgggttag
S P G -

FIG. 32

SEQ ID NO: 83 atggaatggagctgggtctttctcttcttcctgtcagtaacgactggtgtccactccttc
SEQ ID NO: 82 M E W S W V F L F F L S V T T G V H S F
gtgaaccagcacctgtgcggctcccacctggtggaagctctggcactcgtgtgcggcgag
V N Q H L C G S H L V E A L A L V C G E
cggggcttccactacgggggtggcggaggaggttctggtggcggcggaggcatcgtggaa
R G F H Y G G G G G G S G G G G G I V E
cagtgctgcacctccacctgctccctggaccagctggaaaactactgcggtggcggaggt
Q C C T S T C S L D Q L E N Y C G G G G
ggtcaaggaggcggtggacagggtggaggtgggcagggaggaggcgggggagacaaaact
G Q G G G G Q G G G G Q G G G G G D K T
cacacatgcccaccgtgcccagcacctgaactcctggggggaccgtcagtcttcctcttc
H T C P P C P A P E L L G G P S V F L F
ccccccaaaacccaaggacaccctcatgatctcccggacccctgaggtcacatgcgtggtg
P P K P K D T L M I S R T P E V T C V V
gtggacgtgagccacgaagaccctgaggtcaagttcaactggtacgtggacggcgtggag
V D V S H E D P E V K F N W Y V D G V E
gtgcataatgccaagacaaagccgcgggaggagcagtacgccagcacgtaccgtgtggtc
V H N A K T K P R E E Q Y A S T Y R V V
agcgtcctcaccgtcctgcaccaggactggctgaatggcaaggagtacaagtgcaaggtc
S V L T V L H Q D W L N G K E Y K C K V
tccaacaaagccctcccagcccccatcgagaaaaccatctccaaagccaaagggcagccc
S N K A L P A P I E K T I S K A K G Q P
cgagaaccacaggtgtacaccctgcccccatcccgggatgagctgaccaagaaccaggtc
R E P Q V Y T L P P S R D E L T K N Q V
agcctgacctgcctggtcaaaggcttctatcccagcgacatcgccgtggagtgggagagc
S L T C L V K G F Y P S D I A V E W E S
aatgggcagccggagaacaactacaagaccacgcctcccgtgctggactccgacggctcc
N G Q P E N N Y K T T P P V L D S D G S
ttcttcctctacagcaagctcaccgtggacaagagcaggtggcagcaggggaacgtcttc
F F L Y S K L T V D K S R W Q Q G N V F
tcatgctccgtgatgcatgaggctctgcacaaccactacacgcagaagagcctctccctg
S C S V M H E A L H N H Y T Q K S L S L
tctccgggttag
S P G -

FIG. 33

```
SEQ ID NO: 85 atggaatggagctgggtctttctcttcttcctgtcagtaacgactggtgtccactccttc
SEQ ID NO: 84  M  E  W  S  W  V  F  L  F  F  L  S  V  T  T  G  V  H  S  F
              gtgaaccagcacctgtgcggctcccacctggtggaagctctggcactcgtgtgcggcgag
               V  N  Q  H  L  C  G  S  H  L  V  E  A  L  A  L  V  C  G  E
              cggggcttccactacgggggtggcggaggaggttctggtggcggcggaggcatcgtggaa
               R  G  F  H  Y  G  G  G  G  G  G  S  G  G  G  G  G  I  V  E
              cagtgctgcacctccacctgctccctggaccagctggaaaactactgcggtggcggaggt
               Q  C  C  T  S  T  C  S  L  D  Q  L  E  N  Y  C  G  G  G  G
              ggtcaaggaggcggtggacagggtggaggtgggcagggaggaggcgggggagacaaaact
               G  Q  G  G  G  G  Q  G  G  G  G  Q  G  G  G  G  G  D  K  T
              cacacatgcccaccgtgcccagcacctgaactcctggggggaccgtcagtcttcctcttc
               H  T  C  P  P  C  P  A  P  E  L  L  G  G  P  S  V  F  L  F
              cccccaaaacccaaggacaccctcatgatctcccggacccctgaggtcacatgcgtggtg
               P  P  K  P  K  D  T  L  M  I  S  R  T  P  E  V  T  C  V  V
              gtggacgtgagccacgaagaccctgaggtcaagttcaactggtacgtggacggcgtggag
               V  D  V  S  H  E  D  P  E  V  K  F  N  W  Y  V  D  G  V  E
              gtgcataatgccaagacaaagccgcgggaggagcagtacagaagcacgtaccgtgtggtc
               V  H  N  A  K  T  K  P  R  E  E  Q  Y  R  S  T  Y  R  V  V
              agcgtcctcaccgtcctgcaccaggactggctgaatggcaaggagtacaagtgcaaggtc
               S  V  L  T  V  L  H  Q  D  W  L  N  G  K  E  Y  K  C  K  V
              tccaacaaagccctcccagcccccatcgagaaaaccatctccaaagccaaagggcagccc
               S  N  K  A  L  P  A  P  I  E  K  T  I  S  K  A  K  G  Q  P
              cgagaaccacaggtgtacaccctgcccccatcccgggatgagctgaccaagaaccaggtc
               R  E  P  Q  V  Y  T  L  P  P  S  R  D  E  L  T  K  N  Q  V
              agcctgacctgcctggtcaaaggcttctatcccagcgacatcgccgtggagtgggagagc
               S  L  T  C  L  V  K  G  F  Y  P  S  D  I  A  V  E  W  E  S
              aatgggcagccggagaacaactacaagaccacgcctcccgtgctggactccgacggctcc
               N  G  Q  P  E  N  N  Y  K  T  T  P  P  V  L  D  S  D  G  S
              ttcttcctctacagcaagctcaccgtggacaagagcaggtggcagcaggggaacgtcttc
               F  F  L  Y  S  K  L  T  V  D  K  S  R  W  Q  Q  G  N  V  F
              tcatgctccgtgatgcatgaggctctgcacaaccactacacgcagaagagcctctccctg
               S  C  S  V  M  H  E  A  L  H  N  H  Y  T  Q  K  S  L  S  L
              tctccgggttag
               S  P  G  -
```

FIG. 34

SEQ ID NO: 88 atggaatggagctgggtctttctcttcttcctgtcagtaacgactggtgtccactccttc
SEQ ID NO: 87 M E W S W V F L F F L S V T T G V H S F
gtgaaccagcacctgtgcggctcccacctggtggaagctctggcactcgtgtgcggcgag
V N Q H L C G S H L V E A L A L V C G E
cggggcttccactacgggggtggcggaggaggttctggtggcggcggaggcatcgtggaa
R G F H Y G G G G G G S G G G G G I V E
cagtgctgcacctccacctgctccctggaccagctggaaaactactgcggtggcggaggt
Q C C T S T C S L D Q L E N Y C G G G G
ggtgcaggaggcggtggagccggtggaggtggggctggaggaggcggggggagacaaaact
G A G G G G A G G G G A G G G G G D K T
cacacatgcccaccgtgcccagcacctgaactcctggggggaccgtcagtcttcctcttc
H T C P P C P A P E L L G G P S V F L F
cccccaaaacccaaggacaccctcatgatctcccggacccctgaggtcacatgcgtggtg
P P K P K D T L M I S R T P E V T C V V
gtggacgtgagccacgaagaccctgaggtcaagttcaactggtacgtggacggcgtggag
V D V S H E D P E V K F N W Y V D G V E
gtgcataatgccaagacaaagccgcgggaggagcagtacagcagcacgtaccgtgtggtc
V H N A K T K P R E E Q Y S S T Y R V V
agcgtcctcaccgtcctgcaccaggactggctgaatggcaaggagtacaagtgcaaggtc
S V L T V L H Q D W L N G K E Y K C K V
tccaacaaagccctcccagcccccatcgagaaaaccatctccaaagccaaagggcagccc
S N K A L P A P I E K T I S K A K G Q P
cgagaaccacaggtgtacaccctgcccccatcccgggatgagctgaccaagaaccaggtc
R E P Q V Y T L P P S R D E L T K N Q V
agcctgacctgcctggtcaaaggcttctatcccagcgacatcgccgtggagtgggagagc
S L T C L V K G F Y P S D I A V E W E S
aatgggcagccggagaacaactacaagaccacgcctcccgtgctggactccgacggctcc
N G Q P E N N Y K T T P P V L D S D G S
ttcttcctctacagcaagctcaccgtggacaagagcaggtggcagcaggggaacgtcttc
F F L Y S K L T V D K S R W Q Q G N V F
tcatgctccgtgatgcatgaggctctgcacaaccactacacgcagaagagcctctccctg
S C S V M H E A L H N H Y T Q K S L S L
tctccgggttag
S P G -

FIG. 35

```
SEQ ID NO: 90 atggaatggagctgggtctttctcttcttcctgtcagtaacgactggtgtccactccttc
SEQ ID NO: 89  M  E  W  S  W  V  F  L  F  F  L  S  V  T  T  G  V  H  S  F
              gtgaaccagcacctgtgcggctcccacctggtggaagctctggcactcgtgtgcggcgag
               V  N  Q  H  L  C  G  S  H  L  V  E  A  L  A  L  V  C  G  E
              cggggcttccactacgggggtggcggaggaggttctggtggcggcggaggcatcgtggaa
               R  G  F  H  Y  G  G  G  G  G  G  S  G  G  G  G  G  I  V  E
              cagtgctgcacctccacctgctccctggaccagctggaaaactactgcggtggcggaggt
               Q  C  C  T  S  T  C  S  L  D  Q  L  E  N  Y  C  G  G  G  G
              gccggaggcgggggagacaaaactcacacatgcccaccgtgcccagcacctgaactcctg
               A  G  G  G  G  D  K  T  H  T  C  P  P  C  P  A  P  E  L  L
              gggggaccgtcagtcttcctcttccccccaaaacccaaggacaccctcatgatctcccgg
               G  G  P  S  V  F  L  F  P  P  K  P  K  D  T  L  M  I  S  R
              acccctgaggtcacatgcgtggtggtggacgtgagccacgaagaccctgaggtcaagttc
               T  P  E  V  T  C  V  V  V  D  V  S  H  E  D  P  E  V  K  F
              aactggtacgtggacggcgtggaggtgcataatgccaagacaaagccgcgggaggagcag
               N  W  Y  V  D  G  V  E  V  H  N  A  K  T  K  P  R  E  E  Q
              tacagcagcacgtaccgtgtggtcagcgtcctcaccgtcctgcaccaggactggctgaat
               Y  S  S  T  Y  R  V  V  S  V  L  T  V  L  H  Q  D  W  L  N
              ggcaaggagtacaagtgcaaggtctccaacaaagccctcccagcccccatcgagaaaacc
               G  K  E  Y  K  C  K  V  S  N  K  A  L  P  A  P  I  E  K  T
              atctccaaagccaaagggcagccccgagaaccacaggtgtacaccctgcccccatcccgg
               I  S  K  A  K  G  Q  P  R  E  P  Q  V  Y  T  L  P  P  S  R
              gatgagctgaccaagaaccaggtcagcctgacctgcctggtcaaaggcttctatcccagc
               D  E  L  T  K  N  Q  V  S  L  T  C  L  V  K  G  F  Y  P  S
              gacatcgccgtggagtgggagagcaatgggcagccggagaacaactacaagaccacgcct
               D  I  A  V  E  W  E  S  N  G  Q  P  E  N  N  Y  K  T  T  P
              cccgtgctggactccgacggctccttcttcctctacagcaagctcaccgtggacaagagc
               P  V  L  D  S  D  G  S  F  F  L  Y  S  K  L  T  V  D  K  S
              aggtggcagcaggggaacgtcttctcatgctccgtgatgcatgaggctctgcacaaccac
               R  W  Q  Q  G  N  V  F  S  C  S  V  M  H  E  A  L  H  N  H
              tacacgcagaagagcctctccctgtctccgggttag
               Y  T  Q  K  S  L  S  L  S  P  G  -
```

FIG. 36

SEQ ID NO: 100 atggaatggagctgggtctttctcttcttcctgtcagtaacgactggtgtccactcctc
SEQ ID NO: 86 M E W S W V F L F F L S V T T G V H S F
gtgaaccagcacctgtgcggctcccacctggtggaagctctggcactcgtgtgcggcgag
V N Q H L C G S H L V E A L A L V C G E
cggggcttccactacgggggtggcggaggaggttctggtggcggcggaggcatcgtggaa
R G F H Y G G G G G S G G G G G I V E
cagtgctgcacctccacctgctccctggaccagctggaaaactactgcggtggcggaggt
Q C C T S T C S L D Q L E N Y C G G G G
ggtcaaggaggcggtggacagggtggaggtgggcagggaggaggcggggggagacaaaact
G Q G G G G Q G G G G Q G G G G G D K T
cacacatgcccaccgtgcccagcacctgaactcctggggggaccgtcagtcttcctcttc
H T C P P C P A P E L L G G P S V F L F
cccccaaaacccaaggacaccctcatgatctcccggacccctgaggtcacatgcgtggtg
P P K P K D T L M I S R T P E V T C V V
gtggacgtgagccacgaagaccctgaggtcaagttcaactggtacgtggacggcgtggag
V D V S H E D P E V K F N W Y V D G V E
gtgcataatgccaagacaaagccgcgggaggagcagtaccaaagcacgtaccgtgtggtc
V H N A K T K P R E E Q Y Q S T Y R V V
agcgtcctcaccgtcctgcaccaggactggctgaatggcaaggagtacaagtgcaaggtc
S V L T V L H Q D W L N G K E Y K C K V
tccaacaaagccctcccagcccccatcgagaaaaccatctccaaagccaaagggcagccc
S N K A L P A P I E K T I S K A K G Q P
cgagaaccacaggtgtacaccctgcccccatcccgggatgagctgaccaagaaccaggtc
R E P Q V Y T L P P S R D E L T K N Q V
agcctgacctgcctggtcaaaggcttctatcccagcgacatcgccgtggagtgggagagc
S L T C L V K G F Y P S D I A V E W E S
aatgggcagccggagaacaactacaagaccacgcctcccgtgctggactccgacggctcc
N G Q P E N N Y K T T P P V L D S D G S
ttcttcctctacagcaagctcaccgtggacaagagcaggtggcagcaggggaacgtcttc
F F L Y S K L T V D K S R W Q Q G N V F
tcatgctccgtgatgcatgaggctctgcacaaccactacacgcagaagagcctctccctg
S C S V M H E A L H N H Y T Q K S L S L
tctccgggttag
S P G -

FIG. 37

CELLS ENGINEERED TO EXPRESS ULTRA-LONG ACTING INSULIN-FC FUSION PROTEINS

PRIORITY AND RELATED APPLICATIONS

The present application is a continuation of U.S. patent application Ser. No. 17/114,395, filed Dec. 7, 2020, which claims the priority benefit of each of U.S. Provisional Patent Application Ser. No. 62/988,441, filed Mar. 12, 2020, and U.S. Provisional Patent Application Ser. No. 62/950,803, filed Dec. 19, 2019. The contents of each of the aforementioned patent applications are hereby incorporated herein by reference in their entirety.

SEQUENCE LISTING

The following application contains a sequence listing presented in accordance with 37 C.F.R. 1.822. The sequence listing entitled "SequenceListing038CN" is submitted as an ASCII computer readable text file created on Feb. 21, 2022, as 188,021 bytes, which is incorporated by reference herein.

TECHNICAL FIELD

The present technology relates to compositions of insulin-Fc fusion proteins and their use to treat diabetes in humans.

BACKGROUND

The following description of the background of the present technology is provided simply as an aid in understanding the present technology and is not admitted to describe or constitute prior art to the present technology.

Diabetes is a chronic condition characterized by an insulin deficiency and/or ineffective use of insulin. Diabetics that have an absolute deficiency of insulin are categorized as having type 1 or insulin-dependent diabetes mellitus (IDDM). Type 1 diabetics are thought to have a genetic predisposition combined with immunologic destruction of the insulin-producing β-cells of the pancreas. In comparison, diabetics that can still produce some insulin but have a relative deficiency due to insulin resistance or other dysfunction, are classified as having type 2 or non-insulin-dependent diabetes mellitus (NIDDM). Type 2 diabetes is linked to genetic predisposition, obesity, and certain medications. Women can also develop temporary insulin resistance during pregnancy in what is called gestational diabetes. Some adults are diagnosed with latent autoimmune diabetes in adults (LADA), a slow-progressing form of autoimmune diabetes. Similar to type 1 diabetes, in LADA the insulin-producing (3-cells of the pancreas are destroyed but at a slower rate. A small percentage of people are diagnosed with maturity onset diabetes of the young (MODY), which refers to any of several hereditary forms of diabetes mellitus caused by mutations in an autosomal dominant gene disrupting insulin production.

When a type 1 diabetes, LADA, or MODY patient's pancreas does not produce enough insulin, the patient generally exhibits an atypical glycemia phenotype marked by hyperglycemia. In these cases, the patients are treated with chronic insulin injection therapy. In type 2 and gestational diabetes, patients also often exhibit hyperglycemia as they are unable to properly utilize the insulin that is being produced by the pancreas. In these cases, the patients can be treated with oral medication with or without changes in diet and exercise; however, many subjects eventually progress to resemble a type 1 diabetes condition (inflammatory disease in pancreas with significant loss of beta cell mass) and become dependent on exogenous insulin. Left untreated, diabetes can lead to weight loss, loss of appetite, vomiting, dehydration, problems with motor function, coma, and even death.

Approximately 30 million people, or 9.4% of the United States population, have diabetes. Type 1 diabetes accounts for about 5% of all diagnosed cases of diabetes, affecting approximately 1.5 million people. Current diabetes therapies include a variety of short-acting (e.g. Humalog® (Eli Lilly, Indianapolis, Ind.) and NovoLog® (Novo Nordisk, Bagsværd, Denmark)) and long-acting insulin products (e.g. Lantus® (Sanofi, Paris, France) and Levemir® (Novo Nordisk, Bagsværd, Denmark)), which are administered via subcutaneous injection multiple times a day or through a wearable subcutaneous infusion pump. The burden of frequent injections results in a lack of treatment regimen compliance and under-dosing, leading to poor long-term health outcomes. In fact, each year over 7 million hospital discharges related to diabetes are reported among United States adults due to cardiovascular events, amputations, and ketoacidosis. Furthermore, each year over 14 million emergency department visits related to diabetes are reported among United States adults due to hypoglycemia and hyperglycemia crises among other conditions. Among U.S. adults aged 20 years or older with diagnosed diabetes, the estimated prevalence of kidney disease is over 36%. Diabetes is the seventh leading cause of death in the United States with a total estimated annual cost of over $245 billion. Therefore, there is a need for cost effective and less burdensome treatment options for this disease.

SUMMARY OF THE PRESENT TECHNOLOGY

In an aspect, the present disclosure provides a fusion protein comprising an insulin polypeptide and an Fc fragment, wherein the insulin polypeptide and the Fc fragment are connected by a linker, wherein the fusion protein comprises the following sequence:

```
                                          (SEQ ID NO: 87)
FVNQHLCGSHLVEALALVCGERGFHYGGGGGGSGGGGGIVEQCCTSTCSLD

QLENYCGGGGGAGGGGAGGGGAGGGGGDKTHTCPPCPAPELLGGPSVFLFP

PKPKDTLMISRTPEVTCVVVDVSHEDPEVKFNWYVDGVEVHNAKTKPREEQ

YSSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.
```

In some embodiments, the present disclosure provides a fusion protein comprising an insulin polypeptide and an Fc fragment, wherein the insulin polypeptide and the Fc fragment are connected by a linker, wherein the Fc fragment is of human origin and comprises the following sequence: DKTHTCPPCPAPELLGGPSVFLFPPKPKDTLMISRTPE-VTCVVVDVSHEDPEVKFNWYVDGVEV HNAKTKP-REEQY$X_1$STYRVVSVLTVLHQDWLNGKEYKCKVS-NKALPAPIEKTISKAKGQPREP QVYTLPPSRDELT-KNQVSLTCLVKGFYPSDIAVEWESNGQPENNYKTTP-PVLDSDGSFFLYSKL TVDKSRWQQGNVFSCSVM-HEALHNHYTQKSLSLSPG (SEQ ID NO: 77) wherein $X_1$ is S, D, A, or R, and wherein the insulin polypeptide consists of an insulin B-chain analog linked to an insulin A-chain analog via a C-chain, wherein the 16$^{th}$ amino acid from the N-terminus of the insulin B-chain analog (i.e., B16) of the insulin polypeptide is alanine (i.e., B16A).

In some embodiments, the insulin polypeptide comprises the sequence FVNQHLCGSX$_1$LVEALALVCGERGFHYGGGGGGSGGGGGIVEQCCX$_2$STCSLDQLENYC (SEQ ID NO: 9), wherein X$_1$ is not D and X$_2$ is not H. In some embodiments, the insulin polypeptide comprises the following sequence:

```
                                           (SEQ ID NO: 10)
FVNQHLCGSHLVEALALVCGERGFHYGGGGGGSGGGGGIVEQCCTSTCSLD

QLENYC.
```

In some configurations, the linker comprises the sequence: GGGGGQGGGGQGGGGQGGGGG (SEQ ID NO: 13). In configurations, the linker comprises the sequence: GGGGGAGGGGAGGGGAGGGGG (SEQ ID NO: 67). In configurations, the linker comprises the sequence GGGGAGGGG (SEQ ID NO: 11).

In some embodiments, the fusion protein comprises the following sequence:

```
                                           (SEQ ID NO: 89)
FVNQHLCGSHLVEALALVCGERGFHYGGGGGGSGGGGGIVEQCCTSTCSLD

QLENYCGGGGAGGGGDKTHTCPPCPAPELLGGPSVFLFPPKPKDTLMISRT

PEVTCVVVDVSHEDPEVKFNWYVDGVEVHNAKTKPREEQYSSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPG.
```

In some embodiments, the fusion protein comprises the following sequence:

```
                                           (SEQ ID NO: 78)
FVNQHLCGSHLVEALALVCGERGFHYGGGGGGSGGGGGIVEQCCTSTCSLD

QLENYCGGGGGQGGGGQGGGGQGGGGGDKTHTCPPCPAPELLGGPSVFLFP

PKPKDTLMISRTPEVTCVVVDVSHEDPEVKFNWYVDGVEVHNAKTKPREEQ

YSSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.
```

In some embodiments, the fusion protein comprises the following sequence:

```
                                           (SEQ ID NO: 80)
FVNQHLCGSHLVEALALVCGERGFHYGGGGGGSGGGGGIVEQCCTSTCSLD

QLENYCGGGGGQGGGGQGGGGQGGGGGDKTHTCPPCPAPELLGGPSVFLFP

PKPKDTLMISRTPEVTCVVVDVSHEDPEVKFNWYVDGVEVHNAKTKPREEQ

YDSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.
```

In some embodiments, the fusion protein comprises the following sequence:

```
                                           (SEQ ID NO: 82)
FVNQHLCGSHLVEALALVCGERGFHYGGGGGGSGGGGGIVEQCCTSTCSLD

QLENYCGGGGGQGGGGQGGGGQGGGGGDKTHTCPPCPAPELLGGPSVFLFP

PKPKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.
```

In some embodiments, the fusion protein comprises the following sequence:

```
                                           (SEQ ID NO: 84)
FVNQHLCGSHLVEALALVCGERGFHYGGGGGGSGGGGGIVEQCCTSTCSLD

QLENYCGGGGGQGGGGQGGGGQGGGGGDKTHTCPPCPAPELLGGPSVFLFP

PKPKDTLMISRTPEVTCVVVDVSHEDPEVKFNWYVDGVEVHNAKTKPREEQ

YRSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.
```

In some embodiments, the fusion protein comprises domains in the following orientation from N- to C-terminus: (N-terminus)—insulin polypeptide—linker—Fc fragment—(C-terminus).

In some embodiments, the fusion protein is a homodimer. In examples, the percentage homodimer of the fusion protein is greater than 90%. In some examples, the fusion protein is made using HEK293 cells or CHO cells, and the resulting homodimer titer after purification using Protein A beads or a Protein A column is greater than 150 mg/L. In embodiments, the insulin receptor IC50 for the fusion protein is less than or equal to 5000 nM. In some embodiments, the insulin receptor IC50 for the fusion protein is less than or equal to 2400 nM.

In some embodiments, the human FcRn receptor EC50 for the fusion protein is less than or equal to 1000 ng/mL. In examples, the human Fc(gamma)RI receptor assay OD450 Ratio at a biotinylated-Fc(gamma)RI concentration of 3000 ng/mL of the fusion protein is less than or equal to 0.50. In embodiments, the human C1q assay OD450 Ratio at a biotinylated-C1q concentration of 1000 ng/mL is less than or equal to 0.35. In embodiments, the fusion protein is formulated as a pharmaceutical composition. In some examples, the concentration of the fusion protein in the pharmaceutical composition is about 3 mg/mL or greater. In some embodiments, the pharmaceutical composition is suitable for subcutaneous administration.

In embodiments, a physiologically effective amount of the fusion protein or a pharmaceutical composition thereof may be administered to a patient as a method of lowering the blood glucose level of the patient. In examples, the patient is diagnosed with diabetes. In some embodiments, the fusion protein is administered subcutaneously. The fusion protein may be administered daily, twice weekly, or once weekly to the patient. In some examples, the fusion protein is administered once weekly to the patient at a dose between 0.025 and 0.500 mg/kg/week.

In embodiments, a cell may be engineered to express the fusion protein. The cell may be transfected with a nucleic acid encoding the fusion protein. In some examples, the cell is a HEK293 cell or a CHO cell.

In embodiments, the nucleic acid (cDNA) encoding the fusion protein of SEQ ID NO: 87 comprises the following nucleic acid sequence:

(SEQ ID NO: 88)
atggaatggagctgggtctttctcttcttcctgtcagtaacgactggtgtc
cactccttcgtgaaccagcacctgtgcggctcccacctggtggaagctctg
gcactcgtgtgcggcgagegggggcttccactacgggggtggcggaggaggt
tctggtggcggcggaggcatcgtggaacagtgctgcacctccacctgctcc
ctggaccagctggaaaactactgcggtggcggaggtggtgcaggaggcggt
ggagccggtggaggtggggctggaggaggcgggggagacaaaactcacaca
tgcccaccgtgcccagcacctgaactcctggggggaccgtcagtcttcctc
ttccccccaaaacccaaggacaccctcatgatctcccggacccctgaggtc
acatgcgtggtggtggacgtgagccacgaagaccctgaggtcaagttcaac
tggtacgtggacggcgtggaggtgcataatgccaagacaaagccgcgggag
gagcagtacagcagcacgtaccgtgtggtcagcgtcctcaccgtcctgcac
caggactggctgaatggcaaggagtacaagtgcaaggtctccaacaaagcc
ctcccagcccccatcgagaaaaccatctccaaagccaaagggcagccccga
gaaccacaggtgtacaccctgcccccatcccgggatgagctgaccaagaac
caggtcagcctgacctgcctggtcaaaggcttctatcccagcgacatcgcc
gtggagtgggagagcaatgggcagccggagaacaactacaagaccacgcct
cccgtgctggactccgacggctccttcttcctctacagcaagctcaccgtg
gacaagagcaggtggcagcaggggaacgtcttctcatgctccgtgatgcat
gaggetctgcacaaccactacacgcagaagagcctctccctgtctccgggt
tag.

In embodiments, the nucleic acid (cDNA) encoding the fusion protein of SEQ ID NO: 89 comprises the following nucleic acid sequence:

(SEQ ID NO: 90)
atggaatggagctgggtctttctcttcttcctgtcagtaacgactggtgtc
cactccttcgtgaaccagcacctgtgcggctcccacctggtggaagctctg
gcactcgtgtgcggcgagcggggcttccactacgggggtggcggaggaggt
tctggtggcggcggaggcatcgtggaacagtgctgcacctccacctgctcc
ctggaccagctggaaaactactgcggtggcggaggtgccggaggcgggggga
gacaaaactcacacatgcccaccgtgcccagcacctgaactcctgggggga
ccgtcagtcttcctcttccccccaaaacccaaggacaccctcatgatctcc
cggacccctgaggtcacatgcgtggtggtggacgtgagccacgaagaccct
gaggtcaagttcaactggtacgtggacggcgtggaggtgcataatgccaag
acaaagccgcgggaggagcagtacagcagcacgtaccgtgtggtcagcgtc
ctcaccgtcctgcaccaggactggctgaatggcaaggagtacaagtgcaag
gtctccaacaaagccctcccagcccccatcgagaaaaccatctccaaagcc
aaagggcagccccgagaaccacaggtgtacaccctgcccccatcccgggat
gagctgaccaagaaccaggtcagcctgacctgcctggtcaaaggcttctat -continued
cccagcgacatcgccgtggagtgggagagcaatgggcagccggagaacaac
tacaagaccacgcctcccgtgctggactccgacggctccttcttcctctac
agcaagctcaccgtggacaagagcaggtggcagcaggggaacgtcttctca
tgctccgtgatgcatgaggctctgcacaaccactacacgcagaagagcctc
tccctgtctccgggttag.

In embodiments, the nucleic acid (cDNA) encoding the fusion protein of SEQ ID NO: 78 comprises the following nucleic acid sequence:

(SEQ ID NO: 79)
atggaatggagctgggtctttctcttcttcctgtcagtaacg
actggtgtccactccttcgtgaaccagcacctgtgcggctcc
cacctggtggaagctctggcactcgtgtgcggcgagcggggc
ttccactacgggggtggcggaggaggttctggtggcggcgga
ggcatcgtggaacagtgctgcacctccacctgctccctggac
cagctggaaaactactgcggtggcggaggtggtcaaggaggc
ggtggacagggtggaggtgggcagggaggaggcgggggagac
aaaactcacacatgcccaccgtgcccagcacctgaactcctg
gggggaccgtcagtcttcctcttccccccaaaacccaaggac
accctcatgatctcccggacccctgaggtcacatgcgtggtg
gtggacgtgagccacgaagaccctgaggtcaagttcaactgg
tacgtggacggcgtggaggtgcataatgccaagacaaagccg
cgggaggagcagtacagcagcacgtaccgtgtggtcagcgtc
ctcaccgtcctgcaccaggactggctgaatggcaaggagtac
aagtgcaaggtctccaacaaagccctcccagcccccatcgag
aaaaccatctccaaagccaaagggcagccccgagaaccacag
gtgtacaccctgcccccatcccgggatgagctgaccaagaac
caggtcagcctgacctgcctggtcaaaggcttctatcccagc
gacatcgccgtggagtgggagagcaatgggcagccggagaac
aactacaagaccacgcctcccgtgctggactccgacggctcc
ttcttcctctacagcaagctcaccgtggacaagagcaggtgg
cagcaggggaacgtcttctcatgctccgtgatgcatgaggct
ctgcacaaccactacacgcagaagagcctctccctgtctccg
ggttag.

In embodiments, the nucleic acid (cDNA) encoding the fusion protein of SEQ ID NO: 80 comprises the following nucleic acid sequence:

(SEQ ID NO: 81)
atggaatggagctgggtctttctcttcttcctgtcagtaacg
actggtgtccactccttcgtgaaccagcacctgtgcggctcc
cacctggtggaagctctggcactcgtgtgcggcgagcggggc
ttccactacgggggtggcggaggaggttctggtggcggcgga
ggcatcgtggaacagtgctgcacctccacctgctccctggac -continued

```
cagctggaaaactactgcggtggcggaggtggtcaaggaggc

ggtggacagggtggaggtgggcagggaggaggcgggggagac

aaaactcacacatgcccaccgtgcccagcacctgaactcctg

gggggaccgtcagtcttcctcttccccccaaaacccaaggac

accctcatgatctcccggacccctgaggtcacatgcgtggtg

gtggacgtgagccacgaagaccctgaggtcaagttcaactgg

tacgtggacggcgtggaggtgcataatgccaagacaaagccg

cgggaggagcagtacgacagcacgtaccgtgtggtcagcgtc

ctcaccgtcctgcaccaggactggctgaatggcaaggagtac

aagtgcaaggtctccaacaaagccctcccagcccccatcgag

aaaaccatctccaaagccaaagggcagccccgagaaccacag

gtgtacaccdgcccccatcccgggatgagctgaccaagaacc

aggtcagcctgacctgcctggtcaaaggcttctatcccagcg

acatcgccgtggagtgggagagcaatgggcagccggagaaca

actacaagaccacgcctcccgtgctggactccgacggctcct

tcttcctctacagcaagctcaccgtggacaagagcaggtggc

agcaggggaacgtcttctcatgctccgtgatgcatgaggctc

tgcacaaccactacacgcagaagagcctctccctgtctccgg

gttag.
```

In embodiments, the nucleic acid (cDNA) encoding the fusion protein of SEQ ID NO: 82 comprises the following nucleic acid sequence:

```
                                  (SEQ ID NO: 83)
atggaatggagctgggtctttctcttcttcctgtcagtaacg

actggtgtccactccttcgtgaaccagcacctgtgcggctcc

cacctggtggaagctctggcactcgtgtgcggcgagcggggc

ttccactacgggggtggcggaggaggttctggtggcggcgga

ggcatcgtggaacagtgctgcacctccacctgctccctggac

cagctggaaaactactgcggtggcggaggtggtcaaggaggc

ggtggacagggtggaggtgggcagggaggaggcgggggagac

aaaactcacacatgcccaccgtgcccagcacctgaactcctg

gggggaccgtcagtcttcctcttccccccaaaacccaaggac

accctcatgatctcccggacccctgaggtcacatgcgtggtg

gtggacgtgagccacgaagaccctgaggtcaagttcaactgg

tacgtggacggcgtggaggtgcataatgccaagacaaagccg

cgggaggagcagtacgccagcacgtaccgtgtggtcagcgtc

ctcaccgtcctgcaccaggactggctgaatggcaaggagtac

aagtgcaaggtctccaacaaagccctcccagcccccatcgag

aaaaccatctccaaagccaaagggcagccccgagaaccacag

gtgtacaccctgcccccatcccgggatgagctgaccaagaac

caggtcagcctgacctgcctggtcaaaggcttctatcccagc
```

-continued

```
gacatcgccgtggagtgggagagcaatgggcagccggagaac

aactacaagaccacgcctcccgtgctggactccgacggctcc

ttcttcctctacagcaagctcaccgtggacaagagcaggtgg

cagcaggggaacgtcttctcatgctccgtgatgcatgaggct

ctgcacaaccactacacgcagaagagcctctccctgtctccg

ggttag.
```

In embodiments, the nucleic acid (cDNA) encoding the fusion protein of SEQ ID NO: 84 comprises the following nucleic acid sequence:

```
                                  (SEQ ID NO: 85)
atggaatggagctgggtctttctcttcttcctgtcagtaacg

actggtgtccactccttcgtgaaccagcacctgtgcggctcc

cacctggtggaagctctggcactcgtgtgcggcgagcggggc

ttccactacgggggtggcggaggaggttctggtggcggcgga

ggcatcgtggaacagtgctgcacctccacctgctccctggac

cagctggaaaactactgcggtggcggaggtggtcaaggaggc

ggtggacagggtggaggtgggcagggaggaggcgggggagac

aaaactcacacatgcccaccgtgcccagcacctgaactcctg

gggggaccgtcagtcttcctcttccccccaaaacccaaggac

accctcatgatctcccggacccctgaggtcacatgcgtggtg

gtggacgtgagccacgaagaccctgaggtcaagttcaactgg

tacgtggacggcgtggaggtgcataatgccaagacaaagccg

cgggaggagcagtacagaagcacgtaccgtgtggtcagcgtc

ctcaccgtcctgcaccaggactggctgaatggcaaggagtac

aagtgcaaggtctccaacaaagccctcccagcccccatcgag

aaaaccatctccaaagccaaagggcagccccgagaaccacag

gtgtacaccctgcccccatcccgggatgagctgaccaagaac

caggtcagcctgacctgcctggtcaaaggcttctatcccagc

gacatcgccgtggagtgggagagcaatgggcagccggagaac

aactacaagaccacgcctcccgtgctggactccgacggctcc

ttcttcctctacagcaagctcaccgtggacaagagcaggtgg

cagcaggggaacgtcttctcatgctccgtgatgcatgaggct

ctgcacaaccactacacgcagaagagcctctccctgtctccg

ggttag.
```

BRIEF DESCRIPTION OF THE DRAWINGS

FIG. 3 illustrates a side-by-side sequence comparison of SEQ ID NO: 31, SEQ ID NO: 32, SEQ ID NO: 33, SEQ ID NO: 34, and SEQ ID NO: 35. "*" represents complete homology across all sequences at a given sequence position, while ":", "." or spaces refer to conservative, moderate, or very different amino acid mutations across the sequences at a given sequence position respectively.

FIG. 4 illustrates a side-by-side sequence comparison of SEQ ID NO: 31, SEQ ID NO: 36, SEQ ID NO: 37, and SEQ ID NO: 38. "*" represents complete homology across all sequences at a given sequence position, while ":", "." or spaces refer to conservative, moderate, or very different amino acid mutations across the sequences at a given sequence position respectively.

FIG. 7 shows the average anti-drug antibody titer (μg/mL) for N=3 dogs dosed subcutaneously on Day 0 (0.30 mg/kg), Day 28 (0.33 mg/kg), Day 35 (0.33 mg/kg), Day 42 (0.50 mg/kg), Day 49 (1.00 mg/kg) and Day 56 (1.00 mg/kg) with the homodimer of SEQ ID NO: 36.

FIG. 8 illustrates a side-by-side sequence comparison of SEQ ID NO: 39, SEQ ID NO: 40, SEQ ID NO: 41, and SEQ ID NO: 42. "*" represents complete homology across all sequences at a given sequence position, while ":", "." or spaces refer to conservative, moderate, or very different amino acid mutations across the sequences at a given sequence position respectively.

FIG. 12 illustrates a side-by-side sequence comparison of SEQ ID NO: 43, SEQ ID NO: 44, SEQ ID NO: 45, SEQ ID NO: 46, SEQ ID NO: 47 and SEQ ID NO: 48. "*" represents complete homology across all sequences at a given sequence position, while ":", "." or spaces refer to conservative, moderate, or very different amino acid mutations across the sequences at a given sequence position respectively.

FIG. 13 illustrates a side-by-side sequence comparison of SEQ ID NO: 43, SEQ ID NO: 49, SEQ ID NO: 50, SEQ ID NO: 51, and SEQ ID NO: 52. "*" represents complete homology across all sequences at a given sequence position, while ":", "." or spaces refer to conservative, moderate, or very different amino acid mutations across the sequences at a given sequence position respectively.

FIG. 14 illustrates a side-by-side sequence comparison of SEQ ID NO: 43, SEQ ID NO: 48 and SEQ ID NO: 53. "*" represents complete homology across all sequences at a given sequence position, while ":", "." or spaces refer to conservative, moderate, or very different amino acid mutations across the sequences at a given sequence position respectively.

FIG. 15 illustrates a side-by-side sequence comparison of SEQ ID NO: 43, SEQ ID NO: 51, SEQ ID NO: 52 and SEQ ID NO: 54. "*" represents complete homology across all sequences at a given sequence position, while ":", "." or spaces refer to conservative, moderate, or very different amino acid mutations across the sequences at a given sequence position respectively.

FIG. 16 illustrates a side-by-side sequence comparison of SEQ ID NO: 26, SEQ ID NO: 28, SEQ ID NO: 43, SEQ ID NO: 55, SEQ ID NO: 56 and SEQ ID NO: 57. "*" represents complete homology across all sequences at a given sequence position, while ":", "." or spaces refer to conservative, moderate, or very different amino acid mutations across the sequences at a given sequence position respectively.

FIG. 23 shows % fasting blood glucose levels from Day 0 to Day 7 for N=1 dog dosed subcutaneously on Day 0 at 0.16 mg/kg with the homodimer of SEQ ID NO: 59.

FIG. 24 illustrates a side-by-side sequence comparison of SEQ ID NO: 61 and SEQ ID NO: 62. "*" represents complete homology across all sequences at a given sequence position, while ":", "." or spaces refer to conservative, moderate, or very different amino acid mutations across the sequences at a given sequence position respectively.

FIG. 27 illustrates a side-by-side sequence comparison of SEQ ID NO: 76, SEQ ID NO: 91, and SEQ ID NO: 78. "*" represents complete homology across all sequences at a given sequence position, while ":", "." or spaces refer to conservative, moderate, or very different amino acid mutations across the sequences at a given sequence position respectively.

FIG. 28 illustrates a side-by-side sequence comparison of SEQ ID NO: 75, SEQ ID NO: 76, SEQ ID NO: 91, SEQ ID NO: 92, SEQ ID NO: 93, SEQ ID NO: 94, and SEQ ID NO: 95. "*" represents complete homology across all sequences at a given sequence position, while ":", "." or spaces refer to conservative, moderate, or very different amino acid mutations across the sequences at a given sequence position respectively.

FIG. 29 illustrates a side-by-side sequence comparison of SEQ ID NO: 76, SEQ ID NO: 78, SEQ ID NO: 80, SEQ ID NO: 82, SEQ ID NO: 84, and SEQ ID NO: 86. "*" represents complete homology across all sequences at a given sequence position, while ":", "." or spaces refer to conservative, moderate, or very different amino acid mutations across the sequences at a given sequence position respectively.

FIG. 30 illustrates a side-by-side sequence comparison of SEQ ID NO: 87, SEQ ID NO: 96, SEQ ID NO: 78, SEQ ID NO: 97, SEQ ID NO: 89, and SEQ ID NO: 98. "*" represents complete homology across all sequences at a given sequence position, while ":", "." or spaces refer to conservative, moderate, or very different amino acid mutations across the sequences at a given sequence position respectively.

FIG. 31 illustrates the full amino acid sequence including the leader sequence of a fusion protein (SEQ ID NO: 78) and its corresponding nucleic acid sequence (SEQ ID NO: 79).

FIG. 32 illustrates the full amino acid sequence including the leader sequence of a fusion protein (SEQ ID NO: 80) and its corresponding nucleic acid sequence (SEQ ID NO: 81).

FIG. 33 illustrates the full amino acid sequence including the leader sequence of a fusion protein (SEQ ID NO: 82) and its corresponding nucleic acid sequence (SEQ ID NO: 83).

FIG. 34 illustrates the full amino acid sequence including the leader sequence of a fusion protein (SEQ ID NO: 84) and its corresponding nucleic acid sequence (SEQ ID NO: 85).

FIG. 35 illustrates the full amino acid sequence including the leader sequence of a fusion protein (SEQ ID NO: 87) and its corresponding nucleic acid sequence (SEQ ID NO: 88).

FIG. 36 illustrates the full amino acid sequence including the leader sequence of a fusion protein (SEQ ID NO: 89) and its corresponding nucleic acid sequence (SEQ ID NO: 90).

FIG. 37 illustrates the full amino acid sequence including the leader sequence of a fusion protein (SEQ ID NO: 86) and its corresponding nucleic acid sequence (SEQ ID NO: 100).

DETAILED DESCRIPTION

Figure 1:
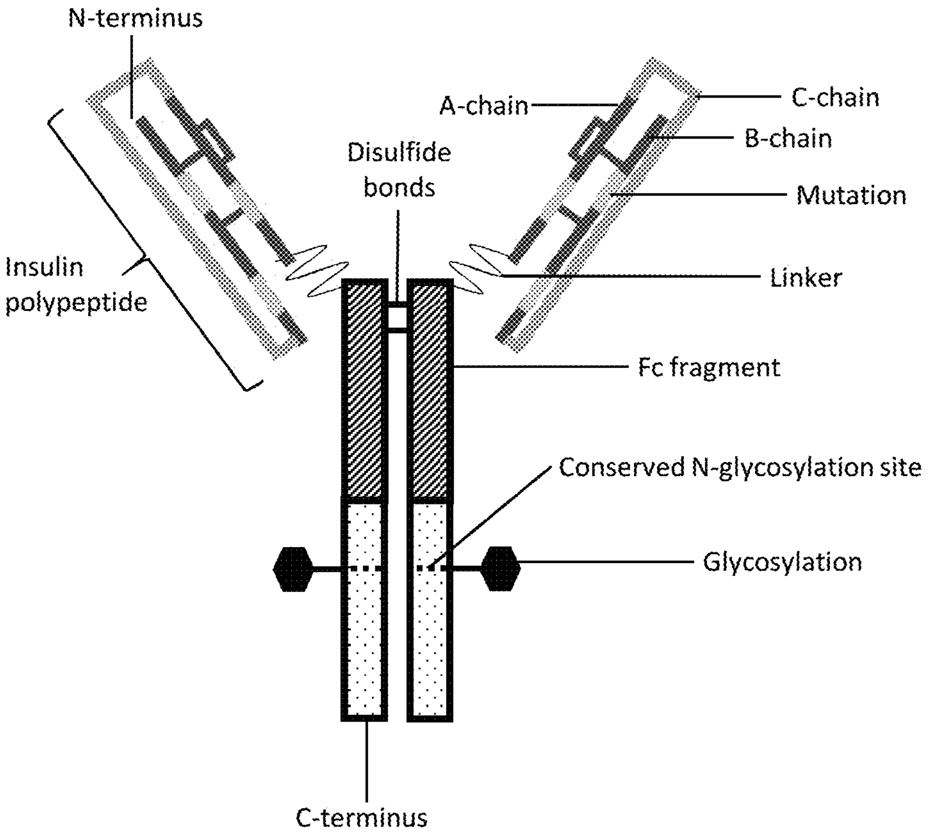
FIG. 1 shows a schematic representation of an exemplary insulin-Fc fusion protein homodimer.

An insulin treatment that requires less frequent dosing (e.g., once-weekly injections) would be less burdensome on patients, leading to better compliance, better glucose control, and ultimately better long-term health outcomes. As disclosed herein, proposed ultra-long acting insulin treatments for human clinical use comprise an insulin-Fc fusion protein making use of a human Fc fragment to prolong their action in vivo. An insulin-Fc fusion protein suitable for an ultra-long acting treatment for diabetes should meet various design goals. An insulin-Fc fusion protein suitable for an ultra-long acting treatment for diabetes should be manufacturable in mammalian cells, for example human embryonic kidney (HEK, e.g. HEK293) cells, with an acceptable titer of the desired homodimer product (e.g., greater than 50 mg/L homodimer titer from transiently transfected HEK cells, greater than 75 mg/L from transiently transfected from HEK cells, greater than 100 mg/L from transiently transfected HEK cells, greater than 150 mg/L from transiently transfected HEK cells, etc.). Only human insulin-Fc fusion protein configurations with a homodimer titer of greater than 150 mg/L are considered useful in the present invention, because experience has demonstrated that homodimer titers less than this level in transiently transfected HEK cells will not likely result in commercial production homodimer titers in stably transfected Chinese hamster ovary (CHO) cells that meet the low manufacturing cost requirements for the relatively commoditized human insulin market.

In addition, the insulin-Fc fusion protein must bind the IR with an appreciable affinity (e.g., IC50 less than 5000 nM, IC50 less than 4000 nM, IC50 less than 3000 nM, IC50 less than 2400 nM, IC50 more preferably less than 2000 nM, etc.) as measured in the 4° C. IM-9 IR binding assay. Based on experience, only molecules exhibiting IR activity IC50 values less than 5000 nM are deemed likely to exhibit the requisite bioactivity. In preferred embodiments, the insulin-Fc fusion protein exhibits an IR activity IC50 value less than 2400 nM, and more preferably less than 2000 nM. The insulin-Fc fusion protein configuration must also exhibit sustained bioactivity in vivo (e.g., demonstrate glucose lowering activity greater than about 2 hours, 6 hours, 9 hours, 12 hours, 18 hours, 1 day, 1.5 days, 2 days, 2.5 days, 3 days, 4 days, 5 days, 6 days, 7 days, or longer) to justify less frequent dosing. The insulin-Fc fusion protein configuration must also demonstrate prolonged system residence time in vivo (e.g., the serum half-life must be greater than 3 days, or longer). The sustained bioactivity and prolonged residence time of a given insulin-Fc fusion protein configuration may be predicted by its ability to bind the FcRn receptor, which is responsible for the prolonged in vivo elimination half-lives of antibodies and Fc-fusion proteins. FcRn receptor activity is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader. Based on experience, insulin-Fc fusion protein configurations exhibiting human FcRn receptor EC50 values less than or equal to 1500 ng/mL (and more preferably less than 1000 ng/mL) are the most likely to exhibit long enough half-lives to justify once-a-week dosing.

Lastly, to be useful for treating a chronic disease such as diabetes, the insulin-Fc fusion protein configuration must not induce the production of anti-drug antibodies, especially antibodies that neutralize the bioactivity of the molecule after repeated dosing. The propensity of a given insulin-Fc fusion protein configuration to induce an adverse immunogenic response may be predicted first by its ability to bind the Fc(gamma)RI receptor, which plays a key role in many immune system effector functions, including phagocytosis of opsonized molecules, release of inflammatory mediators, and antibody-dependent cellular cytotoxicity. Fc(gamma)RI receptor activity is typically measured by the absorbance at a wavelength at 450 nm (OD450) value obtained on a microplate reader in an enzyme-linked immunosorbent assay (ELISA) assay at a given concentration of the insulin-Fc fusion protein. Based on experience, insulin-Fc fusion protein configurations exhibiting human Fc(gamma)RI receptor assay OD450 Ratios (where the reference insulin-Fc fusion protein configuration for the ratio is SEQ ID NO: 76) at a biotinylated-Fc(gamma)RI concentration of 3000 ng/mL less than or equal to 0.50 are likely to exhibit sufficiently low immunogenicity to justify repeated once-a-week dosing. The propensity of a given insulin-Fc fusion protein configuration to induce an adverse immunogenic response may also be predicted by its ability to bind the complement component 1q (C1q), which activates the complement cascade causing phagocytes to clear the bound molecule, inflammation to attract additional phagocytes, and activation of the cell-killing membrane attack complex. C1q activity is typically measured by the OD450 value obtained on a microplate reader in an enzyme-linked immunosorbent assay (ELISA) assay at a given concentration of the insulin-Fc fusion protein configuration that is coated onto a microplate. Based on experience, insulin-Fc fusion protein configurations exhibiting human C1q receptor assay OD450 Ratios (where the reference insulin-Fc fusion protein configuration for the ratio is SEQ ID NO: 76) at a biotinylated-C1q concentration of 1000 ng/mL less than or equal to 0.35 are likely to exhibit sufficiently low immunogenicity to justify repeated once-a-week dosing.

Proposed ultra-long acting insulin treatments for human clinical use comprise an insulin-Fc fusion protein making use of a human Fc fragment to prolong their action in vivo. To understand the behavior of insulin-Fc fusion protein configurations of various designs, insulin-Fc fusion protein configurations useful as ultra-long acting insulins for dogs were considered first. As a human Fc fragment is expected to be immunogenic and therefore capable of inducing the production of anti-drug antibodies in dogs, the human Fc fragment was replaced with a canine Fc fragment.

However, it was unexpectedly found that a simple exchange between the human Fc fragment and any canine Fc fragment in the insulin-Fc fusion protein configuration did not necessarily yield a product with an acceptable homodimer titer (e.g., a homodimer titer greater than 50 mg/L) or a sufficiently high NAOC value (e.g., a NAOC greater than 150% FBGL·days·kg/mg). For example, in some cases only a specific isotype (e.g., canine IgGB) for the Fc fragment resulted in an insulin-Fc fusion protein configuration with a high enough homodimer titer to meet the design goals (e.g., a homodimer titer of canine insulin-Fc fusion protein of greater than 50 mg/L) and an acceptably high NAOC value (e.g., a NAOC greater than 150% FBGL·days·kg/mg). In other cases, specific amino acids of the insulin polypeptide of the insulin-Fc fusion protein configuration were found to be immunogenic in the target species thereby requiring site-directed mutations to find the relatively small number of insulin-Fc fusion protein configurations that were both non-immunogenic and bioactive in the target species with acceptably high NAOC values (e.g., NAOC values greater than 150% FBGL·days·kg/mg) and NAOCR values after the third weekly subcutaneous dose that were greater than 0.50.

In further cases, when the Fc fragments were mutated to prevent glycosylation and thereby further reduce the immunogenicity of the insulin-Fc fusion protein configuration, it was discovered unexpectedly that only specific amino acid mutations in the Fc fragment led to the desired homodimer titers (e.g., homodimer titers for canine insulin-Fc fusion protein configurations of greater than 50 mg/L) and NAOC values (e.g., NAOC greater values than 150% FBGL·days·kg/mg). Furthermore, it was discovered that an additional mutation in the insulin component of the insulin-Fc fusion protein configuration was required to produce these Fc-mutated, non-glycosylated insulin Fc-fusion protein configurations with the desired homodimer titers (e.g., homodimer titers for canine insulin-Fc fusion protein configurations of greater than 50 mg/L) and NAOC values (e.g., NAOC greater values than 150% FBGL·days·kg/mg), while also achieving NAOCR values after the third weekly subcutaneous dose that were greater than 0.50.

For human ultra-long acting insulins, to maximize homodimer titers and reduce manufacturing costs, insulin-Fc fusion protein configurations were produced comprising Fc fragments based on different isotypes of the human IgG molecule (e.g., IgG1 and IgG2). It was discovered rather unexpectedly that switching from an Fc fragment based on the IgG2 molecule to an Fc fragment based on the IgG1 molecule in the insulin-Fc fusion protein configuration increased the average homodimer titer by over 50% without significantly compromising the IR or FcRn binding activity. However, the resulting IgG1-derived insulin-Fc fusion protein configuration was deemed much more likely to interact adversely with the immune system and develop neutralizing antibodies given that its human Fc(gamma)RI receptor assay OD450 Ratio (where the reference insulin-Fc fusion protein configuration for the ratio is SEQ ID NO: 76) at a biotinylated-Fc(gamma)RI concentration of 3000 ng/mL was much greater than 0.50 and its human C1q receptor assay OD450 Ratio (where the reference insulin-Fc fusion protein configuration for the ratio is SEQ ID NO: 76) at biotinylated-C1q concentration of 1000 ng/mL was much greater than 0.35.

In an attempt to reduce unwanted immunogenicity, the insulin-Fc fusion protein configuration was mutated to prevent the glycosylation of the Fc fragment during synthesis in the host cell. Specifically, the conserved asparagine (N)-glycosylation site in the CH2 domain of the heavy chain of the IgG1 Fc region was mutated to different amino acids (e.g., S, D, A, R, and Q) in an attempt to maintain the improved insulin-Fc fusion protein homodimer yields while reducing Fc(gamma)RI and C1q interactions. Interestingly, the S, D, A, and R mutated non-glycosylated insulin-Fc fusion protein configurations gave improved homodimer titers relative to the glycosylated parent configurations; however, the homodimer titer of the insulin-Fc fusion protein configuration with the Q mutation at the conserved asparagine (N)-glycosylation site was too low (i.e., less than the 150 mg/L design goal for human insulin-Fc fusion protein configurations) to support the low cost of manufacturing requirements. Additionally, the Fc(gamma)RI and C1q binding decreased significantly for the S, D, A, and R mutated non-glycosylated insulin-Fc fusion protein configurations. However, in these insulin-Fc fusion protein configurations the improvements in yield and immunogenicity were offset by unexpectedly lower FcRn binding affinity and significantly lower IR binding relative to the glycosylated parent configurations, indicating an unacceptable reduction in bioactivity and residence time in vivo.

As was unexpectedly discovered with the insulin-Fc fusion proteins configurations comprising an Fc fragment of canine origin, it was discovered that by changing a single amino acid in the insulin sequence in human insulin-Fc fusion protein configurations, the improvements in yield and immunogenicity of the S, D, A, and R mutated non-glycosylated insulin-Fc fusion protein configurations were maintained or improved upon, while the IR and FcRn binding affinities increased (e.g. lower IR assay IC50 value), rather than decreased relative to the original glycosylated parent configuration. The resulting non-glycosylated, mutated insulin-Fc fusion protein configurations are expected, therefore, to exhibit acceptable in vivo glucose lowering potencies and prolonged residence times. Unexpectedly, changing the same amino acid in the non-glycosylated insulin-Fc fusion protein configuration with the Q mutation at the conserved asparagine (N)-glycosylation site resulted in a significant decrease in the already poor homodimer titer.

To understand how the properties of the S, D, A, and R non-glycosylated mutant insulin-Fc fusion proteins configurations could be further manipulated, modifications were made to the linker region of the insulin-Fc fusion protein configuration, connecting the insulin polypeptide to the Fc fragment. Test results indicated that without a linker, the homodimer titers of the resulting canine insulin-Fc fusion protein configurations were unacceptably low (i.e., less than 50 mg/L). For insulin-Fc fusion protein configurations comprising linkers of the same length, it was discovered that certain amino acid sequences were preferred over others in terms of homodimer titers, IR and FcRn receptor binding, and Fc(gamma)RI and C1q binding of the insulin-Fc fusion protein configuration.

Provided herein, therefore, are specific manufacturable, high purity, long-acting, bioactive, non-immunogenic insulin-Fc fusion protein configurations, each of which comprises a mutated insulin polypeptide, a non-glycosylated Fc fragment, and a linker between the mutated insulin polypeptide and the non-glycosylated Fc fragment, and wherein the insulin-Fc fusion protein configurations meet the design goals of acceptably high homodimer titers (e.g., homodimer titers greater than 150 mg/L), IR assay IC50 values (e.g., IC50 less than 5000 nM, less than 2400 nM, and more preferably less than 2000 nM), human FcRn receptor EC50 values (e.g., EC50 less than or equal to 1500 ng/L, and more preferably less than 1000 ng/mL), human Fc(gamma)RI receptor OD 450 Ratios (e.g. OD450 Ratios at a biotinylated-Fc(gamma)RI receptor concentration of 3000 ng/mL less than or equal to 0.50 where the reference insulin-Fc fusion protein configuration for the ratio is SEQ ID NO: 76), and human C1q receptor OD 450 Ratios (e.g. OD450 Ratios at a biotinylated-C1q concentration of 1000 ng/mL less than or equal to 0.35 where the reference insulin-Fc fusion protein configuration for the ratio is SEQ ID NO: 76). These exemplary insulin-Fc fusion protein configurations are expected to exhibit sufficiently low immunogenicity long enough half-lives to justify repeated once-a-week dosing, rendering them suitable for the treatment of diabetes.

Definitions

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., insulin) having a chemical structure similar to that of another compound or conjugate but differing from it in at least one aspect.

As used herein, the term "antibody" or "antibody molecule" refers to an immunoglobulin molecule (Ig), immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. As used herein, the term "antibody domain" refers to a variable or constant region of an immunoglobulin. It is documented in the art that antibodies comprise several classes, for example IgA, IgM, or IgG in the case of mammals (e.g., humans). Classes of immunoglobulins can be further classified into different isotypes, such as IgGA, IgGB, IgGC, and IgGD for canines, and IgG1, IgG2, IgG3, and IgG4 for humans. Those skilled in the art will recognize that immunoglobulin isotypes of a given immunoglobulin class will comprise different amino acid sequences, structures, and functional properties from one another (e.g., different binding affinities to Fc(gamma) receptors). "Specifically binds" or "immunoreacts with" means that the antibody reacts with one or more antigenic determinants of the desired antigen and has a lower affinity for other polypeptides, e.g., does not react with other polypeptides.

As used herein, the term "area-under-the-curve" or "AUC" refers to the integrated area under the % FBGL (Fasting Blood Glucose Level) vs. time curve for a subject after a given dose of an insulin-Fc fusion protein is administered. As used herein, the term "area-over-the curve" or "AOC" is used as a measure of the biological potency of an insulin-Fc fusion protein such that the AOC equals the difference between the total possible area under the % FBGL vs. time curve and the AUC value. As used herein, the "normalized area-over-the curve," "normalized AOC," or "NAOC" is the AOC value divided by the actual dose of insulin-Fc fusion protein administered. As used herein, the term "normalized AOC ratio" or "NAOCR" is the ratio of the NAOC resulting from a particular administration of an insulin-Fc fusion protein to the NAOC resulting from the first administration of an insulin-Fc fusion protein in a series of administrations. The NAOCR thus provides a measure of the change in biological activity of an insulin-Fc fusion protein after repeated administrations.

As used herein, the term "bioactivity," "activity," "biological activity," "potency," "bioactive potency," or "biological potency" refers to the extent to which an insulin-Fc fusion protein activates the IR and/or exerts a reduction in blood glucose levels in a target subject. As used herein, "in vitro activity" or "IR activity" refers to the affinity with which an insulin-Fc fusion protein binds to the IR and is typically measured by the concentration at which an insulin-Fc fusion protein displaces half of an insulin reference standard from the IR in a competitive binding assay (i.e., IC50). As used herein, "in vivo activity" refers to the extent and duration of reduction in a target subject's fasting blood glucose level after administration of an insulin-Fc fusion protein.

As used herein, the term "biosynthesis," "recombinant synthesis," or "recombinantly made" refers to the process by which an insulin-Fc fusion protein is expressed within a host cell by transfecting the cell with a nucleic acid molecule (e.g., vector) encoding the insulin-Fc fusion protein (e.g., where the entire insulin-Fc fusion protein is encoded by a single nucleic acid molecule). Exemplary host cells include mammalian cells, e.g., HEK293 cells or CHO cells. The cells can be cultured using standard methods in the art and the expressed insulin-Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a hormone receptor (e.g., an insulin hormone receptor or insulin receptor (IR)) or an Fc receptor which binds to an Fc fragment or the Fc region of an antibody (e.g. an Fc(gamma) receptor, for example Fc(gamma)RI, or an Fc neonatal receptor, for example FcRn). As used herein, "in vitro activity" or "Fc(gamma) receptor activity" or "Fc (gamma) receptor binding" or "FcRn receptor activity" or "FcRn binding" refers to the affinity with which an insulin-Fc fusion protein binds to the Fc receptor (e.g. Fc(gamma) receptor or FcRn receptor) and is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader. Alternatively, the affinity with which an insulin-Fc fusion protein binds to the Fc receptor (e.g. Fc(gamma) receptor or FcRn receptor) is measured by the OD 450 nm value obtained on a microplate reader in an enzyme-linked immunosorbent assay (ELISA) assay at a given concentration of the insulin-Fc fusion protein.

As used herein, the term "C1q" or "complement component 1q" means a protein complex involved in the complement system, which is part of the innate immune system. C1q together with C1r and C1s form the C1 complex. C1q plays a role in involved in specific antigen presentation by dendritic cells to T cells and B cells.

As used herein, the term "fasting blood glucose level" or "FBGL" refers to the average blood glucose level in a target subject at the end of a period during which no food is administered and just prior to the time at which an insulin-Fc fusion protein is administered. As used herein, the term "percent fasting blood glucose level," "% fasting blood glucose level," or "% FBGL" refers to the ratio of a given blood glucose level to the fasting blood glucose level multiplied by 100.

As used herein, the term "immunogenic" or "immunogenicity" refers to the capacity for a given molecule (e.g., an insulin-Fc fusion protein of the present invention) to provoke the immune system of a target subject such that after repeated administrations of the molecule, the subject develops antibodies capable of specifically binding the molecule (i.e., anti-drug antibodies). As used herein, the terms "neutralizing," "neutralizing antibodies", or "neutralizing anti-drug antibodies" refer to the capacity for antibodies to interfere with the compound's biological activity in the target subject. As used herein, the term "immunogenic epitopes," 'immunogenic hot spots," or "hot spots" refers to the mutations or epitopes of a given molecule (e.g., an insulin-Fc fusion protein of the present invention) that are responsible for moderate or strong binding of the anti-drug antibodies.

As used herein, the term "insulin reference standard" is any one of: (i) a naturally occurring insulin from a mammal (e.g., a dog, or a human); (ii) an insulin polypeptide that does not comprise an Fc fragment; or (iii) a standard of care insulin (e.g., a commercially available insulin).

As used herein, the term "monomer" refers to a protein or a fusion protein comprising a single polypeptide. In embodiments, the "monomer" is a protein or a fusion protein, e.g., a single polypeptide, comprising an insulin polypeptide and an Fc fragment polypeptide, wherein the insulin and Fc fragment polypeptides are joined by peptide bonds to form the single polypeptide. In embodiments, the monomer is encoded by a single nucleic acid molecule.

As used herein, "N-terminus" refers to the start of a protein or polypeptide that is initiated by an amino acid containing a free amine group that is the alpha-amino group of the amino acid (e.g. the free amino that is covalently linked to one carbon atom that is located adjacent to a second carbon atom, wherein the second carbon atom is part of the carbonyl group of the amino acid). As used herein, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, "OD450", "optical density at 450 nm", and "absorbance at 450 nm" may be used interchangeably and refer to the use of a microplate reader to read the absorbance of light at 450 nm that is passed through a sample in an assay, e.g. a microplate-based assay, e.g. an enzyme-linked immunosorbent assay, e.g. an ELISA assay.

As used herein, "OD450 Ratio" for a particular assay refers to a way to compare an OD450 value obtained for a first test insulin-Fc fusion protein run at a particular time against an OD450 value obtained for a second test insulin-Fc fusion protein run at another time. The OD450 Ratio is obtained by dividing the OD450 value for a first test article by the OD450 value of a reference insulin-Fc fusion protein. Similarly, a second OD450 Ratio can be obtained for a second test article by dividing the OD450 value for a second test article by the OD450 value of the same reference insulin-Fc fusion protein as used for calculating the OD450 Ratio of the first test article. As a result, the assay properties of a first test insulin-Fc fusion protein and a second test insulin-Fc fusion protein can be compared. The reference insulin-Fc fusion protein configuration used for calculating OD450 Ratios is SEQ ID NO: 76.

As used herein, "pharmacodynamics" or "PD" generally refers to the biological effects of an insulin-Fc fusion protein in a subject. Specifically, herein the PD refers to the measure of the reduction in fasting blood glucose level over time in a subject after the administration of an insulin-Fc fusion protein.

As used herein, "pharmacokinetics" or "PK" generally refers to the characteristic interactions of an insulin-Fc fusion protein and the body of the subject in terms of its absorption, distribution, metabolism, and excretion. Specifically, herein the PK refers to the concentration of an insulin-Fc fusion protein in the blood or serum of a subject at a given time after the administration of the insulin-Fc fusion protein. As used herein, "half-life" refers to the time taken for the concentration of insulin-Fc fusion protein in the blood or serum of a subject to reach half of its original value as calculated from a first order exponential decay model for drug elimination. Insulin-Fc fusion proteins with greater "half-life" values demonstrate greater duration of action in the target subject.

The terms "sequence identity" "sequence homology" "homology" or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences. See, for example Ausubel et al., eds. (1995) *Current Protocols in Molecular Biology*, Chapter 19 (Greene Publishing and Wiley-Interscience, New York); and the ALIGN program Dayhoff (1978) in *Atlas of Polypeptide Sequence and Structure* 5: *Suppl.* 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is described in Smith and Waterman (1981) *Adv. Appl. Math* 2:482-489, herein incorporated by reference. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric—topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" and "patient" are intended to include canine animals and humans having a disease or a disorder, e.g., diabetes or another disease or disorder described herein, or normal subjects.

As used herein, the term "titer" or "yield" refers to the amount of a fusion protein product (e.g., an insulin-Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of insulin-Fc fusion protein expressed by cells and purified via at least one affinity chromatography step (e.g. Protein A or Protein G) and includes monomers of insulin-Fc fusion protein, homodimers of insulin-Fc fusion protein, and higher-order molecular aggregates of homodimers of insulin-Fc fusion protein. As used herein, the term "percent homodimer" or "% homodimer" refers to the proportion of a fusion protein product (e.g., an insulin-Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" a subject having a disease or a disorder refer to subjecting the subject to a regimen, for example the administration of a fusion protein such as a fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve or affect the disease or disorder, or the symptoms of the disease or disorder. The treatment may inhibit deterioration or worsening of a symptom of a disease or disorder.

Insulin-Fc Fusion Protein Components and Structure

The present disclosure relates to a composition of a fusion protein (i.e., an insulin-Fc fusion protein) comprising an insulin polypeptide linked via a peptide linker to a species-specific Fc fragment, and its use to treat diabetes (e.g., in humans and/or dogs). As used herein, the terms "fusion protein" and "insulin-Fc fusion protein" refer to a protein comprising more than one part, for example from different sources (different proteins, polypeptides, cells, etc.), that are covalently linked through peptide bonds. The insulin-Fc fusion proteins are covalently linked by (i) connecting the genes that encode for each part into a single nucleic acid molecule and (ii) expressing in a host cell (e.g., HEK or CHO) the protein for which the nucleic acid molecule encodes as follows: (N-terminus)—insulin polypeptide—linker—Fc fragment—(C-terminus). The fully recombinant synthesis approach is preferred over methods in which the insulin polypeptide and Fc fragments are synthesized separately and then chemically conjugated. The chemical conjugation step and subsequent purification process increase the manufacturing complexity, reduce product yield, and increase cost.

As used herein, the term "dimer" refers to a protein or a fusion protein comprising two polypeptides linked covalently. In embodiments, two identical polypeptides are linked covalently (e.g., via disulfide bonds) forming a "homodimer" (diagrammatically represented in FIG. 1). Disulfide bonds are shown in FIG. 1; the total number of disulfide bonds in actuality may be greater or less than the number shown in FIG. 1. In embodiments, the homodimer is encoded by a single nucleic acid molecule, wherein the homodimer is made recombinantly inside a cell by first forming insulin-Fc fusion protein monomers and by then assembling two identical insulin-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of the insulin-Fc fusion protein homodimers.

Insulin Polypeptide

An insulin polypeptide may be, for example, an insulin or insulin analog produced by β-cells in the islets of Langerhans within the pancreas. Insulin functions by regulating the absorption of glucose from the blood. Upon a stimulus, such as increased protein and glucose levels, insulin is released from β-cells and binds to the IR, initiating a signal cascade that affects many aspects of mammalian (e.g., human) metabolism. Disruption of this process is directly related to several diseases, notably diabetes, insulinoma, insulin resistance, metabolic syndromes, and polycystic ovary syndrome. Insulin analogs of the present disclosure may be related to the structure of insulin yet contain one or more modifications. In some embodiments, the insulin analog comprises at least one amino acid substitution, deletion, addition or chemical modification relative to insulin, which may impact a particular feature or characteristic of the insulin-Fc fusion protein configuration. For example, the modifications or alterations described herein may impact the structure, stability, pH sensitivity, bioactivity, or binding affinity of the insulin-Fc fusion protein configuration to a cell surface receptor (e.g. an insulin hormone receptor) relative to a reference standard.

The amino acid sequence of insulin is strongly conserved throughout evolution, particularly in vertebrates. For example, native canine and porcine insulins differ by only one amino acid from human insulin, native bovine insulin differs by only three amino acids from human insulin, and native feline insulin differs by just four amino acids from human insulin. As used herein, the terms "B-chain or B-chain analog", "C-peptide" or "C-chain", and "A-chain or A-chain analog" refer to the peptide segments of an insulin polypeptide as illustrated in FIG. 1. Insulin is a 51 amino acid hormone containing two peptide chains (i.e., a B-chain and an A-chain) connected via disulfide bonds (e.g., disulfide bonds formed by one or more B-chain cysteine side chain thiols and one or more A-chain cysteine side chain thiols). The A-chain of insulin is 21 amino acids in length and the B-chain of insulin is 30 amino acids in length. In the native form of insulin, the A-chain contains one intrachain disulfide bond formed by two A-chain cysteine side chain thiols. For reference purposes, the sequences for the human insulin B-chain of SEQ ID NO: 1 and the human insulin A-chain of SEQ ID NO: 2 are shown below:

(SEQ ID NO: 1)
FVNQHLCGSHLVEALYLVCGERGFFYTPKT (SEQ ID NO: 2)
GIVEQCCTSICSLYQLENYCN.

As used herein, the term "insulin" or "insulin polypeptide" encompasses mature insulin, preproinsulin, proinsulin, and naturally occurring insulin, or analogs thereof. In embodiments, an insulin polypeptide can be a full-length insulin polypeptide or a fragment thereof. In embodiments, an insulin polypeptide can comprise one or more fragments from mature insulin, preproinsulin, proinsulin, or naturally occurring insulin.

Insulin is normally constructed as a N-terminus—B-chain:C-chain:A-chain—C-terminus polypeptide, wherein the C-chain is cleaved in order to make it bioactive. For reference purposes, the sequence of the entire human insulin molecule including the C-chain (i.e., human proinsulin) is shown below with the C-chain in bold:

(SEQ ID NO: 3)
FVNQHLCGSHLVEALYLVCGERGFFYTPKTRREAEDLQVGQVELGG
GPGAGSLQPLALEGSLQKRGIVEQCCTSICSLYQLENYCN.

The transformation of the single-chain insulin polypeptide into a bioactive two-chain polypeptide is normally accomplished within the β-cells of the islets of Langerhans prior to glucose-stimulated insulin secretion by two endoproteases, Type I endoproteases, PC1 and PC3, that disrupt the C peptide-B chain connection and PC2, and a Type II endoprotease, that cleaves the C peptide-A chain bond at exactly the right sites. However, cell systems used for the biosynthesis of therapeutic molecules such as insulin (e.g. bacteria, yeast, and mammalian (e.g. HEK and CHO) cell systems) do not possess this pathway, and therefore the transformation must take place after expression and harvesting of the single chain polypeptide using chemical or enzymatic methods. All the known techniques for cleaving the C-chain after expression and harvesting rely on first modifying the C-chain such that it terminates in a lysine just before the N-terminus of the A-chain. Then, using an enzyme selected from the trypsin or Lys-C families, which clips peptide bonds specifically at the C-termini of lysine residues, the single chain-insulin polypeptide is cleaved at the C-terminal lysine of the C-chain and at the C-terminal lysine at the $29^{th}$ position from the N-terminus of the B-chain. In some cases, the resulting bioactive two-chain insulin is used without reattaching the clipped amino acid at the $30^{th}$ position from the N-terminus of the B-chain, and in some cases the clipped amino acid at the $30^{th}$ position from the N-terminus of the B-chain is added back to the molecule using an additional enzymatic method. Such a process works well with insulin because it contains only one lysine in its entire two chain polypeptide form. However, this process cannot be used on the insulin-Fc fusion proteins contained herein, because all known Fc fragments contain multiple lysine residues. The enzymatic cleavage process would, therefore, digest the Fc fragment into non-functional parts, thereby eliminating the ability of the Fc fragment to prolong the action of the insulin polypeptide in vivo. Therefore, an insulin-Fc fusion protein of the present invention must comprise an insulin polypeptide that does not require C-chain cleavage and is therefore bioactive in its single chain form.

A number of bioactive single chain insulin polypeptides have been described in the art. In all cases, the single chain insulin polypeptides contain C-chains of specific length and composition as well as A-chains and B-chains mutated at specific amino acid sites in order to achieve electrostatic balance, prevent aggregation, and enhance IR binding and/or downstream signaling to achieve bioactivity at levels comparable to that of the native two-chain insulin. Herein, the location of mutations on peptide segments are notated using the name of the segment (e.g., B-chain, C-chain, A-chain) and the number of the amino acid counting from the N-terminus of the segment. For example, the notation "B16"

refers to the 16th amino acid from the N-terminus of the amino acid sequence of the B-chain. The notation "A8" refers to the 8th amino acid from the N-terminus of the A-chain. Furthermore, if an amino acid is mutated from its native form to a new amino acid at a particular location, the location is appended with the one letter amino acid code for the new amino acid. For example, B16A refers to an alanine mutation at the 16th amino acid from the N-terminus of the amino acid sequence of the B-chain and A8H refers to a histidine mutation at the 8th amino acid from the N-terminus of the amino acid sequence of the A-chain.

U.S. Pat. No. 9,855,318B2 describes a single chain insulin analog with a C-chain ("first linker") of the sequence GGSGGGG (SEQ ID NO: 72), substitutions in the A-chain, and substitutions and deletions in the B-chain (non-native amino acids are in bold and deleted native amino acids represented with a bold Z):

(SEQ ID NO: 7_NULL)
FVNQHLCGSHLVEALELVCGERGFHYGGGGGGSGGGGGIVEQ

CCTSTCSLDQLENYCZ.

The following is a restatement of the sequence shown above but with the absent amino acids of symbol Z removed from the notation of the insulin polypeptide sequence. Again, as before, the non-native amino acids are in bold. Despite the two separate notations, the paired sequences refer to exactly the same insulin polypeptide.

(SEQ ID NO: 7)
FVNQHLCGSHLVEALELVCGERGFHYGGGGGGSGGGGGIVEQC

CTSTCSLDQLENYC

In some embodiments, it was discovered unexpectedly that insulin-Fc fusion protein configurations wherein alanine is substituted for glutamic acid at position 16 from the N-terminus of the B-chain (i.e., B16) in SEQ ID NO: 7 to produce SEQ ID NO: 10, led to improved homodimer titers, IR binding affinity, and FcRn binding of the insulin-Fc fusion protein while preserving reduced immunogenicity as measured by low Fc(gamma)RI and C1q binding affinities. This particular amino acid substitution at B16 was originally motivated by the fact that an alanine in this position is known to be less capable of activating insulin-specific T cells (Alleva, D. G., Gaur, A., Jin, L., Wegmann, D., Gottlieb, P. A., Pahuja, A., Johnson, E. B., Motheral, T., Putnam, A., Crowe, P. D., Ling, N., Boehme, S. A., Conlon, P. J., (2002) *Diabetes* Vol. 51, No. 7 pp 2126-2134). SEQ ID NO: 10 is listed below with each of the non-native amino acids in bold:

(SEQ ID NO: 10)
FVNQHLCGSHLVEALALVCGERGFHYGGGGGGSGGGGGIVEQC

CTSTCSLDQLENYC.

Linker

In some examples, the C-terminus of the insulin polypeptide is connected directly to the N-terminus of the Fc fragment (e.g. no linker or linker absent). In other examples, the successful construction of a recombinantly made insulin-Fc fusion protein requires a linker connecting the insulin polypeptide to the Fc fragment. In embodiments, insulin-Fc fusion protein configurations described herein comprise a peptide linker between the insulin polypeptide and the Fc fragment comprising amino acids (e.g., natural or unnatural amino acids). In embodiments, the peptide linker can be encoded by a nucleic acid molecule, for example such that a single nucleic acid molecule can encode the various peptides within an insulin polypeptide as well as the peptide linker and the Fc fragment. The choice of peptide linker (for example, the length, composition, hydrophobicity, and secondary structure) could impact the manufacturability of the insulin-Fc fusion protein configuration (i.e., the homodimer titer), the chemical and enzymatic stability, the bioactivity (i.e., the NAOC value), parameters that correlate with bioactivity (i.e., the FcRn assay EC50 value), and the immunogenicity of the insulin-Fc fusion protein (Chen, X., Zaro, J., Shen, W. C., *Adv Drug Deliv Rev.* 2013 Oct. 15; 65(10): 1357-1369). Table 1 lists several linkers used in the design of insulin-Fc fusion protein configurations with the goal of improving the homodimer titer and the bioactivity.

TABLE 1

| Peptide Linker Between A-chain and Fc Fragment in an Insulin-Fc Fusion Protein |
|---|
| GGGGAGGGG (SEQ ID NO: 11) |
| GGGGSGGGG (SEQ ID NO: 12) |
| GGGGGAGGGG (SEQ ID NO: 64) |
| GGGGSGGGGSGGGGSGGGG (SEQ ID NO: 65) |
| GGGGKGGGGKGGGGKGGGG (SEQ ID NO: 66) |
| GGGGGAGGGGAGGGGAGGGGG (SEQ ID NO: 67) |
| GGGGGQGGGGQGGGGQGGGGG (SEQ ID NO: 13) |
| SGGGGQGGGGQGGGGQGGGGG (SEQ ID NO: 68) |
| HGGGGQGGGGQGGGGQGGGGG (SEQ ID NO: 69 |
| PGGGGGQGGGGQGGGGQGGGGG (SEQ ID NO: 70) |
| GGGGGQGGGGQGGGGQGGGGGQGGGG (SEQ ID NO: 99) |

In embodiments, the peptide linker comprises the sequence: GGGGGQGGGGQGGGGQGGGGG (SEQ ID NO: 13). In other embodiments, the peptide linker comprises the sequence: GGGGSGGGG (SEQ ID NO: 12). In preferred embodiments, the peptide linker comprises the sequence: GGGGGAGGGGAGGGGAGGGGG (SEQ ID NO: 67) or the sequence: GGGGAGGGG (SEQ ID NO: 11).

In constructing a recombinantly made insulin-Fc fusion protein configuration with a peptide linker like the one of SEQ ID NO: 13, attention must be paid to the possibility of unwanted enzymatic cleavage between the C-terminus of the insulin A-chain and the N-terminus of the peptide linker. Cleavage of the linker and Fc-fragment from the insulin polypeptide would render the insulin-Fc fusion protein configuration incapable of providing an extended duration of bioactivity. A known enzymatic cleavage site exists between asparagine-glycine bonds (Vlasak, J., Ionescu, R., (2011) *MAbs Vol.* 3, No. 3 pp 253-263). In many peptide linker embodiments, including the preferred peptide linker of SEQ ID NO: 13, the N-terminal amino acid is a glycine. Furthermore, the C-terminus of the insulin A-chain (i.e. the 21st amino acid from the N-terminus of the A-chain (i.e., A21)) is an asparagine. Therefore, the A21 asparagine is omitted in the insulin polypeptides of SEQ ID NO: 7, SEQ ID NO: 9, and SEQ ID NO: 10 to eliminate the potentially enzymatically cleavable asparagine-glycine bond that would form between the A-chain and the peptide linker in insulin-Fc fusion protein configurations. Unexpectedly, an insulin-Fc fusion protein configuration constructed from the insulin polypeptide of SEQ ID NO: 8, which retains the asparagine at the C-terminus of the A-chain, demonstrates manufacturability in mammalian cells with an acceptable homodimer titer (i.e., a homodimer titer for the canine insulin-Fc fusion protein of greater than 50 mg/L), an acceptable bioactivity in vivo in dogs (i.e., a NAOC greater than 150% FBGL·days·kg/mg), and sustained levels of bioactivity after multiple doses (i.e., a NAOCR value after the third injection in the dog of greater than 0.5). The results indicate that, contrary to expectations based on prior teachings, there is no risk of enzymatic cleavage or deactivation of insulin-Fc fusion protein configurations containing the asparagine-glycine link between the insulin polypeptide and peptide linker, at least for insulin-Fc fusion protein configurations comprising the Fc fragment sequences disclosed herein.

In another embodiment, it was discovered that for the same insulin polypeptide and Fc fragment compositions, mutating the Glutamine (Q) in SEQ ID NO: 13 to Alanine (A), generating the peptide linker of GGGGGAGGG-GAGGGGAGGGGG (SEQ ID NO: 67), resulted in an insulin-Fc fusion protein configuration with higher homodimer titer, increased binding affinity to the IR, and increased binding affinity to the FcRn receptor.

In another embodiment, it was discovered that for the same insulin polypeptide and Fc fragment compositions, the peptide linker of SEQ ID NO: 67 could be shortened without significantly affecting the homodimer titer or the binding affinity to the FcRn receptor of the insulin-Fc fusion protein, but with a 60% increase in the IR assay IC50 value. The shortened peptide linker comprises the sequence: GGG-GAGGGG (SEQ ID NO: 11).

Fc Fragment

The terms "Fc fragment," "Fc region," "Fc domain," or "Fc polypeptide," are used herein to define a C-terminal region of an immunoglobulin heavy chain. The Fc fragment, region, domain or polypeptide may be a native sequence Fc region or a variant/mutant Fc region. Although the boundaries of the Fc region of an immunoglobulin heavy chain may vary, they generally comprise some or all of the hinge region of the heavy chain, the CH2 region of the heavy chain, and the CH3 region of the heavy chain. The hinge region of a canine or human Fc fragment comprise amino acid sequences that connect the CH1 domain of the heavy chain to the CH2 region of the heavy chain and which contain one or more cysteines that form one or more interheavy chain disulfide bridges to form a homodimer of an Fc fusion protein from two identical but separate monomers of the Fc fusion protein. The hinge region may comprise all or part of a naturally occurring amino acid sequence or a non-naturally occurring amino acid sequence.

An Fc receptor (FcR) refers to a receptor that binds to an Fc fragment or to the Fc region of an antibody. In embodiments, the FcR is a native sequence of the canine or human FcR. In embodiments, the FcR is one which binds an Fc fragment or the Fc region of an IgG antibody (a gamma receptor) and includes without limitation, receptors of the Fc(gamma)RI, Fc(gamma)RIIa, Fc(gamma)R IIb, and Fc(gamma)RIII subclasses, including allelic variants and alternatively spliced forms of these receptors. "FcR" also includes the neonatal receptor, FcRn, which is responsible for the transfer of maternal IgG molecules to the fetus (Guyer et al., 1976 *J. Immunol.*, 117:587; and Kim et al., 1994, *J. Immunol.*, 24:249) and is also responsible for the prolonged in vivo elimination half-lives of antibodies and Fc-fusion proteins in vivo. Those skilled in the art will understand that mammalian FcR from one species (e.g., FcR of human origin) are capable of in vitro binding of insulin-Fc fusion proteins comprising Fc fragments of the same species (e.g., of human origin) and also are sometimes capable of in vitro binding of Fc fragments from another mammalian species (e.g. of canine origin). In embodiments, FcR of human origin are used in vitro (e.g., in an assay) to measure the binding properties of insulin-Fc fusion protein configurations comprising Fc fragments of human or canine origin so as to assess their FcR binding properties. In embodiments, FcR of canine origin are used in vitro (e.g., in an assay) to measure the binding of insulin-Fc fusion protein configurations comprising Fc fragments of canine origin.

In embodiments, the C-terminal lysine that is often found in native canine and human IgG isotype Fc fragment amino acid sequences (i.e., the lysine that represents the last amino acid of the Fc fragment sequence) is omitted to prevent the accidental production of unwanted amino acid sequence variants during manufacturing (e.g., Fc fragments containing the C-terminal lysine becoming mixed with Fc fragments where the C-terminal lysine is omitted, which can occur during production of the desired protein within cells (Dick, L W., (2008) *Biotechnol Bioeng*. August 15; 100(6) pp 1132-43).

In canine insulin-Fc fusion protein embodiments, the Fc fragment comprises the Fc region (e.g., hinge region, CH2 domain, and CH3 domain) of a canine IgGA Fc fragment (SEQ ID NO: 14), a canine IgGB Fc fragment (SEQ ID NO: 15), a canine IgGC Fc fragment (SEQ ID NO: 16), or a canine IgGD Fc fragment (SEQ ID NO: 17). Therefore, in canine insulin-Fc fusion protein configurations, the canine Fc fragment sequences lacking a C-terminal lysine are:

```
                                          (SEQ ID NO: 14)
RCTDTPPCPVPEPLGGPSVLIFPPKPKDILRITRTPEVTCVVLD

LGREDPEVQISWFVDGKEVHTAKTQSREQQFNGTYRVVSVLPIE

HQDWLTGKEFKCRVNHIDLPSPIERTISKARGRAHKPSVYVLPP

SPKELSSSDTVSITCLIKDFYPPDIDVEWQSNGQQEPERKHRMT

PPQLDEDGSYFLYSKLSVDKSRWQQGDPFTCAVMHETLQNHYTD

LSLSHSPG

                                          (SEQ ID NO: 15)
DCPKCPAPEMLGGPSVFIFPPKPKDTLLIARTPEVTCVVVDLDP

EDPEVQISWFVDGKQMQTAKTQPREEQFNGTYRVVSVLPIGHQD

WLKGKQFTCKVNNKALPSPIERTISKARGQAHQPSVYVLPPSRE

ELSKNTVSLTCLIKDFFPPDIDVEWQSNGQQEPESKYRTTPPQL

DEDGSYFLYSKLSVDKSRWQRGDTFICAVMHEALHNHYTQESLS

HSPG

                                          (SEQ ID NO: 16)
CNNCPCPGCGLLGGPSVFIFPPKPKDILVTARTPTVTCVVVDLD

PENPEVQISWFVDSKQVQTANTQPREEQSNGTYRVVSVLPIGHQ

DWLSGKQFKCKVNNKALPSPIEEIISKTPGQAHQPNVYVLPPSR

DEMSKNTVTLTCLVKDFFPPEIDVEWQSNGQQEPESKYRMTPPQ

LDEDGSYFLYSKLSVDKSRWQRGDTFICAVMHEALHNHYTQISL

SHSPG
```

-continued (SEQ ID NO: 17)
CISPCPVPESLGGPSVFIFPPKPKDILRITRTPEITCVVLDLGR
EDPEVQISWFVDGKEVHTAKTQPREQQFNSTYRVVSVLPIEHQD
WLTGKEFKCRVNHIGLPSPIERTISKARGQAHQPSVYVLPPSPK
ELSSSDTVTLTCLIKDFFPPEIDVEWQSNGQPEPESKYHTTAPQ
LDEDGSYFLYSKLSVDKSRWQQGDTFTCAVMHEALQNHYTDLSL
SHSPG.

In human insulin-Fc fusion protein configurations, the human Fc fragment sequences lacking a C-terminal lysine are:

(SEQ ID NO: 73)
DKTHTCPPCPAPELLGGPSVFLFPPKPKDTLMISRTPEVTCVVV
DVSHEDPEVKFNWYVDGVEVHNAKTKPREEQYNSTYRVVSVLTV
LHQDWLNGKEYKCKVSNKALPAPIEKTISKAKGQPREPQVYTLP
PSRDELTKNQVSLTCLVKGFYPSDIAVEWESNGQPENNYKTTPP
VLDSDGSFFLYSKLTVDKSRWQQGNVFSCSVMHEALHNHYTQKS
LSLSPG (SEQ ID NO: 74)
ECPPCPAPPVAGPSVFLFPPKPKDTLMISRTPEVTCVVVDVSHE
DPEVQFNWYVDGVEVHNAKTKPREEQFNSTFRVVSVLTVVHQDW
LNGKEYKCKVSNKGLPAPIEKTISKTKGQPREPQVYTLPPSREE
MTKNQVSLTCLVKGFYPSDIAVEWESNGQPENNYKTTPPMLDSD
GSFFLYSKLTVDKSRWQQGNVFSCSVMHEALHNHYTQKSLSLSPG.

For dogs, the canine IgGA is preferable to minimize any unwanted immunogenicity, due to the IgGA isotype's lack of Fc(gamma) effector function in dogs (much like the human IgG2 isotype in humans). However, in an insulin-Fc fusion protein embodiment containing the insulin polypeptide of SEQ ID NO: 4 and the peptide linker of SEQ ID NO: 11, it was unexpectedly discovered that the insulin-Fc fusion protein configuration comprising the canine IgGA fragment (SEQ ID NO: 14) was highly aggregated with low titers of the desired homodimer (i.e., homodimer titers of the canine insulin-Fc fusion protein of less than 50 mg/L). Furthermore, the insulin-Fc fusion protein configuration was non-bioactive in dogs (i.e., the NAOC value was less than 150% FBGL·days·kg/mg), presumably due to its high level of aggregation (e.g. low % homodimer). Despite mutating the insulin polypeptide of SEQ ID NO: 4, the canine IgGA Fc fragment (SEQ ID NO: 14), and/or the linker, there was no insulin-Fc fusion protein embodiment comprising the canine IgGA Fc fragment that exhibited a low enough degree of aggregation and a high enough titer of the desired homodimer. However, replacing of the canine IgGA Fc fragment (SEQ ID NO: 14) with the canine IgGB Fc fragment (SEQ ID NO: 15) in insulin-Fc fusion protein configurations yielded significantly less aggregated compounds with a comparatively high titer of the desired homodimer. Furthermore, the insulin-Fc fusion protein configuration containing the insulin polypeptide of SEQ ID NO: 4 and the canine IgGB Fc fragment (SEQ ID NO: 15) was bioactive in dogs, exhibiting glucose lowering bioactivity over multiple days (i.e., the NAOC value was greater than 150% FBGL·days·kg/mg).

The preference for the canine IgGB Fc fragment over the canine IgGA Fc fragment was confirmed in insulin-Fc fusion protein configurations containing the insulin polypeptide of SEQ ID NO: 7 and the peptide linker of SEQ ID NO: 13, both of which vary considerably from the insulin polypeptide of SEQ ID NO: 4 and the peptide linker of SEQ ID NO: 11. Insulin-Fc fusion protein configurations containing the insulin polypeptide of SEQ ID NO: 7 and the peptide linker of SEQ ID NO: 13 were synthesized using Fc fragments from the canine IgGA (SEQ ID NO: 14), canine IgGB (SEQ ID NO: 15), canine IgGC (SEQ ID NO: 16), or canine IgGD (SEQ ID NO: 17) immunoglobulins. Using a conventional purification method, only the insulin-Fc fusion protein configurations comprising the canine IgGA and the canine IgGB showed any appreciable protein yields. However as previously seen, the canine IgGA configuration of the insulin-Fc fusion protein was highly aggregated with low levels of bioactivity, whereas the canine IgGB configuration of the insulin-Fc fusion protein exhibited a low degree of aggregation (i.e. high % homodimer), a high titer of the desired homodimer (i.e., a homodimer titer of the canine insulin-Fc fusion protein configurations of greater than 50 mg/L), and appreciable levels of long-duration glucose lowering bioactivity in dogs (i.e., the NAOC value was greater than 150% FBGL·days·kg/mg). Using an alternative purification method, the canine IgGC configuration of the insulin-Fc fusion protein was recovered with low degrees of aggregation, but it was minimally bioactive in dogs (i.e., the NAOC value was less than 150% FBGL·days·kg/mg), presumably due to its low affinity for the FcRn receptor. Therefore, with respect to a dog-specific product, the canine IgGB (SEQ ID NO: 15) is the preferred Fc fragment for all insulin-Fc fusion protein configurations used in dogs, regardless of the choice of insulin polypeptide.

Given that the canine IgGB isotype interacts with the canine Fc(gamma) receptor with higher affinities than the canine IgGA isotype, there could be a risk of unwanted immunogenicity after repeated injections of an insulin-Fc fusion protein configuration comprising canine IgGB. Therefore, various mutations to the canine IgGB Fc fragment were investigated in an effort to preserve greater insulin-Fc fusion protein homodimer titers while decreasing the affinity for the canine Fc(gamma)RI receptor.

One method for reducing the Fc(gamma)RI interaction involves deglycosylating or preventing the glycosylation of the Fc fragment during synthesis of the insulin-Fc fusion protein in the host cell. Each IgG fragment contains a conserved asparagine (N)-glycosylation site in the CH2 domain of each heavy chain of the Fc region. Herein, the notation used to refer to the conserved N-glycosylation site is "cNg". One way to remove the attached glycan from a synthesized insulin-Fc fusion protein is to mutate the cNg site to prevent the attachment of glycans altogether during production in the host cell. Herein, the notation used to describe a cNg mutation is cNg-(substituted amino acid). For example, if the asparagine at the cNg site is mutated to serine, this mutation is notated as "cNg-S".

The absolute position of the cNg site from the N-terminus of the B-chain of the insulin-Fc fusion protein configuration varies depending on the length of the insulin polypeptide, the length of the linker, and any omitted amino acids in the Fc fragment prior to the cNg site. Herein, the notation used to refer to the absolute position of the cNg site in a given insulin-Fc fusion protein sequence (as measured counting from the N-terminus of the B-chain of the insulin-Fc fusion protein) is "NB(number)". For example, if the cNg site is found at the $155^{th}$ amino acid position as counted from the N-terminus of the B-chain, the absolute position of this site is referred to as "cNg-NB155". As a further example, if the cNg site is found at the $155^{th}$ amino acid position as counted from the N-terminus of the B-chain, and the asparagine at this site is mutated to serine, this mutation is noted as "cNg-NB155-S".

In insulin-Fc fusion protein embodiments containing the insulin polypeptide of SEQ ID NO: 4 and the canine IgGB Fc fragment with the cNg-Q, cNg-S, cNg-D, and cNg-K mutations, it was unexpectedly discovered that only the compounds containing the cNg-K and cNg-S mutations exhibited the requisite homodimer titer of the canine insulin-Fc fusion protein of greater than 50 mg/L and lowest Fc(gamma)RI binding affinities. On the other hand, in an insulin-Fc fusion protein embodiment containing the insulin polypeptide of SEQ ID NO: 7 and the canine IgGB Fc fragment with the cNg-S mutation, it was unexpectedly discovered that the resulting insulin-Fc fusion protein was significantly less bioactive in dogs compared to the counterpart insulin-Fc fusion protein configuration but comprising the native canine IgGB Fc (i.e., the NAOC value was significantly lower for the insulin-Fc fusion protein counterpart containing the native glycosylation site amino acid, e.g., cNg-N). The bioactivity of the insulin-Fc fusion protein was unexpectedly restored in the cNg-S mutant (i.e., the NAOC value increased significantly) when the B16 amino acid was mutated to alanine as described above for insulin polypeptide SEQ ID NO: 10. Taken together, there is an unexpected and significant interaction between the choice of cNg mutation on the Fc fragment of the insulin-Fc fusion protein configuration and the composition of the insulin polypeptide such that experimentation is required to identify the preferred insulin-Fc fusion protein embodiments. In specific insulin-Fc fusion protein embodiments, the canine IgGB Fc mutant containing the cNg-S mutation is preferred and the sequence with in bold cNg-S is shown as:

```
                                        (SEQ ID NO: 18)
DCPKCPAPEMLGGPSVFIFPPKPKDTLLIARTPEVTCVVVDLDP

EDPEVQISWFVDGKQMQTAKTQPREEQFSGTYRVVSVLPIGHQD

WLKGKQFTCKVNNKALPSPIERTISKARGQAHQPSVYVLPPSRE

ELSKNTVSLTCLIKDFFPPDIDVEWQSNGQQEPESKYRTTPPQL

DEDGSYFLYSKLSVDKSRWQRGDTFICAVMHEALHNHYTQESLS

HSPG.
```

Generally, the human Fc IgG2 isotype is preferred over the other isotypes due to its lack of Fc(gamma) effector function and therefore its lower propensity to induce unwanted immunogenicity. As an illustration, in one execution of the Fc(gamma)RI binding and C1q binding ELISAs, the insulin-Fc fusion protein embodiment of SEQ ID NO: 76 comprising the human IgG1 fragment exhibited a human Fc(gamma)RI binding assay OD450 at a biotinylated-Fc (gamma)RI concentration of 3000 ng/mL of 2.078, and exhibited a human C1q binding assay OD450 at a biotinylated-C1q concentration of 1000 ng/mL of 3.006, such high values indicating a likelihood of SEQ ID NO: 76 exhibiting immunogenicity in patients. In contrast, in the same execution of the Fc(gamma)RI binding and C1q binding ELISAs, the insulin-Fc fusion protein configuration (SEQ ID NO: 75) comprising the insulin polypeptide of SEQ ID NO: 7, the peptide linker of SEQ ID NO: 13, and the human IgG2 Fc fragment (SEQ ID NO: 74) exhibited a human Fc(gamma)RI binding assay OD450 at a biotinylated-Fc(gamma)RI concentration of 3,000 ng/mL of 0.093 and a human C1q binding assay OD450 at a biotinylated-C1q concentration of 1,000 ng/mL of 0.928, indicating a significantly reduced likelihood of SEQ ID NO: 75 exhibiting immunogenicity in patients.

The absolute value of OD450 measurements for an insulin-Fc fusion protein configuration can vary from one execution of the ELISA to the next, for example due to small variations in execution of the assay. This makes comparisons of absolute value measurements of OD450 for different insulin-Fc fusion protein configurations across different ELISA executions less reliable, even when the concentration of the insulin-Fc fusion configuration under test is held constant. In contrast, the ratio of the OD450 measurement of one insulin-Fc fusion protein configuration in an ELISA execution with the OD450 measurement of a second insulin-Fc fusion protein configuration from the same ELISA execution (again holding the insulin-Fc fusion protein concentrations constant) will be relatively stable for the same two insulin-Fc fusion protein configurations across different ELISA executions. Accordingly, insulin-Fc fusion protein design goals for the OD450 for a human Fc(gamma)RI binding assay and C1q binding assay have been expressed as OD 450 Ratios, where the ratio is made of the absolute OD450 value of the insulin-Fc fusion protein under analysis to the absolute OD 450 value of a reference insulin-Fc fusion protein configuration, where both measurements are made within the same ELISA experiment. The insulin-Fc fusion protein configuration sample biotinylated-Fc(gamma)RI concentration in the Fc(gamma)RI binding ELISA OD450 is set to 3000 ng/mL and the insulin-Fc fusion protein configuration sample biotinylated-C1q concentration in the C1q binding ELISA OD450 is set to 1000 ng/mL for all samples tested.

The insulin-Fc fusion protein configuration of SEQ ID NO: 76 (comprising the human IgG1 Fc fragment) is used as the reference insulin-Fc fusion protein for the Fc(gamma)RI binding ELISA and C1q binding ELISA OD450 Ratio calculations. The Fc(gamma)RI binding ELISA OD450 Ratio for the insulin-Fc fusion protein configuration of SEQ ID NO: 75 (comprising the human IgG2 Fc fragment) using the measured OD450 values given above is:

$$Fc(\text{gamma})RI \text{ binding } ELISA\ OD450 \text{ Ratio}_{\left(\frac{SEQ\ ID\ NO:75}{SEQ\ ID\ NO:76}\right)} = \frac{0.093}{2.078} = 0.045$$

The C1q binding ELISA OD450 Ratio for the insulin-Fc fusion protein configuration of SEQ ID NO: 75 using the measured OD450 values given above is:

$$C1q \text{ binding } ELISA\ OD450 \text{ Ratio}_{\left(\frac{SEQ\ ID\ NO:75}{SEQ\ ID\ NO:76}\right)} = \frac{0.928}{3.06} = 0.309$$

The Fc(gamma)RI binding ELISA OD450 Ratio and the C1q binding ELISA OD450 Ratio of the insulin-Fc fusion protein configuration of SEQ ID NO: 75 (hIgG2) with respect to the insulin-Fc fusion protein configuration of SEQ ID NO: 76 (hIgG1) represents an aspirational benchmark that was used in creating the design goals for evaluating the Fc(gamma)RI binding and C1q binding for different insulin-Fc fusion configurations in order to reduce the propensity for unwanted immunogenicity. Accordingly, the design goal established for human Fc(gamma)RI binding (where the biotinylated-Fc(gamma)RI concentration of the insulin-Fc fusion protein under test is 3000 ng/mL) is an OD450 Ratio<0.50 and the design goal established for human C1q binding (where the biotinylated-C1q concentration of the insulin-Fc fusion protein under test is 1000 ng/mL) is an OD450 ratio<0.35.

The resulting average homodimer titer from two separate syntheses of this insulin-Fc fusion protein configuration (SEQ ID NO: 75) comprising the human IgG2 Fc fragment was 117 mg/L.

By comparison, in an insulin-Fc fusion protein embodiment (SEQ ID NO: 76) comprising the same insulin polypeptide of SEQ ID NO: 7, the same peptide linker of SEQ ID NO: 13, and the human IgG1 fragment (SEQ ID NO: 73) it was found that the insulin-Fc fusion protein exhibited an average homodimer titer from two separate syntheses of 180 mg/L, which was over 50% greater than that obtained for the analogous insulin-Fc fusion protein configuration comprising the human IgG2 fragment. Given that the human IgG1 isotype interacts with the human Fc(gamma)RI receptor with higher affinities than the human IgG2 isotype, there could be a risk of unwanted immunogenicity after repeated injections of an insulin-Fc fusion protein configuration comprising human IgG1.

Therefore, various mutations to the human IgG1 Fc fragment were investigated in an effort to preserve greater insulin-Fc fusion protein homodimer titers while decreasing the affinity for the human Fc(gamma)RI receptor and C1q.

As discussed previously, one method for reducing the Fc(gamma)RI interaction involves deglycosylating or preventing the glycosylation of the Fc fragment during synthesis of the insulin-Fc fusion protein in the host cell. One way to remove the attached glycan from a synthesized insulin-Fc fusion protein is to mutate the cNg site to prevent the attachment of glycans altogether during production in the host cell.

The mutated human IgG1 Fc fragment generalized configuration with cNg site in bold is as follows: DKTHTCPPCPAPELLGGPSVFLFPPKPKDTLMISRTPEVTCVVVDVSHEDPEVKFNWYVDGVEV HNAKTKPREEQY$X_1$STYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPG (SEQ ID NO: 77), where in examples $X_1$ is S, D, A, R or Q.

The human IgG1 Fc fragment comprising the insulin polypeptide of SEQ ID NO: 7, the peptide linker of SEQ ID NO: 13, and the human IgG1 Fc fragment of SEQ ID NO: 77 where $X_1$ is S (i.e., with the cNg-NB155-S mutation) is shown below:

(SEQ ID NO: 91)
FVNQHLCGSHLVEALELVCGERGFHYGGGGGGSGGGGGIVEQCC
TSTCSLDQLENYCGGGGGQGGGGQGGGGQGGGGGDKTHTCPPCP
APELLGGPSVFLFPPKPKDTLMISRTPEVTCVVVDVSHEDPEVK
FNWYVDGVEVHNAKTKPREEQYSSTYRVVSVLTVLHQDWLNGKE
YKCKVSNKALPAPIEKTISKAKGQPREPQVYTLPPSRDELTKNQ
VSLTCLVKGFYPSDIAVEWESNGQPENNYKTTPPVLDSDGSFFL
YSKLTVDKSRWQQGNVFSCSVMHEALHNHYTQKSLSLSPG

It was unexpectedly discovered that the non-glycosylated insulin-Fc fusion protein embodiment of SEQ ID NO: 91 gave improved homodimer titers relative to the glycosylated parent material (SEQ ID NO: 76). Additionally, the human Fc(gamma)RI assay OD450 Ratio at a biotinylated-Fc (gamma)RI concentration of 3000 ng/mL for the insulin-Fc fusion protein embodiment of SEQ ID NO: 91 against the reference insulin-Fc fusion protein of SEQ ID NO: 76 was less than 0.50 and the human C1q binding assay OD450 Ratio at a biotinylated-C1q concentration of 1,000 ng/mL for the insulin-Fc fusion protein configuration of SEQ ID NO: 91 against the reference insulin-Fc fusion protein of SEQ ID NO: 76 was less than 0.35. However, the resulting non-glycosylated insulin-Fc fusion protein of SEQ ID NO: 91 with respect to its parent glycosylated insulin-Fc fusion protein of SEQ ID NO: 76 exhibited decreased IR binding (increased IR assay IC50 value) and decreased FcRn binding affinity (increased EC50 value), indicating a high likelihood of an unacceptable reduction in bioactivity with residence time in vivo respectively.

Insulin-Fc Fusion Proteins

Provided herein are insulin-Fc fusion protein configurations comprising an insulin polypeptide, an Fc fragment, and a linker between the insulin polypeptide and the Fc fragment. In embodiments, the insulin polypeptide comprises domains in the following orientation from N- to C-termini: (N-terminus)—B-chain—C-chain—A-chain—(C-terminus). In embodiments, the insulin polypeptide is located on the N-terminal side of the Fc fragment. In embodiments, the fusion protein comprises domains in the following orientation from N- to C-termini: (N-terminus)—insulin polypeptide—linker—Fc fragment—(C-terminus) (e.g., (N-terminus)—B-chain—C-chain—A-chain—linker—Fc fragment—(C-terminus)) as illustrated in FIG. 1.

Canine Insulin-Fc Fusion Proteins

In embodiments, the preferred non-immunogenic, bioactive insulin polypeptide of SEQ ID NO: 5 was combined with the preferred canine IgGB Fc fragment of SEQ ID NO: 15 using the preferred linker of SEQ ID NO: 13 to produce a family of high homodimer titer-yielding, non-aggregated, bioactive, non-immunogenic canine insulin-Fc fusion configurations of SEQ ID NO: 20 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 20 with non-native amino acids in bold:

(SEQ ID NO: 20)
FVNQHLCGS$X_1$LVEALELVCGERGFHYGGGGGGSGGGGGIVEQC
C$X_2$STCSLDQLENYC$X_3$GGGGGQGGGGQGGGGQGGGGGDCPKCPA
PEMLGGPSVFIFPPKPKDTLLIARTPEVTCVVVDLDPEDPEVQI
SWFVDGKQMQTAKTQPREEQFNGTYRVVSVLPIGHQDWLKGKQF
TCKVNNKALPSPIERTISKARGQAHQPSVYVLPPSREELSKNTV
SLTCLIKDFFPPDIDVEWQSNGQQEPESKYRTTPPQLDEDGSYF
LYSKLSVDKSRWQRGDTFICAVMHEALHNHYTQESLSHSPG, where $X_1$ is not D, $X_2$ is not H, and $X_3$ is absent or N.

In preferred canine insulin-Fc fusion protein embodiments comprising SEQ ID NO: 20, $X_1$ is H, $X_2$ is T, and $X_3$ is absent or N. The selections produce the high homodimer titer-yielding, non-aggregated, bioactive, non-immunogenic canine insulin-Fc fusion protein configurations of SEQ ID NO: 21 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 21 with non-native amino acids in bold:

(SEQ ID NO: 21)

FVNQHLCGSHLVEALELVCGERGFHYGGGGGGSGGGGGIVEQCC

TSTCSLDQLENYCX$_3$GGGGGQGGGGQGGGGQGGGGGDCPKCPAP

EMLGGPSVFIFPPKPKDTLLIARTPEVTCVVVDLDPEDPEVQIS

WFVDGKQMQTAKTQPREEQFNGTYRVVSVLPIGHQDWLKGKQFT

CKVNNKALPSPIERTISKARGQAHQPSVYVLPPSREELSKNTVS

LTCLIKDFFPPDIDVEWQSNGQQEPESKYRTTPPQLDEDGSYFL

YSKLSVDKSRWQRGDTFICAVMHEALHNHYTQESLSHSPG, where $X_3$ is absent or N.

In preferred embodiments, $X_3$ is absent in SEQ ID NO: 21 to produce the high homodimer-yielding, non-aggregated, bioactive, non-immunogenic canine insulin-Fc fusion protein of SEQ ID NO: 26 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 26 with non-native amino acids in bold:

(SEQ ID NO: 26)

FVNQHLCGSHLVEALELVCGERGFHYGGGGGGSGGGGGIVEQCCTSTCSL

DQLENYCGGGGGQGGGGQGGGGQGGGGGDCPKCPAPEMLGGPSVFIFPPK

PKDTLLIARTPEVTCVVVDLDPEDPEVQISWFVDGKQMQTAKTQPREEQF

NGTYRVVSVLPIGHQDWLKGKQFTCKVNNKALPSPIERTISKARGQAHQP

SVYVLPPSREELSKNTVSLTCLIKDFFPPDIDVEWQSNGQQEPESKYRTT

PPQLDEDGSYFLYSKLSVDKSRWQRGDTFICAVMHEALHNHYTQESLSHS

PG.

In preferred embodiments, $X_3$ is N in SEQ ID NO: 21 to produce the high homodimer titer-yielding, non-aggregated, bioactive, non-immunogenic canine insulin-Fc fusion protein of SEQ ID NO: 28 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 28 with non-native amino acids in bold:

(SEQ ID NO: 28)

FVNQHLCGSHLVEALELVCGERGFHYGGGGGGSGGGGGIVEQCCTSTCSL

DQLENYCNGGGGGQGGGGQGGGGQGGGGGDCPKCPAPEMLGGPSVFIFPP

KPKDTLLIARTPEVTCVVVDLDPEDPEVQISWFVDGKQMQTAKTQPREEQ

FNGTYRVVSVLPIGHQDWLKGKQFTCKVNNKALPSPIERTISKARGQAHQ

PSVYVLPPSREELSKNTVSLTCLIKDFFPPDIDVEWQSNGQQEPESKYRT

TPPQLDEDGSYFLYSKLSVDKSRWQRGDTFICAVMHEALHNHYTQESLSH

SPG.

In preferred embodiments, the preferred non-glycosylated, cNg-S mutated canine IgGB Fc fragment of SEQ ID NO: 18 is combined with the preferred B16A mutated insulin polypeptide sequence of SEQ ID NO: 9 using the preferred linker of SEQ ID NO: 13 to produce a family of high homodimer titer-yielding, non-aggregated, bioactive, non-immunogenic canine insulin-Fc fusion proteins of SEQ ID NO: 22 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 22 with non-native amino acids in bold:

(SEQ ID NO: 22)

FVNQHLCGSX$_1$LVEALALVCGERGFHYGGGGGGSGGGGGIVEQCCX$_2$STC

SLDQLENYCGGGGGQGGGGQGGGGQGGGGGDCPKCPAPEMLGGPSVFIFP

PKPKDTLLIARTPEVTCVVVDLDPEDPEVQISWFVDGKQMQTAKTQPREE

QFSGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYR

TTPPQLDEDGSYFLYSKLSVDKSRWQRGDTFICAVMHEALHNHYTQESLS

HSPG, where $X_1$ is not D and $X_2$ is not H.

In a preferred embodiment, $X_1$ is H and $X_2$ is T in SEQ ID NO: 22 to produce the high homodimer titer-yielding, non-aggregated, bioactive, non-immunogenic canine insulin-Fc fusion protein of SEQ ID NO: 30 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 30 with non-native amino acids in bold:

(SEQ ID NO: 30)

FVNQHLCGSHLVEALALVCGERGFHYGGGGGGSGGGGGIVEQCCTSTCSL

DQLENYCGGGGGQGGGGQGGGGQGGGGGDCPKCPAPEMLGGPSVFIFPPK

PKDTLLIARTPEVTCVVVDLDPEDPEVQISWFVDGKQMQTAKTQPREEQF

SGTYRVVSVLPIGHQDWLKGKQFTCKVNNKALPSPIERTISKARGQAHQP

SVYVLPPSREELSKNTVSLTCLIKDFFPPDIDVEWQSNGQQEPESKYRTT

PPQLDEDGSYFLYSKLSVDKSRWQRGDTFICAVMHEALHNHYTQESLSHS

PG.

The unexpected discovery of the highly manufacturable and effective ultra-long acting canine insulin-Fc fusion protein embodiment of SEQ ID NO: 30, led the inventors to attempt to produce similarly manufacturable and effective ultra-long acting insulin-Fc fusion protein configurations for human patients.

Human Insulin-Fc Fusion Proteins

Further experiments were done to determine if other non-glycosylated insulin-Fc fusion protein configurations exhibited the same behavior. The human IgG1 Fc fragment generalized configuration with cNg site in bold is as follows: DKTHTCPPCPAPELLGGPSVFLFPPKPKDTLMISRTPE-VTCVVVDVSHEDPEVKFNWYVDGVEV HNAKTKP-REEQYX$_1$STYRVVSVLTVLHQDWLNGKEYKCKVS-NKALPAPIEKTISKAKGQPREP QVYTLPPSRDELT-KNQVSLTCLVKGFYPSDIAVEWESNGQPENNYKTT-PPVLDSDGSFFLYSKL TVDKSRWQQGNVFSCSVMH-EALHNHYTQKSLSLSPG (SEQ ID NO: 77), where $X_1$ is S, D, A, R or Q.

Insulin-Fc fusion protein embodiments comprising the insulin polypeptide of SEQ ID NO: 7 (no B16A mutation) with the linker of SEQ ID NO: 13 and with the human IgG1 Fc fragment configuration with cNg mutation options to prevent glycosylation (SEQ ID NO: 77 where $X_1$ is S, D, A, R or Q) are shown below:

(SEQ ID NO: 91)

FVNQHLCGSHLVEALELVCGERGFHYGGGGGGSGGGGGIVEQCCTSTCSLDQLENYCGGGGG

QGGGGQGGGGQGGGGGDKTHTCPPCPAPELLGGPSVFLFPPKPKDTLMISRTPEVTCVVVDVS

HEDPEVKFNWYVDGVEVHNAKTKPREEQYSSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG (SEQ ID NO: 92)

FVNQHLCGSHLVEALELVCGERGFHYGGGGGGSGGGGGIVEQCCTSTCSLDQLENYCGGGGG

QGGGGQGGGGQGGGGGDKTHTCPPCPAPELLGGPSVFLFPPKPKDTLMISRTPEVTCVVVDVS

HEDPEVKFNWYVDGVEVHNAKTKPREEQYDSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG (SEQ ID NO: 93)

FVNQHLCGSHLVEALELVCGERGFHYGGGGGGSGGGGGIVEQCCTSTCSLDQLENYCGGGGG

QGGGGQGGGGQGGGGGDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG (SEQ ID NO: 94)

FVNQHLCGSHLVEALELVCGERGFHYGGGGGGSGGGGGIVEQCCTSTCSLDQLENYCGGGGG

QGGGGQGGGGQGGGGGDKTHTCPPCPAPELLGGPSVFLFPPKPKDTLMISRTPEVTCVVVDVS

HEDPEVKFNWYVDGVEVHNAKTKPREEQYRSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG (SEQ ID NO: 95)

FVNQHLCGSHLVEALELVCGERGFHYGGGGGGSGGGGGIVEQCCTSTCSLDQLENYCGGGGG

QGGGGQGGGGQGGGGGDKTHTCPPCPAPELLGGPSVFLFPPKPKDTLMISRTPEVTCVVVDVS

HEDPEVKFNWYVDGVEVHNAKTKPREEQYQSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

In embodiments containing the insulin polypeptide of SEQ ID NO: 7 using the preferred linker of SEQ ID NO: 13 and the human IgG1 Fc fragment of SEQ ID NO: 77 wherein $X_1$ is S (cNg-NB155-S—SEQ ID NO: 91), D (cNg-NB155-D—SEQ ID NO: 92), A (cNg-NB155-A—SEQ ID NO: 93), R (cNg-NB155-R—SEQ ID NO: 94), or Q (cNg-NB155-Q—SEQ ID NO: 95), it was unexpectedly discovered that each of these non-glycosylated insulin-Fc fusion proteins gave improved homodimer titers relative to the glycosylated parent material (SEQ ID NO: 76). Additionally, for each of the deglycosylated insulin-Fc fusion proteins of SEQ ID NO: 91, SEQ ID NO: 92, SEQ ID NO: 93, SEQ ID NO: 94 and SEQ ID NO: 95, the human Fc(gamma)RI assay OD450 Ratios at a biotinylated-Fc(gamma)RI concentration of 3000 ng/mL (where the reference insulin-Fc fusion protein used in OD450 Ratio calculations is the insulin-Fc fusion protein of SEQ ID NO: 76) were all less than 0.50 and the human C1q binding assay OD450 Ratios at a biotinylated-C1q concentration of 1,000 ng/mL (where the reference insulin-Fc fusion protein used in OD450 Ratio calculations is the insulin-Fc fusion protein of SEQ ID NO: 76) were also less than 0.35. However, the deglycosylated insulin-Fc fusion proteins of SEQ ID NO: 91, SEQ ID NO: 92, SEQ ID NO: 93, SEQ ID NO: 94 and SEQ ID NO: 95 all demonstrated lower IR binding affinities (higher IR assay IC50 values) and lower FcRn binding affinities (higher EC50 values) relative to the glycosylated parent material (SEQ ID NO: 76), indicating a high likelihood of these compounds displaying an unacceptable reduction in bioactivity and residence time in vivo. Unexpectedly, in the embodiment comprising the insulin polypeptide of SEQ ID NO: 7 using the preferred linker of SEQ ID NO: 13 and the human IgG1 Fc fragment of SEQ ID NO: 77 wherein $X_1$ is Q (SEQ ID NO: 95), the resulting non-glycosylated insulin-Fc fusion protein gave a homodimer titer of 136 mg/L, such that this insulin-Fc fusion protein configuration did not meet the design goal for homodimer titer of 150 mg/L.

FIG. 28 illustrates a side-by-side sequence comparison of SEQ ID NO: 75 (comprising native human IgG2) and SEQ ID NO: 76 (comprising native human IgG1), with sequences comprising the variants of SEQ ID NO: 77, that is SEQ ID NO: 91, SEQ ID NO: 92, SEQ ID NO: 93, SEQ ID NO: 94, and SEQ ID NO: 95. "*" represents complete homology across all sequences at a given sequence position, while ":", "." or spaces refer to conservative, moderate, or very different amino acid mutations across the sequences at a given sequence position respectively.

Applying the learning from the unexpected results with respect to the canine insulin-Fc fusion protein configurations discussed previously, the $16^{th}$ amino acid on the B-chain (B16) of the insulin polypeptide in the insulin-Fc fusion protein embodiments of SEQ ID NO: 91, SEQ ID NO: 92, SEQ ID NO: 93 and SEQ ID NO: 94 was mutated to alanine, resulting in SEQ ID NO: 78 (with cNg-NB155-S), SEQ ID NO: 80 (with cNg-NB155-D), SEQ ID NO: 82 (with cNg-NB155-A), SEQ ID NO: 84 (with cNg-NB155-R). Acceptable insulin receptor binding was unexpectedly restored in the insulin-Fc fusion protein configurations of SEQ ID NO: 78, SEQ ID NO: 80, SEQ ID NO: 82 and SEQ ID NO: 84 (i.e., the IR binding and FcRn receptor binding affinities increased significantly) when the B16 amino acid was mutated to alanine as described above resulting in the insulin polypeptide of SEQ ID NO: 10, without compromising the increased homodimer titers or the reduction in Fc(gamma)RI and C1q binding affinities.

In a preferred embodiment, the human insulin-Fc fusion protein configuration of SEQ ID NO: 78 comprises the insulin polypeptide of SEQ ID NO: 10, the linker of SEQ ID NO: 13, and the cNg-NB155-S mutant of the human IgG1 Fc fragment of SEQ ID NO: 77. The insulin-Fc fusion protein of SEQ ID NO: 78 exhibits a homodimer titer greater than 150 mg/L. The following shows the insulin-Fc fusion protein of SEQ ID NO: 78 with the B16A and cNg-NB155-S mutations in bold:

(SEQ ID NO: 78)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYSSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

Similar to the unexpected discovery with canine insulin-Fc fusion protein configurations, the bioactivity of the non-glycosylated insulin-Fc fusion protein embodiment of SEQ ID NO: 78 comprising the B16A mutation and a human IgG1 Fc fragment with the cNg-NB155-S mutation was unexpectedly restored (i.e., the IR binding and FcRn receptor binding affinities increased significantly) as compared to the bioactivity of the non-glycosylated insulin-Fc fusion protein embodiment of SEQ ID NO: 91 which lacked the B16A mutation. The insulin-Fc fusion protein embodiment of SEQ ID NO: 78 demonstrated an IR assay IC50 value less than 2400 nM and more preferably less than 2000 nM, a human FcRn assay EC50 value less than 1500 ng/L and more preferably less than 1000 ng/mL, a human Fc(gamma) RI assay OD450 Ratio at a biotinylated-Fc(gamma)RI concentration of 3,000 ng/mL less than 0.50 (where the reference insulin-Fc fusion protein used in OD450 Ratio calculations is the insulin-Fc fusion protein of SEQ ID NO: 76), and a human C1q binding assay OD450 Ratio at a biotinylated-C1q concentration of 1,000 ng/mL (where the reference insulin-Fc fusion protein used in OD450 Ratio calculations is the insulin-Fc fusion protein of SEQ ID NO: 76) less than 0.35.

In a preferred embodiment, the insulin-Fc fusion protein of SEQ ID NO: 80 comprises the insulin polypeptide of SEQ ID NO: 10, the linker of SEQ ID NO: 13, and the cNg-NB155-D mutant of the Fc fragment of SEQ ID NO: 77 ($X_1$ is D). The insulin-Fc fusion protein of SEQ ID NO: 80 exhibits a homodimer titer greater than 150 mg/L, an IR assay IC50 value less than 2400 nM, a human FcRn assay EC50 value less than 1000 ng/mL, a human Fc(gamma)RI assay OD450 Ratio at a biotinylated-Fc(gamma)RI concentration of 3,000 ng/mL less than 0.50, and a human C1q binding assay OD450 Ratio at a biotinylated-C1q concentration of 1,000 ng/mL less than 0.35. The following shows SEQ ID NO: 80 with the B16A and cNg-NB155-D mutations in bold:

(SEQ ID NO: 80)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYDSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

In a preferred embodiment, the insulin-Fc fusion protein of SEQ ID NO: 82 comprises the insulin polypeptide of SEQ ID NO: 10, the linker of SEQ ID NO: 13, and the cNg-NB155-A mutant of the Fc fragment of SEQ ID NO: 77 ($X_1$ is A). The insulin-Fc fusion protein of SEQ ID NO: 82 exhibits a homodimer titer greater than 150 mg/L, an IR assay IC50 value less than 2400 nM, a human FcRn assay EC50 value less than 1000 ng/mL, a human Fc(gamma)RI assay OD450 Ratio at a biotinylated-Fc(gamma)RI concentration of 3,000 ng/mL less than 0.50, and a human C1q binding assay OD450 Ratio at a biotinylated-C1q concentration of 1,000 ng/mL less than 0.35. The following shows SEQ ID NO: 82 with the B16A and cNg-NB155-A mutations in bold:

(SEQ ID NO: 82)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYASTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

In a preferred embodiment, the insulin-Fc fusion protein of SEQ ID NO: 84 comprises the insulin polypeptide of SEQ ID NO: 10, the linker of SEQ ID NO: 13, and the cNg-NB155-R mutant of the Fc fragment of SEQ ID NO: 77 ($X_1$ is R). The insulin-Fc fusion protein of SEQ ID NO: 84 exhibits a homodimer titer greater than 150 mg/L, an IR assay IC50 value less than 2400 nM, a human FcRn assay EC50 value less than 1000 ng/mL, a human Fc(gamma)RI assay OD450 Ratio at a biotinylated-Fc(gamma)RI concentration of 3,000 ng/mL less than 0.50, and a human C1q binding assay OD450 Ratio at a biotinylated-C1q concentration of 1,000 ng/mL less than 0.35. The following shows SEQ ID NO: 84 with the B16A and cNg-NB155-R mutations in bold:

(SEQ ID NO: 84)

FVNQHLCGSHLVEALALVCGERGFHYGGGGGGSGGGGGIVEQCCTSTCSL

DQLENYCGGGGGQGGGGQGGGGQGGGGGDKTHTCPPCPAPELLGGPSVFL

FPPKPKDTLMISRTPEVTCVVVDVSHEDPEVKFNWYVDGVEVHNAKTKPR

EEQYRSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPG.

As was the case with SEQ ID NO: 78, the bioactivity of the non-glycosylated insulin-Fc fusion protein configurations comprising human IgG1 FC fragments with the cNg-NB155-D, cNg-NB155-A, cNg-NB155-R and cNg-NB155-Q mutations (SEQ ID NO: 92, SEQ ID NO: 93, SEQ ID NO: 94 and SEQ ID NO: 95) was restored (i.e., the IR binding and FcRn receptor binding affinities increased significantly) when the $16^{th}$ amino acid on the B-chain (B16) of the insulin polypeptide was mutated to alanine (resulting in the insulin polypeptide of SEQ ID NO: 10), without compromising the increased homodimer titers or the reduction in Fc(gamma)RI and C1q binding affinities of the non-glycosylated insulin-Fc fusion protein configurations of SEQ ID NO: 92, SEQ ID NO: 93, and SEQ ID NO: 94 (as previously discussed, the homodimer titer of the insulin-Fc fusion protein configuration of SEQ ID NO: 95 did not meet the design goal of 150 mg/L).

However, the insulin-Fc fusion protein of SEQ ID NO: 86 comprising the insulin polypeptide of SEQ ID NO: 10, the linker of SEQ ID NO: 13, and the cNg-NB155-Q mutant of the Fc fragment of SEQ ID NO: 77 ($X_1$ is Q) did not exhibit the reduction in Fc(gamma)RI and C1q binding affinities of the non-glycosylated insulin-Fc fusion protein configuration of SEQ ID NO: 95, however the homodimer titer of the insulin-Fc fusion protein configuration of SEQ ID NO: 86 dropped further from that of SEQ ID NO: 95 to 111 mg/L, which does not meet the design goal of an insulin-Fc fusion protein homodimer titer greater than 150 mg/L. The following shows SEQ ID NO: 86 with the B16A and cNg-NB155-Q mutations in bold:

(SEQ ID NO: 86)

FVNQHLCGSHLVEALALVCGERGFHYGGGGGGSGGGGGIVEQCCTSTCSL

DQLENYCGGGGGQGGGGQGGGGQGGGGGDKTHTCPPCPAPELLGGPSVFL

FPPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

-continued

TTPPVLDSDGSFFLYSKLTVDKSRWQQGNVFSCSVMHEALHNHYTQKSLS

LSPG.

These results indicate that there is an unexpected and significant interaction between the choice of cNg mutation on the human IgG1 Fc fragment and the composition of the insulin polypeptide such that experimentation is required to identify the preferred configurations with respect to IR and FcRn binding affinities of the resulting insulin-Fc fusion proteins.

In some configurations, insulin-Fc fusion protein configurations described herein do not include a leader amino acid sequence at the N-terminus. In other configurations, insulin-Fc fusion protein configurations described herein includes a leader sequence, e.g., at the N-terminus. In some embodiments, an exemplary leader sequence includes the amino acid sequence: MEWSWVFLFFLSVTTGVHS (SEQ ID NO: 24). In some embodiments, insulin-Fc fusion protein configurations described herein are encoded by a nucleic acid molecule comprising a leader sequence, e.g., for expression (e.g., recombinant expression) in cells (e.g., eukaryotic, e.g., mammalian cells). In certain embodiments, the leader sequence is cleaved off, e.g., in the cell culture, during expression. An exemplary nucleic acid sequence encoding a leader sequence includes the nucleic acid sequence: atggaatggagctgggtctttctcttcttcctgtcagtaacgactggtgtccactcc (SEQ ID NO: 23). In embodiments, the exemplary nucleic acid of SEQ ID NO: 23 encodes the exemplary leader sequence of SEQ ID NO: 24.

In a preferred embodiment comprising the insulin-Fc fusion protein configuration of SEQ ID NO: 78, the nucleic acid sequence (leader sequence in bold) is:

(SEQ ID NO: 79)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtcaaggag gcggtggacagggtggaggtgggcagggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacagcagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc -continued tcatgctccgtgatgcatgaggctctgcacaaccactacacgcagaagag cctctccctgtctccgggttag.

In a preferred embodiment comprising the insulin-Fc fusion protein configuration of SEQ ID NO: 80, the nucleic acid sequence (leader sequence in bold) is:

(SEQ ID NO: 81)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtcaaggag gcggtggacagggtggaggtgggcagggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacgacagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

In an embodiment comprising the insulin-Fc fusion protein configuration of SEQ ID NO: 82, the nucleic acid sequence (leader sequence in bold) is:

(SEQ ID NO: 83)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtcaaggag gcggtggacagggtggaggtgggcagggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacgccagcacgtaccgtgtggtcagcgtcctca -continued ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

In a preferred embodiment comprising the insulin-Fc fusion protein configuration of SEQ ID NO: 84, the nucleic acid sequence (leader sequence in bold) is:

(SEQ ID NO: 85)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtcaaggag gcggtggacagggtggaggtgggcagggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacagaagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

In a preferred embodiment comprising the insulin-Fc fusion protein configuration of SEQ ID NO: 86, the nucleic acid sequence (leader sequence in bold) is:

(SEQ ID NO: 100)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtcaaggag -continued gcggtggacagggtggaggtgggcagggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtaccaaagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

In some applications, it may be desirable to covalently modify the insulin-Fc fusion protein to further modify its properties. For example, the insulin-Fc fusion protein may be conjugated to various lengths of polyethylene glycol (PEG) molecules to further extend its circulating half-life as described in Dozier, J.; Distefano, M. Site-Specific PEGylation of Therapeutic Proteins. *Int. J. Mol. Sci.* 2015, 16(10), 25831-25864). One such method of conjugation relies on a class of enzymes called transglutaminases (TGases) which create a covalent bond between a primary amine (e.g. at the terminus of a PEG molecule) and the carboxamide group of glutamine (e.g. Q on a target protein, e.g. on a target insulin-Fc fusion protein) via an acyl transfer reaction (Dozier, J.; Distefano, M., page 25853). The Q at position NB153 of the insulin-Fc fusion proteins of SEQ ID NO: 86, and SEQ ID NO: 95 is a preferred TGase conjugation site, but because each of the insulin-Fc fusion proteins comprises a GGGGGQGGGGQGGGGQGGGGG (SEQ ID NO: 13) linker, the linker will also be conjugated at the Q residues. Therefore, to minimize unwanted TGase conjugation at the linker Q sites, alanine (A) for glutamine (Q) mutations in the linker were tested. Accordingly, in a preferred embodiment, the insulin-Fc fusion protein of SEQ ID NO: 87 comprises the insulin polypeptide of SEQ ID NO: 10, the linker of GGGGGAGGGGAGGGGAGGGGG (SEQ ID NO: 67), and the cNg-NB155-S mutant of the Fc fragment of SEQ ID NO: 77 ($X_1$ is S). The insulin-Fc fusion protein of SEQ ID NO: 87 exhibits a homodimer titer greater than 150 mg/L, an IR assay IC50 value less than 2400 nM, a human FcRn assay EC50 value less than 1000 ng/mL, a human Fc(gamma)RI assay OD450 Ratio at biotinylated-Fc(gamma)RI concentration of 3,000 ng/mL less than 0.50, and a human C1q binding assay OD450 Ratio at a biotinylated-C1q concentration of 1,000 ng/mL less than 0.35. The following shows SEQ ID NO: 87 with the B16A and cNg-NB155-S mutations as well as the linker sequence in bold:

(SEQ ID NO: 87)

FVNQHLCGSHLVEALALVCGERGFHYGGGGGGSGGGGGIVEQCCTSTCSL

DQLENYCGGGGGAGGGGAGGGGAGGGGGDKTHTCPPCPAPELLGGPSVFL

FPPKPKDTLMISRTPEVTCVVVDVSHEDPEVKFNWYVDGVEVHNAKTKPR

EEQYSSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPG.

In an embodiment comprising the insulin-Fc fusion protein of SEQ ID NO: 87, the nucleic acid sequence (leader sequence in bold) is:

(SEQ ID NO: 88)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtgcaggag gcggtggagccggtggaggtggggctggaggaggcgggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacagcagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

Linker length in Fc-fusion protein conjugates has been known to affect characteristics of the fusion protein ranging from yield to bioactivity. Accordingly, an insulin-Fc fusion protein configuration with a shorter linker was tested to determine any gain or loss of yield or function due to the length of the linker. In another preferred embodiment, the insulin-Fc fusion protein of SEQ ID NO: 89 comprises the insulin polypeptide of SEQ ID NO: 10, the linker of GGGGAGGGG (SEQ ID NO: 11), and the cNg-NB155-S mutant of the Fc fragment of SEQ ID NO: 77 ($X_1$ is S). The insulin-Fc fusion protein of SEQ ID NO: 89 exhibits a homodimer titer greater than 150 mg/L, an IR assay IC50 value less than 2400 nM, a human FcRn assay EC50 value less than 1000 ng/mL, a human Fc(gamma)RI assay OD450 Ratio at a biotinylated-Fc(gamma)RI concentration of 3,000 ng/mL less than 0.50, and a human C1q binding assay OD450 Ratio at a biotinylated-C1q concentration of 1,000 ng/mL less than 0.35.

The following shows SEQ ID NO: 89 with the B16A and cNg-NB155-S mutations as well as the linker sequence in bold:

(SEQ ID NO: 89)

FVNQHLCGSHLVEALALVCGERGFHYGGGGGGSGGGGGIVEQCCTSTCSL

DQLENYCGGGGAGGGGDKTHTCPPCPAPELLGGPSVFLFPPKPKDTLMIS

RTPEVTCVVVDVSHEDPEVKFNWYVDGVEVHNAKTKPREEQYSSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPG.

In an embodiment comprising the insulin-Fc fusion protein of SEQ ID NO: 89, the nucleic acid sequence (leader sequence in bold) is:

(SEQ ID NO: 90)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtgccggaggcg gggagacaaaactcacacatgcccaccgtgcccagcacctgaactcctg gggggaccgtcagtcttcctcttccccccaaaacccaaggacaccctcat gatctcccggacccctgaggtcacatgcgtggtggtggacgtgagccacg aagaccctgaggtcaagttcaactggtacgtggacggcgtggaggtgcat aatgccaagacaaagccgcgggaggagcagtacagcagcacgtaccgtgt ggtcagcgtcctcaccgtcctgcaccaggactggctgaatggcaaggagt acaagtgcaaggtctccaacaaagccctcccagcccccatcgagaaaacc atctccaaagccaaagggcagccccgagaaccacaggtgtacaccctgcc cccatcccgggatgagctgaccaagaaccaggtcagcctgacctgcctgg tcaaaggcttctatcccagcgacatcgccgtggagtgggagagcaatggg cagccggagaacaactacaagaccacgcctcccgtgctggactccgacgg ctccttcttcctctacagcaagctcaccgtggacaagagcaggtggcagc aggggaacgtcttctcatgctccgtgatgcatgaggctctgcacaaccac tacacgcagaagagcctctccctgtctccgggttag.

In general preferred configurations, the less-immunogenic, non-glycosylated, cNg-mutated human IgG1 Fc fragments of SEQ ID NO: 77 ($X_1$ is S, D, A, or R) combined with the preferred B16A-mutated insulin polypeptide of SEQ ID NO: 10 and with various linkers (SEQ ID NO: 11, SEQ ID NO: 13, SEQ ID NO: 67) produce a family of high homodimer titer-yielding, bioactive, non-immunogenic human insulin-Fc fusion protein configurations that are expected to exhibit sufficient in vivo potency and duration of action to enable chronic, once-a-week dosing in diabetic patients.

Insulin-Fc Fusion Protein Production

In embodiments, a fusion protein can be expressed by a cell as described in more detail in the Examples section.

Expression and Purification

In embodiments, an insulin-Fc fusion protein can be expressed recombinantly, e.g., in a eukaryotic cell, e.g., mammalian cell or non-mammalian cell. Exemplary mammalian cells used for expression include HEK cells (e.g., HEK293 cells) or CHO cells. CHO cells can be subdivided into various strains or subclasses, (e.g. CHO DG44, CHO-M, and CHO-K1), and some of these cell strains may be genetically engineered for optimal use with a particular type of nucleic acid molecule (e.g., a vector comprising DNA) or a particular cell growth media composition as described in the Examples section. In embodiments, cells are transfected with a nucleic acid molecule (e.g., vector) encoding the insulin-Fc fusion protein (e.g., where the entire insulin-Fc fusion protein is encoded by a single nucleic acid molecule). In embodiments, HEK293 cells are transfected with a vector that encodes for the insulin-Fc fusion protein, but only results in temporary expression of the insulin-Fc fusion protein for a period of time (e.g., 3 days, 4 days, 5, days, 7 days, 10 days, 12 days, 14 days, or more) before the host cell stops expressing appreciable levels of the insulin-Fc fusion protein (i.e., transient transfection). HEK293 cells that are transiently transfected with nucleic acid sequences encoding for insulin-Fc fusion proteins often allow for more rapid production of recombinant proteins which facilitates making and screening multiple insulin-Fc fusion protein candidates. In embodiments, CHO cells are transfected with a vector that is permanently incorporated into the host cell DNA and leads to consistent and permanent expression (i.e., stable transfection) of the insulin-Fc fusion protein as long as the cells are cultured appropriately. CHO cells and CHO cell lines that are stably transfected with nucleic acids encoding for insulin-Fc fusion proteins often take longer to develop, but they often produce higher total protein yields and are more amenable to manufacturing low cost products (e.g., products for the relatively commoditized human insulin market). Cells and cell lines can be cultured using standard methods in the art.

In preferred embodiments, HEK cells comprising any one of the cDNA sequences with SEQ ID NO: 79 (corresponding to the insulin-Fc fusion protein embodiment of SEQ ID NO: 78), SEQ ID NO: 81 (corresponding to the insulin-Fc fusion protein embodiment of SEQ ID NO: 80), SEQ ID NO: 83 (corresponding to the insulin-Fc fusion protein embodiment of SEQ ID NO: 82), SEQ ID NO: 85 (corresponding to the insulin-Fc fusion protein embodiment of SEQ ID NO: 84), SEQ ID NO: 88 (corresponding to the insulin-Fc fusion protein embodiment of SEQ ID NO: 87), and SEQ ID NO: 90 (corresponding to the insulin-Fc fusion protein embodiment of SEQ ID NO: 89) are used to express insulin-Fc fusion proteins. In preferred embodiments, CHO cells comprising any one of the cDNA sequences with SEQ ID NO: 79 (corresponding to the insulin-Fc fusion protein embodiment of SEQ ID NO: 78), SEQ ID NO: 81 (corresponding to the insulin-Fc fusion protein embodiment of SEQ ID NO: 80), SEQ ID NO: 83 (corresponding to the insulin-Fc fusion protein embodiment of SEQ ID NO: 82), SEQ ID NO: 85 (corresponding to the insulin-Fc fusion protein embodiment of SEQ ID NO: 84), SEQ ID NO: 88 (corresponding to the insulin-Fc fusion protein embodiment of SEQ ID NO: 87), and SEQ ID NO: 90 (corresponding to the insulin-Fc fusion protein embodiment of SEQ ID NO: 89) are used to express insulin-Fc fusion proteins.

In some embodiments, the insulin-Fc fusion protein is purified or isolated from the cells (e.g., by lysis of the cells). In other embodiments, the insulin-Fc fusion protein is secreted by the cells and purified or isolated from the cell culture media in which the cells were grown. Purification of the insulin-Fc fusion protein can include using column chromatography (e.g., affinity chromatography) or using other separation methods based on differences in size, charge, and/or affinity for certain molecules. In embodiments, purification of the insulin-Fc fusion protein involves selecting or enriching for proteins containing an Fc fragment, e.g., by using Protein A beads or a Protein A column that cause proteins containing an Fc fragment to become bound with high affinity at neutral solution pH to the Protein A covalently conjugated to the Protein A beads. The bound insulin-Fc fusion protein may then be eluted from the Protein A beads by a change in a solution variable (e.g. a decrease in the solution pH). Other separation methods such as ion exchange chromatography and/or gel filtration chromatography can also be employed alternatively or additionally. In embodiments, purification of the insulin-Fc fusion protein further comprises filtering or centrifuging the protein preparation. In embodiments, further purification of the insulin-Fc fusion protein comprises diafiltration, ultrafiltration, and filtration through porous membranes of various sizes, as well as final formulation with excipients.

The purified insulin-Fc fusion protein can be characterized, e.g., for purity, total protein yield, structure, and/or activity, using a variety of methods, e.g., absorbance at 280 nm (e.g., to determine total protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to an anti-insulin antibody). Exemplary methods of characterization are also described in the Examples section.

In embodiments, the total protein yield of an insulin-Fc fusion protein after production in transiently transfected HEK cells and protein A purification is greater than 5 mg/L, 10 mg/L, or 20 mg/L. In preferred embodiments, the total protein yield of a human insulin-Fc fusion protein after production in transiently transfected HEK cells and protein A purification is greater than 100 mg/L (e.g., greater than 150 mg/L). In embodiments, the % homodimer of an insulin-Fc fusion protein after production in transiently transfected HEK cells and protein A purification is greater than 70% (e.g., greater than 80%, greater than 85%, greater than 90%, greater than 95%, greater than 96%, greater than 97%, greater than 98%, greater than 99%). In preferred embodiments, the homodimer titer of a human insulin-Fc fusion protein after production in transiently transfected HEK cells and protein A purification, calculated as the product between the insulin-Fc fusion total protein yield and the % homodimer is greater than 100 mg/L (e.g., greater than 150 mg/L). Only human insulin-Fc fusion protein configurations with a homodimer titer of greater than 150 mg/L were considered useful in the present invention, because experience has demonstrated that homodimer titers less than this level will not likely result in commercial production titers in CHO cells that meet the stringently low manufacturing cost requirements for the relatively commoditized human insulin market.

In embodiments, the total protein yield of an insulin-Fc fusion protein after production in stably transfected CHO cells (e.g., CHO cell lines or CHO cell clones) and protein A purification is greater than 100 mg of insulin-Fc fusion protein per L (e.g. mg/L of culture media). In preferred embodiments, the total protein yield of an insulin-Fc fusion protein after production in stably transfected CHO cells (e.g. CHO cell lines or CHO cell clones) and protein A purification is greater than 150 mg insulin-Fc fusion protein/L of culture media (e.g., greater than 200 mg/L, greater than 300 mg/L, greater than 400 mg/L, greater than 500 mg/L, greater than 600 mg/L or more). In embodiments, the % homodimer of an insulin-Fc fusion protein after production in stably transfected CHO cells (e.g. CHO cell lines or CHO cell clones) and protein A purification is greater than 70% (e.g., greater than 80%, greater than 85%, greater than 90%, greater than 95%, greater than 96%, greater than 97%, greater than 98%, greater than 99%). In embodiments, the homodimer titer of an insulin-Fc fusion protein after production in stably transfected CHO cells (e.g. CHO cell lines or CHO cell clones) and protein A purification, calculated as the product between the insulin-Fc fusion total protein yield and the % homodimer is greater than 150 mg/L (e.g., greater than 200 mg/L, greater than 300 mg/L, greater than 400 mg/L, greater than 500 mg/L, greater than 600 mg/L or more).

Functional Features of Insulin-Fc Fusion Proteins

Described herein are methods for interacting with the insulin receptors to lower blood glucose in the target subject (e.g., dogs or humans), wherein the methods comprise administering to the subject an insulin-Fc fusion protein, e.g., a fusion protein described herein. In some embodiments, the subject has been diagnosed with diabetes (e.g., canine diabetes for dogs, or type 1 diabetes or type 2 diabetes for humans).

In embodiments, an insulin-Fc fusion protein described herein binds to the IR with an appreciable affinity as measured by the IC50 in the 4° C. IM-9 IR binding assay described in Example 12 (e.g. IC50 less than 5000 nM, IC50 less than 4000 nM, IC50 less than 3000 nM, IC less than 2400 nM, IC50 less than 2000 nM). Based on experience, only compounds exhibiting IR activity IC50 values less than 5000 nM, preferably less than 2400 nM and more preferably less than 2000 nM, were deemed likely to exhibit bioactivity in the target subject. Generally, higher affinity IR binding (i.e., lower IC50 values) is preferred. However, it is well-known that the clearance of insulin and insulin analogs (e.g., insulin polypeptides described herein) is governed primarily through binding to the IR followed by IR internalization and degradation within the cell. Therefore, insulin-Fc fusion protein configurations with too high of an IR binding affinity (i.e., too low of an IC50, e.g. an IC50 less than 500 nM) may be cleared too quickly from circulation resulting in a lower than desired duration of glucose-lowering bioactivity in the target subject.

In embodiments, the insulin-Fc fusion protein configurations described herein bind to the FcRn receptor with an affinity that is higher than that of an insulin-Fc fusion protein reference standard as measured according to Example 19. In some embodiments, the FcRn receptor affinity of the insulin-Fc fusion protein configurations as described herein and as measured by the human FcRn receptor assay EC50 value is less than or equal to 1500 ng/mL, and more preferably less than or equal to 1000 ng/mL.

In embodiments, the insulin-Fc fusion proteins described herein are capable of lowering glucose levels (e.g., blood glucose levels) after administration in a subject. In embodiments, the glucose lowering activity of the insulin-Fc fusion proteins is greater than that of an insulin reference standard. In some embodiments, the duration of activity of the insulin-Fc fusion proteins can be measured by a decrease, e.g., a statistically significant decrease, in fasting blood glucose relative to a pre-dose fasting blood glucose level. In embodiments, the duration of activity of the insulin-Fc fusion proteins (e.g., the time during which there is a statistically significant decrease in fasting blood glucose level in a subject relative to a pre-dose level) is longer than about 2 hours. In embodiments, the duration of activity of the insulin-Fc fusion proteins (e.g., the time during which there is a statistically significant decrease in blood glucose level in a subject relative to a pre-dose level) is longer than about 6 hours, 9 hours, 12 hours, 18 hours, 1 day, 1.5 days, 2 days, 2.5 days, 3 days, 4 days, 5 days, 6 days, 7 days, or longer. In embodiments, the insulin-Fc fusion proteins are long-acting (e.g., have a long half-life, e.g., in serum).

In embodiments, the serum half-life of the insulin-Fc fusion proteins described herein in the target subject is longer than that of an insulin reference standard or control formulation. In embodiments, the serum half-life of the insulin-Fc fusion proteins (e.g., in the blood of a subject upon administration) in the target subject is longer than about 2 hours. In embodiments, the serum half-life of the insulin-Fc fusion protein in the target subject is about 0.5 days, 1 day, 2 days, or 2.5 days. In preferred embodiments, the serum half-life of the insulin-Fc fusion protein in the target subject is about 3 days or longer.

In embodiments, the combination of potency and duration of bioactivity of the insulin-Fc fusion proteins described herein may be quantified by calculating the area over the percent fasting blood glucose (% FBGL) curve normalized to a given dose in mg/kg (NAOC) with units of % FBGL·days·kg/mg. In embodiments, the NAOC of the insulin-Fc fusion proteins described herein is greater than 150% FBGL·days·kg/mg (e.g. greater than 200% FBGL·days·kg/mg, greater than 250% FBGL·days·kg/mg or more). Again, based on experience, at NAOC values greater than 150% FBGL·days·kg/mg, the dose requirements in the target subject will be sufficiently low so as to achieve an acceptable treatment cost. In embodiments, the NAOC of the insulin-Fc fusion proteins must be maintained after repeated dosing in the target subject (i.e., the ratio of the NAOC after the third dose to the NAOC after the first dose of the insulin-Fc fusion protein is greater than 0.5 (e.g., greater than 0.6, greater than 0.7, greater than 0.8, greater than 0.9, or more).

In some embodiments, the insulin-Fc fusion protein configurations described herein bind to the Fc(gamma) receptor with an affinity that is lower than that of an insulin-Fc fusion protein reference standard as measured according to Example 15. In some embodiments, the ratio of the Fc(gamma) receptor affinity of the insulin-Fc fusion proteins to that of an insulin-Fc fusion protein reference standard (i.e., the insulin-Fc fusion protein of SEQ ID NO: 76) is less than 0.50 (e.g. less than 0.40, less than 0.30, less than 0.20). In some embodiments, the Fc(gamma) receptor affinity of the insulin-Fc fusion protein as measured by the human Fc(gamma)RI receptor assay OD450 Ratio at 3000 ng/mL biotinylated-Fc(gamma)RI (with respect to the reference insulin-Fc fusion protein of SEQ ID NO: 76) is less than or equal to 0.50.

In some embodiments, the insulin-Fc fusion protein configurations described herein bind to C1q with an affinity that is lower than that of an insulin-Fc fusion protein reference standard as measured according to Example 16. In some embodiments, the ratio of the C1q binding affinity of the insulin-Fc fusion proteins to that of an insulin-Fc fusion protein reference standard (i.e., the insulin-Fc fusion protein of SEQ ID NO: 76) is less than 0.50 (e.g. less than 0.40, less than 0.30, less than 0.20). In some embodiments, the C1q binding affinity of the insulin-Fc fusion proteins as measured by the human C1q binding assay OD450 Ratio at a biotinylated-C1q concentration of 1000 ng/mL (with respect to the reference insulin-Fc fusion protein of SEQ ID NO: 76) is less than or equal to 0.35.

Methods of Treatment and Characteristics of Subject Selection

Described herein are methods for treating diabetes (e.g., type 1 diabetes or type 2 diabetes in humans), the methods comprising the administration of an insulin-Fc fusion protein (e.g., an insulin-Fc fusion protein configuration as described herein) to a target subject.

In embodiments, a reference standard used in any method described herein comprises a reference treatment or reference therapy. In some embodiments, the reference comprises a standard of care agent for diabetes treatment (e.g., a standard of care agent for canine diabetes or a standard of care agent for type 1 diabetes in humans or a standard of care agent for type 2 diabetes in humans). In some embodiments, the reference standard is a commercially available insulin or insulin analog. In some embodiments, the reference standard comprises a long-lasting insulin, intermediate-lasting insulin, short-lasting insulin, rapid-acting insulin, short-acting, intermediate-acting, long-acting insulin. In some embodiments, the reference standard for canine insulin comprises Vetsulin®, Prozinc®, insulin NPH, insulin glargine (Lantus®) or recombinant human insulin. In some embodiments, the reference standard for human insulin comprises Humalog®, NovoLog®, Novolin®R (Novo Nordisk, Bagsværd, Denmark), Novolin®N (Novo Nordisk, Bagsværd, Denmark), Humulin®R (Eli Lilly, Indianapolis, Ind.), Humulin®N (Eli Lilly, Indianapolis, Ind.), Lantus®, and Levemir®, or generic recombinant human insulin.

In embodiments, a reference standard used in any method described herein includes an outcome, e.g., outcome described herein, of a diabetes therapy (e.g., a canine diabetes therapy or a human diabetes therapy).

In embodiments, a reference standard is a level of a marker (e.g., blood glucose or HbA1c) in the target subject prior to initiation of a therapy, e.g., an insulin-Fc fusion protein therapy described herein; where the target subject has diabetes. In embodiments, the blood glucose level in a target subject is greater than 200 mg/dL (e.g. greater than 250 mg/dL, 300 mg/dL, 350 mg/dL, 400 mg/dL or more) prior to initiation of therapy. In embodiments, the fructosamine level in a dog is greater than 250 micromol/L, 350 micromol/L (e.g. greater than 400 micromol/L, 450 micromol/L, 500 micromol/L, 550 micromol/L, 600 micromol/L, 650 micromol/L, 700 micromol/L, 750 micromol/L or more) prior to initiation of therapy. In embodiments, the HbA1c level in a human target subject is greater than 7 mmol/L (e.g. greater than 7.5 mmol/L, 8 mmol/L, 9 mmol/L, 10 mmol/L, 11 mmol/L, 12 mmol/L, or more) prior to initiation of therapy. In embodiments, a reference standard is a measure of the presence of, the progression of, or the severity of the disease. In embodiments, a reference standard is a measure of the presence of or the severity of the disease symptoms prior to initiation of a therapy, e.g., an insulin-Fc fusion protein therapy described herein, e.g., where the target subject has diabetes.

Pharmaceutical Compositions and Routes of Administration

Provided herein are pharmaceutical compositions containing an insulin-Fc fusion protein configuration as described herein that can be used to lower blood glucose in target subjects. The amount and concentration of the insulin-Fc fusion protein in the pharmaceutical compositions, as well as the quantity of the pharmaceutical composition administered to a target subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of *Comprehensive Medicinal Chemistry* (Corwin Hansch; Chairman of Editorial Board), Pergamon Press 1990.

Formulations of the present disclosure include those suitable for parenteral administration. The phrases "parenteral administration" and "administered parenterally" as used herein means modes of administration other than enteral and topical administration, usually by intravenous or subcutaneous injection.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., polysorbate-20, Tween-20 or Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, the concentration of the insulin-Fc fusion protein in the aqueous carrier is about 3 mg/mL. In some embodiments, the concentration of the insulin-Fc fusion protein in the aqueous carrier is about 6 mg/mL. In some embodiments, the concentration of the insulin-Fc fusion protein in the aqueous carrier is about 8 mg/mL, 9 mg/mL, 10 mg/mL, 12 mg/mL, 15 mg/mL or more.

In some embodiments, the insulin-Fc fusion protein is administered as a bolus, infusion, or an intravenous push. In some embodiments, the fusion protein is administered through syringe injection, pump, pen, needle, or indwelling catheter. In some embodiments, the insulin-Fc fusion protein is administered by a subcutaneous bolus injection. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Dosages

Actual dosage levels of an insulin-Fc fusion protein of the configurations described herein can be varied so as to obtain an amount of the active ingredient that is effective to achieve the desired therapeutic response for a particular target subject (e.g., dog or human). The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the subject being treated, and like factors well known in the medical arts.

In general, a suitable dose of an insulin-Fc fusion protein will be the amount that is the lowest dose effective to produce a therapeutic effect. Such an effective dose will generally depend upon the factors described above. Generally, intravenous and subcutaneous doses of the insulin-Fc fusion protein for a target subject will range from about 0.001 to about 1 mg per kilogram (e.g. mg/kg) of body weight per day, e.g., about 0.001 to 1 mg/kg/day, about 0.01 to 0.1 mg/kg/day, about 0.1 to 1 mg/kg/day, or about 0.01 to 1 mg/kg/day. In still other embodiments, the fusion protein is administered at a dose between 0.025 and 4 mg per kilogram of body weight per week, e.g., between 0.025 and 1.0 mg/kg/week.

The present disclosure contemplates formulation of the insulin-Fc fusion protein in any of the aforementioned pharmaceutical compositions and preparations. Furthermore, the present disclosure contemplates administration via any of the foregoing routes of administration. One of skill in the art can select the appropriate formulation and route of administration based on the condition being treated and the overall health, age, and size of the subject being treated.

EXAMPLES

The present technology is further illustrated by the following Examples, which should not be construed as limiting in any way.

General Methods, Assays, and Materials

Example 1: Synthesis and Methods of Making an Insulin-Fc Fusion Protein in HEK293 Cells Insulin-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a suspension of HEK293 cells using the (LakePharma, Belmont, Calif.) standard operating procedure for transient transfection. After 20 hours, the cells were counted to determine the viability and viable cell count, and the titer was measured by FortéBio® Octet® (Pall FortéBio LLC, Fremont, Calif.). Additional readings were taken throughout the transient transfection production run. The culture was harvested on or after day 5.

Example 2: Synthesis and Methods of Making an Insulin-Fc Fusion Protein in CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension-adapted CHO cells were cultured in a humidified 5% $CO_2$ incubator at 37° C. in a chemically defined media (CD OptiCHO; Invitrogen, Carlsbad, Calif.). No serum or other animal-derived products were used in culturing the CHO cells.

Approximately 80 million suspension-adapted CHO cells, growing in CD OptiCHO media during the exponential growth phase, were transfected by electroporation using MaxCyte® STX® system (MaxCyte, Inc., Gaithersburg, Md.) with 80 μg DNA to a create a stable CHO cell line for each insulin-Fc fusion protein (DNA construct contains the full-length sequence of the insulin-Fc fusion protein). After twenty-four hours, the transfected cells were counted and placed under selection for stable integration of the insulin-Fc fusion genes. The transfected cells were seeded into CD OptiCHO selection media containing between 0-100 μM methionine sulfoximine (MSX) at a cell density of $0.5\times10^6$ cells/mL in a shaker flask and were incubated at 37° C. with 5% $CO_2$. During a selection process, the cells were spun down and resuspended in fresh selection media every 2-3 days until the CHO stable pool recovered its growth rate and viability. The cell culture was monitored for growth and titer.

The cells were grown to $2.5\times10^6$ cells per mL. At the time of harvest for cell banking, the viability was above 95%. The cells were then centrifuged, and the cell pellet was resuspended in the CD OptiCHO media with 7.5% dimethyl sulfoxide (DMSO) to a cell count of $15\times10^6$ cells per mL per vial. Vials were cryopreserved for storage in liquid nitrogen.

A small-scale-up production was performed using the CHO cells as follows. The cells were scaled up for production in CD OptiCHO growth medium containing 100 μM MSX at 37° C. and fed every 2-4 days as needed, with CD OptiCHO growth medium supplemented with glucose and additional amino acids as necessary for approximately 14-21 days. The conditioned media supernatant harvested from the stable pool production run was clarified by centrifuge spinning. The protein was run over a Protein A (Mab Select, GE Healthcare, Little Chalfont, United Kingdom) column pre-equilibrated with binding buffer. Washing buffer was then passed through the column until the OD280 value (NanoDrop, Thermo Scientific) was measured to be at or near background levels. The insulin-Fc fusion protein was eluted using a low pH buffer, elution fractions were collected, and the OD280 value of each fraction was recorded. Fractions containing the target insulin-Fc fusion protein were pooled and optionally further filtered using a 0.2 μM membrane filter.

The cell line was optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein was accomplished as described above in growth medium without MSX, or optionally in growth medium containing MSX, to obtain a cell culture supernatant containing the recombinant, CHO-made, insulin-Fc fusion protein. The MSX concentration was optionally increased over time to exert additional selectivity for clones capable of yielding higher product titers.

Example 3: Synthesis and Methods of Making an Insulin-Fc Fusion Protein in CHO Cells A CHO cell line is originally derived from CHO-K1 (LakePharma, Belmont, Calif.), and the endogenous glutamine synthetase (GS) genes are knocked out by recombinant technology using methods known in the art. Stable expression DNA vectors are designed and optimized for CHO expression and GS selection and incorporated into a high expression mammalian vector (LakePharma, Belmont, Calif.). The sequence of each completed construct is confirmed prior to initiating scale up experiments. The suspension-adapted CHO cells are cultured in a humidified 5% $CO_2$ incubator at 37° C. in a chemically defined media (CD OptiCHO; Invitrogen, Carlsbad, Calif.). No serum or other animal-derived products are used in culturing the CHO cells.

Approximately 80 million suspension-adapted CHO cells, growing in CD OptiCHO media during the exponential growth phase, are transfected by electroporation using MaxCyte® STX® system (MaxCyte, Inc., Gaithersburg, Md.) with 80 μg DNA to a create a stable CHO cell line for each insulin-Fc fusion protein (DNA construct contains the full-length sequence of the insulin-Fc fusion protein). After twenty-four hours, the transfected cells are counted and placed under selection for stable integration of the insulin-Fc fusion genes. The transfected cells are seeded into CD OptiCHO selection media containing between 0-100 μM methionine sulfoximine (MSX) at a cell density of $0.5\times10^6$ cells/mL in a shaker flask and are incubated at 37° C. with 5% $CO_2$. During a selection process, the cells are spun down and resuspended in fresh selection media every 2-3 days until the CHO stable pool recovered its growth rate and viability. The cell culture is monitored for growth and titer.

The cells are grown to $2.5\times10^6$ cells per mL. At the time of harvest for cell banking, the viability is to remain above 95%. The cells are then centrifuged, and the cell pellet resuspended in the CD OptiCHO media with 7.5% dimethyl sulfoxide (DMSO) to a cell count of $15\times10^6$ cells per mL per vial. Vials are cryopreserved for storage in liquid nitrogen.

A small-scale-up production is performed using the CHO cells as follows. The cells are scaled up for production in CD OptiCHO growth medium containing 100 μM MSX at 37° C. and fed every 2-4 days as needed, with CD OptiCHO growth medium supplemented with glucose and additional amino acids as necessary for approximately 14-21 days. The conditioned media supernatant harvested from the stable pool production run is clarified by centrifuge spinning. The protein is run over a Protein A (Mab Select, GE Healthcare, Little Chalfont, United Kingdom) column pre-equilibrated with binding buffer. Washing buffer is then passed through the column until the OD280 value (NanoDrop, Thermo Scientific) is measured to be at or near background levels. The insulin-Fc fusion protein is eluted using a low pH buffer, elution fractions are collected, and the OD280 value of each fraction is recorded. Fractions containing the target insulin-Fc fusion protein are pooled and optionally further filtered using a 0.2 μM membrane filter.

The cell line is optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein is accomplished as described above in growth medium without MSX, or optionally in growth medium containing MSX, to obtain a cell culture supernatant containing the recombinant, CHO-made, insulin-Fc fusion protein. The MSX concentration is optionally increased over time to exert additional selectivity for clones capable of yielding higher product titers.

Example 4: Purification of an Insulin-Fc Fusion Protein

Purification of an insulin-Fc fusion protein was performed as follows. Conditioned media supernatants containing the secreted insulin-Fc fusion protein were harvested from the transiently transfected HEK, stably transfected HEK, or stably transfected CHO production runs and were clarified by centrifugation. The supernatant containing the desired insulin-Fc fusion protein was run over a Protein A column, washed with various wash buffers including 0.15-0.50M sodium chloride, and then eluted using a low pH solution. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography (e.g. using an anion exchange bead resin or a cation exchange bead resin), gel filtration chromatography, or other methods was performed as necessary.

Example 5: Purification of an Insulin-Fc Fusion Protein

Purification of an insulin-Fc fusion protein is performed as follows. Conditioned media supernatants containing the secreted insulin-Fc fusion protein are harvested from the transiently transfected HEK, stably transfected HEK, or stably transfected CHO production runs and are clarified by centrifugation. The supernatant containing the desired insulin-Fc fusion protein is run over a Protein A column, washed with various wash buffers including 0.15-0.50M sodium chloride, and then eluted using a low pH solution. Afterwards, the eluted fractions containing the desired protein are pooled and buffer exchanged into 200 mM HEPES, 100 mM NaCl, 50 mM NaOAc, pH 7.0 buffer. A final filtration step is performed using a 0.2 μm membrane filter. The final protein concentration is calculated from the solution optical density at 280 nm. Further optional purification by ion-exchange chromatography (e.g. using an anion exchange bead resin or a cation exchange bead resin), gel filtration chromatography, or other methods is performed as necessary.

Example 6: Structure Confirmation by Non-Reducing and Reducing CE-SDS

Capillary electrophoresis sodium dodecyl sulfate (CE-SDS) analysis was performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (e.g. using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 7: Structure Confirmation by Non-Reducing and Reducing CE-SDS

Capillary electrophoresis sodium dodecyl sulfate (CE-SDS) analysis is performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram is plotted. Under non-reducing conditions, the sample is run against known molecular weight (MW) protein standards, and the eluting peak represents the 'apparent' MW of the insulin-Fc fusion protein homodimer.

Under reducing conditions (e.g. using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 8: Sequence Identification by LC-MS with Glycan Removal for Compounds Containing Glycan To obtain an accurate estimate of the insulin-Fc fusion protein mass via mass spectroscopy (MS) in cases where the insulin-Fc fusion protein is naturally glycosylated, the sample was first treated to remove naturally occurring glycan that might interfere with the MS analysis. 100 μL of a 2.5 mg/mL insulin-Fc fusion protein dissolved in 200 mM HEPES, 100 mM NaCl, 50 mM NaOAc, pH 7.0 buffer solution was first buffer exchanged into 0.1 M Tris, pH 8.0 buffer containing 5 mM EDTA using a Zeba desalting column (Pierce, ThermoFisher Scientific, Waltham, Mass.). 1.67 μL of PNGase F enzyme (Prozyme N-glycanase) was added to this solution in order to remove N-linked glycan present in the fusion protein (e.g., glycan linked to the side chain of the asparagine located at the cNg-N site), and the mixture was incubated at 37° C. overnight in an incubator. The sample was then analyzed via LC-MS (NovaBioassays, Woburn, Mass.) resulting in a molecular mass of the molecule which corresponds to the desired homodimer without the glycan. This mass was then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass was the measured mass minus 2 Da to correct for the enzymatic modification of the insulin-Fc fusion protein structure in the analytical sample.

In cases where the insulin-Fc fusion protein amino acid composition prevents natural glycosylation from occurring at the cNg site, LC-MS (NovaBioassays, Woburn, Mass.) was used to directly obtain an accurate estimate of the insulin-Fc fusion protein mass without pretreatment of the molecule with PNGase enzyme.

Example 9: Sequence Identification by LC-MS with Glycan Removal for Compounds Containing Glycan To obtain an accurate estimate of the insulin-Fc fusion protein mass via mass spectroscopy (MS) in cases where the insulin-Fc fusion protein is naturally glycosylated, the sample is first treated to remove naturally occurring glycan that might interfere with the MS analysis. 100 μL of a 2.5 mg/mL insulin-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, Mass.). 1.67 μL of PNGase F enzyme (Prozyme N-glycanase) is added to this solution in order to remove N-linked glycan present in the fusion protein (e.g., glycan linked to the side chain of the asparagine located at the cNg-N site), and the mixture is incubated at 37° C. overnight in an incubator. The sample is then analyzed via LC-MS (NovaBioassays, Woburn, Mass.) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

In cases where the insulin-Fc fusion protein amino acid composition prevents natural glycosylation from occurring at the cNg site, LC-MS (NovaBioassays, Woburn, Mass.) can be used to directly obtain an accurate estimate of the insulin-Fc fusion protein mass without pretreatment of the molecule with PNGase enzyme.

Example 10: % Homodimer by Size-Exclusion Chromatography

Size-exclusion chromatography (SEC-HPLC) of insulin-Fc fusion proteins was carried out using a Waters 2795HT HPLC (Waters Corporation, Milford, Mass.) connected to a 2998 Photodiode array at a wavelength of 280 nm. 100 μL or less of a sample containing an insulin-Fc fusion protein of interest was injected into a MAbPac SEC-1, 5 μm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g. multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained.

Example 11: % Homodimer by Size-Exclusion Chromatography

Size-exclusion chromatography (SEC-HPLC) of insulin-Fc fusion proteins is carried out using a Waters 2795HT HPLC (Waters Corporation, Milford, Mass.) connected to a 2998 Photodiode array at a wavelength of 280 nm. 100 μL or less of a sample containing an insulin-Fc fusion protein of interest is injected into a MAbPac SEC-1, 5 μm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g. multimers of insulin-Fc fusion protein homodimers) will elute at earlier retention times, and the non-aggregated homodimers will elute at later retention times. In separating the mixture of homodimers from aggregated multimeric homodimers via analytical SEC-HPLC, the purity of the insulin-Fc fusion protein solution in terms of the percentage of non-aggregated homodimer is ascertained.

Example 12: In Vitro IM-9 Insulin Receptor (IR) Binding of an Exemplary Insulin-Fc Fusion Protein at 4° C.

Human IM-9 cells (ATTC #CCL-159) that express human IR were cultured and maintained in complete RPMI 5% FBS medium at 70-80% confluency. Cultures of IM-9 cells were centrifuged at 250×g (~1000 rpm) for 10 min to pellet the cells. Cells were washed once with HBSS or PBS buffer, resuspended in cold FACS staining medium (HBSS/2 mM EDTA/0.1% Na-azide+4% horse serum) to a concentration of $8\times10^6$ cells/mL and kept on ice or at 4° C. until test solutions were made. The insulin-Fc protein was diluted in FACS buffer in 1:3 serial dilutions as 2× concentrations in 1.2 mL tubes (approx. 60 μL volume of each dilution), and the solutions were kept cold on ice until ready for pipetting.

Biotinylated-RHI was diluted in FACS staining medium to a concentration of 1.25 μg/mL. 40 μL of the serially diluted test compound and 8 μL of 1.25 μg/mL Biotin-RHI were added into each well of a V bottom microtiter plate, mixed by slow vortexing, and placed on ice. 40 μL of an IM-9 cell suspension ($8\times10^6$ cells/mL) was then added to each well by multichannel pipette, mixed again gently and incubated on ice for 30 min to allow competitive binding on the IR on IM-9 cells. Cells were then washed twice with 275 μL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells were then resuspended in 404, of FACS staining medium containing 1:100 diluted Streptavidin-PE (Life Technologies) for 20 min on ice. Cells were then washed once with 275 μL of ice-cold FACS buffer and finally fixed with 3% paraformaldehyde for 10 min at room temp. Cells were then washed once with 275 μL of ice-cold FACS buffer and resuspended in 250 μl of FACS buffer for analysis.

The V-bottom plates containing cells were then analyzed on a Guava 8-HT flow cytometer (Millipore). Biotinylated-RHI binding to IR was quantitated by the median fluorescence intensity (MFI) of the cells on the FACS FL-2 channel for each concentration of the test compound. Control wells were labeled only with biotinylated-RHI and were used to calculate the percent (%) inhibition resulting from each test compound concentration. The % inhibition by test compounds of biotinylated-RHI binding on IM-9 cells was plotted against log concentrations of the test compound, and the resulting IC50 values were calculated using GraphPad Prism (GraphPad Software, La Jolla, Calif.) for the test compounds. Lower IC50 values of the test compound therefore indicate greater levels of biotinylated-RHI inhibition at lower concentrations indicating stronger binding of the insulin-Fc fusion protein to the IR. A control compound, such as unlabeled recombinant human insulin (RHI) was also used as an internal standard to generate an RHI IC50 against which a given compound IC50 could be ratioed (IC50(compound)/IC50(RHI)). Lower IC50 ratios have more similar binding to RHI (stronger binding to IR), while higher IC50 ratios have weaker binding to the IR relative to RHI.

Example 13: In Vitro IM-9 Insulin Receptor (IR) Binding of an Exemplary Insulin-Fc Fusion Protein at 4° C.

Human IM-9 cells (ATTC #CCL-159) that express human IR are cultured and maintained in complete RPMI 5% FBS medium at 70-80% confluency. Cultures of IM-9 cells are centrifuged at 250×g (~1000 rpm) for 10 min to pellet the cells. Cells are washed once with HBSS or PBS buffer, resuspended in cold FACS staining medium (HBSS/2 mM EDTA/0.1% Na-azide+4% horse serum) to a concentration of $8\times10^6$ cells/mL and kept on ice or at 4° C. until test solutions are made. The insulin-Fc protein is diluted in FACS buffer in 1:3 serial dilutions as 2× concentrations in 1.2 mL tubes (approx. 60 μL volume of each dilution), and the solutions are kept cold on ice until ready for pipetting.

Biotinylated-RHI is diluted in FACS staining medium to a concentration of 1.25 μg/mL. 40 μL of the serially diluted test compound and 8 μL of 1.25 μg/mL Biotin-RHI are added into each well of a V bottom microtiter plate, mixed by slow vortexing, and placed on ice. 40 μL of an IM-9 cell suspension ($8\times10^6$ cells/mL) is then added to each well by multichannel pipette, mixed again gently and incubated on ice for 30 min to allow competitive binding on the IR on IM-9 cells. Cells are then washed twice with 275 μL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells are then resuspended in 40 μL of FACS staining medium containing 1:100 diluted Streptavidin-PE (Life Technologies) for 20 min on ice. Cells are then washed once with 275 μL of ice-cold FACS buffer and finally fixed with 3% paraformaldehyde for 10 min at room temp. Cells are then washed once with 275 μL of ice-cold FACS buffer and resuspended in 250 μl of FACS buffer for analysis.

The V-bottom plates containing cells are then analyzed on a Guava 8-HT flow cytometer (Millipore). Biotinylated-RHI binding to IR is quantitated by the median fluorescence intensity (MFI) of the cells on the FACS FL-2 channel for each concentration of the test compound. Control wells are labeled only with biotinylated-RHI and are used to calculate the percent (%) inhibition resulting from each test compound concentration. The % inhibition by test compounds of biotinylated-RHI binding on IM-9 cells is plotted against log concentrations of the test compound, and the resulting IC50 values are calculated using GraphPad Prism (GraphPad Software, La Jolla, Calif.) for the test compounds. Lower IC50 values of the test compound therefore indicate greater levels of biotinylated-RHI inhibition at lower concentrations indicating stronger binding of the insulin-Fc fusion protein to the IR. A control compound, such as unlabeled recombinant human insulin (RHI) is also used as an internal standard to generate an RHI IC50 against which a given compound IC50 could be ratioed (IC50(compound)/IC50(RHI)). Lower IC50 ratios have more similar binding to RHI (stronger binding to IR), while higher IC50 ratios have weaker binding to the IR relative to RHI.

Example 14: In Vitro Human Fc(Gamma)RI Binding Affinity Assay

The binding of insulin-Fc fusion proteins to the Fc(gamma)RI at pH 7.4 was conducted using an ELISA assay as follows using human Fc(gamma)RI (i.e., rhFc(gamma)RI). Insulin-Fc fusion proteins were diluted to 10 μg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated rhFc(gamma)RI (recombinant human Fc(gamma) RI; R&D Systems) were prepared in PBST/10% Superblock buffer from 3000 ng/mL to 4.1 ng/mL and loaded at 100 μL/well onto the microplate strips coated with insulin-Fc fusion protein. The microtiter plate was incubated for 1 hour at room temperature after which time the microplate strips were washed 5 times with PBST and then loaded with 100 μL/well of streptavidin-HRP diluted 1:10000 in PBST/10% Superblock buffer. After incubating for 45 min, the microplate strips were washed again 5 times with PBST. TMB was added to reveal the bound Fc(gamma)RI proteins and stopped with ELISA stop reagent (Boston Bioproducts). The plate was read in an ELISA plate reader at 450 nm, and the OD450 values (proportional to the binding of rhFc(gamma) RI to insulin-Fc protein) were plotted against log concentrations of rhFc(gamma)RI added to each well to generate binding curves using GraphPad Prism software. For groupings of compounds with somewhat similar curves, the OD450 at one of the higher concentrations, for instance at rhFc(gamma)RI concentrations of 3000 ng/mL, can be used to identify differences between coated insulin-Fc fusion protein compounds. In order to compare differences across multiple insulin-Fc fusion proteins run at different times, the human Fc(gamma)RI assay OD450 Ratio was calculated as the OD450 value of a test insulin-Fc fusion protein compound obtained at a biotinylated-Fc(gamma)RI concentration of 3000 ng/mL, divided by the OD450 value of a reference insulin-Fc fusion protein of SEQ ID NO: 76 obtained at a biotinylated-Fc(gamma)RI concentration of 3000 ng/mL.

Example 15: In Vitro Human Fc(Gamma)RI Binding Affinity Assay

The binding of insulin-Fc fusion proteins to the Fc(gamma)RI at pH 7.4 is conducted using an ELISA assay as follows using human Fc(gamma)RI (i.e., rhFc(gamma)RI). Insulin-Fc fusion proteins are diluted to 10 μg/mL in sodium bicarbonate buffer at pH 9.6 and coated on Maxisorp (Nunc) microtiter plates overnight at 4° C., after which the microplate strips are washed 5 times with PBST (PBS/0.05% Tween-20) buffer and blocked with Superblock blocking reagent (ThermoFisher). Serial dilutions of biotinylated rhFc (gamma)RI (recombinant human Fc(gamma)RI; R&D Systems) are prepared in PBST/10% Superblock buffer from 3000 ng/mL to 4.1 ng/mL and loaded at 100 μL/well onto the microplate strips coated with insulin-Fc fusion protein. The microtiter plate is incubated for 1 hour at room temperature after which time the microplate strips are washed 5 times with PBST and then loaded with 100 μL/well of streptavidin-HRP diluted 1:10000 in PBST/10% Superblock buffer. After incubating for 45 min, the microplate strips are washed again 5 times with PBST. TMB is added to reveal the bound Fc(gamma)RI proteins and is stopped with ELISA stop reagent (Boston Bioproducts). The plate is read in an ELISA plate reader at 450 nm, and the OD450 values (proportional to the binding of rhFc(gamma)RI to insulin-Fc protein) are plotted against log concentrations of rhFc(gamma)RI added to each well to generate binding curves using GraphPad Prism software. For groupings of compounds with somewhat similar curves, the OD450 at one of the higher concentrations, for instance at rhFc(gamma)RI concentrations of 3000 ng/mL, can be used to identify differences between coated insulin-Fc fusion protein compounds. In order to compare differences across multiple insulin-Fc fusion proteins run at different times, the human Fc(gamma)RI assay OD450 Ratio is calculated as the OD450 value of a test insulin-Fc fusion protein compound obtained at a biotinylated-Fc(gamma)RI concentration of 3000 ng/mL, divided by the OD450 value of a reference insulin-Fc fusion protein of SEQ ID NO: 76 obtained at a biotinylated-Fc (gamma)RI concentration of 3000 ng/mL.

Example 16: In Vitro C1 q Binding Affinity Assay

The binding of insulin-Fc fusion proteins to complement component C1q at pH 7.4 was conducted using an ELISA assay as follows using human complement component C1q. Insulin-Fc fusion proteins were diluted to 10 μg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated complement component C1q (human complement component C1q; Sigma-Aldrich) were prepared in PBST/10% Superblock buffer from 1000 ng/mL to 1.4 ng/mL and loaded at 100 μL/well onto the microplate strips coated with insulin-Fc fusion protein. The microtiter plate was incubated for 1 hour at room temperature after which the microplate strips were washed 5 times with PBST and then loaded with 100 μL/well of streptavidin-HRP diluted 1:12000 in PBST/10% Superblock buffer. After incubating for 45 min, the microplate strips were washed again 5 times with PBST. TMB was added to reveal the bound complement C1q proteins and stopped with ELISA stop reagent (Boston Bioproducts). The plate absorbance was read in an ELISA plate reader at 450 nm (0D450), and the OD450 values (proportional to the binding of complement component C1q to insulin-Fc protein) were plotted against log concentrations of complement component C1q added to each well to generate binding curves using GraphPad Prism software. For groupings of compounds with somewhat similar curves, the OD450 at one of the higher concentrations, for instance at complement component C1q concentrations of 1000 ng/mL, was used to identify differences between coated insulin-Fc fusion protein compounds. In order to further compare differences across multiple insulin-Fc fusion proteins run at different times, the human C1q assay OD450 Ratio was calculated as the OD450 of a test insulin-Fc fusion protein compound obtained at a biotinylated-C1q concentration of 1000 ng/mL, divided by the OD450 of a reference insulin-Fc fusion protein of SEQ ID NO: 76 obtained at a biotinylated-C1q concentration of 1000 ng/mL.

Example 17: In Vitro C1 q Binding Affinity Assay

The binding of insulin-Fc fusion proteins to complement component C1q at pH 7.4 is conducted using an ELISA assay as follows using human complement component C1q. Insulin-Fc compounds are diluted to 10 μg/mL in sodium bicarbonate buffer at pH 9.6 and coated on Maxisorp (Nunc) microtiter plates overnight at 4° C., after which the microplate strips are washed 5 times with PBST (PBS/0.05% Tween-20) buffer and blocked with Superblock blocking reagent (ThermoFisher). Serial dilutions of biotinylated complement component C1q (human complement component C1q; Sigma-Aldrich) are prepared in PBST/10% Superblock buffer from 1000 ng/mL to 1.4 ng/mL and loaded at 100 μL/well onto the microplate strips coated with insulin-Fc fusion protein. The microtiter plate is incubated for 1 hour at room temperature after which the microplate strips are washed 5 times with PBST and then loaded with 100 μL/well of streptavidin-HRP diluted 1:12000 in PBST/10% Superblock buffer. After incubating for 45 min, the microplate strips are washed again 5 times with PBST. TMB is added to reveal the bound complement C1q proteins and stopped with ELISA stop reagent (Boston Bioproducts). The plate absorbance is read in an ELISA plate reader at 450 nm (OD450), and the OD450 values (proportional to the binding of complement component C1q to insulin-Fc protein) are plotted against log concentrations of complement component C1q added to each well to generate binding curves using GraphPad Prism software. For groupings of compounds with somewhat similar curves, the OD450 at one of the higher concentrations, for instance at complement component C1q concentrations of 1000 ng/mL, can be used to identify differences between coated insulin-Fc fusion protein compounds. In order to further compare differences across multiple insulin-Fc fusion proteins run at different times, the human C1q assay OD450 Ratio is calculated as the OD450 of a test insulin-Fc fusion protein compound obtained at a biotinylated-C1q concentration of 1000 ng/mL, divided by the OD450 of a reference insulin-Fc fusion protein of SEQ ID NO: 76 obtained at a biotinylated-C1q concentration of 1000 ng/mL.

Example 18: In Vitro Measurement of Insulin-Fc Fusion Protein Affinity for the Canine FcRn Receptor In vitro binding affinity of insulin-Fc fusion proteins containing Fc fragments of canine IgG origin to the canine FcRn receptor was measured via an ELISA technique conducted at a solution pH of 5.5. The slightly acidic pH is the preferred binding environment for Fc fragment-containing molecules to bind to the FcRn receptor. In vivo, cells express FcRn on their surfaces and internally in the endosomes. As molecules containing Fc fragments are brought into the cell through natural processes (e.g. pinocytosis or endocytosis), the pH changes to a lower pH in the endosomes, where the FcRn receptor binds to Fc fragment-containing molecules that would otherwise be degraded in the endosomal-lysosomal compartments, thereby allowing these molecules to recycle back to the cellular surface where the pH is closer to neutral (e.g., pH 7.0-7.4). Neutral pH disfavors binding to the FcRn receptor and allows release of the Fc-fragment containing molecules back into circulation. This is a primary mechanism by which Fc fragment-containing molecules exhibit prolonged circulatory pharmacokinetic half-lives in vivo.

Insulin-Fc fusion proteins comprising Fc fragments of canine origin were diluted to 10 μg/ml in sodium bicarbonate pH 9.6 buffer and coated in duplicate on Maxisorb ELISA plate strips for 1-2 hours at RT. The strips were then washed 4 times with PBST (PBS/0.1% Tween-20) buffer and blocked with Superblock blocking reagent (ThermoFisher). Strips for FcRn binding were then washed again twice with pH 5.5 MES/NaCl/Tween (50 mM MES/150 mM NaCl/0.1% Tween-20) buffer before addition of the FcRn reagent (biotinylated canine FcRn; Immunitrack). Serial dilutions (1:3× dilutions) of biotinylated FcRn reagent were prepared in pH 5.5 MES/NaCl/Tween/10% Superblock buffer at concentrations from 1000 ng/ml to 0.45 ng/mL and loaded at 100 μL/well using a multichannel pipettor onto the strips coated with the insulin-Fc fusion protein compounds. The assay plate was then incubated for 1 hour at room temperature. FcRn binding strips were washed 4 times with pH 5.5 MES/NaCl/Tween buffer and then loaded with 100 μl/well streptavidin-HRP diluted 1:10000 in pH 5.5 MES/NaCl/10% Superblock buffer. After incubating for 45 minutes, strips were washed again 4 times with pH 5.5 MES/NaCl/Tween buffer. TMB was finally added to reveal the bound biotinylated-canine FcRn reagent, and the color development was stopped with the ELISA stop reagent. The plate was read in an ELISA plate reader at a wavelength of 450 nm. The OD values (proportional to the binding of canine-FcRn to the insulin-Fc fusion protein test compounds) were plotted against log concentrations of FcRn added to each well to generate binding curves using GraphPad Prism software. EC50 values for each binding curve were calculated to compare between different compounds.

Example 19: In Vitro Measurement of Insulin-Fc Fusion Protein Affinity for the Human FcRn Receptor In vitro binding affinity of insulin-Fc fusion proteins containing Fc fragments of human IgG origin to the human FcRn receptor was measured via an ELISA technique conducted at a solution pH of 5.5. The slightly acidic pH is the preferred binding environment for Fc fragment-containing molecules to bind to the FcRn receptor. In vivo, cells express FcRn on their surfaces and internally in the endosomes. As molecules containing Fc fragments are brought into the cell through natural processes (e.g. pinocytosis or endocytosis), the pH changes to a lower pH in the endosomes, where the FcRn receptor binds to Fc fragment-containing molecules that would otherwise be degraded in the endosomal-lysosomal compartments, thereby allowing these molecules to recycle back to the cellular surface where the pH is closer to neutral (e.g., pH 7.0-7.4). Neutral pH disfavors binding to the FcRn receptor and allows release of the Fc-fragment containing molecules back into circulation. This is a primary mechanism by which Fc fragment-containing molecules exhibit prolonged circulatory pharmacokinetic half-lives in vivo.

Insulin-Fc fusion proteins comprising Fc fragments were diluted to 10 μg/mL in sodium bicarbonate pH 9.6 buffer and coated in duplicate on Maxisorb ELISA plate strips for 1-2 hours at RT. The strips were then washed 5 times with PBST (PBS/0.1% Tween-20) buffer and blocked with Superblock blocking reagent (ThermoFisher). Strips for FcRn binding were then washed again 3 times with pH 5.5 MES/NaCl/Tween (50 mM MES/150 mM NaCl/0.1% Tween-20) buffer before addition of the FcRn reagent (biotinylated human FcRn; Immunitrack). Serial dilutions (1:3× dilutions) of biotinylated FcRn reagent were prepared in pH 5.5 MES/NaCl/Tween/5% Superblock buffer at concentrations from 6000 ng/mL to 8.23 ng/mL and loaded at 100 μL/well using a multichannel pipettor onto the strips coated with the insulin-Fc fusion protein compounds. The assay plate was then incubated for 1.5 hours at room temperature. FcRn binding strips were washed 4 times with pH 5.5 MES/NaCl/Tween buffer and then loaded with 100 μl/well streptavidin-HRP diluted 1:10000 in pH 5.5 MES/NaCl/5% Superblock buffer. After incubating for 45 minutes, strips were washed again 5 times with pH 5.5 MES/NaCl/Tween buffer. TMB was finally added to reveal the bound biotinylated-FcRn reagent, and the color development was stopped with the ELISA stop reagent. The plate was read in an ELISA plate reader at a wavelength of 450 nm. The OD450 values (proportional to the binding of human-FcRn to the insulin-Fc fusion protein test compounds) were plotted against log concentrations of FcRn added to each well to generate binding curves using GraphPad Prism software. EC50 values for each binding curve were calculated to compare between different compounds.

Example 20: In Vitro Measurement of Insulin-Fc Fusion Protein Affinity for the Human FcRn Receptor In vitro binding affinity of insulin-Fc fusion proteins containing Fc fragments of human IgG origin to the human FcRn receptor is measured via an ELISA technique conducted at a solution pH of 5.5. The slightly acidic pH is the preferred binding environment for Fc fragment-containing molecules to bind to the FcRn receptor. In vivo, cells express FcRn on their surfaces and internally in the endosomes. As molecules containing Fc fragments are brought into the cell through natural processes (e.g. pinocytosis or endocytosis), the pH changes to a lower pH in the endosomes, where the FcRn receptor binds to Fc fragment-containing molecules that would otherwise be degraded in the endosomal-lysosomal compartments, thereby allowing these molecules to recycle back to the cellular surface where the pH is closer to neutral (e.g., pH 7.0-7.4). Neutral pH disfavors binding to the FcRn receptor and allows release of the Fc-fragment containing molecules back into circulation. This is a primary mechanism by which Fc fragment-containing molecules exhibit prolonged circulatory pharmacokinetic half-lives in vivo.

Insulin-Fc fusion proteins comprising Fc fragments are diluted to 10 μg/mL in sodium bicarbonate pH 9.6 buffer and coated in duplicate on Maxisorb ELISA plate strips for 1-2 hours at RT. The strips are then washed 5 times with PBST (PBS/0.1% Tween-20) buffer and blocked with Superblock blocking reagent (ThermoFisher). Strips for FcRn binding are then washed again 3 times with pH 5.5 MES/NaCl/Tween (50 mM MES/150 mM NaCl/0.1% Tween-20) buffer before addition of the FcRn reagent (biotinylated human FcRn; Immunitrack). Serial dilutions (1:3× dilutions) of biotinylated FcRn reagent are prepared in pH 5.5 MES/NaCl/Tween/5% Superblock buffer at concentrations from 6000 ng/mL to 8.23 ng/mL and loaded at 100 μL/well using a multichannel pipettor onto the strips coated with the insulin-Fc fusion protein compounds. The assay plate is then incubated for 1.5 hours at room temperature. FcRn binding strips are washed 4 times with pH 5.5 MES/NaCl/Tween buffer and then loaded with 100 μl/well streptavidin-HRP diluted 1:10000 in pH 5.5 MES/NaCl/5% Superblock buffer. After incubating for 45 minutes, strips are washed again 5 times with pH 5.5 MES/NaCl/Tween buffer. TMB is finally added to reveal the bound biotinylated-FcRn reagent, and the color development is stopped with the ELISA stop reagent. The plate is read in an ELISA plate reader at a wavelength of 450 nm. The OD450 values (proportional to the binding of human-FcRn to the insulin-Fc fusion protein test compounds) are plotted against log concentrations of FcRn added to each well to generate binding curves using GraphPad Prism software. EC50 values for each binding curve are calculated to compare between different compounds.

Example 21: Generalized Procedure for Determination of In Vivo Pharmacodynamics (PD) after Single Administration of Canine Insulin Fc-Fusion Proteins in Dogs Insulin-Fc fusion proteins were assessed for their effects on fasting blood glucose levels in dogs as follows. N=1, 2, 3 or more healthy, antibody-naïve, dogs weighing approximately 10-15 kg were used, one for each insulin-Fc fusion protein. Animals were also observed twice daily for signs of anaphylaxis, lethargy, distress, pain, etc., and, optionally for some compounds, treatment was continued for an additional three weekly subcutaneous injections or more to observe if the glucose lowering capability of the compounds lessened over time, a key sign of potential induction of neutralizing anti-drug antibodies. On day 0, the animals received a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 min and at 1, 2, 3, 4, 5, 6, and 7 days post injection.

For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from day 0 to day 7 were plotted to assess the bioactivity of a given insulin-Fc fusion protein.

Example 22: Generalized Procedure for Determination of In Vivo Pharmacodynamics (PD) after Repeated Administration of Canine Insulin-Fc Fusion Proteins in Dogs Insulin-Fc fusion proteins were assessed for their effects on blood glucose levels over repeated injections as follows. Healthy, antibody-naïve, dogs weighing approximately between 10 kg and 20 kg were used, and each animal was administered doses of an insulin-Fc fusion protein. Animals were observed twice daily for signs of anaphylaxis, lethargy, distress, pain, and other negative side effects, and optionally for some compounds, treatment was continued for up to an additional two to five subcutaneous injections to observe if the glucose lowering capability of the compounds decreased over time, indicating the possible presence of neutralizing anti-drug antibodies in vivo. On day 0, the animals received a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 min and at 1, 2, 3, 4, 5, 6, and 7 days post injection.

Subsequent subcutaneous injections were given no more frequently than once-weekly, and in some cases the injections were given at different intervals based on the pharmacodynamics of a given insulin-Fc fusion protein formulation. Subsequent injections for each insulin-Fc fusion protein were adjusted to higher or lower doses, depending on the demonstrated pharmacodynamics of the insulin-Fc fusion protein. For instance, if the dose of a first injection on day 0 was found to be ineffective at lowering blood glucose, the subsequent dose levels of injected insulin-Fc fusion protein were adjusted upward. In a similar manner, if the dose of a first injection on day 0 was found to lower glucose in too strong a manner, then subsequent dose levels of injected insulin-Fc fusion protein were adjusted downward. It was also found that interim doses or final doses could be adjusted in a similar manner as needed. For each dose, blood was collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from throughout the study were plotted against time which allows the bioactivity of a fusion protein to be determined.

To determine the bioactivity of each dose, an area-over-the-curve (AOC) analysis was conducted as follows. After constructing the % FBGL versus time data, the data were then entered into data analysis software (GraphPad Prism, GraphPad Software, San Diego Calif.). The software was used to first conduct an area-under-the curve analysis (AUC) to integrate the area under the % FBGL vs. time curve for each dose. To convert the AUC data into the desired AOC data, the following equation was used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL·days, a calculation gave the following for AOC: AOC=(100% FBGL×7 days)−(500% FBGL·days)=200% FBGL days. The analysis was performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose was calculated as follows: NAOC=AOC/D with units of % FBGL·days·kg/mg; where D is the actual dose injected into the animal in mg/kg. NAOC values were calculated for each injection in a series of injections for a given animal and were averaged across a group of animals receiving the same insulin-Fc fusion protein formulation.

The NAOC ratio (NAOCR) was calculated for each injection in a series of injections for a given animal by taking the NAOC values for each injection (e.g. injections 1, 2, 3, . . . N) and dividing each NAOC for a given injection by the NAOC from injection 1 as follows: NAOCR=(NAOC (Nth injection)/NAOC(injection 1)). By evaluating the NAOCR of a given insulin-Fc fusion protein formulation for the $N^{th}$ injection in a series of injections, it was possible to determine whether the in vivo glucose lowering activity of a given insulin-Fc fusion protein had substantially retained its bioactivity over a series of N doses (e.g., NAOCR for the Nth dose of greater than 0.5) or whether the in vivo glucose lowering activity of a given insulin-Fc fusion protein had lost a substantial portion of its potency (e.g., NAOCR of the $N^{th}$ dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection was greater than 0.5 (i.e., the NAOCR of the third subcutaneous injection was greater than 0.5).

Example 23: Generalized Procedure for the Determination of In Vivo Pharmacokinetics (PK) of Canine Insulin-Fc Fusion Proteins in Canine Serum An assay was constructed for measuring the concentrations of insulin-Fc fusion proteins comprising Fc fragments of a canine isotype in canine serum as follows. The assay comprised a sandwich ELISA format in which therapeutic compounds in serum samples were captured by an anti-insulin/proinsulin monoclonal antibody (mAb) coated on the ELISA plates and were then detected by an HRP-conjugated anti-canine IgG Fc specific antibody followed by use of a TMB substrate system for color development. Maxisorp ELISA Plates (Nunc) were coated with the anti-insulin mAb clone D6C4 (Biorad) in coating buffer (pH=9.6 sodium carbonate-sodium biocarbonate buffer) at 5 μg/ml overnight at 4° C. Plates were then washed 5 times with PBST (PBS+0.05% Tween 20) and blocked for a minimum of one hour at room temperature (or overnight at 4C) with SuperBlock blocking solution (ThermoFisher). Test serum samples were diluted to 1:20 in PBST/SB/20% HS sample dilution buffer (PBS+0.1% Tween 20+10% SuperBlock+20% horse serum). For making a standard curve, the insulin-Fc fusion protein of interest was diluted in sample dilution buffer (PBST/SB/20% HS)+5% of pooled beagle serum (BioIVT) from a concentration range of 200 ng/ml to 0.82 ng/ml in 1:2.5 serial dilutions. Standards and diluted serum samples were added to the blocked plates at 100 μl/well in duplicate and were incubated for 1 hour at room temperature. Following incubation, samples and standards were washed 5 times with PBST. HRP-conjugated goat anti-canine IgG Fc (Sigma) detection antibody was diluted to about 1:15,000 in PBST/SB/20% HS buffer and 100 μl was added to all the wells and incubated for 45 minutes at room temperature in the dark. Plates were washed 5 times with PBST and once with deionized water and were developed by the addition of 100 μl/well TMB (Invitrogen) for 8-10 minutes at room temperature. Color development was then stopped by the addition of 100 μl/well ELISA Stop Solution (Boston Bioproducts) and the absorbance was read at 450 nm using a SpectraMax plate reader (Molecular Devices) within 30 minutes. Concentrations of insulin-Fc fusion protein compounds in the samples were calculated by interpolation on a 4-PL curve using SoftMaxPro software.

Example 24: Assay Protocol for Measuring Anti-Drug Antibodies in Canine Serum

Maxisorp ELISA Plates (Nunc) were coated with the insulin-Fc fusion protein of interest diluted in coating buffer (pH=9.6 Carbonate-Biocarbonate buffer) at 10 μg/mL overnight at 4° C. for measuring ADAs against the test compound. For measuring ADAs against the insulin portion of the insulin-Fc fusion protein containing an Fc fragment of canine IgG origin, plates were coated with purified insulin at 30 μg/mL in coating buffer. Plates were then washed 5 times with PBST (PBS+0.05% Tween 20) and blocked for at least 1 hour (or overnight) with SuperBlock blocking solution (ThermoFisher, Waltham Mass.). For calculating the ADAs in canine IgG units, strips were directly coated with 1:2 serial dilutions of canine IgG (Jackson Immunoresearch Laboratories, West Grove Pa.) in pH=9.6 Carb-Biocarb coating buffer at concentrations between 300-4.69 ng/ml overnight at 4° C. and used to create a 7-point pseudo-standard curve. The standards strip plates were also washed and blocked with SuperBlock blocking solution for at least 1 hour (or overnight).

Test serum samples were diluted to greater than or equal to 1:100 (typically tested as 1:200) in PBST/SB/20% HS sample dilution buffer (PBS+0.1% Tween 20+10% SuperBlock+20% horse serum) and added to the insulin-Fc fusion protein coated (or RHI coated) strips at 100 μL/well in duplicate. Duplicate strips of canine IgG coated standard strips were also added to each plate and filled with PBST/SB (PBS+0.1% Tween 20+10% SuperBlock) buffer at 100 μL/well. Plates were incubated for 1 hour at room temperature and then washed 5 times with PBST. For detection of ADAs, HRP-conjugated Goat anti-feline IgG F(ab')2 (anti-feline IgG F(ab')2 reagent was cross-reacted to canine antibodies; Jackson Immunoresearch Laboratories, West Grove Pa.), which was diluted in PBST/SB to 1:10000 and added at 100 μL/well to both sample and standard wells and incubated for 45 minutes at room temperature in the dark. Plates were washed 5 times with PBST and then one time with deionized water and then developed by adding 100 μL/well TMB substrate (Invitrogen, ThermoFisher Scientific, Waltham Mass.) for 15-20 minutes at room temperature in the dark. Color development was then stopped by addition of 100 μL/well of ELISA Stop Solution (Boston Bioproducts) and the absorbance was read at 450 nm using a SpectraMax plate reader within 30 minutes. The anti-drug antibody concentration was determined by interpolating the OD values in the 4-PL pseudo-standard curve using SoftMax Pro Software (Molecular Devices, San Jose Calif.).

To demonstrate the specificity of the detected ADAs, an "inhibition" assay was carried out. In the drug inhibition ADA assay, serum samples were diluted 1:100 in PBST/SB/20% HS buffer and mixed with an equal volume of 300 μg/mL of the relevant therapeutic compound (final sample dilution at 1:200 and final inhibitory compound at 150 μg/mL) and were incubated for 30-40 minutes at room temperature to allow anti-drug antibodies to bind the free inhibitor (i.e., the therapeutic compound). After pre-incubation, the samples were added to insulin-Fc fusion protein coated (or RHI coated) strips at 100 μL/well in duplicate. Samples diluted 1:200 in PBST/SB/20% HS buffer without the inhibitory compound were also tested in the sample plates along with duplicate strips of canine IgG coated standards. Remaining steps of the assay procedure were carried out as described above. The ADAs measured in the drug-inhibited wells were matched with the non-inhibited ADA concentrations to assess the specificity of the ADAs. If significant inhibition of ADA signals was observed in the drug-inhibited wells, this meant the ADAs were specific to the therapeutic compound.

Example 25: Generalized Procedure for Determination of In Vivo Pharmacodynamics (PD) after a Single Administration of Human Insulin Fc-Fusion Proteins in Mice Insulin-Fe fusion proteins were assessed for their effects on fasting blood glucose levels as follows. Data was collected from N=3 balb/c mice or diabetic wt NOD mice (Jackson Laboratories) per group. The animals were fasted one hour before the experiment and then at time=0 hours, the mice received a single subcutaneous administration of a pharmaceutical composition containing an insulin Fc-fusion protein homodimer at a concentration of 300 μg/kg of insulin-Fc fusion protein in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a final solution pH of between 7.0-8.0 adjusted using sodium hydroxide and/or hydrochloric acid.

For each time point, a sample of blood was collected, and a glucose level reading was immediately determined using a glucose meter (AlphaTRAK® 2 pet glucometer), which requires approximately one drop of blood. Average % fasting blood glucose levels (% FBGL) from 0 to 9 hours were plotted to assess the bioactivity of a given insulin-Fc fusion protein.

Example 26: Generalized Procedure for Determination of In Vivo Pharmacodynamics (PD) after a Single Administration of Human Insulin Fc-Fusion Proteins in Mice Insulin-Fc fusion proteins are assessed for their effects on fasting blood glucose levels as follows. Data is collected from N=3 balb/c mice or diabetic wt NOD mice (Jackson Laboratories) per group. The animals are fasted one hour before the experiment and then at time=0 hours, the mice receive a single subcutaneous administration of a pharmaceutical composition containing an insulin Fc-fusion protein homodimer at a concentration of 300 μg/kg of insulin-Fc fusion protein in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a final solution pH of between 7.0-8.0 adjusted using sodium hydroxide and/or hydrochloric acid.

For each time point, a sample of blood is collected, and a glucose level reading is immediately determined using a glucose meter (AlphaTRAK® 2 pet glucometer), which requires approximately one drop of blood. Average % fasting blood glucose levels (% FBGL) from 0 to 9 hours are plotted to assess the bioactivity of a given insulin-Fc fusion protein.

Example 27: Assay Procedure for Immunogenic Epitope Identification

Maxisorp ELISA microplates (Nunc) are coated with a library of insulin-Fc fusion protein homodimer compounds with known amino acid sequences, and the coated plates are blocked in a similar manner as described in the anti-drug antibody ELISA assay of Example 25, except that each compound in the library is coated on a separate individual strip of ELISA microplate wells. The compounds in the library comprise a range of insulin-Fc fusion proteins with different insulin polypeptide amino acid compositions, including various B-chain, C-chain, and A-chain amino acid mutations, different linker compositions, and different Fc fragment compositions, including some of human origin. Separately, some plate strip wells are directly coated with 1:2 serial dilutions of canine IgG (Jackson Immunoresearch Laboratories, West Grove Pa.) for calculating the anti-drug antibodies (ADA) in canine IgG units, respectively, as described in Example 24.

Serum obtained from individual dogs receiving repeated doses of an insulin-Fc fusion protein is first screened on the anti-drug antibody ELISA assay of Example 24. Serum samples demonstrating moderate or high positivity (e.g. moderate or high titers of antibodies) on the assay of Example 24 are serially diluted (1:200 to 1:8000) in PBST/SB/20% HS sample dilution buffer (PBS+0.1% Tween 20+10% SuperBlock+20% horse serum) and added to the plates coated with the library of insulin-Fc fusion protein compounds for 1 hour at RT. Following incubation, the plates are washed 5 times with PBST. For detection of canine antibodies capable of cross-reacting to the coated compound library, HRP conjugated goat anti-feline IgG F(ab')2 (Jackson Immunoresearch Laboratories, West Grove Pa.), which is cross-reactive to canine IgGs, is diluted in PBST/SB to 1:10000 and added at 100 μL/well to both sample and standard wells and incubated for 45 min at RT in the dark. Plates are washed 5 times with PBST, once with deionized water, and developed by the adding 100 μL/well TMB substrate (Invitrogen, ThermoFisher Scientific, Waltham Mass.) for 15-20 min at RT in the dark. Color development is then stopped by addition of 100 μL/well of ELISA Stop Solution (Boston Bioproducts, Ashland Mass.) and absorbance is read at 450 nm using a SpectraMax plate reader within 30 min. Anti-compound cross-reactive antibody concentrations present in the serum samples are determined by interpolating the OD values in the 4-PL pseudo-standard curve against the directly coated canine IgG antibody controls using SoftMax Pro Software (Molecular Devices, San Jose Calif.).

By correlating the resulting antibody concentrations from the assay with the known amino acid compositions of the coated insulin-Fc fusion protein library, one can determine whether particular amino acid mutations or epitopes are responsible for causing none, some, most, or all of the total antibody signal on the assay, indicating no binding, weak binding, or strong binding to various insulin-Fc fusion protein homodimers. The mutations or epitopes responsible for moderate or strong binding are herein referred to as immunogenic "hot spots".

Example 28: Design Process for Obtaining Canine Insulin-Fc Fusion Proteins with High Homodimer Titers and Acceptable Levels of Acute and Repeated Dose Bioactivity The process for meeting the design goals described in the Detailed Description of the Invention comprised the following steps. First, the insulin polypeptide of SEQ ID NO: 4 or SEQ ID NO: 5 was combined with a species-specific Fc fragment of a particular IgG isotype and a linker such that the resulting insulin-Fc fusion protein was most likely to yield a long acting bioactivity product with minimal immunogenicity (e.g., a species-specific IgG isotype was chosen with minimal Fc(gamma)receptor I binding). The DNA sequence coding for the desired fusion protein was prepared, cloned into a vector (LakePharma, San Carlos, Calif.), and the vector was then used to transiently transfect HEK cells according to the procedure described in Example 1. The insulin-Fc fusion protein was then purified according to Example 4 and the overall protein yield and % homodimer measured according to Example 10. Only candidates with a homodimer titer of greater than 50 mg/L were considered acceptable, because titers less than this level are not likely to result in commercial production titers that meet the stringently low manufacturing cost requirements for veterinary products. Selected insulin-Fc fusion proteins were then screened for indicators of bioactivity through in vitro insulin receptor binding studies as described in Example 12. Based on experience, only compounds that exhibited IR activity IC50 values less than 5000 nM were deemed likely to exhibit bioactivity in the target species. Although the in vitro IR IC50 value is a useful qualitative screening tool, it utilizes human IM-9 cells which express the human insulin receptor and therefore it may not capture some of the small differences in affinity between the canine IR and the human IR. Furthermore, factors other than insulin receptor binding may influence a compound's bioactivity in vivo (e.g., affinity for canine FcRn to allow for extended pharmacokinetic elimination half-lives in vivo). Therefore, selected insulin-Fc fusion proteins that were acceptable from a manufacturing and IR activity IC50 value standpoint were further screened for bioactivity dogs to screen out any materials with less than the desired potency and/or duration of bioactivity (e.g., NAOC of less than 150% FBGL·days·kg/mg). Again, based on experience, at NAOC values of greater than 150% FBGL·days·kg/mg, the dose requirements in the target species will be sufficiently low so as to reach an acceptable treatment cost. Lastly, an additional evaluation criterion was added which is mentioned rarely if ever in the art. As discussed in more detail in the Examples below, many insulin-Fc fusion protein embodiments that exhibit acceptable NAOC levels in the target species after the first dose, unexpectedly fail to maintain that level of bioactivity after repeated doses. Furthermore, in most cases the reduction in repeated dose bioactivity in the target species is correlated with the development of neutralizing anti-drug antibodies. This propensity to generate anti-drug antibodies and the failure to maintain activity render such insulin-Fc fusion proteins impractical for use in treating a chronic disease such as canine diabetes. Therefore, only the insulin-Fc fusions proteins exhibiting acceptable levels of repeated dose bioactivity (e.g., NAOCR values greater than 0.5 for the third dose relative to the first dose) with minimal levels of anti-drug antibodies were deemed acceptable for use in the present invention.

Example 29: Design Process for Obtaining Human Insulin-Fc Fusion Proteins with High Homodimer Titers and Acceptable Levels of Acute and Repeated Dose Bioactivity The process for meeting the design goals described in the Detailed Description of the invention comprised the following steps. First, the insulin polypeptide of SEQ ID NO: 7 or SEQ ID NO: 10 was combined with a human Fc fragment of a particular IgG isotype (IgG2 or IgG1) and a linker such that the resulting insulin-Fc fusion protein was most likely to yield a long acting bioactivity product. The DNA sequence coding for the desired fusion protein was prepared, cloned into a vector (LakePharma, San Carlos, Calif.), and the vector was then used to transiently transfect HEK cells according to the procedure described in Example 1. The insulin-Fc fusion protein was then purified according to Example 4 and the total protein yield and % homodimer was measured according to Example 10 and the homodimer titer calculated. Only candidates with a homodimer titer of greater than 150 mg/L were considered acceptable, because homodimer titers less than this level are not likely to translate to high homodimer titer CHO stably infected cell lines, and therefore not likely to result in commercial production titers that meet the low manufacturing cost requirements for the relatively commoditized human insulin market. Selected insulin-Fc fusion protein configurations were then screened for indicators of bioactivity through in vitro IR binding studies as described in Example 12. Based on experience, only compounds that exhibited IR activity IC50 values less than 2400 nM and more preferably less than 2000 nM were deemed likely to exhibit bioactivity in vivo. The in vitro IR IC50 value is a useful qualitative screening tool, as the assay utilizes human IM-9 cells which express the human IR, and the greater binding (lower IR IC50 values) would be expected to give greater in vivo potency for a given dose compared to compounds with decreased binding (higher IR IC50 values). Furthermore, factors other than IR binding may influence a compound's bioactivity in vivo. For example, the affinity of Fc fusion proteins for the human FcRn receptor is related to a compound's in vivo pharmacokinetic elimination half-life. Extended in vivo half-life of insulin-Fc fusion proteins of several days or more correlates well with EC50 values less than 1500 ng/mL and more preferably less than 1000 ng/mL, as measured by an in vitro human FcRn binding assay (Example 19).

Selected insulin-Fc fusion protein configurations that were acceptable in the areas of manufacturing, IR activity IC50 value, and human FcRn activity EC50 value were further screened for their potential for in vivo immunogenicity by testing the human Fc(gamma)RI receptor and human C1q binding affinities. Molecules that bind more strongly to these immune system components are more likely to go through increased antigen cell presentation (APC) and exhibit a greater immunogenicity profile as measured by anti-drug antibodies. Anti-drug antibodies are unwanted and may hinder the in vivo pharmacokinetic half-life of the molecule, may neutralize the activity of the drug, or may perform both functions. The impact of potential anti-drug antibodies on insulin-Fc in vivo performance could be quite problematic. Therefore, work was performed to screen candidate insulin-Fc fusion proteins against Fc(gamma)RI (Example 14) and C1q (Example 16) to mitigate the risk of unwanted antigen presentation and potential anti-drug antibody-inducing immunogenicity (Guilliams, Martin & Bruhns, Pierre & Saeys, Yvan & Hammad, Hamida & Lambrecht, Bart. (2014). The function of Fc gamma receptors in dendritic cells and macrophages. *Nature reviews. Immunology.* 14. 10.1038/nri3582). The design goal established for human Fc(gamma)RI binding (where the biotinylated-Fc(gamma)RI concentration of the insulin-Fc fusion protein under test is 3000 ng/mL) is an OD450 Ratio<0.50 (with respect to the insulin-Fc fusion protein configuration of SEQ ID NO: 76) and the design goal established for C1q binding (where the biotinylated-C1q concentration of the insulin-Fc fusion protein under test is 1000 ng/mL) is an OD450 ratio<0.35 (with respect to the insulin-Fc fusion protein configuration of SEQ ID NO: 76).

As described elsewhere, human IgG1 Fc containing insulin-Fc fusion protein configurations were unexpectedly found to be much higher yielding than the human IgG2 Fc containing configurations and were therefore preferred with respect to manufacturability. However, human IgG1 Fc containing insulin-Fc fusion protein configurations, when containing natural N-linked glycosylation at the cNg site often display very high binding to both Fc(gamma)RI and C1q, and strong binding to one or both of these moieties has been correlated to a high potential for enhanced antigen presentation and immunogenicity in vivo (Kouser, L., Madhukaran, S. P., Shastri, A., Saraon, A., Ferluga, J., Al-Mozaini, M., & Kishore, U. (2015). Emerging and Novel Functions of Complement Protein C1q. *Frontiers in Immunology,* 6, 317. doi:10.3389/fimmu.2015.00317). Therefore, several variants of hIgG1 isotype, Fc-containing insulin-Fc fusion protein configurations were tested by first screening compounds whose native glycosylation site (cNg) was mutated to prevent natural glycosylation during biosynthesis. These molecules were then further mutated to improve their properties by manipulating the insulin polypeptide composition. Lastly, several linker variants of different composition and length were examined to identify whether various design properties could be further optimized. After screening through multiple rounds of optimization, only the insulin-Fc fusions protein configurations exhibiting acceptable levels of homodimer titer, IR binding, FcRn binding, Fc(gamma)RI binding, and C1q binding were deemed acceptable for use in the present invention.

Results—Insulin-Fc Fusion Proteins Comprising a Canine Fc Fragment

Example 30: Canine Insulin-Fc Fusion Protein Comprising the Canine Fc IgGA Isotype An attempt was made to produce an insulin-Fc fusion protein comprising the insulin polypeptide sequence of SEQ ID NO: 4 and the Fc fragment of the canine IgGA isotype (SEQ ID NO: 14) using the peptide linker of SEQ ID NO: 11. The full amino acid sequence for the resulting insulin-Fc fusion protein is as follows:

```
                                     (SEQ ID NO: 31)
FVNQHLCGSDLVEALALVCGERGFFYTDPTGGGPRRGIVEQCCHSICSLY

QLENYCNGGGGAGGGGRCTDTPPCPVPEPLGGPSVLIFPPKPKDILRITR

TPEVTCVVLDLGREDPEVQISWFVDGKEVHTAKTQSREQQFNGTYRVVSV

LPIEHQDWLTGKEFKCRVNHIDLPSPIERTISKARGRAHKPSVYVLPPSP

KELSSSDTVSITCLIKDFYPPDIDVEWQSNGQQEPERKHRMTPPQLDEDG

SYFLYSKLSVDKSRWQQGDPFTCAVMHETLQNHYTDLSLSHSPG.
```

The insulin-Fc fusion protein of SEQ ID NO: 31 was synthesized in HEK cells according to Example 1 and purified according to Example 4. The protein yield was 22 mg/L after the Protein A purification step. The structure of the insulin-Fc fusion protein was confirmed according to Example 6 by non-reducing and reducing CE-SDS, and the sequence was further identified by LC-MS with glycan removal according to Example 8. The % homodimer was measured by size-exclusion chromatography according to Example 10 and determined to be 24%, indicating a high degree of homodimer aggregates. The resulting homodimer titer was therefore only 5 mg/L. In summary, manufacturing of the insulin-Fc fusion protein of SEQ ID NO: 31 in HEK cells resulted in a high level of aggregates and a low homodimer titer (5 mg/L), which did not meet the design goal of a homodimer titer of greater than 50 mg/L.

Nevertheless, the insulin-Fc fusion protein of SEQ ID NO: 31 as evaluated for bioactivity. First, the insulin receptor binding of the insulin-Fc fusion protein of SEQ ID NO: 31 was measured according to Example 12, resulting in an IC50 value of 2,733 nM indicating that the compound is likely to be bioactive in vivo (i.e. IC50 less than 5000 nM).

Figure 2:
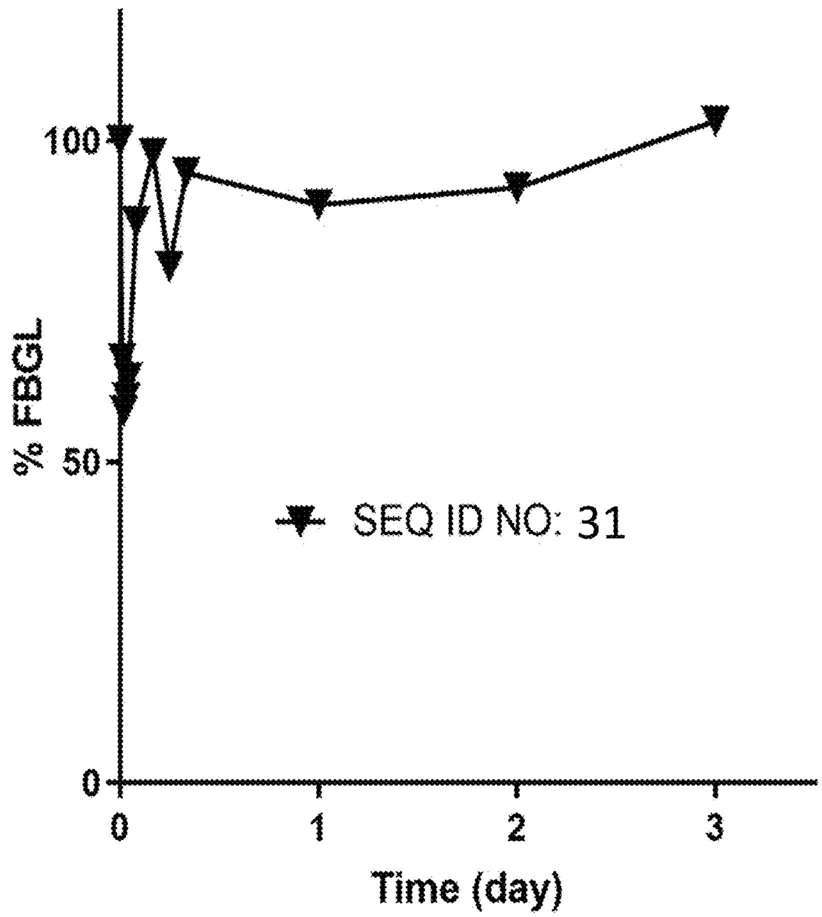
FIG. 2 shows average % fasting blood glucose levels from Day 0 to Day 3 for N=3 dogs dosed intravenously on Day 0 at 0.2 mg/kg with the homodimer of SEQ ID NO: 31.

Next, the in vivo pharmacodynamics (PD) of the insulin-Fc fusion protein of SEQ ID NO: 31 was measured after a single intravenous administration of the compound to N=3 canines, according to Example 21. FIG. 2 shows the percent fasting blood glucose level of SEQ NO: 31 as a function of time. The NAOC for SEQ ID NO: 31 was calculated to be 105% FBGL·days·kg/mg according to the procedure of Example 22. The in vivo half-life of SEQ ID NO: 31 was calculated to be less than one day using the method of Example 23. The relatively low NAOC was likely the result of the high amount of aggregates in the sample (i.e., low % homodimer), but what soluble homodimer remained in circulation still only had a pharmacokinetic elimination half-life of less than one day which was deemed unlikely support of once-weekly administration.

Example 31: Mutations of the Fc Fragment Region of Insulin-Fc Fusion Proteins Comprising the Canine IgGA Isotype In an attempt to increase the % homodimer content, improve the bioactivity, and increase the half-life of the insulin-Fc fusion protein of SEQ ID NO: 31, mutations were inserted into the Fc fragment CH3 region to try to prevent intermolecular association (e.g., Fc fragment-Fc fragment interactions between molecules) and encourage stronger binding to the FcRn receptor (e.g., higher affinity for the FcRn) to increase recycling and systemic circulation time. The following insulin-Fc fusion proteins were synthesized in HEK cells according to Example 1, purified according to Example 4, and tested according to Example 6, Example 8 and Example 10, the test results of which are shown below in Table 2. The sequence alignment of SEQ ID NO: 32, SEQ ID NO: 33, SEQ ID NO: 34, and SEQ ID NO: 35 against SEQ ID NO: 31 and the differences in amino acid sequences are shown in FIG. 3.

```
                                                              (SEQ ID NO: 32)
FVNQHLCGSDLVEALALVCGERGFFYTDPTGGGPRRGIVEQCCHSICSLYQLENYCNGGGGAG

GGGRCTDTPPCPVPEPLGGPSVLIFPPKPKDILRITRTPEVTCVVLDLGREDPEVQISWFVDGKEV

HTAKTQSREQQFNGTYRVVSVLPIEHQDWLTGKEFKCRVNHIDLPSPIERTISKARGRAHKPSV

YVLPPSPKELSSSDTVSITCLIKDFYPPDIDVEWQSNGQQEPERKHRWITPPQLDEDGSYFLYSKL

SVDKSRWQQGDPFTCAVLHEALHSHYTQKSLSLSPG

                                                              (SEQ ID NO: 33)
FVNQHLCGSDLVEALALVCGERGFFYTDPTGGGPRRGIVEQCCHSICSLYQLENYCNGGGGAG

GGGRCTDTPPCPVPEPLGGPSVLIFPPKPKDILRITRTPEVTCVVLDLGREDPEVQISWFVDGKEV

HTAKTQSREQQFNGTYRVVSVLPIEHQDWLTGKEFKCRVNHIDLPSPIERTISKARGRAHKPSV

YVLPPSPKELSSSDTVSITCLIKDFYPPDIDVEWQSNGQQEPERKHRMTPPQLDEDGSYFLYSKL

SVDKSRWQQGDPFTCAVLHETLQSHYTDLSLSHSPG
```

-continued (SEQ ID NO: 34)

```
FVNQHLCGSDLVEALALVCGERGFFYTDPTGGGPRRGIVEQCCHSICSLYQLENYCNGGGGAG

GGGRCTDTPPCPVPEPLGGPSVLIFPPKPKDILRITRTPEVTCVVLDLGREDPEVQISWFVDGKEV

HTAKTQSREQQFNGTYRVVSVLPIEHQDWLTGKEFKCRVNHIDLPSPIERTISKARGRAHKPSV

YVLPPSPKELSSSDTVSITCLIKDFYPPDIDVEWQSNGQQEPERKHRMTPPQLDEDGSYFLYSKL

SVDKSRWQQGDPFTCAVMHETLQSHYTDLSLSHSPG
```

(SEQ ID NO: 35)

```
FVNQHLCGSDLVEALALVCGERGFFYTDPTGGGPRRGIVEQCCHSICSLYQLENYCNGGGGAG

GGGRCTDTPPCPVPEPLGGPSVLIFPPKPKDILRITRTPEVTCVVLDLGREDPEVQISWFVDGKEV

HTAKTQSREQQFNGTYRVVSVLPIEHQDWLTGKEFKCRVNHIDLPSPIERTISKARGRAHKPSV

YVLPPSPKELSSSDTVSITCLIKDFYPPDIDVEWQSNGQQEPERKHRMTPPQLDEDGSYFLYSKL

SVDKSRWQQGDPFTCAVLHETLQNHYTDLSLSHSPG
```

The insulin-Fc fusion proteins based on canine IgGA variants are listed in Table 2 along with the corresponding protein yields, % homodimer, and homodimer titers. The results show that the various mutations to the IgGA Fc fragment, instead of improving the % homodimer and homodimer titer, gave rise to highly aggregated proteins with extremely low homodimer titers of less than 5 mg/L. As such, the in vivo bioactivity and pharmacokinetics of the compounds could not be evaluated.

TABLE 2

Homodimer titers for sequences utilizing a native or mutated canine IgGA Fc fragment CH3 region

| SEQ ID NO: | Protein Yield (mg/L) | % Homodimer | Homodimer Titer (mg/L) |
|---|---|---|---|
| SEQ ID NO: 31 | 22 | 24% | 5 |
| SEQ ID NO: 32 | 33 | 0% | 0 |
| SEQ ID NO: 33 | 57 | 0% | 0 |
| SEQ ID NO: 34 | 67 | 0% | 0 |
| SEQ ID NO: 35 | 80 | 0% | 0 |

Example 32: Canine Insulin-Fc Fusion Protein Using Other Canine Fc Fragment Isotypes As described above, canine IgGA is thought to be the preferred isotype for the Fc fragment to produce non-immunogenic insulin-Fc fusion protein for dogs due to its lack of Fc(gamma) I effector function in canines (much like the human IgG2 isotype in humans). However, insulin-Fc fusion proteins manufactured with a canine IgGA Fc fragment were highly aggregated with an unacceptably low homodimer titer and unacceptably low levels of bioactivity and duration of action. Therefore, Fc fragments from the other canine IgG isotypes (canine IgGB of SEQ ID NO: 15), canine IgGC of SEQ ID NO: 16, and canine IgGD of SEQ ID NO: 17) were evaluated as replacements for the canine IgGA Fc fragment of the insulin-Fc fusion of SEQ ID NO: 31. The three insulin-Fc fusion proteins containing Fc fragments based on the canine IgGB, IgGC, and IgGD isotypes were synthesized using the same insulin polypeptide of SEQ ID NO: 4 and peptide linker of SEQ ID NO: 11 as were used to make the insulin-Fc fusion protein of SEQ ID NO: 31. The proteins were manufactured in HEK293 cells according to Example 1. The insulin-Fc fusion proteins were then purified using a Protein A column according to Example 4. The structures of the insulin-Fc fusion proteins were confirmed according to Example 6 by non-reducing and reducing CE-SDS, and the sequences were further identified by LC-MS with glycan removal according to Example 8. The % homodimer was measured by size-exclusion chromatography according to Example 10. Their sequences are shown below and their sequence alignment comparison against SEQ ID NO: 31 is shown in FIG. 4:

(SEQ ID NO: 36)

```
FVNQHLCGSDLVEALALVCGERGFFYTDPTGGGPRRGIVEQCCHSICSLYQLENYCNGGGGAG

GGGDCPKCPAPEMLGGPSVFIFPPKPKDTLLIARTPEVTCVVVDLDPEDPEVQISWFVDGKQMQ

TAKTQPREEQFNGTYRVVSVLPIGHQDWLKGKQFTCKVNNKALPSPIERTISKARGQAHQPSVY

VLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPG
```

(SEQ ID NO: 37)

```
FVNQHLCGSDLVEALALVCGERGFFYTDPTGGGPRRGIVEQCCHSICSLYQLENYCNGGGGAG

GGGCNNCPCPGCGLLGGPSVFIFPPKPKDILVTARTPTVTCVVVDLDPENPEVQISWFVDSKQV

QTANTQPREEQSNGTYRVVSVLPIGHQDWLSGKQFKCKVNNKALPSPIEEIISKTPGQAHQPNV
```

-continued

```
YVLPPSRDEMSKNTVTLTCLVKDFFPPEIDVEWQSNGQQEPESKYRMTPPQLDEDGSYFLYSKL

SVDKSRWQRGDTFICAVMHEALHNHYTQISLSHSPG
```

(SEQ ID NO: 38)

```
FVNQHLCGSDLVEALALVCGERGFFYTDPTGGGPRRGIVEQCCHSICSLYQLENYCNGGGGAG

GGGCISPCPVPESLGGPSVFIFPPKPKDILRITRTPEITCVVLDLGREDPEVQISWFVDGKEVHTAK

TQPREQQFNSTYRVVSVLPIEHQDWLTGKEFKCRVNHIGLPSPIERTISKARGQAHQPSVYVLPP

SPKELSSSDTVTLTCLIKDFFPPEIDVEWQSNGQPEPESKYHTTAPQLDEDGSYFLYSKLSVDKSR

WQQGDTFTCAVMHEALQNHYTDLSLSHSPG
```

The resulting protein yields, % homodimer, and homodimer titers are given in Table 3. Unexpectedly, only the insulin-Fc fusion protein of SEQ ID NO: 36 comprising an Fc fragment based on the canine IgGB isotype demonstrated a homodimer titer which met the design criteria of greater than 50 mg/L. The insulin-Fc fusion protein of SEQ ID NO: 37 comprising an Fc fragment based on the canine IgGC isotype did not yield any compound at all, and the insulin-Fc fusion protein of SEQ ID NO: 38 comprising an Fc fragment based on the canine IgGD isotype demonstrated an appreciable protein yield but with a high degree of aggregation and therefore an unacceptably low homodimer titer.

In vitro insulin receptor binding for the insulin-Fc fusion proteins of SEQ ID NO: 36 and SEQ ID NO: 38 was tested according to the procedure of Example 12. The insulin-Fc fusion protein of SEQ ID NO: 38 demonstrated an IC50 of greater than 5000 nM, indicating that the compound was highly unlikely to show bioactivity in vivo. However, the insulin-Fc fusion protein of SEQ ID NO: 36 demonstrated an IC50 of 28 nM indicating that this sequence was likely to be bioactive in vivo.

TABLE 3

Homodimer titers for sequences utilizing native canine IgGB, IgGC, and IgGD Fc fragments

| SEQ ID NO: | IgG Fragment | Protein Yield (mg/L) | % Homodimer | Homodimer Titer mg/L) | IR Binding, IC50 (nM) |
|---|---|---|---|---|---|
| SEQ ID NO: 31 | IgGA | 21 | 24% | 5 | 2,733 |
| SEQ ID NO: 36 | IgGB | 80 | 93% | 74 | 28 |
| SEQ ID NO: 37 | IgGC | 0 | 0% | 0 | DNM* |
| SEQ ID NO: 38 | IgGD | 134 | 12% | 16 | >5000 |

*DNM = Did Not Measure

Figure 5:
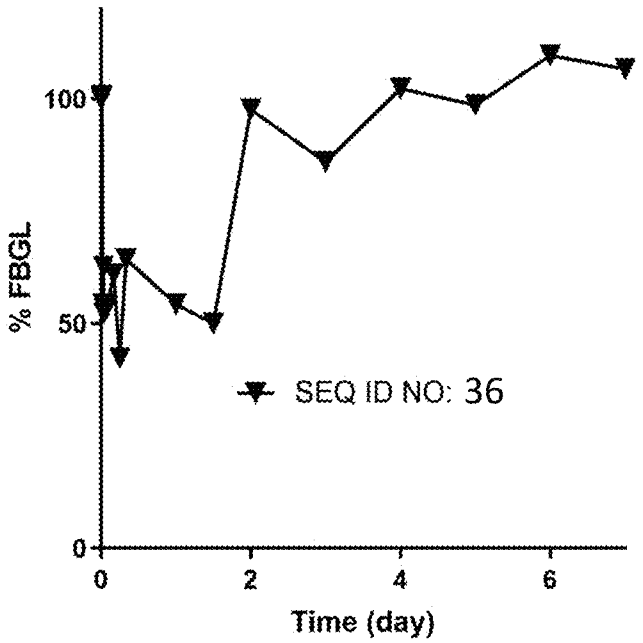
FIG. 5 shows average % fasting blood glucose levels from Day 0 to Day 7 for N=3 dogs dosed intravenously on Day 0 at 0.2 mg/kg with the homodimer of SEQ ID NO: 36.
Figure 6:
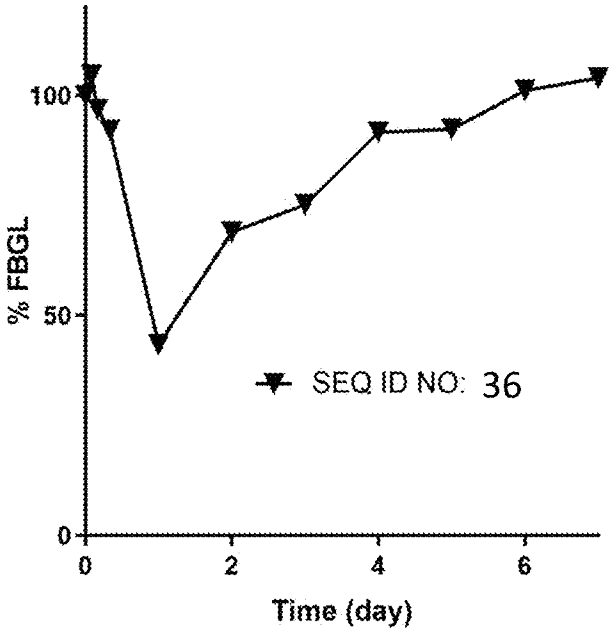
FIG. 6 shows average % fasting blood glucose levels from Day 0 to Day 7 for N=6 dogs dosed subcutaneously on Day 0 at 0.33 mg/kg with the homodimer of SEQ ID NO: 36.

Example 33: In Vivo Efficacy of an Insulin-Fc Fusion Protein Comprising the Insulin Polypeptide of SEQ ID NO: 4 with a Canine IgGB Isotype Fc Fragment Given the promising homodimer titer and insulin receptor activity results in Example 32, the insulin-Fc fusion protein of SEQ ID NO: 36 was tested for in vivo bioactivity according to Example 21 following an intravenous injection in each of N=3 healthy, antibody-naïve, beagle dogs weighing approximately 10 kg. In a separate experiment, the compound was administered subcutaneously to N=3 naïve beagle dogs. FIG. 5 shows the % FBGL versus time for a single intravenous administration of the insulin-Fc fusion protein of SEQ ID NO: 36, and FIG. 6 shows the % FBGL vs. time for a single subcutaneous administration of the insulin-Fc fusion protein of SEQ ID NO: 36, both of which demonstrate that the insulin-Fc fusion protein of SEQ ID NO: 36 is significantly bioactive in dogs.

The NAOC was calculated according to the procedure of Example 22 to determine the relative bioactivity and duration of action of the insulin-Fc fusion protein. The NAOC of the insulin-Fc fusion protein of SEQ ID NO: 36 injected intravenously was 399% FBGL·days·kg/mg which was 3.8 times the NAOC of the insulin-Fc fusion protein of SEQ ID NO: 31 injected intravenously, illustrating significantly increased bioactivity for the insulin-Fc fusion protein comprising the canine IgGB Fc fragment versus the insulin-Fc fusion protein comprising the canine IgGA Fc fragment. The NAOC of the insulin-Fc fusion protein of SEQ ID NO: 36 injected subcutaneously was 366% FBGL·days·kg/mg, demonstrating a level of bioactivity via subcutaneous administration that is similar to that obtained via intravenous administration.

Example 34: In Vivo Immunogenicity Screening after Repeated Subcutaneous Doses of the Insulin-Fc Fusion Protein Comprising the Insulin Polypeptide of SEQ ID NO: 4 with a Canine IgGB Isotype Fc Fragment The repeated dose subcutaneous bioactivity of the insulin-Fc fusion protein of SEQ ID NO: 36 was tested in dogs as per the method described in Example 22. N=3 animals were dosed subcutaneously at day 0, at day 35, and at day 42, and the % FBGL was measured for the 7-day window after each dose according to Example 22. The NAOC and NAOCR were calculated according to the procedure of Example 22 for each repeated subcutaneous injection. As illustrated in Table 4, repeated subcutaneous dosing in dogs unexpectedly revealed a significant decay in bioactivity by the third dose as measured by a significant decrease in the NAOCR (i.e., the NAOC for the third injection was only 0.40, or 40%, of the NAOC for the first injection).

TABLE 4

NAOC per dose and NAOCR for repeated doses of SEQ ID NO: 36

| Injection Number of SEQ ID NO: 36 | NAOC (% FBGL· days · kg/mg) | NAOCR (ratioed to Week 1) |
|---|---|---|
| 1 | 330 | 1.0 |
| 2 | 339 | 1.1 |
| 3 | 115 | 0.4 |

Without being bound to any particular explanation it was postulated that the cause of the significant reduction in bioactivity of the insulin-Fc fusion protein of SEQ ID NO: 36 after the third repeated subcutaneous dose in dogs was due to the development of anti-drug antibodies that neutralized its biological activity. Anti-drug antibodies may be directed against the insulin polypeptide, linker, or Fc-fragment portions of an insulin-Fc fusion protein. The immunogenic response manifests as interactions between antigen presenting cells, T-helper cells, B-cells, and their associated cytokines, which may lead to the production of endogenous antibodies against the drug (e.g. anti-drug antibodies). Binding antibodies are all isotypes capable of binding the insulin-Fc fusion protein, and these may be detected in an immunoassay as described in Example 24. Neutralizing antibodies that inhibit functional activity of the insulin-Fc fusion protein are generally directed against an epitope that is required for bioactivity. To assess whether this was the case, serum that was collected prior to the administration of each dose and at the end of the experiment described in Example 11 and Example 12 was tested to quantify the levels of anti-drug antibodies according to Example 24. As shown in FIG. 7, levels of anti-drug antibodies did indeed increase with multiple subcutaneous administrations of the compound, indicating that the generation of neutralizing anti-drug antibodies were the likely cause for the reduction in the NAOCR after the third injection of the insulin Fc-fusion protein of SEQ ID NO: 36.

Example 35: Non-Glycosylated Insulin-Fc Fusion Protein Comprising the Insulin Polypeptide of SEQ ID NO: 4 with Canine IgGB Isotype Fc Fragments to Reduce the Potential Risk of Immunogenicity As shown in Example 32 and Example 33, the insulin-Fc fusion protein of SEQ ID NO: 36 showed acceptable % homodimer content, homodimer titer, and bioactivity in dogs; however, its use for a chronic disease such as diabetes is compromised by the reduction in bioactivity (Example 34) and generation of anti-drug antibodies (Example 34) with repeated subcutaneous dosing. Without being bound to any particular theory, one possible cause of the generation of anti-drug antibodies and the reduction in bioactivity is the increased interaction of the canine IgGB Fc fragment with various receptors of the canine immune system (e.g. Fc(gamma) receptors, e.g. Fc(gamma)RI). Nevertheless, the canine IgGB isotype was the only one of the four canine IgG isotypes that, when used for the Fc fragment, resulted in an insulin-Fc fusion protein meeting the manufacturability and single-dose bioactivity design goals (Example 28). As described in the Detailed Description of the Invention, one method for reducing the Fc(gamma) interaction involves mutating the Fc fragment cNg site to prevent glycosylation during synthesis in the host cell. Therefore, cNg site mutations were made to the Fc fragment region of SEQ ID NO: 36 to reduce the binding affinity of the Fc fragment for Fc(gamma) receptors in vivo, as measured by binding in an in vitro human Fc(gamma)RI assay described in Example 14. Verification of the lack of glycan were performed using the LC-MS method of Example 8, but with omission of the PNGase F treatment step. The position of the cNg site in the insulin-Fc fusion protein of SEQ ID NO: 36 is cNg-NB139. Mutations to SEQ ID NO: 36 included SEQ ID NO: 39 comprising a mutation of cNg-NB139-Q, SEQ ID NO: 40 comprising a mutation of cNg-NB139-S, SEQ ID NO: 41 comprising a mutation of cNg-NB139-D, and SEQ ID NO: 42 comprising a mutation of cNg-NB139-K. The full amino acid sequences of the cNg-mutated insulin-Fc fusion proteins are listed below (with the NB139 position in bold) and the resulting sequence alignments are shown in FIG. 8 (Clustal Omega):

(SEQ ID NO: 39)

FVNQHLCGSDLVEALALVCGERGFFYTDPTGGGPRRGIVEQCCHSICSLYQLENYCNGGGGAG

GGGDCPKCPAPEMLGGPSVFIFPPKPKDTLLIARTPEVTCVVVDLDPEDPEVQISWFVDGKQMQ

TAKTQPREEQFQGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 40)

FVNQHLCGSDLVEALALVCGERGFFYTDPTGGGPRRGIVEQCCHSICSLYQLENYCNGGGGAG

GGGDCPKCPAPEMLGGPSVFIFPPKPKDTLLIARTPEVTCVVVDLDPEDPEVQISWFVDGKQMQ

TAKTQPREEQFSGTYRVVSVLPIGHQDWLKGKQFTCKVNNKALPSPIERTISKARGQAHQPSVY

VLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 41)

FVNQHLCGSDLVEALALVCGERGFFYTDPTGGGPRRGIVEQCCHSICSLYQLENYCNGGGGAG

GGGDCPKCPAPEMLGGPSVFIFPPKPKDTLLIARTPEVTCVVVDLDPEDPEVQISWFVDGKQMQ

TAKTQPREEQFDGTYRVVSVLPIGHQDWLKGKQFTCKVNNKALPSPIERTISKARGQAHQPSVY

VLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPG

-continued

```
                                                  (SEQ ID NO: 42)
FVNQHLCGSDLVEALALVCGERGFFYTDPTGGGPRRGIVEQCCHSICSLYQLENYCNGGGGAG

GGGDCPKCPAPEMLGGPSVFIFPPKPKDTLLIARTPEVTCVVVDLDPEDPEVQISWFVDGKQMQ

TAKTQPREEQFKGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLS

VDKSRWQRGDTFICAVMHEALHNHYTQESLSHSPG.
```

The insulin-Fc fusion proteins were manufactured in HEK293 cells according to Example 1 and purified using a Protein A column according to Example 4. The structures of the insulin-Fc fusion proteins were confirmed according to Example 6 by non-reducing and reducing CE-SDS, and the sequences were further identified by LC-MS with glycan removal according to Example 8. The % homodimer was measured by size-exclusion chromatography according to Example 10. As shown in Table 5, the homodimer titers of the insulin-Fc fusion proteins of SEQ ID NO: 40, SEQ ID NO: 41, and SEQ ID NO: 42 meet the design goal, while unexpectedly the insulin-Fc fusion protein of SEQ ID NO: 39 containing the cNg-NB139-Q mutation did not meet the design goal for homodimer titer.

TABLE 5

Homodimer titers for cNg variations of SEQ ID NO: 36

| SEQ ID NO: | cNg Mutation | Protein Yield (mg/L) | % Homodimer | Homodimer Titer (mg/L) |
|---|---|---|---|---|
| SEQ ID NO: 39 | cNg-Q | 37 | 98% | 36 |
| SEQ ID NO: 40 | cNg-S | 77 | 98% | 75 |
| SEQ ID NO: 41 | cNg-D | 88 | 98% | 86 |
| SEQ ID NO: 42 | cNg-K | 68 | 98% | 67 |

To determine which of the remaining three compounds was most likely to exhibit reduced immunogenicity, the Fc(gamma) receptor binding was measured according to the procedure of Example 15. Low Fc(gamma) receptor binding is most likely to correlate with minimum immunogenicity. Table 6 compares the Fc(gamma) receptor I binding of these insulin-Fc fusion proteins with the Fc(gamma) receptor binding of the insulin-Fc fusion protein of SEQ ID NO: 36 demonstrating unexpectedly that the insulin-Fc fusion protein of SEQ ID NO: 41, containing the cNg-D mutation, exhibits an Fc (gamma) receptor binding activity that is approximately twice that of the insulin-Fc fusion proteins of SEQ ID NO: 40, containing the cNg-S mutation and SEQ ID NO: 42 containing the cNg-K mutation. Therefore, only the insulin-Fc fusion proteins comprising the latter two compounds containing the cNg-S mutation and the cNg-K mutations were deemed suitable for repeated dose bioactivity testing in dogs.

TABLE 6

Fc(gamma) receptor binding for cNg variations of SEQ ID NO: 36

| SEQ ID NO: | cNg Mutation | OD 450 nm Log[Fc(gamma) RI] (ng/mL) | OD 450 nm Minus Assay Back-ground | Ratio to SEQ ID NO: 36 |
|---|---|---|---|---|
| SEQ ID NO: 36 | Native cNg | 0.386 | 0.323 | 1.00 |
| SEQ ID NO: 40 | cNg-S | 0.140 | 0.077 | 0.24 |
| SEQ ID NO: 41 | cNg-D | 0.204 | 0.141 | 0.44 |
| SEQ ID NO: 42 | cNg-K | 0.126 | 0.063 | 0.20 |
| Assay background (no compound) | N/A | 0.063 | 0.000 | N/A |

Example 36: Evaluation of In Vivo Bioactivity and Immunogenicity of an Insulin Polypeptide of SEQ ID NO: 4 with the Non-Glycosylated cNg-K and cNg-S Canine IgGB Isotype Fc Fragments To determine if the insulin-Fc fusion protein of SEQ ID NO: 40, containing the cNg-S mutation, improved the repeated dose bioactivity performance in dogs, the compound was administered subcutaneously to N=1 dog on day 0, day 7, day 14, and on day 28 according to the procedure of Example 22. When the dog's % FBGL dropped too low, the dog was given food to raise the blood glucose to a safe level. The NAOC for the first injection was 191% FBGL·days·kg/mg, showing that the insulin-Fc fusion protein of SEQ ID NO: 40 was satisfactorily bioactive in vivo. The NAOC and NAOCR were also measured for each subsequent dose according to the general procedure of Example 22, calculated from the time the dose was administered until just before the next dose was administered. The NAOC and the NAOCR shown in Table 7 illustrate that the insulin-Fc fusion protein of SEQ ID NO: 40 exhibited an NAOCR that decreased significantly on doses 3 and 4 of a four dose regimen. Therefore, the insulin-Fc fusion protein of SEQ ID NO: 40, containing the cNg-S mutation, was unable to demonstrate repeated dose bioactivity in dogs despite having a low Fc(gamma)RI binding four times lower than that of the insulin-Fc fusion protein of SEQ ID NO: 36.

TABLE 7

NAOC per dose for repeated doses of SEQ ID NO: 40

| Injection Number of SEQ ID NO: 40 | NAOC (% FBGL · days · kg/mg) | NAOCR |
|---|---|---|
| 1 | 191 | 1.0 |
| 2 | 240 | 1.3 |

TABLE 7-continued

| NAOC per dose for repeated doses of SEQ ID NO: 40 | | |
|---|---|---|
| Injection Number of SEQ ID NO: 40 | NAOC (% FBGL · days · kg/mg) | NAOCR |
| 3 | 0 | 0.0 |
| 4 | 39 | 0.2 |

To determine if the insulin-Fc fusion protein of SEQ ID NO: 42, containing the cNg-K mutation, improved the repeated dose bioactivity performance in dogs, the compound was administered subcutaneously to N=1 dog on day 0, day 7, day 14, and on day 28 according to the procedure of Example 22. When the dog's % FBGL dropped too low, the dog was given food to raise the blood glucose to a safe level. The NAOC for the first injection was 449% FBGL·days·kg/mg, showing that the insulin-Fc fusion protein of SEQ ID NO: 42 was satisfactorily bioactive in vivo. The pharmacokinetic profile of the compound was also measured by the method of Example 23 using ELISA, and a two-compartment model was fit to the data to determine its elimination half-life which was about 0.9 days. The NAOC and NAOCR were also measured for each subsequent dose according to the general procedure of Example 22, calculated from the time the dose was administered until just before the next dose was administered. The NAOC and the NAOCR shown in Table 8 illustrate that the insulin-Fc fusion protein of SEQ ID NO: 42 maintains an NAOCR greater than 0.6 throughout the four doses. Therefore, unexpectedly, the insulin-Fc fusion protein of SEQ ID NO: 42, containing the cNg-K mutation, was the only non-glycosylated mutant of the insulin-Fc fusion protein of SEQ ID NO: 36 resulting in significantly improved repeated dose bioactivity in dogs.

TABLE 8

| NAOC per dose for repeated doses of SEQ ID NO: 42 | | |
|---|---|---|
| Injection Number of SEQ ID NO: 42 | NAOC (% FBGL · days · kg/mg) | NAOCR |
| 1 | 449 | 1.0 |
| 2 | 361 | 0.8 |
| 3 | 259 | 0.6 |
| 4 | 638 | 1.4 |

Figure 9:
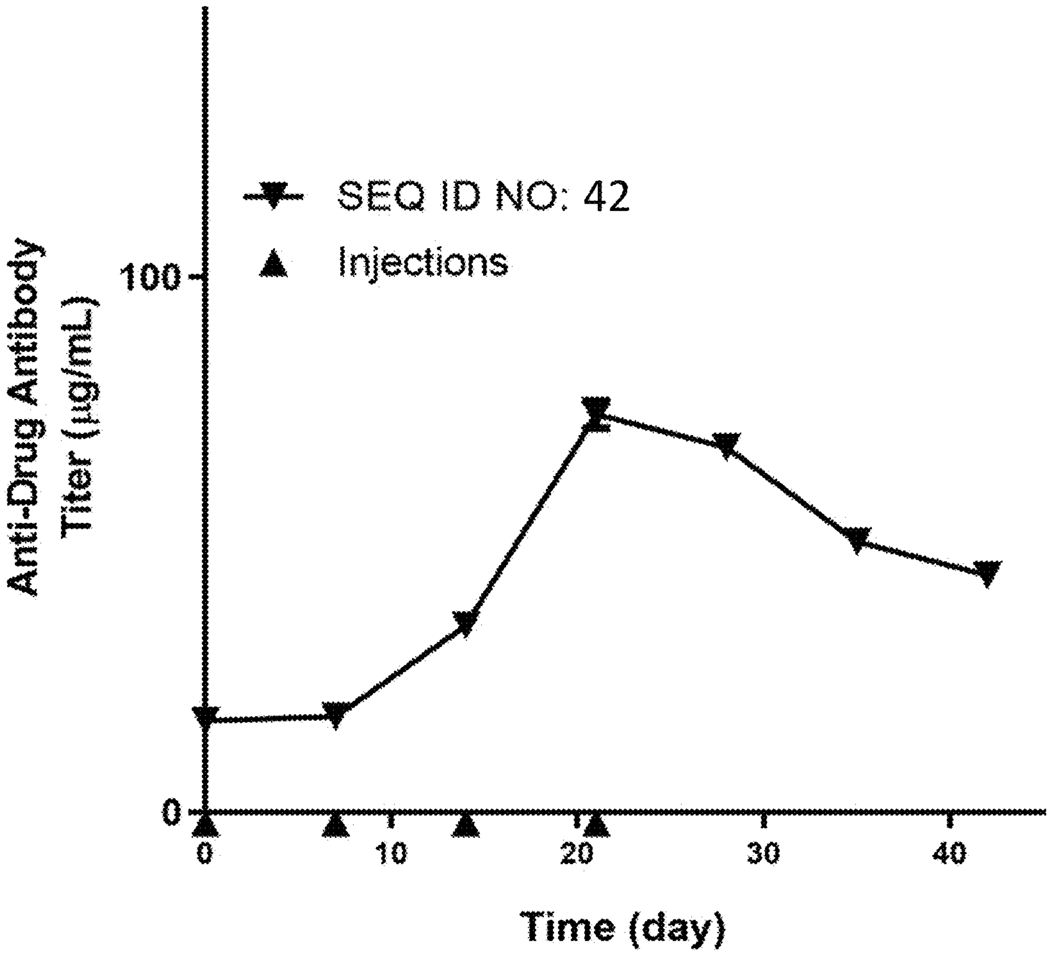
FIG. 9 shows the average anti-drug antibody titer (μg/mL) for N=1 dog dosed subcutaneously on Day 0 (0.33 mg/kg), Day 7 (0.50 mg/kg), Day 14 (0.50 mg/kg), and Day 21 (0.50 mg/kg) with the homodimer of SEQ ID NO: 42.

The levels of anti-drug and anti-insulin antibodies were also measured throughout the course of treatment (28 days) and for an additional two weeks according to Example 24. FIG. 9 illustrates that the insulin-Fc fusion protein of SEQ ID NO: 42 still generated anti-drug antibodies with repeated subcutaneous dosing in dogs, but the anti-drug antibody titers were much lower than those generated by the insulin-Fc fusion protein of SEQ ID NO: 36 (Example 32).

Example 37: Screening of Canine Serum Containing Anti-Drug Antibodies and Identification of Potential Immunogenic Epitopes at the B10D and A8H Positions of the Insulin Polypeptide Mutating the cNg site of the canine IgGB Fc fragment to a Lys (i.e., cNg-K) did improve the repeated dose bioactivity of the insulin-fusion protein comprising the insulin polypeptide of SEQ ID NO: 4 and the peptide linker of SEQ ID NO: 11 (Example 36), but the resulting insulin-Fc fusion protein of SEQ ID NO: 42 still gave rise to anti-drug antibodies (Example 36). It was hypothesized, therefore, that the insulin polypeptide of SEQ ID NO: 4 may unexpectedly contain specific epitopes (i.e., immunogenic "hot spots") against which the dog's immune system is directed. Therefore, the binding specificity of the antibodies present in the serum samples described in Example 24 were evaluated according to the general procedure of Example 27. The analysis of the antibody-containing serum samples from the repeated dosing of the insulin-Fc fusion protein of SEQ ID NO: 36 (Example 32) against the coated insulin-Fc fusion protein library demonstrated that there were unexpectedly two primary "hot spots" present within the insulin polypeptide sequence of SEQ ID NO: 5: the aspartic acid mutation at the 10th position from the N-terminus of the B-chain (i.e., B10), and, separately, the histidine mutation at the 8th position from the N-terminal end of the A-chain (i.e., A8). The results suggest that insulin-Fc fusion proteins comprising insulin polypeptide amino acid compositions containing these two particular amino acid mutations are likely to be immunogenic in dogs and therefore likely to give rise to anti-drug antibodies that neutralize the bioactivity after repeated injections. Therefore, it was determined that insulin polypeptides that do not contain the B10 aspartic acid and A8 histidine are preferred for insulin-Fc fusion proteins that need to be repeatedly dosed in dogs over long periods long-term (e.g., to treat canine diabetes).

Example 38: An Insulin-Fc Fusion Protein Comprising the Insulin Polypeptide of SEQ ID NO: 4 and a Non-Glycosylated Canine IgGB Isotype Fc Fragment in which the B10D and ABH Mutations of the Insulin Polypeptide are Restored to Native Compositions to Reduce the Potential Risk of Immunogenicity To evaluate whether replacing the "hot spot" mutations would improve the immunogenicity and repeated dose bioactivity of insulin-Fc fusion proteins comprising the insulin polypeptide of SEQ ID NO: 4 and the canine IgGB isotype fragment, an exemplary insulin-Fc fusion protein (SEQ ID NO: 43) was synthesized in which the B10 and A8 amino acids of the insulin polypeptide were restored to their native histidine and threonine compositions, respectively (SEQ ID NO: 63) listed below with non-native amino acids in bold.

(SEQ ID NO: 63)

FVNQHLCGSHLVEALALVCGERGFFYTDPTGGGPRRGIVEQCCTSICSLY

QLENYCN.

Furthermore, given the additional potential benefits of the non-glycosylated cNg mutants, the insulin-Fc fusion protein of SEQ ID NO: 43 contains the cNg-Q mutation. The entire amino acid sequence of the insulin-Fc fusion protein of SEQ ID NO: 43 is given below:

(SEQ ID NO: 43)

FVNQHLCGSHLVEALALVCGERGFFYTDPTGGGPRRGIVEQCCTSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFQGTYRVVSVLPI

GHQDWLKGKQFTCKVNNKALPSPIERTISKARGQAHQPSVYVLPPSREEL

-continued

SKNTVSLTCLIKDFFPPDIDVEWQSNGQQEPESKYRTTPPQLDEDGSYFL

YSKLSVDKSRWQRGDTFICAVMHEALHNHYTQESLSHSPG.

The insulin-Fc fusion protein of SEQ ID NO: 43 was manufactured in HEK293 cells according to Example 1 and purified using a Protein A column according to Example 4. The resulting protein yield was only 21 mg/L. The structure was confirmed according to Example 6 by non-reducing and reducing CE-SDS, and the sequence was further identified by LC-MS with glycan removal according to Example 8. The % homodimer as measured by size-exclusion chromatography according to Example 10, was 98.0% indicating that the protein was relatively free of aggregates.

Figure 10:
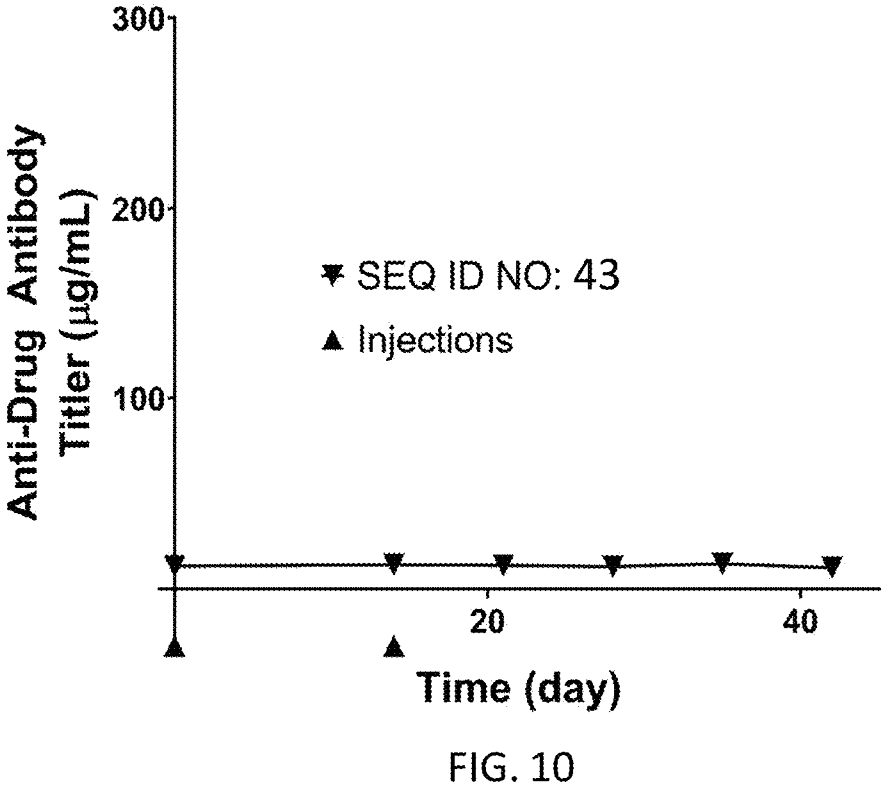
FIG. 10 shows the average anti-drug antibody titer (μg/mL) for N=1 dogs dosed subcutaneously on Day 0 (0.33 mg/kg) and Day 14 (0.16 mg/kg) with the homodimer of SEQ ID NO: 43.

Despite the relatively low homodimer titer of 21 mg/L, the insulin-Fc fusion protein of SEQ ID NO: 43 was evaluated in dogs for in vivo bioactivity and immunogenicity according to the procedures of Example 22, Example 23, and Example 24, respectively. FIG. 10 demonstrates that restoration of the B10D and A8H mutations to their native amino acids (i.e., B10H and A8T) in the insulin-Fc fusion protein of SEQ ID NO: 43 did significantly reduce the immunogenicity of the parent compound (SEQ ID NO: 36).

Figure 11:
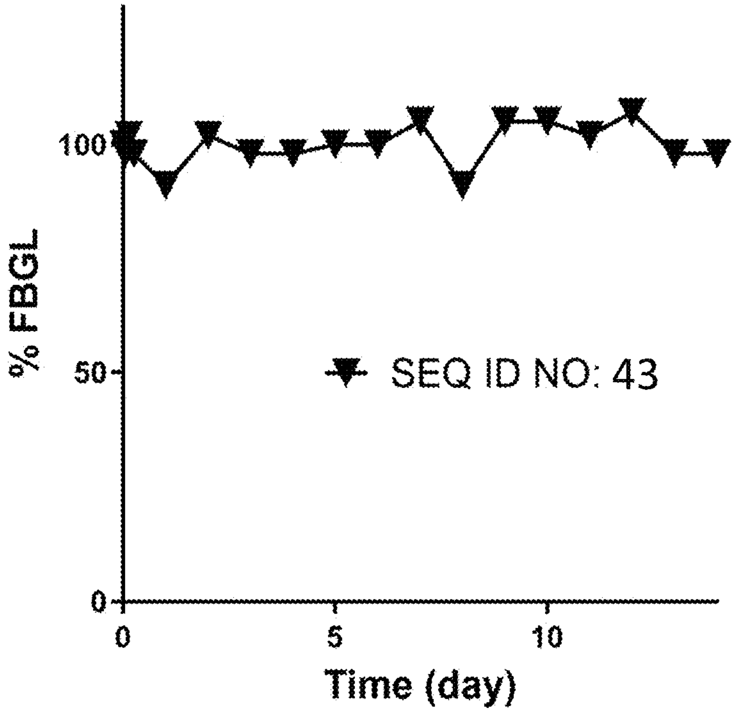
FIG. 11 shows average % fasting blood glucose levels from Day 0 to Day 7 for N=2 dogs dosed subcutaneously on Day 0 at 0.33 mg/kg with the homodimer of SEQ ID NO: 43.

However, as shown in FIG. 11, the insulin-Fc fusion protein of SEQ ID NO: 43 containing the native B10 and A8 amino acids was not bioactive (i.e., the NAOC was essentially zero).

Example 39: Attempts to Incorporate Additional B-Chain and A-Chain Mutations into the Insulin Polypeptide of SEQ ID NO: 63 to Improve the Bioactivity of the Associated Insulin-Fc Fusion Proteins Containing the Canine IgGB Fc Fragment The fact that the insulin-Fc fusion protein of SEQ ID NO: 43 did not generate anti-drug antibodies (Example 38) compared to the insulin-Fc fusion protein of SEQ ID NO: 36 (Example 33) provides strong evidence for the theory that the B10D and A8H mutations in the insulin polypeptide of SEQ ID NO: 4 are likely the immunogenic epitopes responsible for the production of anti-drug antibodies. However, the lack of in vivo potency of the insulin-Fc fusion protein of SEQ ID NO: 43 compared to that of SEQ ID NO: 36 indicates that these two amino acid mutations are also responsible for achieving acceptable levels of bioactivity. The lack of in vivo potency for the insulin-Fc fusion protein of SEQ ID NO: 43 correlates with its high IC50 (shown in Table 9 below) as measured by the insulin receptor binding assay according to the method of Example 12. Therefore, further efforts were required to increase the insulin-Fc fusion protein bioactivity (i.e., decrease the insulin receptor binding assay IC50 value to less than 5000 nM, or more preferably less than 4000 nM, or even more preferably less than 3000 nM) while maintaining a low degree of immunogenicity by keeping the native B10 and A8 amino acids in the insulin polypeptide.

It is known that various portions of the insulin B-chain and A-chain are required for strong binding to the IR (Hubbard S. R., "Structural biology: Insulin meets its receptor", Nature. 2013; 493(7431):171-172). Therefore, portions of the B-chain or A-chain were modified while keeping the B10 and A8 the same as in native insulin and the C-chain and peptide linker constant. Several of these insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. Their sequences are shown below, and the resulting sequence alignments against SEQ ID NO: 43 are shown in FIG. 12 (Clustal Omega).

(SEQ ID NO: 44)

FVNQHLCGSHLVQALYLVCGERGFFYTDPTGGGPRRGIVEQCCTSICSLYQLENYCGGGGAGG

GGDCPKCPAPEMLGGPSVFIFPPKPKDTLLIARTPEVTCVVVDLDPEDPEVQISWFVDGKQMQT

AKTQPREEQFSGTYRVVSVLPIGHQDWLKGKQFTCKVNNKALPSPIERTISKARGQAHQPSVYV

LPPSREELSKNTVSLTCLIKDFFPPDIDVEWQSNGQQEPESKYRTTPPQLDEDGSYFLYSKLSVD

KSRWQRGDTFICAVMHEALHNHYTQESLSHSPG (SEQ ID NO: 45)

FVNQHLCGSELVEALALVCGERGFFYTDPTGGGPRRGIVEQCCTSICSLYQLENYCGGGGAGG

GGDCPKCPAPEMLGGPSVFIFPPKPKDTLLIARTPEVTCVVVDLDPEDPEVQISWFVDGKQMQT

AKTQPREEQFSGTYRVVSVLPIGHQDWLKGKQFTCKVNNKALPSPIERTISKARGQAHQPSVYV

LPPSREELSKNTVSLTCLIKDFFPPDIDVEWQSNGQQEPESKYRTTPPQLDEDGSYFLYSKLSVD

KSRWQRGDTFICAVMHEALHNHYTQESLSHSPG (SEQ ID NO: 46)

FVNQHLCGSHLVEALALVCGEAGFFYTDPTGGGPRRGIVEQCCTSICSLYQLENYCGGGGAGG

GGDCPKCPAPEMLGGPSVFIFPPKPKDTLLIARTPEVTCVVVDLDPEDPEVQISWFVDGKQMQT

AKTQPREEQFSGTYRVVSVLPIGHQDWLKGKQFTCKVNNKALPSPIERTISKARGQAHQPSVYV

LPPSREELSKNTVSLTCLIKDFFPPDIDVEWQSNGQQEPESKYRTTPPQLDEDGSYFLYSKLSVD

KSRWQRGDTFICAVMHEALHNHYTQESLSHSPG

-continued (SEQ ID NO: 47)
FVNQHLCGSHLVEALALVCGERGFYYTDPTGGGPRRGIVEQCCTSICSLYQLENYCGGGGAGG
GGDCPKCPAPEMLGGPSVFIFPPKPKDTLLIARTPEVTCVVVDLDPEDPEVQISWFVDGKQMQT
AKTQPREEQFSGTYRVVSVLPIGHQDWLKGKQFTCKVNNKALPSPIERTISKARGQAHQPSVYV
LPPSREELSKNTVSLTCLIKDFFPPDIDVEWQSNGQQEPESKYRTTPPQLDEDGSYFLYSKLSVD
KSRWQRGDTFICAVMHEALHNHYTQESLSHSPG (SEQ ID NO: 48)
FVNQHLCGSHLVEALALVCGERGFFYTDPTGGGPRRGIVEQCCTSICSLYQLENYCGGGGAGG
GGDCPKCPAPEMLGGPSVFIFPPKPKDTLLIARTPEVTCVVVDLDPEDPEVQISWFVDGKQMQT
AKTQPREEQFSGTYRVVSVLPIGHQDWLKGKQFTCKVNNKALPSPIERTISKARGQAHQPSVYV
LPPSREELSKNTVSLTCLIKDFFPPDIDVEWQSNGQQEPESKYRTTPPQLDEDGSYFLYSKLSVD
KSRWQRGDTFICAVMHEALHNHYTQESLSHSPG

TABLE 9

% homodimer, homodimer titers, and IR IC50 values for various SEQ ID NOs.

| SEQ ID NO: | % Homodimer | HEK homodimer titer (mg/L) | IR IC50 (nM) |
|---|---|---|---|
| SEQ ID NO: 43 | 98.0% | 21 | >5000 |
| SEQ ID NO: 44 | 97.6% | 9 | 2624 |
| SEQ ID NO: 45 | 81.4% | 17 | 633 |
| SEQ ID NO: 46 | 99.1% | 22 | >5000 |
| SEQ ID NO: 47 | 96.6% | 25 | 2402 |
| SEQ ID NO: 48 | 98.0% | 6 | >5000 |

In only three cases (SEQ ID NO: 44, SEQ ID NO: 45, and SEQ ID NO: 47 did the proposed mutations improve the IR binding (i.e., lower the IC50 value) as compared to SEQ ID NO: 43. However, none of the mutations resulted in compounds that meet the manufacturing design goal of a homodimer titer greater than 50 mg/L, and in some cases, the mutations lead to significantly reduced manufacturability (e.g., homodimer titers less than 20 mg/L).

Example 40: Attempts to Incorporate C-Chain Mutations into the Insulin Polypeptide of SEQ ID NO: 63 to Improve the Bioactivity of the Associated Insulin-Fc Fusion Proteins Containing the Canine IgGB Fc Fragment The results obtained in Example 39 showed that all attempts to mutate the A-chain and B-chain of the insulin polypeptide of SEQ ID NO: 63 resulted in unacceptably low HEK homodimer titers of the associated insulin-Fc fusion (i.e., homodimer titers less than or equal to 25 mg/L). Therefore, there was a need for further experimentation. In the present example, the C-chain composition of the insulin polypeptide of SEQ ID NO: 63 was mutated by making it longer or by increasing its flexibility. Native insulin (e.g. human insulin) has been shown to undergo a significant conformational change that involves movement of both the B-chain and A-chain folding as it binds to the insulin receptor (e.g., as described by Menting, et al., *Nature,* 2013; 493(7431): pp 241-245). Native insulin, unlike the insulin polypeptides of the present invention, is freely able to undergo this conformational change at the insulin receptor, because it is a two-chain polypeptide in its native form, connected only through two disulfide bonds with no C-chain constraining the mobility of the A- and B-chains. Without being bound by any particular theory, it was hypothesized that the C-chain contained within the insulin polypeptide of SEQ ID NO: 63 was too inflexible (e.g. an amino acid composition and sequence that does not permit facile movement between the B-chain and A-chain) and/or too short (e.g. not enough amino acids between the C-terminus of the B-chain and the N-terminus of the A-chain) thus preventing the insulin polypeptide from undergoing the necessary change in molecular shape required for strong binding to the insulin receptor. Therefore, several insulin-Fc fusion proteins were synthesized based on the insulin-Fc fusion protein of SEQ ID NO: 43 with variations in the insulin polypeptide C-chain as shown below with the resulting sequence alignments against SEQ ID NO: 43 shown in FIG. 13 (Clustal Omega).

(SEQ ID NO: 49)
FVNQHLCGSHLVQALYLVCGERGFFYTDPTQRGGGGGQRGIVEQCCTSICSLYQLENYCGGGG
AGGGGDCPKCPAPEMLGGPSVFIFPPKPKDTLLIARTPEVTCVVVDLDPEDPEVQISWFVDGKQ
MQTAKTQPREEQFSGTYRVVSVLPIGHQDWLKGKQFTCKVNNKALPSPIERTISKARGQAHQPS
VYVLPPSREELSKNTVSLTCLIKDFFPPDIDVEWQSNGQQEPESKYRTTPPQLDEDGSYFLYSKL
SVDKSRWQRGDTFICAVMHEALHNHYTQESLSHSPG (SEQ ID NO: 50)
FVNQHLCGSHLVEALALVCGERGFFYTDPTGGGGGGSGGGGGIVEQCCTSICSLYQLENYCGG
GGAGGGGDCPKCPAPEMLGGPSVFIFPPKPKDTLLIARTPEVTCVVVDLDPEDPEVQISWFVDG
KQMQTAKTQPREEQFSGTYRVVSVLPIGHQDWLKGKQFTCKVNNKALPSPIERTISKARGQAH

-continued

```
QPSVYVLPPSREELSKNTVSLTCLIKDFFPPDIDVEWQSNGQQEPESKYRTTPPQLDEDGSYFLY
SKLSVDKSRWQRGDTFICAVMHEALHNHYTQESLSHSPG
```

(SEQ ID NO: 51)

```
FVNQHLCGSHLVEALALVCGERGFFYTDPGGGGGGGGGIVEQCCTSICSLYQLENYCGGGGAG
GGGDCPKCPAPEMLGGPSVFIFPPKPKDTLLIARTPEVTCVVVDLDPEDPEVQISWFVDGKQMQ
TAKTQPREEQFSGTYRVVSVLPIGHQDWLKGKQFTCKVNNKALPSPIERTISKARGQAHQPSVY
VLPPSREELSKNTVSLTCLIKDFFPPDIDVEWQSNGQQEPESKYRTTPPQLDEDGSYFLYSKLSV
DKSRWQRGDTFICAVMHEALHNHYTQESLSHSPG
```

(SEQ ID NO: 52)

```
FVNQHLCGSHLVEALALVCGERGFFYTPGGGGGGGGGIVEQCCTSICSLYQLENYCGGGGAGG
GGDCPKCPAPEMLGGPSVFIFPPKPKDTLLIARTPEVTCVVVDLDPEDPEVQISWFVDGKQMQT
AKTQPREEQFSGTYRVVSVLPIGHQDWLKGKQFTCKVNNKALPSPIERTISKARGQAHQPSVYV
LPPSREELSKNTVSLTCLIKDFFPPDIDVEWQSNGQQEPESKYRTTPPQLDEDGSYFLYSKLSVD
KSRWQRGDTFICAVMHEALHNHYTQESLSHSPG
```

TABLE 10

% homodimer, homodimer titers, and IR IC50 values for various SEQ ID NOs.

| SEQ ID NO: | % Homodimer | HEK homodimer titer (mg/L) | IR IC50 (nM) |
|---|---|---|---|
| SEQ ID NO: 43 | 98.0% | 21 | >5000 |
| SEQ ID NO: 49 | 94.0% | 8 | 4176 |
| SEQ ID NO: 50 | 99.6% | 37 | 1609 |
| SEQ ID NO: 51 | 98.3% | 42 | >5000 |
| SEQ ID NO: 52 | 98.6% | 33 | 4720 |

The insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. The results are shown in Table 10. In only one case, (SEQ ID NO: 50) which comprises the longest C-chain (GGGGGGSGGGG—SEQ ID NO: 71), did a C-chain mutation significantly improve the insulin receptor binding affinity (IC50 less than 3000 nM) compared to that of the insulin-Fc fusion protein of SEQ ID NO: 43. However, none of these C-chain-mutated insulin-Fc fusion proteins exhibited a homodimer titer greater than the manufacturing design goal of 50 mg/L. In fact, in one case (SEQ ID NO: 49) the C-chain mutation unexpectedly led to significantly lower homodimer titers.

Example 41: Attempts to Incorporate Peptide Linker Mutations into Insulin-Fc Fusion Proteins Containing the Insulin Polypeptide of SEQ ID NO: 63 and the Canine IgGB Fc Fragment to Improve Bioactivity Without being bound by any particular theory, another possible reason for the poor insulin receptor binding of the insulin-Fc fusion protein of SEQ ID NO: 43 was thought to involve the steric hindrance between the insulin polypeptide and the insulin receptor resulting from the close proximity of the much larger Fc fragment molecule attached to the insulin polypeptide through the peptide linker. Shorter peptide linkers or more tightly folded peptide linkers were thought to potentially exacerbate this issue, while longer peptide linkers or peptide linkers that are resistant to folding back on themselves (e.g., linkers with more molecular stiffness) may alleviate this issue by creating more space between the insulin polypeptide and the Fc fragment. The increased space between the insulin polypeptide and the Fc fragment would also increase the distance between the insulin receptor and the Fc fragment leading to less interference during insulin receptor binding. The peptide linker of SEQ ID NO: 11 (i.e., GGGGAGGGG) used to construct the insulin-Fc fusion protein of SEQ ID NO: 43 was hypothesized to be potentially too short and/or too flexible, because the amino acids that comprise the linker contain no side chains (i.e., it contains only glycine and alanine amino acids). Therefore, to test this hypothesis, two other insulin-Fc fusion protein variants of the insulin-Fc fusion protein of SEQ ID NO: 43 were synthesized. The insulin-Fc fusion protein of SEQ ID NO: 48 contained the same peptide linker as was used to construct the insulin-Fc fusion protein of SEQ ID NO: 43 but with an insulin polypeptide in which the asparagine at the $21^{st}$ position from the N-terminus of the A chain (i.e., A21) was absent (i.e., des-A21). This particular mutation was incorporated to see whether the junction between the A-chain and the peptide linker affects the protein yield and/or bioactivity of the molecule. The other insulin-Fc fusion protein of SEQ ID NO: 53 contains this des-A21N A-chain mutation and a peptide linker that is more than twice the length of that used to construct the insulin-Fc fusion protein of SEQ ID NO: 43. In this longer peptide linker, alanine is disfavored and instead is replaced with a glutamine, which contains a polar amide side chain. The glutamine substitutions were expected to increase the hydrophilic nature of the peptide linker and potentially prevent the linker from folding back against itself. The sequences are shown below with the resulting sequence alignments against SEQ ID NO: 43 shown in FIG. 14 (Clustal Omega).

(SEQ ID NO: 53)
FVNQHLCGSHLVEALALVCGERGFFYTDPTGGGPRRGIVEQCCTSICSLYQLENYCGGGGGQG
GGGQGGGGQGGGGGDCPKCPAPEMLGGPSVFIFPPKPKDTLLIARTPEVTCVVVDLDPEDPEV
QISWFVDGKQMQTAKTQPREEQFSGTYRVVSVLPIGHQDWLKGKQFTCKVNNKALPSPIERTIS
KARGQAHQPSVYVLPPSREELSKNTVSLTCLIKDFFPPDIDVEWQSNGQQEPESKYRTTPPQLDE
DGSYFLYSKLSVDKSRWQRGDTFICAVMHEALHNHYTQESLSHSPG (SEQ ID NO: 48)
FVNQHLCGSHLVEALALVCGERGFFYTDPTGGGPRRGIVEQCCTSICSLYQLENYCGGGGAGG
GGDCPKCPAPEMLGGPSVFIFPPKPKDTLLIARTPEVTCVVVDLDPEDPEVQISWFVDGKQMQT
AKTQPREEQFSGTYRVVSVLPIGHQDWLKGKQFTCKVNNKALPSPIERTISKARGQAHQPSVYV
LPPSREELSKNTVSLTCLIKDFFPPDIDVEWQSNGQQEPESKYRTTPPQLDEDGSYFLYSKLSVD
KSRWQRGDTFICAVMHEALHNHYTQESLSHSPG

TABLE 11

% homodimer, homodimer titers, and IR IC50 values for various SEQ ID NOs.

| SEQ ID NO: | % Homodimer | HEK Homodimer titer (mg/L) | IR IC50 (nM) |
|---|---|---|---|
| SEQ ID NO: 43 | 98.0% | 21 | >5000 |
| SEQ ID NO: 48 | 98.0% | 6 | >5000 |
| SEQ ID NO: 53 | 99.6% | 11 | 1281 |

The two insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. The results are given in Table 11. The incorporation of a longer peptide linker of different composition (GGGGGQGGGGQGGGGQGGGGG (SEQ ID NO: 13) for SEQ ID NO: 53 vs. GGGGAGGGG (SEQ ID NO: 11) for SEQ ID NO: 43) did improve the insulin receptor binding as measured by a significant reduction in the IC50 value, indicating that longer linkers may be a strategy for increasing insulin receptor binding for other insulin-Fc fusion proteins. However, the incorporation of a longer linker still did not improve the homodimer titers to above the manufacturing design goal of greater than 50 mg/L.

Example 42: Attempts to Delete Portions of the B-Chain of the Insulin Polypeptide of SEQ ID NO: 63 to Improve the Homodimer Titer of the Associated Insulin-Fc Fusion Proteins Containing the Canine IgGB Fc Fragment The results from Example 41 demonstrate that the peptide linker can be modified to increase the insulin receptor binding affinity of the insulin-Fc fusion protein of SEQ ID NO: 43, which contains the native B10 and A8 amino acids. However, the peptide linker mutation failed to increase the homodimer titer enough to meet the manufacturing design goal. Because the homodimer titer is a function of several properties, including the intracellular synthesis and processing within cells, it was hypothesized that perhaps the insulin-Fc molecule was self-associating (i.e., aggregating) during and after synthesis either intramolecularly between the two monomers of the homodimer or intermolecularly between two or more separate homodimers. This aggregation would lead to unacceptably low homodimer titers obtained from the cell culture supernatants during the production process described in Example 1, Example 4, and Example 10. This potential interaction between the insulin-Fc fusion protein molecules could be due, in part, to insulin's well-known propensity to self-associate and form aggregates. One method known in the art to reduce the propensity for insulin to self-associate involves mutating the amino acids near the C-terminus of the B-chain. For example, insulin lispro (B28K; B29P mutations) and insulin aspart (B28D mutation) are well-known commercial two-chain insulins with non-native B-chain mutations that prevent association and aggregation thus giving rise to a predominantly monomeric form of insulin in solution. Another approach to prevent aggregation involves amino acid structural deletions. For example, a two-chain insulin known as despentapeptide insulin (DPPI; see Brange J., Dodson G. G., Edwards J., Holden P. H., Whittingham J. L. 1997b. "A model of insulin fibrils derived from the x-ray crystal structure of a monomeric insulin (despentapeptide insulin)" *Proteins* 27 507-516), is identical to native two-chain human insulin except that the five C-terminal amino acids of the B-chain (YTPKT) are removed. DPPI has a lower binding affinity to the insulin receptor as compared to the native two-chain human insulin, but it is completely monomeric in solution, meaning that there is no significant association or aggregation between DPPI molecules. Therefore, in an attempt to decrease the potential for intramolecular and intermolecular self-association and improve the insulin-Fc fusion protein homodimer titer, several variants of the insulin-Fc fusion protein of SEQ ID NO: 43 were constructed using partial B-chain amino acid truncation and B-chain amino acid mutations as described above for DPPI, insulin lispro, and insulin aspart. The sequences are shown below with the resulting sequence alignments against SEQ ID NO: 43 shown in FIG. 15 (Clustal Omega).

(SEQ ID NO: 51)
FVNQHLCGSHLVEALALVCGERGFFYTDPGGGGGGGGGIVEQCCTSICSLYQLENYCGGGGAG

GGGDCPKCPAPEMLGGPSVFIFPPKPKDTLLIARTPEVTCVVVDLDPEDPEVQISWFVDGKQMQ

TAKTQPREEQFSGTYRVVSVLPIGHQDWLKGKQFTCKVNNKALPSPIERTISKARGQAHQPSVY

VLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 52)
FVNQHLCGSHLVEALALVCGERGFFYTPGGGGGGGGGIVEQCCTSICSLYQLENYCGGGGAGG

GGDCPKCPAPEMLGGPSVFIFPPKPKDTLLIARTPEVTCVVVDLDPEDPEVQISWFVDGKQMQT

AKTQPREEQFSGTYRVVSVLPIGHQDWLKGKQFTCKVNNKALPSPIERTISKARGQAHQPSVYV

LPPSREELSKNTVSLTCLIKDFFPPDIDVEWQSNGQQEPESKYRTTPPQLDEDGSYFLYSKLSVD

KSRWQRGDTFICAVMHEALHNHYTQESLSHSPG (SEQ ID NO: 54)
FVNQHLCGSHLVEALALVCGERGFFYTQGGGGGGGGGIVEQCCTSICSLYQLENYCGGGGAGG

GGDCPKCPAPEMLGGPSVFIFPPKPKDTLLIARTPEVTCVVVDLDPEDPEVQISWFVDGKQMQT

AKTQPREEQFSGTYRVVSVLPIGHQDWLKGKQFTCKVNNKALPSPIERTISKARGQAHQPSVYV

LPPSREELSKNTVSLTCLIKDFFPPDIDVEWQSNGQQEPESKYRTTPPQLDEDGSYFLYSKLSVD

KSRWQRGDTFICAVMHEALHNHYTQESLSHSPG

TABLE 12

% homodimer, homodimer titers, and IR IC50 values for various SEQ ID NOs.

| SEQ ID NO: | % Homodimer | HEK Homodimer titer (mg/L) | IR IC50 (nM) |
|---|---|---|---|
| SEQ ID NO: 43 | 98.0% | 21 | >5000 |
| SEQ ID NO: 51 | 98.3% | 42 | 1915 |
| SEQ ID NO: 54 | 99.4% | 22 | 2195 |
| SEQ ID NO: 52 | 98.6% | 33 | 1930 |

The insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. The results are given in Table 12. The homodimer titer of the resulting compounds was only significantly increased in one case (SEQ ID NO: 51), but unexpectedly, the insulin receptor affinity was improved for all of the mutated compounds (SEQ ID NO: 51, SEQ ID NO: 54, and SEQ ID NO: 52).

Example 43: Attempts to Combine B-Chain, C-Chain, and A-Chain Mutations, B-Chain Truncation, and Linker Mutations to the Insulin-Fc Fusion Protein of SEQ ID NO: 43 to Further Improve Homodimer Titer and Bioactivity As shown in Example 39, Example 40, Example 41 and Example 42, no single strategy successfully incorporated an insulin polypeptide comprising the non-immunogenic native B10 and A8 amino acids with the canine IgGB Fc fragment to form an insulin-Fc fusion protein with acceptable insulin receptor activity and homodimer titer. Therefore, the concepts of a longer C-chain, a longer peptide linker, and truncation of the C-terminal amino acids of the B-chain were combined. In addition, to potentially further decrease the propensity for self-association and aggregation, additional point mutations were introduced to the native insulin hydrophobic amino acid residue sites using less hydrophobic amino acids, including those with side groups that are negatively or positively charged at physiological pH. Example mutations included tyrosine to alanine, tyrosine to glutamic acid, isoleucine to threonine, and phenylalanine to histidine. Furthermore, to simplify the analysis, in all cases the cNg site of the canine IgGB Fc fragment was restored to its native asparagine. The sequences for these insulin-Fc fusion protein variants are shown below with the resulting sequence alignments against SEQ ID NO: 43 shown in FIG. 16 (Clustal Omega).

(SEQ ID NO: 55)
FVNQHLCGSHLVEALELVCGERGFFYTPKTGGSGGGGGIVEQCCTSTCSLDQLENYCGGGGGQ

GGGGQGGGGQGGGGGDCPKCPAPEMLGGPSVFIFPPKPKDTLLIARTPEVTCVVVDLDPEDPE

VQISWFVDGKQMQTAKTQPREEQFNGTYRVVSVLPIGHQDWLKGKQFTCKVNNKALPSPIERT

ISKARGQAHQPSVYVLPPSREELSKNTVSLTCLIKDFFPPDIDVEWQSNGQQEPESKYRTTPPQL

DEDGSYFLYSKLSVDKSRWQRGDTFICAVMHEALHNHYTQESLSHSPG

-continued (SEQ ID NO: 56)
FVNQHLCGSHLVEALELVCGERGFHYGGGGGGSGGGGGIVEQCCTSTCSLDQLENYCNHGGG

GQGGGGQGGGGQGGGGGDCPKCPAPEMLGGPSVFIFPPKPKDTLLIARTPEVTCVVVDLDPED

PEVQISWFVDGKQMQTAKTQPREEQFNGTYRVVSVLPIGHQDWLKGKQFTCKVNNKALPSPIE

RTISKARGQAHQPSVYVLPPSREELSKNTVSLTCLIKDFFPPDIDVEWQSNGQQEPESKYRTTPP

QLDEDGSYFLYSKLSVDKSRWQRGDTFICAVMHEALHNHYTQESLSHSPG (SEQ ID NO: 28)
FVNQHLCGSHLVEALELVCGERGFHYGGGGGGSGGGGGIVEQCCTSTCSLDQLENYCNGGGG

GQGGGGQGGGGQGGGGGDCPKCPAPEMLGGPSVFIFPPKPKDTLLIARTPEVTCVVVDLDPED

PEVQISWFVDGKQMQTAKTQPREEQFNGTYRVVSVLPIGHQDWLKGKQFTCKVNNKALPSPIE

RTISKARGQAHQPSVYVLPPSREELSKNTVSLTCLIKDFFPPDIDVEWQSNGQQEPESKYRTTPP

QLDEDGSYFLYSKLSVDKSRWQRGDTFICAVMHEALHNHYTQESLSHSPG (SEQ ID NO: 26)
FVNQHLCGSHLVEALELVCGERGFHYGGGGGGSGGGGGIVEQCCTSTCSLDQLENYCGGGGG

QGGGGQGGGGQGGGGGDCPKCPAPEMLGGPSVFIFPPKPKDTLLIARTPEVTCVVVDLDPEDP

EVQISWFVDGKQMQTAKTQPREEQFNGTYRVVSVLPIGHQDWLKGKQFTCKVNNKALPSPIER

TISKARGQAHQPSVYVLPPSREELSKNTVSLTCLIKDFFPPDIDVEWQSNGQQEPESKYRTTPPQ

LDEDGSYFLYSKLSVDKSRWQRGDTFICAVMHEALHNHYTQESLSHSPG (SEQ ID NO: 57)
FVNQHLCGSHLVEALELVCGERGFFYGGGGGGSGGGGGIVEQCCTSTCSLDQLENYCGGGGG

QGGGGQGGGGQGGGGGDCPKCPAPEMLGGPSVFIFPPKPKDTLLIARTPEVTCVVVDLDPEDP

EVQISWFVDGKQMQTAKTQPREEQFNGTYRVVSVLPIGHQDWLKGKQFTCKVNNKALPSPIER

TISKARGQAHQPSVYVLPPSREELSKNTVSLTCLIKDFFPPDIDVEWQSNGQQEPESKYRTTPPQ

LDEDGSYFLYSKLSVDKSRWQRGDTFICAVMHEALHNHYTQESLSHSPG

TABLE 13

% homodimer, homodimer titers, and IR IC50 values for various SEQ ID NOs.

| SEQ ID NO: | % Homodimer | HEK homodimer titer (mg/L) | IR IC50 (nM) |
|---|---|---|---|
| SEQ ID NO: 43 | 98.0% | 21 | >5000 |
| SEQ ID NO: 55 | 97.9% | 69 | 3869 |
| SEQ ID NO: 56 | 99.5% | 101 | 554 |
| SEQ ID NO: 28 | 99.7% | 107 | 1247 |
| SEQ ID NO: 57 | 99.7% | 128 | 2043 |
| SEQ ID NO: 26 | 99.4% | 187 | 2339 |

The insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. The results are given in Table 13. The results show that a combination of decreasing the hydrophobicity of certain B-chain and A-chain amino acids, using longer and more flexible C-peptide sequences, truncating several C-terminal B-chain amino acids, and using a longer peptide linker resulted in several useful insulin-Fc fusion proteins that meet the minimum homodimer titer and insulin receptor binding activity design criteria. SEQ ID NO: 56, SEQ ID NO: 28, SEQ ID NO: 26, and SEQ ID NO: 57 showed more preferable insulin receptor IC50 values (less than 3000 nM) and more preferable HEK homodimer titer values (greater than 100 mg/L) than either SEQ ID NO: 43 or SEQ ID NO: 55. Surprisingly, changing just a few amino acids leads to a multifold improvement in insulin receptor affinity, and, in the case of the insulin-Fc fusion protein of SEQ ID NO: 26 a dramatic increase in homodimer titer over the original insulin-Fc fusion protein of SEQ ID NO: 43.

Example 44: In Vivo Bioactivity, Repeated Dose Bioactivity, and Immunogenicity of Insulin-Fc Fusion Proteins Constructed from the Insulin Polypeptide of SEQ ID NO: 7, the Peptide Linker of SEQ ID NO: 13, and the Canine IgGB Fc Fragment of SEQ ID NO: 15

Given the positive homodimer titer and insulin receptor binding activity results from Example 43, two of the most promising insulin-Fc fusion proteins (SEQ ID NO: 26 and SEQ ID NO: 28) were tested in dogs to evaluate the repeated dose bioactivity and immunogenicity. Each compound comprises the longer, more hydrophilic peptide linker of SEQ ID NO: 13 and the more manufacturable, less aggregated canine IgGB Fc fragment of SEQ ID NO: 15. Most importantly, both insulin-Fc fusion proteins comprise insulin polypeptides with the putatively less immunogenic native B10 and A8 amino acids (i.e. general SEQ ID NO: 6). In the case of the insulin-Fc fusion protein of SEQ ID NO: 28, the asparagine at position A21 is present (i.e. the insulin polypeptide comprises SEQ ID NO: 8). In the case of the insulin-Fc fusion protein of SEQ ID NO: 26, the asparagine at position A21 is absent (i.e. the insulin polypeptide comprises SEQ ID NO: 7).

Figure 17:
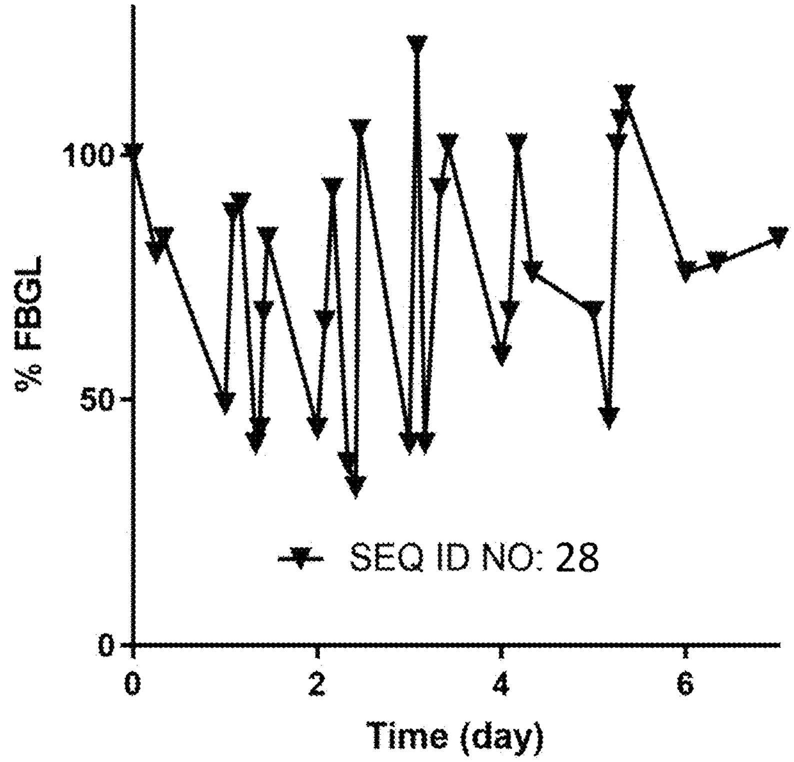
FIG. 17 shows % fasting blood glucose levels from Day 0 to Day 7 for N=1 dog dosed subcutaneously on Day 0 at 0.16 mg/kg with the homodimer of SEQ ID NO: 28.

The in vivo bioactivity of the insulin-Fc fusion protein of SEQ ID NO: 28 was tested in N=1 dog according to the procedure of Example 21. The results shown in FIG. 17 for a single subcutaneous dose demonstrate that the insulin-Fc fusion protein of SEQ ID NO: 28 is indeed bioactive in vivo with an NAOC of 1076% FBGL·days·kg/mg calculated according to the procedure in Example 22. The insulin-Fc fusion protein of SEQ ID NO: 28 pharmacokinetic profile was measured by the method of Example 23 using ELISA, and a two-compartment model was fit to the data to determine its elimination half-life which was 3.5 days.

The repeated dose bioactivity was then evaluated by continuing to subcutaneously administer the insulin-Fc fusion protein of SEQ ID NO: 28 to N=1 dog on day 14, day 28, and day 42 after the initial injection according to the procedure of Example 15. When the dog's % FBGL dropped too low, the dog was given food to raise the blood glucose to a safe level. The NAOC and NAOCR were measured for each subsequent dose according to the general procedure of Example 22, calculated from the time the dose was administered until just before the next dose was administered. The NAOC and the NAOCR shown in Table 14 illustrate that the insulin-Fc fusion protein of SEQ ID NO: 28 maintains an NAOCR greater than 0.8 throughout the four doses thus meeting the repeated dose bioactivity design goal.

TABLE 14

NAOC per dose for repeated doses of SEQ ID NO: 28

| Injection# | Day | NAOC (% FBGL · days · kg/mg) | NAOCR |
|---|---|---|---|
| 1 | 0 | 1076 | 1.0 |
| 2 | 14 | 1005 | 0.9 |
| 3 | 28 | 900 | 0.8 |
| 4 | 42 | 838 | 0.8 |

Figure 18:
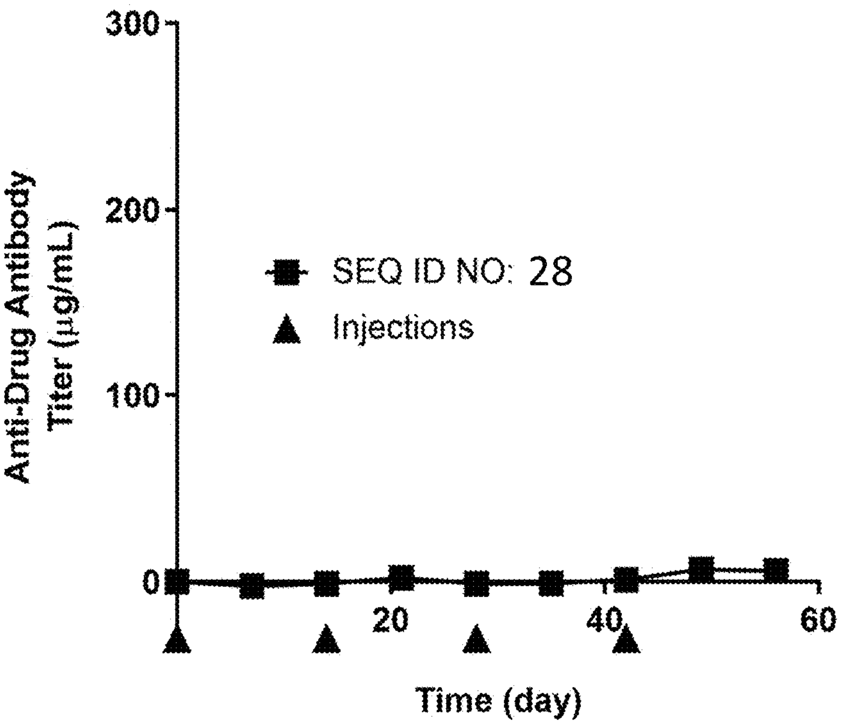
FIG. 18 shows the anti-drug antibody titer (μg/mL) for N=1 dog dosed subcutaneously on Day 0 (0.16 mg/kg), Day 14 (0.16 mg/kg), Day 28 (0.16 mg/kg), and Day 42 (0.16 mg/kg) with the homodimer of SEQ ID NO: 28.

The immunogenicity of the insulin-Fc fusion protein of SEQ ID NO: 28 was tested according to the procedure of Example 24. FIG. 18 demonstrates that the insulin-Fc fusion protein of SEQ ID NO: 28 exhibits no apparent immunogenicity in vivo in agreement with the maintenance of in vivo bioactivity throughout the repeated dose experiment.

Figure 19:
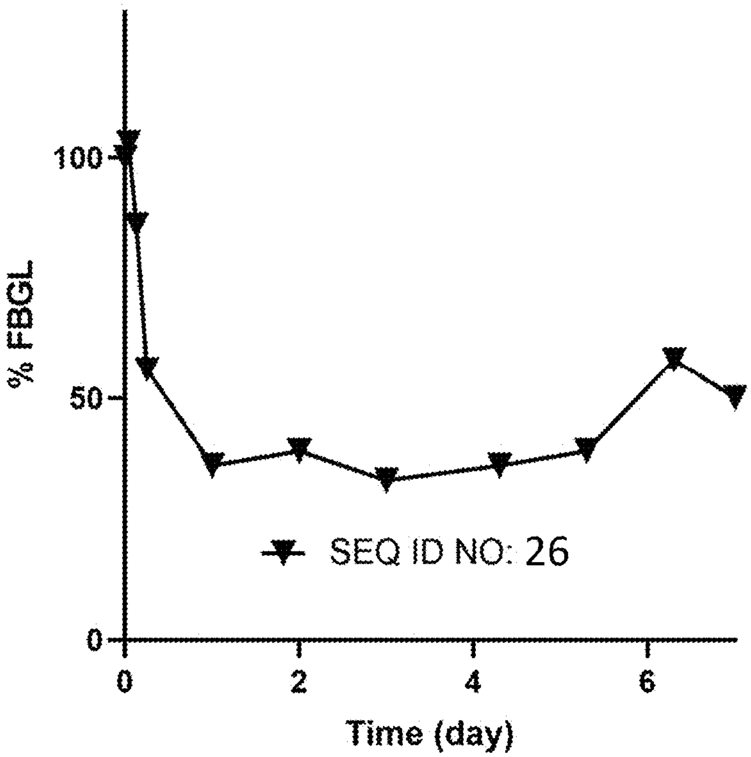
FIG. 19 shows % fasting blood glucose levels from Day 0 to Day 7 for N=1 dog dosed subcutaneously on Day 0 at 0.33 mg/kg with the homodimer of SEQ ID NO: 26.
Figure 20:
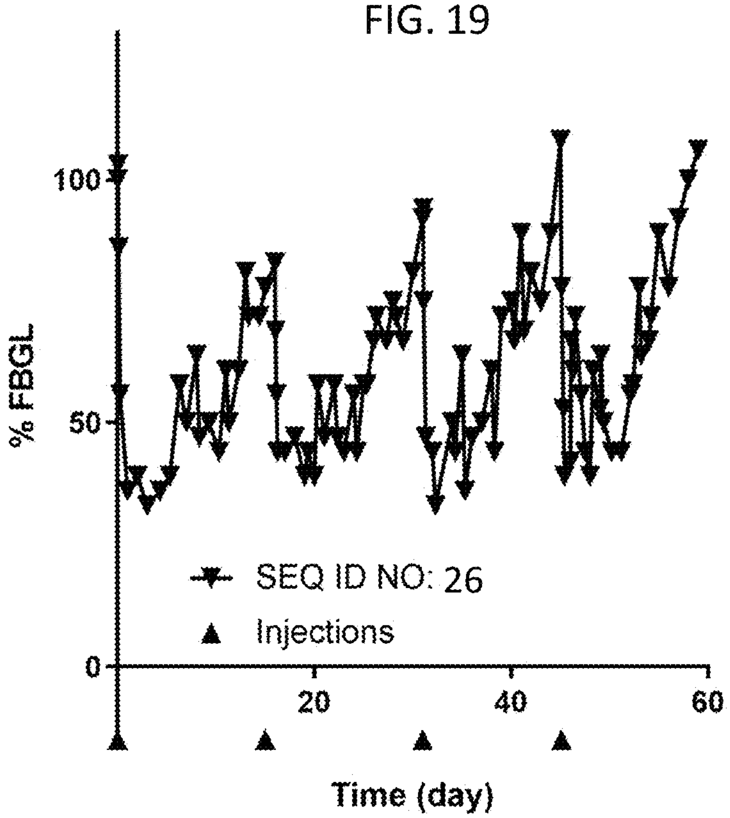
FIG. 20 shows % fasting blood glucose levels from Day 0 to Day 60 for N=1 dog dosed subcutaneously on Day 0 (0.33 mg/kg), Day 15 (0.16 mg/kg), Day 31 (0.16 mg/kg) and Day 45 (0.15 mg/kg) with the homodimer of SEQ ID NO: 26.

The insulin-Fc fusion protein of SEQ ID NO: 26, with the asparagine at A21 of the insulin polypeptide chain absent, was also evaluated for repeated dose bioactivity performance in dogs. The compound was administered subcutaneously to N=1 dog on day 0, day 14, day 28, and on day 42 according to the procedure of Example 22. When the dog's % FBGL dropped too low, the dog was given food to raise the blood glucose to a safe level. The NAOC for the first injection was an impressive 2278% FBGL·days·kg/mg, showing that the insulin-Fc fusion protein of SEQ ID NO: 26 was satisfactorily bioactive in vivo at almost twice the potency of the insulin-Fc fusion protein of SEQ ID NO: 28. The pharmacokinetic profile of the insulin-Fc fusion protein was measured by the method of Example 23 using ELISA, and a two-compartment model was fit to the data to determine its elimination half-life which was 4.1±0.7 days. FIG. 19 and FIG. 20 show the single dose blood glucose control and the multidose, multiweek blood glucose control for animals receiving the homodimer of SEQ ID NO: 26. The NAOC and NAOCR were also measured for each subsequent dose according to the general procedure of Example 22, calculated from the time the dose was administered until just before the next dose was administered. The NAOC and the NAOCR shown in Table 15 illustrate that the insulin-Fc fusion protein of SEQ ID NO: 26 maintains an NAOCR greater than or equal to 1.0 throughout the four doses thus meeting the repeated dose bioactivity design goal described in Example 29.

Figure 21:
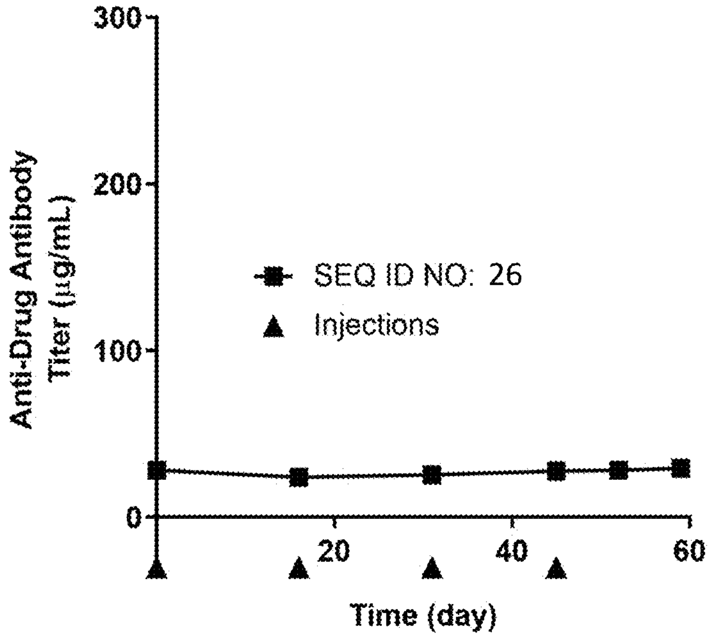
FIG. 21 shows the anti-drug antibody titer (μg/mL) for N=1 dogs dosed subcutaneously on Day 0 (0.33 mg/kg), Day 15 (0.16 mg/kg), Day 31 (0.16 mg/kg) and Day 45 (0.15 mg/kg) with the homodimer of SEQ ID NO: 26.

The immunogenicity of the insulin-Fc fusion protein of SEQ ID NO: 26 was tested according to the procedure of Example 24. FIG. 21 demonstrates that the insulin-Fc fusion protein of SEQ ID NO: 26 exhibits no apparent immunogenicity in vivo in agreement with the maintenance of in vivo bioactivity throughout the repeated dose experiment.

TABLE 15

NAOC per dose for repeated doses of SEQ ID NO: 26

| Injection# | Day | NAOC (% FBGL · days · kg/mg) | NAOCR |
|---|---|---|---|
| 1 | 0 | 2278 | 1.0 |
| 2 | 14 | 4029 | 1.8 |
| 3 | 28 | 3450 | 1.5 |
| 4 | 42 | 3257 | 1.4 |

As discussed in the Detailed Description of the invention, a known enzymatic cleavage site exists between asparagine-glycine bonds (Vlasak, J., Ionescu, R., (2011) *MAbs Vol.* 3, *No.* 3 pp 253-263). Omitting the asparagine at the 21st amino acid in the A chain (i.e., A21) in the insulin polypeptide of SEQ ID NO: 7 contained in the insulin-Fc fusion protein of SEQ ID NO: 26 with the peptide linker of SEQ ID NO: 13, eliminates the possibility of enzymatic cleavage of the asparagine-glycine bond between the C-terminus of the A-chain and the N-terminus of the peptide linker. However, the insulin-Fc fusion protein of SEQ ID NO: 28 comprises the peptide linker of SEQ ID NO: 13 and the insulin polypeptide of SEQ ID NO: 8, which keeps the asparagine at A21. Therefore, it would have been expected that the insulin-Fc fusion protein of SEQ ID NO: 28 would have been enzymatically digested during synthesis or in vivo following subcutaneous administration. However, rather unexpectedly the insulin-Fc fusion protein of SEQ ID NO: 28 was manufacturable in HEK cells with an acceptable homodimer titer and demonstrated acceptable bioactivity in vivo with no signs of enzymatic digestion compromising its bioactivity.

Example 45: Confirmation of the Canine IgGB Isotype Fc Fragment for Optimal Manufacturability and In Vivo Efficacy of Insulin-Fc Fusion Proteins Comprising the Preferred Insulin Polypeptide of SEQ ID NO: 7 and the Preferred Peptide Linker of SEQ ID NO: 13

Having discovered a new insulin polypeptide and peptide linker combination resulting in non-immunogenic, high yielding, high purity, and highly bioactive insulin-Fc fusion proteins as described in Example 43 and Example 44, a question remained as to whether the canine IgGB Fc fragment was still the preferred isotype with respect to homodimer titer and bioactivity as was the case for the insulin-Fc fusion proteins in Example 32 and Example 33. Therefore, additional insulin-Fc fusion proteins were designed wherein the insulin polypeptide (SEQ ID NO: 7) and peptide linker (SEQ ID NO: 13) of the insulin-Fc fusion protein of SEQ ID NO: 26 were kept constant, and the canine IgGB Fc fragment of SEQ ID NO: 15 was replaced by the canine IgGA Fc fragment of SEQ ID NO: 14, the canine IgGC Fc fragment of SEQ ID NO: 16, or the canine IgGD Fc fragment of SEQ ID NO: 17. The sequences for these resulting insulin-Fc fusion protein variants are shown below:

(SEQ ID NO: 26)
```
FVNQHLCGSHLVEALELVCGERGFHYGGGGGGSGGGGGIVEQCCTSTCS
LDQLENYCGGGGGQGGGGQGGGGQGGGGGDCPKCPAPEMLGGPSVFIFP
PKPKDTLLIARTPEVTCVVVDLDPEDPEVQISWFVDGKQMQTAKTQPRE
EQFNGTYRVVSVLPIGHQDWLKGKQFTCKVNNKALPSPIERTISKARGQ
AHQPSVYVLPPSREELSKNTVSLTCLIKDFFPPDIDVEWQSNGQQEPES
KYRTTPPQLDEDGSYFLYSKLSVDKSRWQRGDTFICAVMHEALHNHYTQ
ESLSHSPG
```

(SEQ ID NO: 58)
```
FVNQHLCGSHLVEALELVCGERGFHYGGGGGGSGGGGGIVEQCCTSTCS
LDQLENYCGGGGGQGGGGQGGGGQGGGGGRCTDTPPCPVPEPLGGPSVL
IFPPKPKDILRITRTPEVTCVVLDLGREDPEVQISWFVDGKEVHTAKTQ
SREQQFNGTYRVVSVLPIEHQDWLTGKEFKCRVNHIDLPSPIERTISKA
RGRAHKPSVYVLPPSPKELSSSDTVSITCLIKDFYPPDIDVEWQSNGQQ
EPERKHRMTPPQLDEDGSYFLYSKLSVDKSRWQQGDPFTCAVMHETLQN
HYTDLSLSHSPG
```

(SEQ ID NO: 59)
```
FVNQHLCGSHLVEALELVCGERGFHYGGGGGGSGGGGGIVEQCCTSTCS
LDQLENYCGGGGGQGGGGQGGGGQGGGGGCNNCPCPGCGLLGGPSVFIF
PPKPKDILVTARTPTVTCVVVDLDPENPEVQISWFVDSKQVQTANTQPR
EEQSNGTYRVVSVLPIGHQDWLSGKQFKCKVNNKALPSPIEEIISKTPG
```

-continued
```
QAHQPNVYVLPPSRDEMSKNTVTLTCLVKDFFPPEIDVEWQSNGQQEPE
SKYRMTPPQLDEDGSYFLYSKLSVDKSRWQRGDTFICAVMHEALHNHYT
QISLSHSPG
```

-continued (SEQ ID NO: 60)
```
FVNQHLCGSHLVEALELVCGERGFHYGGGGGGSGGGGGIVEQCCTSTCS
LDQLENYCGGGGGQGGGGQGGGGQGGGGGCISPCPVPESLGGPSVFIFP
PKPKDILRITRTPEITCVVLDLGREDPEVQISWFVDGKEVHTAKTQPRE
QQFNSTYRVVSVLPIEHQDWLTGKEFKCRVNHIGLPSPIERTISKARGQ
AHQPSVYVLPPSPKELSSSDTVTLTCLIKDFFPPEIDVEWQSNGQPEPE
SKYHTTAPQLDEDGSYFLYSKLSVDKSRWQQGDTFTCAVMHEALQNHYT
DLSLSHSPG.
```

The insulin-Fc fusion proteins were manufactured in HEK293 cells according to Example 1 and purified using a Protein A or Protein G columns according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. Additionally, the insulin-Fc fusion protein affinities for the canine FcRn receptor were measured according to Example 15. As is shown in Table 16, the insulin-Fc fusion protein of SEQ ID NO: 26 comprising the canine IgGB Fc fragment demonstrated the highest homodimer titer of these sequences. The insulin-Fc fusion protein of SEQ ID NO: 58 comprising the canine IgGA Fc fragment exhibited poor homodimer titer when purified using a Protein A column; however, when it purified using a Protein G column, the homodimer titer was significantly improved, exceeding the design goal of greater than 50 mg/L. The same was true for the insulin-Fc fusion protein of SEQ ID NO: 59 comprising the canine IgGC Fc fragment. The insulin-Fc fusion protein of SEQ ID NO: 60 comprising the canine IgGD Fc fragment did not yield any compound when purified with either a Protein A or a Protein G column. Therefore, as was demonstrated with the insulin-Fc fusion protein of SEQ ID NO: 36 containing a different insulin polypeptide (SEQ ID NO: 4) and peptide linker (SEQ ID NO: 11), the canine IgGB was the preferred Fc fragment with respect to homodimer titer (see Example 32).

TABLE 16

Homodimer titers, IR binding, and FcRn binding for sequences utilizing native canine IgGA, IgGB, IgGC, and IgGD Fc fragments

| SEQ ID NO: | Fc Fragment IgG Isotype | Protein Yield Protein A/ (Protein G) (mg/L) | % Homodimer Protein A/ (Protein G) | Homodimer Titer (mg/L) | IR Binding, IC50 (nM) | FcRn Binding, EC50 (ng/mL) | First dose NAOC (% FBGL · days · kg/mg) |
|---|---|---|---|---|---|---|---|
| SEQ ID NO: 26 | IgGB | 187/(DNM) | 99%/(DNM) | 185 | 2339 | 599 | 2278 |
| SEQ ID NO: 58 | IgGA | 10/(69) | 45%/(91%) | 62‡ | 2586# | 1610 | 174 |
| SEQ ID NO: 59 | IgGC | 0/(86) | 0%/(94%) | 81‡ | 2084‡ | >200000 | 39 |
| SEQ ID NO: 60 | IgGD | 0/(0) | (DNM)/(DNM) | 0 | DNM | DNM | DNM |

DNM = did not measure;
# = purified via Protein A;
‡ = purified by Protein G.

Figure 22:
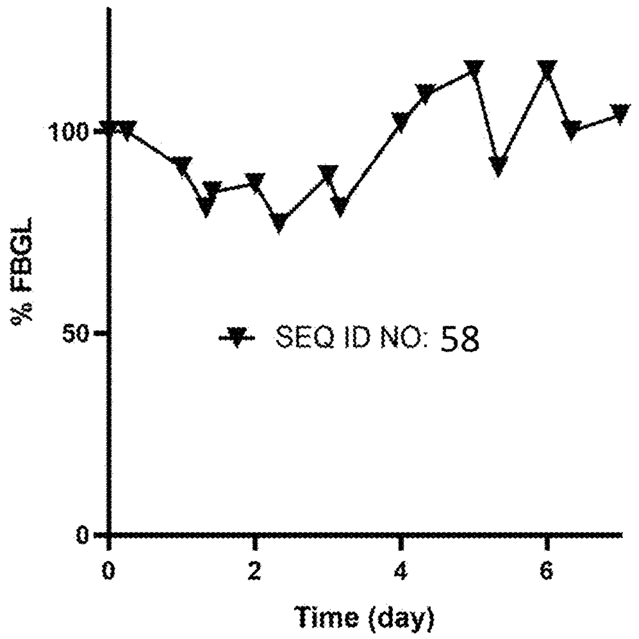
FIG. 22 shows % fasting blood glucose levels from Day 0 to Day 7 for N=1 dog dosed subcutaneously on Day 0 at 0.16 mg/kg with the homodimer of SEQ ID NO: 58.

The in vivo bioactivity of the insulin-Fc fusion protein of SEQ ID NO: 58 comprising the canine IgGA Fc fragment that was purified via Protein G was tested according to the procedure of Example 21. The results illustrated in FIG. 22 show that the insulin-Fc fusion protein of SEQ ID NO: 58 is only somewhat bioactive in vivo with a NAOC of only 174% FBGL·days·kg/mg calculated according to Example 22.

The in vivo bioactivity of the insulin-Fc fusion protein of SEQ ID NO: 59 comprising the canine IgGC Fc fragment was purified via Protein G tested according to the procedure of Example 21. The results illustrated in FIG. 23 show that the insulin-Fc fusion protein of SEQ ID NO: 59 is only somewhat bioactive in vivo with a NAOC of only 39% FBGL·days·kg/mg calculated according to Example 22.

Therefore, as was demonstrated with the insulin-Fc fusion protein of SEQ ID NO: 36 containing a different insulin polypeptide (SEQ ID NO: 4 and peptide linker (SEQ ID NO: 11), the canine IgGB was the preferred Fc fragment with respect to bioactivity (see Example 32 and Example 33 and Table 16 above).

Example 46: Non-Glycosylated Insulin-Fc Fusion Proteins Comprising the Insulin Polypeptide of SEQ ID NO: 8, the Peptide Linker of SEQ ID NO: 13, and the Canine IgGB Fc Fragment to Reduce the Potential Risk of Immunogenicity While the insulin-Fc fusion protein of SEQ ID NO: 26 meets all of the design goals (Example 28), there may or may not be a risk of immunogenicity over extended periods of treatment (e.g., 6 months, 1 year, 2 years or more) which could compromise the use of this insulin-Fc fusion protein for treating diabetes should this occur. As described in the Detailed Description of the Invention and in Example 34 and Example 35, one possible cause of a reduction in bioactivity after repeated doses is the unwanted interaction of the canine IgGB Fc fragment with the dog's immune system resulting in the production of neutralizing anti-drug antibodies. However, the results shown in Example 45 demonstrate that unexpectedly, the canine IgGB isotype was the only option of the four canine IgG isotypes that yielded the desired manufacturability and bioactivity. Therefore, further Fc mutations were explored to achieve non-glycosylated insulin-Fc fusion proteins with low Fc(gamma)RI receptor binding, which should reduce the long-term, chronic immunogenicity risk.

As described in the Detailed Description of the Invention, one method for reducing the Fc(gamma)RI interaction involves mutating the Fc fragment cNg site to prevent glycosylation during synthesis in the host cell. Therefore, cNg site mutations were made to the Fc fragment region of SEQ ID NO: 26 to reduce the binding affinity of the Fc fragment for Fc(gamma) receptors in vivo, as measured by binding in an in vitro human Fc(gamma)RI assay described in Example 15. The position of the cNg site in the insulin-Fc fusion protein of SEQ ID NO: 26 is cNg-NB151. Mutations to SEQ ID NO: 26 included SEQ ID NO: 62 comprising a cNg-NB151-S mutation and SEQ ID NO: 61 comprising the same cNg-NB151-S mutation as well as a NB119-A mutation. The NB119-A was incorporated in a further attempt to reduce the interaction with Fc(gamma)RI as has been described only for use in mouse antibodies by Lo, M. et al. "Effector attenuating substitutions that maintain antibody stability and reduce toxicity in mice", J. Biol. Chem. (2017), pp. 1-20. The full amino acid sequences of the resulting insulin-Fc fusion proteins are listed below (NB119 and NB151 sites in bold for clarity) along with their sequence alignments (Clustal Omega) which are shown in FIG. 24:

(SEQ ID NO: 61)
FVNQHLCGSHLVEALELVCGERGFHYGGGGGGSGGGGGIVEQCCTSTCS

LDQLENYCGGGGGQGGGGQGGGGQGGGGGDCPKCPAPEMLGGPSVFIFP

PKPKDTLLIARTPEVTCVVVALDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG (SEQ ID NO: 62)
FVNQHLCGSHLVEALELVCGERGFHYGGGGGGSGGGGGIVEQCCTSTCS

LDQLENYCGGGGGQGGGGQGGGGQGGGGGDCPKCPAPEMLGGPSVFIFP

PKPKDTLLIARTPEVTCVVVDLDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG.

The insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10, and their insulin receptor binding affinities were measured according to Example 12. As shown in Table 17, incorporating the cNg-NB151-S mutations on the Fc fragment decreased the % homodimer, indicating an unacceptably high level of aggregation (i.e., the % homodimer dropped to just above 70%).

TABLE 17

Homodimer titers for non-glycosylated insulin-Fc fusion proteins of SEQ ID NO: 61 and 104

| SEQ ID NO: | IgG Fragment | Relevant Mutations | Protein Yield (mg/L) | % Homodimer | Homodimer Titer (mg/L) | IR Binding, IC50 (nM) |
|---|---|---|---|---|---|---|
| SEQ ID NO: 26 | IgGB | cNg-NB-151-N | 187 | 99% | 185 | 2339 |
| SEQ ID NO: 61 | IgGB | cNg-NB-151-S, NB119-A | 78 | 73% | 57 | 3093 |
| SEQ ID NO: 62 | IgGB | cNg-NB151-S | 130 | 71% | 93 | 2302 |

Figure 25:
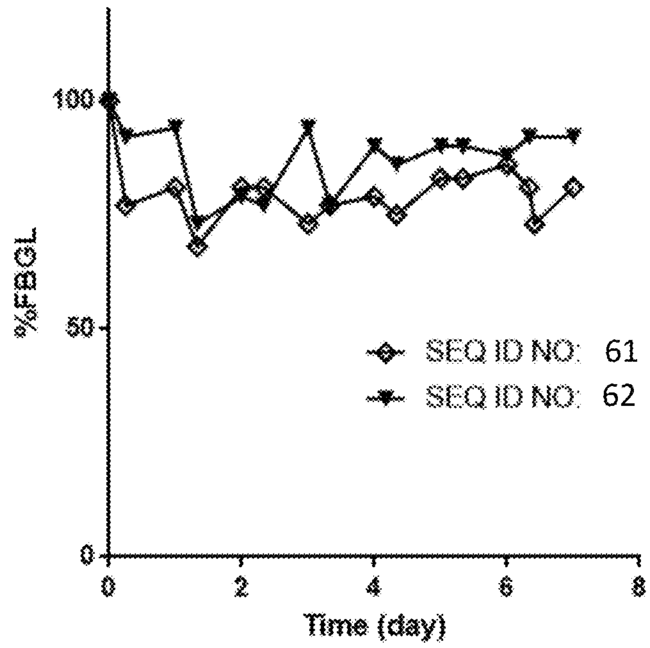
FIG. 25 shows % fasting blood glucose levels from Day 0 to Day 7 for N=1 dog dosed subcutaneously on Day 0 at 0.16 mg/kg with the homodimer of SEQ ID NO: 61, and % fasting blood glucose levels from Day 0 to Day 7 for N=1 dog dosed subcutaneously on Day 0 at 0.16 mg/kg with the homodimer of SEQ ID NO: 62.

The in vivo bioactivity of the insulin-Fc fusion proteins of SEQ ID NO: 61 and SEQ ID NO: 62 was tested in N=1 dog each according to the procedure of Example 21. The results shown in FIG. 25 for a single subcutaneous dose demonstrate that both compounds were significantly less bioactive in vivo than the insulin-Fc fusion protein of SEQ ID NO: 26 (NAOC for SEQ ID NO: 62=574% FBGL·days·kg/mg; NAOC for SEQ ID NO: 61=921% FBGL·days·kg/mg). The results indicate that incorporating cNg-NB151-S mutations on the Fc fragment to produce non-glycosylated versions of the insulin-Fc fusion protein of SEQ ID NO: 26 unexpectedly decreased the in vivo bioactivity of the resulting compounds.

In an attempt to lessen the degree of aggregation and improve the bioactivity of the insulin-Fc fusion protein of SEQ ID NO: 62 containing the cNg-NB151-S site mutation, various insulin-polypeptide B-chain variants were investigated with mutations in the region thought to be responsible for aggregation. The insulin-Fc fusion proteins were manufactured in HEK293 cells according to Example 1 and purified using a Protein A column according to Example 4. Their structures were confirmed according to Example 6 by non-reducing and reducing CE-SDS, and the sequences were further identified by LC-MS with glycan removal according to Example 8. Their % homodimer content was measured by size-exclusion chromatography according to Example 10. Among the B-chain variants tested, one insulin Fc-fusion protein (SEQ ID NO: 30) containing a tyrosine to alanine substitution at the $16^{th}$ amino acid from the N-terminus of the B-chain (i.e., B16) was unexpectedly found to have high homodimer titers (105 mg/L) with low aggregation (99% homodimer), resulting in a homodimer titer of 104 mg/L. The insulin receptor binding measured according to Example 12 was acceptable with an IC50 of 2040 nM. The FcRn receptor binding affinity EC50 value measured according to Example 16 was 1194 ng/mL. The pharmacokinetic profile of the insulin-Fc fusion protein of SEQ ID NO: 30 was measured by the method of Example 23 using ELISA, and a two-compartment model was fit to the data to determine its elimination half-life which was 4.1±0.7 days. The sequence of SEQ ID NO: 30 is shown below (B16A and cNg-NB151-S mutations in bold for clarity).

(SEQ ID NO: 30)

FVNQHLCGSHLVEALALVCGERGFHYGGGGGGSGGGGGIVEQCCTSTCS

LDQLENYCGGGGGQGGGGQGGGGQGGGGGDCPKCPAPEMLGGPSVFIFP

PKPKDTLLIARTPEVTCVVVDLDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG.

Figure 26:
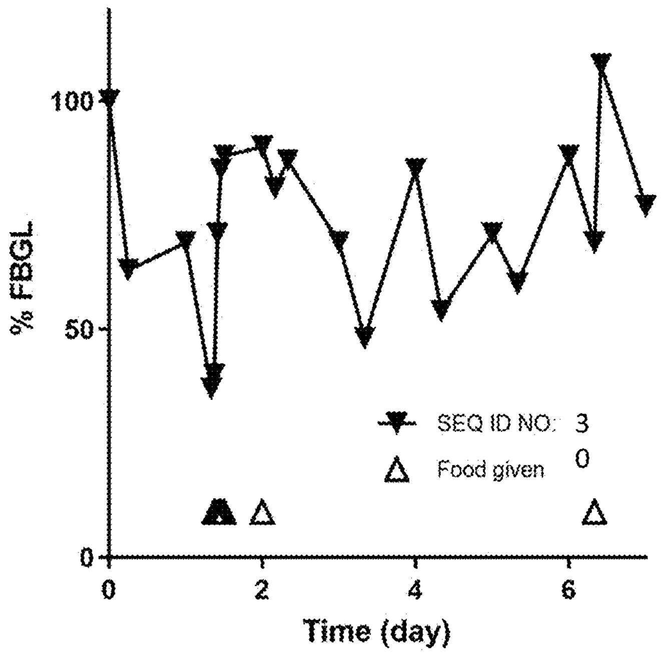
FIG. 26 shows % fasting blood glucose levels from Day 0 to Day 7 for N=1 dog dosed subcutaneously with the homodimer of SEQ ID NO: 30 in addition to the times that the dog was given food.

The insulin-Fc fusion protein of SEQ ID NO: 30 was then evaluated for repeated dose bioactivity performance in dogs. The compound was administered subcutaneously to N=1 dog on day 0, day 7, day 14, and on day 28 according to the procedure of Example 22. When the dog's % FBGL dropped too low, the dog was given food to raise the blood glucose to a safe level. Unexpectedly, compared to the insulin-Fc fusion protein of SEQ ID NO: 62, the NAOC for the first injection of the insulin-Fc fusion protein of SEQ ID NO: 30 containing the B16A mutation, was significantly higher (1185% FBGL·days·kg/mg). The first dose in vivo bioactivity plot is shown in FIG. 26. The pharmacokinetic profile of the compound was also measured by the method of Example 23 using ELISA, and a two-compartment model was fit to the data to determine its elimination half-life which was 3.5 days. The NAOC and NAOCR were also measured for each subsequent dose according to the general procedure of Example 22, calculated from the time the dose was administered until just before the next dose was administered. The NAOC and the NAOCR shown in Table 18 illustrate that the insulin-Fc fusion protein of SEQ ID NO: 30 maintains an NAOCR greater than or equal to 0.6 throughout the four doses thus meeting the repeated dose bioactivity design goal. Taken together, the results indicate that it was necessary to mutate the insulin B-chain sequence to obtain a suitable, non-glycosylated cNg-S variant of SEQ ID NO: 26. Therefore, the insulin polypeptide of SEQ ID NO: 10 was preferred for non-glycosylated insulin-Fc fusion proteins comprising cNg-mutated canine IgGB Fc fragments.

TABLE 18

NAOC per dose for repeated doses of SEQ ID NO: 30

| Injection# | Day | NAOC (% FBGL · days · kg/mg) | NAOCR |
|---|---|---|---|
| 1 | 0 | 1185 | 1.0 |
| 2 | 7 | 954 | 0.8 |
| 3 | 14 | 764 | 0.6 |
| 4 | 28 | 991 | 0.8 |

Finally, select compounds were tested for their likelihood to interact with the immune system by measuring their Fc(gamma) receptor binding activity according to the procedure of Example 15. Table 19 compares the Fc(gamma) receptor I binding of these insulin-Fc fusion proteins with the Fc(gamma) receptor binding of the insulin-Fc fusion protein of SEQ ID NO: 36. It can be seen that the non-glycosylated insulin-Fc fusion proteins (achieved through a cNg-S mutation) exhibited the lowest Fc(gamma) receptor binding ratio to SEQ ID NO: 36.

TABLE 19

Fc(gamma) receptor binding for cNg variations of SEQ ID NO: 36

| SEQ ID NO: | Species / Fc Isotype | Glycosylation Mutation | OD450 nm at a Fc(gamma)RI concentration of 3000 (ng/mL) | OD450 nm Minus Assay Background | Ratio to SEQ ID NO: 36 |
|---|---|---|---|---|---|
| SEQ ID NO: 36 | Canine / IgGB | Native cNg | 0.428 | 0.371 | 1.00 |
| SEQ ID NO: 26 | Canine / IgGB | Native cNg | 0.368 | 0.311 | 0.84 |
| SEQ ID NO: 58 | Canine / IgGA | Native cNg | 0.253 | 0.196 | 0.53 |
| SEQ ID NO: 62 | Canine / IgGB | cNg-S | 0.175 | 0.118 | 0.32 |

TABLE 19-continued

Fc(gamma) receptor binding for cNg variations of SEQ ID NO: 36

| SEQ ID NO: | Species / Fc Isotype | Glycosylation Mutation | OD450 nm at a Fc(gamma)RI concentration of 3000 (ng/mL) | OD450 nm Minus Assay Background | Ratio to SEQ ID NO: 36 |
|---|---|---|---|---|---|
| SEQ ID NO: 61 | Canine / IgGB | cNg-S and NB119-A | 0.166 | 0.109 | 0.29 |
| SEQ ID NO: 30 | Canine / IgGB | cNg-S and B16A | 0.177 | 0.120 | 0.32 |

Example 47: Exemplary CHO-Based Production Runs Using Preferred Insulin-Fc Fusion Proteins Comprising Fc Fragments of Canine IgGB Origin Made Via Stably Transfected CHO Cell Lines Separate CHO cell lines stably transfected with vectors encoding for SEQ ID NO: 26, or SEQ ID NO: 30 were constructed as described in Example 2. Fed-batch shake flask 14-day production runs (0.5-2.0 L media scale) were seeded at 0.5 million cells/mL in an incubator-shaker set at 37° C. and 5% carbon dioxide, and the runs were conducted as described in Example 2 above, except that CD OptiCHO was substituted for Dynamis as the growth media (ThermoFisher) and Efficient Feed C (ThermoFisher) was used as the feed. Feed was added at 3% v/v starting on production run day 3, and on day 4, the shake-flask temperature was adjusted to 32° C. and the incubator-shaker carbon dioxide concentration was lowered from 5% to 2%. During the run, the cells increased to between 8-14 million cells/mL, and on Day 14 the production run was harvested to remove the cells and the culture supernatant was purified and tested to obtain the insulin-Fc fusion protein as described in Example 4, Example 6, Example 8, and Example 10. Table 20 describes the manufacturing data obtained from the production runs with stably transfected CHO cell lines.

TABLE 20

Homodimer titers for non-glycosylated insulin-Fc fusion proteins of SEQ ID NO: 26 and SEQ ID NO: 30

| SEQ ID NO: | Protein Yield (mg/L) | % Homodimer | Homodimer Titer (mg/L) |
|---|---|---|---|
| SEQ ID NO: 26 | 485 | 99.3% | 482 |
| SEQ ID NO: 30 | 260 | 99.0% | 257 |

Example 48: Exemplary CHO-Based Production Runs Using Preferred Insulin-Fc Fusion Proteins Comprising Fc Fragments of Canine IgGB Origin Made Via Stably Transfected CHO Cell Lines A CHO cell line stably transfected with vectors encoding for SEQ ID NO: 28 is constructed as described in Example 2. Fed-batch shake flask 14-day production runs (0.5-2.0 L media scale) is seeded at 0.5 million cells/mL in an incubator-shaker set at 37° C. and 5% carbon dioxide, and the run is conducted as described in Example 2, except that CD OptiCHO is substituted for Dynamis as the growth media (ThermoFisher) and Efficient Feed C (ThermoFisher) is used as the feed. Feed is added at 3% v/v starting on production run day 3, and on day 4, the shake-flask temperature is adjusted to 32° C. and the incubator-shaker carbon dioxide concentration is lowered from 5% to 2%. On Day 14, the production run is harvested to remove the cells, and the culture supernatant is purified and tested to obtain the insulin-Fc fusion protein as described in Example 4, Example 6, Example 8, and Example 10. The resulting production run is expected to give a protein yield of greater than 200 mg/L, greater than 95% homodimer, and greater than 190 mg/L homodimer titer of SEQ ID NO: 28.

Results—Insulin-Fc Fusion Proteins Comprising a Human Fc Fragment

Example 49: Insulin-Fc Fusion Proteins Comprising Fc Fragment of the Human Fc IgG1 and IgG2 Isotypes An attempt was made to produce an insulin-Fc fusion protein comprising the insulin polypeptide sequence of SEQ ID NO: 7 and the Fc fragment of the human IgG2 isotype (SEQ ID NO: 74) using the peptide linker of SEQ ID NO: 13. The full amino acid sequence for the resulting insulin-Fc fusion protein is as follows:

```
                                             (SEQ ID NO: 75)
FVNQHLCGSHLVEALELVCGERGFHYGGGGGGSGGGGGIVEQCCTSTCS

LDQLENYCGGGGGQGGGGQGGGGQGGGGGECPPCPAPPVAGPSVFLFPP

KPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSL

SLSPG.
```

A further attempt was made to produce an insulin-Fc fusion protein comprising the insulin polypeptide sequence of SEQ ID NO: 7 and the Fc fragment of the human IgG1 isotype (SEQ ID NO: 73) using the peptide linker of SEQ ID NO: 13. The full amino acid sequence for the resulting insulin-Fc fusion protein is as follows:

```
                                             (SEQ ID NO: 76)
FVNQHLCGSHLVEALELVCGERGFHYGGGGGGSGGGGGIVEQCCTSTCS

LDQLENYCGGGGGQGGGGQGGGGQGGGGGDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQP
```

-continued

ENNYKTTPPVLDSDGSFFLYSKLTVDKSRWQQGNVFSCSVMHEALHNHY

TQKSLSLSPG.

The insulin-Fc fusion protein configurations of SEQ ID NO: 75 and SEQ ID NO: 76 were synthesized in HEK cells according to Example 1 and purified according to Example 4. The total protein yields gave average homodimer titers as shown in Table 21 after two separate synthesis and Protein A purification steps for each insulin-Fc fusion protein configuration. The structures of the insulin-Fc fusion protein configurations were confirmed according to Example 6 by non-reducing and reducing CE-SDS, and the sequences were further identified by LC-MS with glycan removal according to Example 8. The % homodimer was measured by size-exclusion chromatography according to Example 10 and determined as shown in Table 21 below. In summary, manufacturing of the insulin-Fc fusion protein of SEQ ID NO: 76 in HEK cells resulted in acceptable aggregate and homodimer titer levels, which meet the design goal of a homodimer titer of greater than 150 mg/L, while the manufacturing of the insulin-Fc fusion protein of SEQ ID NO: 75 in HEK cells did not meet the homodimer titer design goal.

Next, the insulin-Fc fusion protein of SEQ ID NO: 76 was evaluated for the potential for in vivo bioactivity. First, the IR binding of the insulin-Fc fusion protein of SEQ ID NO: 76 was measured according to Example 12, resulting in an IC50 value of 1799 nM indicating that the compound is likely to be bioactive in vivo (i.e., IC50 less than 2400 nM). The FcRn assay EC50 value was 578 ng/mL, indicating a strong likelihood of having a prolonged in vivo bioactivity profile when measured in a canine screening study (e.g., as described in Example 28) or in a human diabetic patient.

Next, the propensity for unwanted immunogenic potential was screened by measuring each compound's in vitro binding to the Fc(gamma)RI and C1q by the methods of Example 14 and Example 16. The insulin-Fc fusion protein of SEQ ID NO: 75 demonstrated Fc(gamma)RI and C1q assay OD450 Ratios (where the reference insulin-Fc fusion protein in the OD450 Ratio is SEQ ID NO: 76) of 0.045 and 0.309 respectively, indicating that the homodimer of SEQ ID NO: 75 did meet the design goals (Example 29) for Fc(gamma)RI binding (assay OD450 Ratio less than 0.50) and the C1q binding (assay OD450 Ratio less than 0.35). However, as described above, the yield of the insulin-Fc fusion protein of SEQ ID NO: 75 in HEK cells did not meet the homodimer titer design goal.

Example 50: cNg Mutation of the Fc Fragment Region of an Insulin-Fc Fusion Protein Comprising the Human IgG1 Isotype In an attempt to maintain % homodimer content, IR binding affinity, and acceptable binding affinity to the FcRn receptor of the insulin-Fc fusion protein of SEQ ID NO: 76, a cNg-S mutation was inserted into the Fc fragment CH3 region to try to decrease binding to Fc(gamma)RI and C1q, resulting in the insulin-Fc fusion protein configuration of SEQ ID NO: 91 as follows:

(SEQ ID NO: 91)

FVNQHLCGSHLVEALELVCGERGFHYGGGGGGSGGGGGIVEQCCTSTCS

LDQLENYCGGGGGQGGGGQGGGGQGGGGGDKTHTCPPCPAPELLGGPSV

FLFPPKPKDTLMISRTPEVTCVVVDVSHEDPEVKFNWYVDGVEVHNAKT

KPREEQYSSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHY

TQKSLSLSPG.

The non-glycosylated insulin-Fc fusion protein configuration of SEQ ID NO: 91 was synthesized in HEK cells according to Example 1, purified according to Example 4, and tested according to Example 6, Example 8, Example 10, Example 12, Example 14 and Example 16 with results as shown in Table 22, together with the results of the parent glycosylated insulin-Fc fusion protein configuration of SEQ ID NO: 76 showing total protein yields, % homodimer, and homodimer titers. The results show that the cNg-S mutation within the human IgG1 Fc fragment of SEQ ID NO: 76 resulting in the insulin-Fc fusion protein configuration of SEQ ID NO: 91 did result in desirable decreases in Fc(gamma)RI affinity and C1q affinity. The homodimer titer of the insulin-Fc fusion protein configuration of SEQ ID NO: 91 increased significantly relative to the homodimer titer of the insulin-Fc fusion protein configuration of SEQ ID NO: 76. Despite the improvement in homodimer titer, the insulin-Fc fusion protein configuration of SEQ ID NO: 91 gave IR assay IC50 values that were greater than 2400 nM (outside of the design criteria of less than 2400 nM) and substantially higher (i.e., lower IR affinity) than that of SEQ ID NO: 76, indicating that this insulin-Fc fusion protein configuration was not likely to exhibit acceptable potency or meet the design goals (Example 29).

TABLE 21

Homodimer titers and receptor binding data for sequences utilizing an Fc fragment of IgG1 or IgG2 isotype

| Candidate ID | Species/Fc Isotype | Transiently Transfected HEK293 Yield (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated-Fc(gamma)RI | Human C1q Assay OD450 Ratio at 1,000 ng/mL biotinylated-C1q |
|---|---|---|---|---|---|---|---|---|
| SEQ ID NO: 75 | Human/IgG2 | 118# | 99.5 | 117# | 1726 | 462 | 0.045 | 0.309 |
| SEQ ID NO: 76 | Human/IgG1 | 181# | 99.5 | 180# | 1799 | 578 | 1.000* | 1.000* |

#= averaged from two independent experiments.

^= averaged from three independent experiments.

*= ratio of reference insulin-Fc fusion protein against itself.

TABLE 22

| Homodimer titers and receptor binding data for sequences comprising an Fc fragment of IgG1 and cNg mutations | | | | | | | | |
|---|---|---|---|---|---|---|---|---|
| Candidate ID | Fc Isotype/ Mutation | Transiently Transfected HEK293 Yield (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated-Fc(gamma)RI | Human C1q Assay OD450 Ratio at 1,000 ng/mL biotinylated-C1q |
| SEQ ID NO: 76 | hIgG1/ cNg-NB155 | 181[#] | 99.5 | 180 | 1799 | 578 | 1.000 | 1.000 |
| SEQ ID NO: 91 | hIgG1/ cNg-NB155-S | 193 | 98.1 | 189 | 2937 | 943 | 0.199 | 0.102 |

[#]= averaged from two independent experiments.
DNT = did not test.

Example 51: Human Insulin-Fc Fusion Protein Using Mutated Insulin Polypeptide (SEQ ID NO: 10), Linker (SEQ ID NO: 13), and Fc IgG1 Isotype with cNg-S Mutation As described above, a cNg-S, IgG1 isotype Fc fragment mutation produced an insulin-Fc fusion protein configuration with significantly reduced affinity for the Fc(gamma)RI and C1q, but this insulin-Fc fusion protein configuration has IR receptor affinity that is unacceptably low (i.e., IC50 value greater than 2400 nM). Therefore, a mutation to the insulin polypeptide was made and the resulting materials was screened against the IR IC50 assay in an effort to see if the mutation led to improved IR affinity. A switch from tyrosine to alanine was made at the $16^{th}$ amino acid from the N-terminus of the B-chain (i.e., B16A) to give the insulin polypeptide of SEQ ID NO: 10. The mutated insulin polypeptide of SEQ ID NO: 10 and peptide linker SEQ ID NO: 13 were used with the cNg mutated Fc fragment of SEQ ID NO: 77 with $X_1$ is S, resulting in the insulin-Fc fusion protein configuration of SEQ ID NO: 78. The cNg-S mutation in the insulin-Fc fusion protein configuration was made to the Fc fragment region to reduce the binding affinity of the Fc fragment for Fc(gamma) receptors in vivo, as measured by binding in an in vitro human Fc(gamma)RI assay described in Example 15. The position of the cNg-S site in the insulin-Fc fusion protein of SEQ ID NO: 78 is cNg-NB155, comprising a mutation at the cNg site from “N” to “5”.

The insulin-Fc fusion protein configuration of SEQ ID NO: 78 was manufactured in HEK293 cells according to Example 1 and purified using a Protein A column according to Example 4. The structure of the insulin-Fc fusion protein of SEQ ID NO: 78 was confirmed according to Example 6 by non-reducing and reducing CE-SDS, and the sequence was further identified by LC-MS without glycan removal according to Example 8. The compound MW of SEQ ID NO: 78 was assessed by the LC-MS method of Example 8 without enzymatic deglycosylation. The target mass of SEQ ID NO: 78 is 65046.9 Da and the found mass was 65046.7 Da, which confirmed the compound amino acid composition and homodimer structure of SEQ ID NO: 78 were correct.

The % homodimer was measured by size-exclusion chromatography according to Example 10. The full amino acid sequence of the cNg-mutated insulin-Fc fusion proteins is listed below (with the NB155 position in bold):

```
                                            (SEQ ID NO: 78)
FVNQHLCGSHLVEALALVCGERGFHYGGGGGGSGGGGGIVEQCCTSTCS

LDQLENYCGGGGGQGGGGQGGGGQGGGGGDKTHTCPPCPAPELLGGPSV

FLFPPKPKDTLMISRTPEVTCVVVDVSHEDPEVKFNWYVDGVEVHNAKT

KPREEQYSSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHY

TQKSLSLSPG.
```

The resulting total protein yield, % homodimer, and homodimer titer of the insulin-Fc fusion protein configuration of SEQ ID NO: 78 is given in Table 23 and compared to that of SEQ ID NO: 76 and SEQ ID NO: 91. Including the B16A mutation in the insulin polypeptide sequence with the non-glycosylated cNg-S mutated insulin-Fc fusion protein improved the homodimer titer relative to SEQ ID NO: 76. In vitro IR binding for the insulin-Fc fusion protein of SEQ ID NO: 78 was tested according to the procedure of Example 12. The inclusion of the B16A mutation into the insulin polypeptide of SEQ ID NO: 10 in the insulin-Fc fusion protein of SEQ ID NO: 78 led to marked improvements in IR affinity (i.e., lower IR IC50 assay values) compared to SEQ ID NO: 91 in which the insulin polypeptide contained the B16E mutation (SEQ ID NO: 7). This is especially surprising, given that this B16A mutation in a different insulin-Fc fusion protein (SEQ ID NO: 3 in U.S. Pat. No. 10,597,435) gave IR IC50 assay values of greater than 5000 nM and showed no glucose-lowering bioactivity in vivo. The sequence alignment of SEQ ID NO: 76, SEQ ID NO: 78 and SEQ ID NO: 91 highlighting the differences in amino acid sequences is shown in FIG. 27. “*” represents complete homology across all sequences at a given sequence position, while “:”, “.” or spaces refer to conservative, moderate, or very different amino acid mutations across the sequences at a given sequence position respectively.

TABLE 23

Homodimer titers and receptor binding data for sequences comprising an Fc fragment of IgG1, cNg mutations and B16A mutation.

| Candidate ID | Fc Isotype/ Mutation | Transiently Transfected HEK293 Yield (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated-Fc(gamma)RI | Human C1q Assay OD450 Ratio at 1,000 ng/mL biotinylated-C1q |
|---|---|---|---|---|---|---|---|---|
| SEQ ID NO: 76 | hIgG1/ cNg-NB155 | 181[#] | 99.5 | 180 | 1799 | 578 | 1.000 | 1.000 |
| SEQ ID NO: 91 | hIgG1/ cNg-NB155-S | 193 | 98.1 | 189 | 2937 | 943 | 0.199 | 0.102 |
| SEQ ID NO: 78 | hIgG1/B16A/ cNg-NB155-S | 189 | 93.2 | 176 | 1162 | 825 | 0.197 | 0.169 |

Furthermore, inclusion of the B16A mutation in the insulin polypeptide (resulting in SEQ ID NO: 10) of the insulin-Fc fusion protein of SEQ ID NO: 78 led to acceptable FcRn binding as measured by the procedure in Example 19, indicating that this insulin-Fc fusion protein will likely exhibit prolonged in vivo pharmacokinetic half-life and demonstrate a prolonged glucose-lowering bioactivity profile in vivo. It was noted that the FcRn binding affinity for SEQ ID NO: 78 is greater (as demonstrated by a lower EC50 measurement in the FcRn binding assay) than that of the similar insulin-Fc fusion protein not containing the B16A mutation (SEQ ID NO: 91), further highlighting that the inclusion of the B16A mutation unexpectedly impacts FcRn receptor affinity in addition to IR receptor affinity. It is thought that this incremental increases in FcRn receptor affinity may be desirable, since higher FcRn affinities often correlate with longer therapeutic pharmacokinetic half-lives in vivo.

The Fc(gamma)RI and C1q binding properties were measured by the methods of Example 14 and Example 16 for the insulin-Fc fusion protein of SEQ ID NO: 78 and were shown to be acceptable. The C1q binding affinity was also much lower for the insulin-Fc fusion protein of SEQ ID NO: 78, showing greater than 80% reduction in C1q binding relative to the insulin-Fc fusion protein of SEQ ID NO: 76. Thus, the insulin-Fc fusion protein of SEQ ID NO: 78 met the design goals (Example 29) for manufacturability, in vivo potency, prolonged in vivo bioactivity, and a low potential for immunogenicity.

Example 52: Alternate cNg Mutations of the Fc Fragment Region of Insulin-Fc Fusion Proteins Comprising the Human IgG1 Isotype In further attempt to create insulin-Fc fusion protein configurations with prolonged in vivo bioactivity and a low potential for immunogenicity while maintaining similar % homodimer content and IR binding affinity to the insulin-Fc fusion protein of SEQ ID NO: 76, and acceptable binding affinity to the FcRn receptor, alternate cNg mutations were inserted into the Fc fragment CH3 region to try to decrease binding to Fc(gamma)RI and C1q, resulting in SEQ ID NO: 92, SEQ ID NO: 93, SEQ ID NO: 94, and SEQ ID NO: 95. The insulin-Fc fusion protein embodiments were synthesized in HEK cells according to Example 1, purified according to Example 4, and tested according to Example 6, Example 8, Example 10, Example 12, Example 14 and Example 16 with results as shown in Table 24. The sequence alignment of SEQ ID NO: 92, SEQ ID NO: 93, SEQ ID NO: 94, and SEQ ID NO: 95 against SEQ ID NO: 75, SEQ ID NO: 76 and SEQ ID NO: 91 highlighting the differences in amino acid sequences are shown in FIG. 28 (Clustal Omega). "*" represents complete homology across all sequences at a given sequence position, while ":", "." or spaces refer to conservative, moderate, or very different amino acid mutations across the sequences at a given sequence position respectively.

The full amino acid sequences for the insulin-Fc fusion protein embodiments are shown below, with the cNg mutations in bold.

(SEQ ID NO: 92)

FVNQHLCGSHLVEALELVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYDSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG (SEQ ID NO: 93)

FVNQHLCGSHLVEALELVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYASTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG (SEQ ID NO: 94)

FVNQHLCGSHLVEALELVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYRSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG

-continued (SEQ ID NO: 95)

FVNQHLCGSHLVEALELVCGERGFHYGGGGGGSGGGGGIVEQCCTSTCS

LDQLENYCGGGGGQGGGGQGGGGQGGGGGDKTHTCPPCPAPELLGGPSV

FLFPPKPKDTLMISRTPEVTCVVVDVSHEDPEVKFNWYVDGVEVHNAKT

KPREEQYQSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHY

TQKSLSLSPG.

The insulin-Fc fusion protein embodiments above comprising the human IgG1 Fc fragment of SEQ ID NO: 77 where X1 is D, A, R, and Q, are listed in Table 24 along with SEQ ID NO: 76, illustrating the corresponding total protein yields, % homodimer, and homodimer titers. The results show that the various mutations to the cNg site contained within the human IgG1 Fc fragment for SEQ ID NO: 92, SEQ ID NO: 93, SEQ ID NO: 94 and SEQ ID NO: 95 did result in desirable decreases in Fc(gamma)RI affinity and C1q affinity. The homodimer titer of SEQ ID NO: 92, SEQ ID NO: 93, and SEQ ID NO: 94 increased significantly relative to SEQ ID NO: 76. The homodimer titer of SEQ ID NO: 95 was too low to meet design goals (Example 29) and so insulin receptor binding was not assessed. Despite the improvements in homodimer titer, SEQ ID NO: 92, SEQ ID NO: 93, and SEQ ID NO: 94 gave IR assay IC50 values that were greater than 2400 nM in all cases and substantially higher (i.e., lower IR affinity) than that of SEQ ID NO: 76. The IR assay IC50 values in all cases were greater than the design criterion of less than 2400 nM, indicating that these insulin-Fc fusion protein embodiments were not likely to exhibit acceptable potency and cost of goods. None of SEQ ID NO: 91, SEQ ID NO: 92, SEQ ID NO: 93, SEQ ID NO: 94, and SEQ ID NO: 95 meet the design goals (Example 29).

TABLE 24

Homodimer titers and receptor binding data for sequences comprising an Fc fragment of IgG1 and cNg mutations

| Candidate ID | Fc Isotype/ Mutation | Transiently Transfected HEK293 Yield (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated- Fc(gamma)RI | Human C1q Assay OD450 Ratio at 1,000 ng/mL biotinylated-C1q |
|---|---|---|---|---|---|---|---|---|
| SEQ ID NO: 76 | hIgG1/ cNg-NB155 | 181[#] | 99.5 | 180 | 1799 | 578 | 1.000 | 1.000 |
| SEQ ID NO: 92 | hIgG1/ cNg-NB155-D | 243 | 97.8 | 238 | 2438 | 883 | 0.379 | 0.116 |
| SEQ ID NO: 93 | hIgG1/ cNg-NB155-A | 228 | 96.7 | 220 | 2852 | 900 | 0.245 | 0.151 |
| SEQ ID NO: 94 | hIgG1/ cNg-NB155-R | 219 | 94.7 | 207 | 3767 | 913 | 0.150 | 0.127 |
| SEQ ID NO: 95 | hIgG1/ cNg-NB155-Q | 139 | 97.6 | 136 | DNT | 775 | 0.192 | 0.222 |

[#]= averaged from two independent experiments.
DNT = did not test.

Example 53: Human Insulin-Fc Fusion Proteins Using Insulin Polypeptide (SEQ ID NO: 10), Linker (SEQ ID NO: 13), and Fc IgG1 Isotypes Comprising Various cNg Mutations As described above, cNg-site, IgG1 isotype Fc fragment mutations produce insulin-Fc fusion protein with significantly reduced affinities for the Fc(gamma)RI and C1q, but these compounds have IR receptor affinities that are unacceptably low (i.e., IC50 values greater than 2400 nM). Therefore, the same mutation that was made to the insulin polypeptide in SEQ ID NO: 78 (a switch from tyrosine to alanine was made at the 16$^{th}$ amino acid from the N-terminus of the B-chain (i.e., B16A) to give the insulin polypeptide of SEQ ID NO: 10) was made and the resulting insulin-Fc fusion protein configurations were screened against the IR IC50 assay in an effort to see if any of the mutated insulin polypeptides led to improved IR affinity. The mutated insulin polypeptide of SEQ ID NO: 10 and peptide linker SEQ ID NO: 13 were used to make the insulin-Fc fusion protein configurations of SEQ ID NO: 80, SEQ ID NO: 82, SEQ ID NO: 84, and SEQ ID NO: 86 as shown below. Each of these insulin-Fc fusion protein configurations comprise cNg site mutations that were made to the Fc fragment region to reduce the binding affinity of the Fc fragment for Fc(gamma) receptors in vivo, as measured by binding in an in vitro human Fc(gamma)RI assay described in Example 15. The position of the cNg site in the insulin-Fc fusion protein configurations of SEQ ID NO: 80, SEQ ID NO: 82, SEQ ID NO: 84, and SEQ ID NO: 86 is cNg-NB155. The insulin-Fc fusion protein of SEQ ID NO: 80 comprises a mutation at the cNg site from “N” to “D”. The insulin-Fc fusion protein of SEQ ID NO: 82 comprises a mutation at the cNg site from “N” to “A”. The insulin-Fc fusion protein of SEQ ID NO: 84 comprises a mutation at the cNg site from “N” to “R”. The insulin-Fc fusion protein of SEQ ID NO: 86 comprises a mutation at the cNg site from “N” to “Q”.

The proteins were manufactured in HEK293 cells according to Example 1. Surprisingly, the homodimer titer for the insulin-Fc fusion protein configuration of SEQ ID NO: 86 comprising the cNg-NB155-Q mutation together with the B16A mutation was significantly lower than required to meet the design goal for homodimer titer. The insulin-Fc fusion protein configurations s of SEQ ID NO: 80, SEQ ID NO: 82, and SEQ ID NO: 84 were then purified using a Protein A column according to Example 4. The structures of the insulin-Fc fusion protein configurations were confirmed according to Example 6 by non-reducing and reducing CE-SDS, and the sequences were further identified by LC-MS without glycan removal according to Example 8. The compound MW of the insulin-Fc fusion protein of SEQ ID NO: 80 was assessed by the LC-MS method of Example 8 without enzymatic deglycosylation. The target mass of SEQ ID NO: 80 is 65102.9 Da and the found mass was 65102.8 Da, which confirmed the compound amino acid composition and homodimer structure of SEQ ID NO: 80 were correct. The compound MW of the insulin-Fc fusion protein of SEQ ID NO: 82 was assessed by the LC-MS method of Example 8 without enzymatic deglycosylation. The target mass of SEQ ID NO: 82 is 65014.9 Da and the found mass was 65014.9 Da, which confirmed the compound amino acid composition and homodimer structure of SEQ ID NO: 82 were correct. The compound MW of the insulin-Fc fusion protein of SEQ ID NO: 84 was assessed by the LC-MS method of Example 8 without enzymatic deglycosylation. The target mass of SEQ ID NO: 84 is 65185.1 Da and the found mass was 65184.8 Da, which confirmed the compound amino acid composition and homodimer structure of SEQ ID NO: 84 were correct.

The % homodimer was measured by size-exclusion chromatography according to Example 10. The full amino acid sequences of the cNg-mutated insulin-Fc fusion protein configurations are listed below (SEQ ID NO: 80, SEQ ID NO: 82, SEQ ID NO: 84, and SEQ ID NO: 86 with the NB155 position in bold) and the resulting sequence alignments are shown against SEQ ID NO: 76 and SEQ ID NO: 78 in FIG. 29 (Clustal Omega). "*" represents complete homology across all sequences at a given sequence position, while ":", "." or spaces refer to conservative, moderate, or very different amino acid mutations across the sequences at a given sequence position respectively.

(SEQ ID NO: 80)
FVNQHLCGSHLVEALALVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYDSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG (SEQ ID NO: 82)
FVNQHLCGSHLVEALALVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYASTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG (SEQ ID NO: 84)
FVNQHLCGSHLVEALALVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYRSTYRVVSVLTVLHQDWLNGKEYKCKVSNKALPAPIEKTISK
AKGQPREPQVYTLPPSRDELTKNQVSLTCLVKGFYPSDIAVEWESNGQP

-continued

ENNYKTTPPVLDSDGSFFLYSKLTVDKSRWQQGNVFSCSVMHEALHNHY
TQKSLSLSPG (SEQ ID NO: 86)
FVNQHLCGSHLVEALALVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYQSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG.

The resulting total protein yields, % homodimer, and homodimer titers are given in Table 25. With the exception of SEQ ID NO: 86 as described above, including the B16A mutation in the insulin polypeptide sequence with the non-glycosylated cNg mutated insulin-Fc fusion protein embodiments improved the homodimer titers relative to SEQ ID NO: 76. The cNg-NB155-D composition exhibited the highest homodimer titer at 222 mg/L. In vitro IR binding for the insulin-Fc fusion proteins was tested according to the procedure of Example 12. As was the case with SEQ ID NO: 78, the inclusion of the B16A mutation into the insulin polypeptides of the insulin-Fc fusion protein embodiments of SEQ ID NO: 80, SEQ ID NO: 82, and SEQ ID NO: 84 led to marked improvements in IR affinity (i.e., lower IR IC50 assay values) compared to the insulin-Fc fusion protein configurations of SEQ ID NO: 92, SEQ ID NO: 93, and SEQ ID NO: 94 in which the insulin polypeptide contained the B16E mutation.

Furthermore, inclusion of the B16A mutation in the insulin polypeptides of the insulin-Fc fusion proteins of SEQ ID NO: 80, SEQ ID NO: 82, and SEQ ID NO: 84 led to acceptable FcRn binding for these insulin-Fc fusion protein embodiments as measured by the procedure in Example 19, indicating that these compounds will likely exhibit prolonged in vivo pharmacokinetic half-lives and demonstrate prolonged glucose-lowering bioactivity profiles in vivo. It was noted that the FcRn binding affinities for the insulin-Fc fusion protein configurations containing the B16A mutation (SEQ ID NO: 80, SEQ ID NO: 82, and SEQ ID NO: 84) were significantly greater (e.g. lower EC50's in the FcRn binding assay) than those of the similar insulin-Fc fusion protein configurations not containing the B16A mutation (SEQ ID NO: 92, SEQ ID NO: 93, and SEQ ID NO: 94), further highlighting that the inclusion of the B16A mutation unexpectedly impacts FcRn receptor affinity in addition to IR receptor affinity. It is thought that these incremental increases FcRn receptor affinity may be desirable, since higher FcRn affinities often correlate with longer therapeutic pharmacokinetic half-lives in vivo.

The Fc(gamma)RI and C1q binding properties were measured by the methods of Example 14 and Example 16 for the insulin-Fc fusion protein configurations of SEQ ID NO: 80, SEQ ID NO: 82, and SEQ ID NO: 84, and were shown to be acceptable. Additionally, the Fc(gamma)RI binding affinities decreased very significantly with the cNg-NB155-R (SEQ ID NO: 84) mutation, demonstrating greater than 80% reduction in Fc(gamma)RI binding relative to the insulin-Fc fusion protein of SEQ ID NO: 76. The C1q binding affinities were also much lower for the insulin-Fc fusion proteins of SEQ ID NO: 80, SEQ ID NO: 82, and SEQ ID NO: 84, with all of these insulin-Fc fusion protein embodiments showing greater than 80% reduction in C1q binding relative to the insulin-Fc fusion protein of SEQ ID NO: 76. Thus, the insulin-Fc fusion proteins of SEQ ID NO: 80, SEQ ID NO: 82, and SEQ ID NO: 84 met the design goals (Example 29) for manufacturability, in vivo potency, prolonged in vivo bioactivity, and a low potential for immunogenicity.

TABLE 25

Homodimer titers and receptor binding data for sequences comprising an Fc fragment of IgG1

| Candidate ID | Fc Isotype/ Mutation | Transiently Transfected HEK293 Yield (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated-Fc(gamma)RI | Human C1q Assay OD450 Ratio at 1,000 ng/mL biotinylated-C1q |
|---|---|---|---|---|---|---|---|---|
| SEQ ID NO: 76 | hIgG1/ cNg-NB155 | 181[#] | 99.5 | 180 | 1799 | 578 | 1.000 | 1.000 |
| SEQ ID NO: 80 | hIgG1/B16A/ cNg-NB155-D | 234 | 94.9 | 222 | 881 | 788 | 0.346 | 0.109 |
| SEQ ID NO: 82 | hIgG1/B16A/ cNg/NB155-A | 227 | 93.1 | 211 | 1125 | 690 | 0.267 | 0.181 |
| SEQ ID NO: 84 | hIgG1/B16A/ cNg-NB155-R | 193 | 96.1 | 185 | 911 | 696 | 0.167 | 0.173 |
| SEQ ID NO: 86 | hIgG1/B16A/ cNg-NB155-Q | 114 | 97.1 | 111 | DNT | 750 | 0.192 | 0.311 |

[#]= averaged from two independent experiments.
DNT = did not test.

Example 54: Human Insulin-Fc Fusion Proteins with an Insulin Polypeptide SEQ ID NO: 10, the Fc IgG1 Isotype Comprising the cNg-S Mutation, and Various Linkers As described above, the IgG1 isotype Fc fragment mutations at the cNg site and mutations on the insulin polypeptide led to unexpected changes in the material properties, including for the IR, FcRn, Fc(gamma)RI receptor, and C1q binding. To better understand how the linker composition impacted these properties, a particular insulin-Fc fusion protein configuration (SEQ ID NO: 78) containing the B16A-mutated insulin polypeptide of SEQ ID NO: 10, the non-glycosylated hIgG1 Fc fragment with the cNg-S mutation (SEQ ID NO: 77 where $X_1$ is S), and the linker sequence of SEQ ID NO: 13 was chosen as the starting point from which the linker length and composition were modified as shown in Table 26 below.

TABLE 26

Sequence ID NOs and linker amino acid compositions, and position of cNg-S site

| Candidate ID | Linker Amino Acid Sequence | Position of the cNg Site |
|---|---|---|
| SEQ ID NO: 96 | GGGGGQGGGGQGGGGQG GGGGQGGGG (SEQ ID NO: 99) | cNg-NB160-S |
| SEQ ID NO: 78 | GGGGGQGGGGQGGGGQG GGGG (SEQ ID NO: 13) | cNg-NB155-S |

TABLE 26-continued

Sequence ID NOs and linker amino acid compositions, and position of cNg-S site

| Candidate ID | Linker Amino Acid Sequence | Position of the cNg Site |
|---|---|---|
| SEQ ID NO: 97 | GGGGQGGGG (SEQ ID NO: 19) | cNg-NB143-S |

TABLE 26-continued

Sequence ID NOs and linker amino acid compositions, and position of cNg-S site

| Candidate ID | Linker Amino Acid Sequence | Position of the cNg Site |
|---|---|---|
| SEQ ID NO: 98 | <Linker Absent> | cNg-NB136-S |
| SEQ ID NO: 87 | GGGGGAGGGGAGGGGAG GGGG (SEQ ID NO: 67) | cNg-NB155-S |
| SEQ ID NO: 89 | GGGGAGGGG (SEQ ID NO: 11) | cNg-NB143-S |

The insulin-Fc fusion protein embodiments of SEQ ID NO: 96, SEQ ID NO: 97, SEQ ID NO: 98, SEQ ID NO: 87, and SEQ ID NO: 89 were manufactured in HEK293 cells according to Example 1. The insulin-Fc fusion protein configurations were then purified using a Protein A column according to Example 4. The structures of the insulin-Fc fusion protein configurations were confirmed according to Example 6 by non-reducing and reducing CE-SDS, and the sequences were further identified by LC-MS without glycan removal according to Example 8. Verification of the lack of glycan was performed using the LC-MS method of Example 8, but with omission of the PNGase F treatment step. The compound MW of the insulin-Fc fusion protein configuration of SEQ ID NO: 87 was assessed by the LC-MS method of Example 8 without enzymatic deglycosylation. The target mass is 64704.6 Da and the found mass was 64704.4 Da, which confirmed the compound amino acid composition and homodimer structure of SEQ ID NO: 87 were correct. The compound MW of the insulin-Fc fusion protein configuration of SEQ ID NO: 89 was assessed by the LC-MS method of Example 8 without enzymatic deglycosylation. The target mass is 63279.2 Da and the found mass was 63278.8 Da, which confirmed the compound amino acid composition and homodimer structure of SEQ ID NO: 89 were correct.

The % homodimer was measured by size-exclusion chromatography according to Example 10. In vitro IM-9 IR binding IC50 was measured as described in Example 12, Fc(gamma) receptor binding affinity was measured using an in vitro human Fc(gamma)RI assay as described in Example 15, C1q binding affinity was measured as described in Example 16, and affinity for the human FcRn receptor was measured as described in Example 19. The results are given in Table 27.

-continued

SNGQPENNYKTTPPVLDSDGSFFLYSKLTVDKSRWQQGNVFSCSVMHEA

LHNHYTQKSLSLSPG (SEQ ID NO: 97)

FVNQHLCGSHLVEALALVCGERGFHYGGGGGGSGGGGGIVEQCCTSTCS

LDQLENYCGGGGQGGGGDKTHTCPPCPAPELLGGPSVFLFPPKPKDTLM

ISRTPEVTCVVVDVSHEDPEVKFNWYVDGVEVHNAKTKPREEQYSSTYR

VVSVLTVLHQDWLNGKEYKCKVSNKALPAPIEKTISKAKGQPREPQVYT

TABLE 27

Homodimer titers and receptor binding data for sequences comprising a B16A, Fc fragment of IgG1, cNg-S mutations, and various linker compositions

| Candidate ID | Transiently Transfected HEK293 Titer (mg/L) | % Homodimer | Homodimer Titer (mg/L) | IR Assay IC50 (nM) | Human FcRn Assay EC50, (ng/mL) | Human Fc(gamma)RI Assay OD450 Ratio at 3,000 ng/mL biotinylated-Fc(gamma)RI | Human C1q Assay OD450 Ratio at 1,000 ng/mL biotinylated-C1q |
|---|---|---|---|---|---|---|---|
| SEQ ID NO: 96 | 227 | 94.2 | 214 | 760 | 672 | 0.216 | 0.166 |
| SEQ ID NO: 78 | 189 | 93.2 | 176 | 1162 | 825 | 0.197 | 0.169 |
| SEQ ID NO: 97 | 187 | 95.5 | 179 | 954 | 679 | 0.208 | 0.314 |
| SEQ ID NO: 98 | 40 | 94.8 | 38 | 526 | 401 | 0.146 | 0.311 |
| SEQ ID NO: 87 | 224 | 95.2 | 213 | 789 | 701 | 0.193 | 0.204 |
| SEQ ID NO: 89 | 193 | 94.5 | 182 | 1265 | 657 | 0.192 | 0.305 |

The full amino acid sequences of the resulting insulin-Fc fusion proteins are listed below (with the cNg-S position in bold). FIG. 30 (Clustal Omega) illustrates a side-by-side sequence comparison of SEQ ID NO: 87, SEQ ID NO: 96, SEQ ID NO: 78, SEQ ID NO: 97, SEQ ID NO: 89, and SEQ ID NO: 98. "*" represents complete homology across all sequences at a given sequence position, while ":", "." or spaces refer to conservative, moderate, or very different amino acid mutations across the sequences at a given sequence position respectively.

(SEQ ID NO: 87)

FVNQHLCGSHLVEALALVCGERGFHYGGGGGGSGGGGGIVEQCCTSTCS

LDQLENYCGGGGGAGGGGAGGGGAGGGGGDKTHTCPPCPAPELLGGPSV

FLFPPKPKDTLMISRTPEVTCVVVDVSHEDPEVKFNWYVDGVEVHNAKT

KPREEQYSSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFScSVMHEALHNHY

TQKSLSLSPG (SEQ ID NO: 96)

FVNQHLCGSHLVEALALVCGERGFHYGGGGGGSGGGGGIVEQCCTSTCS

LDQLENYCGGGGGQGGGGQGGGGQGGGGGQGGGGDKTHTCPPCPAPELL

GGPSVFLFPPKPKDTLMISRTPEVTCVVVDVSHEDPEVKFNWYVDGVEV

HNAKTKPREEQYSSTYRVVSVLTVLHQDWLNGKEYKCKVSNKALPAPIE

KTISKAKGQPREPQVYTLPPSRDELTKNQVSLTCLVKGFYPSDIAVEWE

-continued

LPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG (SEQ ID NO: 89)

FVNQHLCGSHLVEALALVCGERGFHYGGGGGGSGGGGGIVEQCCTSTCS

LDQLENYCGGGGAGGGGDKTHTCPPCPAPELLGGPSVFLFPPKPKDTLM

ISRTPEVTCVVVDVSHEDPEVKFNWYVDGVEVHNAKTKPREEQYSSTYR

VVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG (SEQ ID NO: 98)

FVNQHLCGSHLVEALALVCGERGFHYGGGGGGSGGGGGIVEQCCTSTCS

LDQLENYCDKTHTCPPCPAPELLGGPSVFLFPPKPKDTLMISRTPEVTC

VVVDVSHEDPEVKFNWYVDGVEVHNAKTKPREEQYSSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPG.

The results indicate that in the insulin-Fc fusion protein configurations without a linker, wherein the C-terminal end of the insulin polypeptide is directly linked to the N-terminal end of the Fc fragment (SEQ ID NO: 98), the homodimer titer is unacceptably low (i.e., 38 mg/L). In the insulin-Fc fusion protein configurations with the glycine-glutamine linker composition (SEQ ID NO: 97, SEQ ID NO: 78, and SEQ ID NO: 96) comprising at least nine amino acids in length, there did not appear to be any significant trends in physiochemical properties that varied with linker length. A comparison of the insulin-Fc fusion protein configuration of SEQ ID NO: 87, containing a linker of glycine-alanine composition, with the insulin-Fc fusion protein configuration of SEQ ID NO: 78 containing a linker of glycine-glutamine composition, suggested that for an identical linker length of 21 amino acids, the insulin-Fc fusion protein configuration of SEQ ID NO: 87 demonstrated improved homodimer titer, stronger IR binding, and stronger FcRn binding, while having nearly identical Fc(gamma)RI and C1q binding properties. Therefore, while the insulin-Fc fusion protein configurations of SEQ ID NO: 96, SEQ ID NO: 97, SEQ ID NO: 87, and SEQ ID NO: 89 all met the design goals (Example 29), the homodimer of SEQ ID NO: 87 is a preferred embodiment.

Example 55: In Vivo Efficacy of Insulin-Fc Fusion Proteins Comprising the B16A Insulin Polypeptide Mutant, Human IgG1 Isotype Fc Fragment with cNg-NB155-X Site Mutations, and Linker (SEQ ID NO: 13)

Given the promising homodimer titer, IR activity, and FcRn activity results in Example 53, the insulin-Fc fusion proteins of SEQ ID NO: 78, SEQ ID NO: 80, SEQ ID NO: 82, and SEQ ID NO: 84 will be tested for in vivo bioactivity according to Example 22 following a subcutaneous injection in each of N=3 healthy, antibody-naïve, beagle dogs weighing approximately 10 kg. A plot of % FBGL versus time for a single subcutaneous administration of each insulin-Fc fusion protein of SEQ ID NO: 78, SEQ ID NO: 80, SEQ ID NO: 82, and SEQ ID NO: 84 will be constructed, and the % FBGL vs. time data is expected to demonstrate that the insulin-Fc fusion proteins of SEQ ID NO: 78, SEQ ID NO: 80, SEQ ID NO: 82, and SEQ ID NO: 84 are significantly bioactive in dogs.

Example 56: In Vivo Efficacy of Insulin-Fc Fusion Proteins Comprising the B16A Insulin Polypeptide Mutant, Human IgG1 Isotype Fc Fragment with cNg-NB155-S Mutation, and Linker (SEQ ID NO: 11)

Given the promising homodimer titer, IR activity, and FcRn activity results in Example 54, the insulin-Fc fusion protein of SEQ ID NO: 89 will be tested for in vivo bioactivity according to Example 22 following a subcutaneous injection in each of N=3 healthy, antibody-naïve, beagle dogs weighing approximately 10 kg. A plot of % FBGL versus time for a single subcutaneous administration of the insulin-Fc fusion protein of SEQ ID NO: 89 will be constructed, and the % FBGL vs. time data is expected to demonstrate that the insulin-Fc fusion protein of SEQ ID NO: 89 is significantly bioactive in dogs.

Example 57: In Vivo Efficacy of Insulin-Fc Fusion Proteins Comprising the B16A Insulin Polypeptide Mutant, Human IgG1 Isotype Fc Fragment with cNg-NB155-S Mutation, and Linker (SEQ ID NO: 67)

Given the promising homodimer titer, IR activity, and FcRn activity results in Example 54, the insulin-Fc fusion protein of SEQ ID NO: 87 will be tested for in vivo bioactivity according to Example 22 following a subcutaneous injection in each of N=3 healthy, antibody-naïve, beagle dogs weighing approximately 10 kg. A plot of % FBGL versus time for a single subcutaneous administration of the insulin-Fc fusion protein of SEQ ID NO: 87 will be constructed, and the % FBGL vs. time data is expected to demonstrate that the insulin-Fc fusion protein of SEQ ID NO: 87 is significantly bioactive in dogs.

Example 58: Exemplary CHO-Based Production Runs Using Preferred Insulin-Fc Fusion Proteins Comprising Fc Fragments of Human IgG1 Origin Made Via Stably Transfected CHO Cell Lines Separate CHO cell lines stably transfected with vectors encoding for the insulin-Fc fusion protein configurations of SEQ ID NO: 78, SEQ ID NO: 80, SEQ ID NO: 82, SEQ ID NO: 84, SEQ ID NO: 87, and SEQ ID NO: 89 will be constructed as described in Example 2. Fed-batch shake flask 14-day production runs (0.5-2.0 L media scale) will be seeded at 0.5 million cells/mL in an incubator-shaker set at 37° C. and 5% carbon dioxide, and the runs will be conducted as described in Example 2, except that CD OptiCHO will be substituted for Dynamis as the growth media (ThermoFisher) and Efficient Feed C (ThermoFisher) will be used as the feed. Feed will be added at 3% v/v starting on production run day 3, and on day 4, the shake-flask temperature will be adjusted to 32° C. and the incubator-shaker carbon dioxide concentration will be lowered from 5% to 2%. During the run, the cell densities will increase to between 8-14 million cells/mL, and on Day 14 the production run will be harvested to remove the cells and the culture supernatant purified and tested to obtain the insulin-Fc fusion proteins as described in Example 4, Example 6, Example 8, and Example 10. The manufacturing and in vitro testing data from the separate production runs of the insulin-Fc fusion protein configurations of SEQ ID NO: 78, SEQ ID NO: 80, SEQ ID NO: 82, SEQ ID NO: 84, SEQ ID NO: 87 and SEQ ID NO: 89 with stably transfected CHO cell lines are expected to exhibit homodimer titers greater than those obtained in the transiently transfected HEK293 cells, with IR, FcRn receptor, Fc(gamma)RI receptor binding and C1q binding properties that meet the design goals (Example 29).

Example 59: In Vivo Pharmacodynamics (PD) after a Single Administration of Human Insulin Fc-Fusion Proteins in Mice Insulin-Fc fusion proteins were assessed for their effects on fasting blood glucose levels as follows. Data was collected from N=3 balb/c mice or diabetic wt NOD mice (Jackson Laboratories) per group. The animals were fasted one hour before the experiment and then at time=0 hours, the mice received a single subcutaneous administration of a pharmaceutical composition containing an insulin Fc-fusion protein homodimer at a concentration of 300 μg/kg of insulin-Fc fusion protein in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a final solution pH of between 7.0-8.0 adjusted using sodium hydroxide and/or hydrochloric acid.

Figure 38:
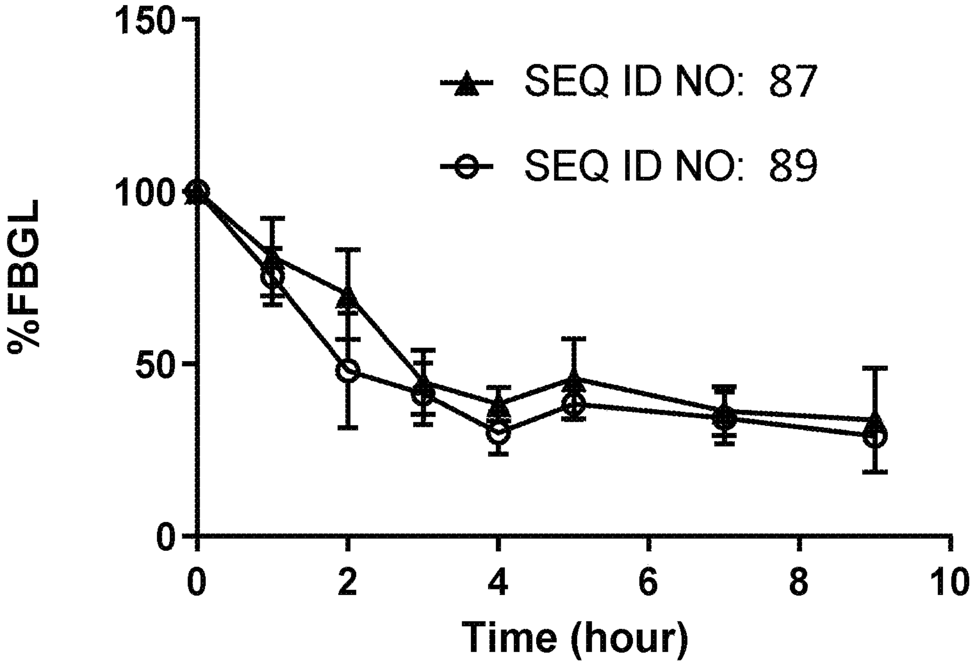
FIG. 38 shows average % fasting blood glucose levels from Hour 0 to Hour 10 for N=12 Balb/c mice fasted 1 hour before subcutaneous injection at a dose of 300 μg/kg with the homodimers of SEQ ID NO: 87 and SEQ ID NO: 89.

For each time point, a sample of blood was collected, and a glucose level reading was immediately determined using a glucose meter (AlphaTRAK® 2 pet glucometer), which requires approximately one drop of blood. Average % fasting blood glucose levels (% FBGL) from 0 to 9 hours were plotted to assess the bioactivity of a given insulin-Fc fusion protein configuration. The results shown in FIG. 38 for a single subcutaneous dose of SEQ ID NO: 87 and SEQ ID NO: 89 demonstrate that both compounds showed significant bioactivity in mice.

Example 60: In Vivo Pharmacodynamics (PD) after a Single Administration of Human Insulin Fc-Fusion Proteins in Mice Insulin-Fe fusion proteins are assessed for their effects on fasting blood glucose levels as follows. Data is collected from N=3 balb/c mice or diabetic wt NOD mice (Jackson Laboratories) per group. The animals are fasted one hour before the experiment and then at time=0 hours, the mice receive a single subcutaneous administration of a pharmaceutical composition containing an insulin Fc-fusion protein homodimer at a concentration of 300 μg/kg of insulin-Fc fusion protein in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a final solution pH of between 7.0-8.0 adjusted using sodium hydroxide and/or hydrochloric acid.

For each time point, a sample of blood is collected, and a glucose level reading is immediately determined using a glucose meter (AlphaTRAK® 2 pet glucometer), which requires approximately one drop of blood. Average % fasting blood glucose levels (% FBGL) from 0 to 9 hours are plotted to assess the bioactivity of a given insulin-Fc fusion protein configuration. It is expected that a single subcutaneous dose of SEQ ID NO: 78, SEQ ID NO: 80, SEQ ID NO: 82, or SEQ ID NO: 84 will demonstrate that these insulin-Fc fusion proteins show significant bioactivity in mice.

Example 61: Exemplary Insulin-Fc Fusion Protein Domains and Sequences

Exemplary insulin-Fc fusion protein amino acid sequences and corresponding DNA sequences used in the above Examples are shown in FIG. 31, FIG. 32, FIG. 33, FIG. 34, FIG. 35, FIG. 36 and FIG. 37.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

SEQUENCE LISTING

```
<160> NUMBER OF SEQ ID NOS: 100

<210> SEQ ID NO 1
<211> LENGTH: 30
<212> TYPE: PRT
<213> ORGANISM: Artificial Sequence
<220> FEATURE:
<223> OTHER INFORMATION: Human insulin B-chain

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 2
<211> LENGTH: 21
<212> TYPE: PRT
<213> ORGANISM: Artificial Sequence
<220> FEATURE:
```

-continued

```
<223> OTHER INFORMATION: Human insulin A-chain

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 3
<211> LENGTH: 86
<212> TYPE: PRT
<213> ORGANISM: Artificial Sequence
<220> FEATURE:
<223> OTHER INFORMATION: Human ProInsulin

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85


<210> SEQ ID NO 4
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 4

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55


<210> SEQ ID NO 5
<211> LENGTH: 58
<212> TYPE: PRT
<213> ORGANISM: Artificial Sequence
<220> FEATURE:
<223> OTHER INFORMATION: Insulin Polypeptide
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H
<220> FEATURE:
<221> NAME/KEY: Xaa
<222> LOCATION: (58)..(58)
<223> OTHER INFORMATION: Xaa is absent or N
```

<400> SEQUENCE: 5

Phe Val Asn Gln His Leu Cys Gly Ser Xaa Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Xaa Ser Thr Cys
35 40 45

Ser Leu Asp Gln Leu Glu Asn Tyr Cys Xaa
50 55

<210> SEQ ID NO 6
<211> LENGTH: 58
<212> TYPE: PRT
<213> ORGANISM: Artificial Sequence
<220> FEATURE:
<223> OTHER INFORMATION: Insulin Polypeptide
<220> FEATURE:
<221> NAME/KEY: Xaa
<222> LOCATION: (58)..(58)
<223> OTHER INFORMATION: Xaa is absent or N

<400> SEQUENCE: 6

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Xaa
50 55

<210> SEQ ID NO 7
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 7

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys
50 55

<210> SEQ ID NO 8
<211> LENGTH: 58
<212> TYPE: PRT
<213> ORGANISM: Artificial Sequence
<220> FEATURE:
<223> OTHER INFORMATION: Insulin Polypeptide

<400> SEQUENCE: 8

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

```
Ser Gly Gly Gly Gly Gly Ile Val Glu Gln Cys Cys Thr Ser Thr Cys
        35                  40                  45

Ser Leu Asp Gln Leu Glu Asn Tyr Cys Asn
    50                  55


<210> SEQ ID NO 9
<211> LENGTH: 57
<212> TYPE: PRT
<213> ORGANISM: Artificial Sequence
<220> FEATURE:
<223> OTHER INFORMATION: Insulin Polypeptide
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 9

Phe Val Asn Gln His Leu Cys Gly Ser Xaa Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys
    50                  55


<210> SEQ ID NO 10
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 10

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55


<210> SEQ ID NO 11
<211> LENGTH: 9
<212> TYPE: PRT
<213> ORGANISM: Artificial Sequence
<220> FEATURE:
<223> OTHER INFORMATION: Linker

<400> SEQUENCE: 11

Gly Gly Gly Gly Ala Gly Gly Gly Gly
1               5


<210> SEQ ID NO 12
<211> LENGTH: 9
<212> TYPE: PRT
<213> ORGANISM: Artificial Sequence
<220> FEATURE:
<223> OTHER INFORMATION: Linker
```

<400> SEQUENCE: 12

Gly Gly Gly Gly Ser Gly Gly Gly Gly
1 5

<210> SEQ ID NO 13
<211> LENGTH: 21
<212> TYPE: PRT
<213> ORGANISM: Artificial Sequence
<220> FEATURE:
<223> OTHER INFORMATION: Linker

<400> SEQUENCE: 13

Gly Gly Gly Gly Gly Gln Gly Gly Gly Gly Gln Gly Gly Gly Gly Gln
1 5 10 15

Gly Gly Gly Gly Gly
20

<210> SEQ ID NO 14
<211> LENGTH: 228
<212> TYPE: PRT
<213> ORGANISM: Artificial Sequence
<220> FEATURE:
<223> OTHER INFORMATION: Fc Fragment dIgGA

<400> SEQUENCE: 14

Arg Cys Thr Asp Thr Pro Pro Cys Pro Val Pro Glu Pro Leu Gly Gly
1 5 10 15

Pro Ser Val Leu Ile Phe Pro Pro Lys Pro Lys Asp Ile Leu Arg Ile
20 25 30

Thr Arg Thr Pro Glu Val Thr Cys Val Val Leu Asp Leu Gly Arg Glu
35 40 45

Asp Pro Glu Val Gln Ile Ser Trp Phe Val Asp Gly Lys Glu Val His
50 55 60

Thr Ala Lys Thr Gln Ser Arg Glu Gln Gln Phe Asn Gly Thr Tyr Arg
65 70 75 80

Val Val Ser Val Leu Pro Ile Glu His Gln Asp Trp Leu Thr Gly Lys
85 90 95

Glu Phe Lys Cys Arg Val Asn His Ile Asp Leu Pro Ser Pro Ile Glu
100 105 110

Arg Thr Ile Ser Lys Ala Arg Gly Arg Ala His Lys Pro Ser Val Tyr
115 120 125

Val Leu Pro Pro Ser Pro Lys Glu Leu Ser Ser Ser Asp Thr Val Ser
130 135 140

Ile Thr Cys Leu Ile Lys Asp Phe Tyr Pro Pro Asp Ile Asp Val Glu
145 150 155 160

Trp Gln Ser Asn Gly Gln Gln Glu Pro Glu Arg Lys His Arg Met Thr
165 170 175

Pro Pro Gln Leu Asp Glu Asp Gly Ser Tyr Phe Leu Tyr Ser Lys Leu
180 185 190

Ser Val Asp Lys Ser Arg Trp Gln Gln Gly Asp Pro Phe Thr Cys Ala
195 200 205

Val Met His Glu Thr Leu Gln Asn His Tyr Thr Asp Leu Ser Leu Ser
210 215 220

His Ser Pro Gly
225

<210> SEQ ID NO 15
<211> LENGTH: 224

<212> TYPE: PRT
<213> ORGANISM: Artificial Sequence
<220> FEATURE:
<223> OTHER INFORMATION: Fc Fragment dIgGB

<400> SEQUENCE: 15

```
Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
            20                  25                  30

Pro Glu Val Thr Cys Val Val Val Asp Leu Asp Pro Glu Asp Pro Glu
        35                  40                  45

Val Gln Ile Ser Trp Phe Val Asp Gly Lys Gln Met Gln Thr Ala Lys
    50                  55                  60

Thr Gln Pro Arg Glu Glu Gln Phe Asn Gly Thr Tyr Arg Val Val Ser
65                  70                  75                  80

Val Leu Pro Ile Gly His Gln Asp Trp Leu Lys Gly Lys Gln Phe Thr
                85                  90                  95

Cys Lys Val Asn Asn Lys Ala Leu Pro Ser Pro Ile Glu Arg Thr Ile
            100                 105                 110

Ser Lys Ala Arg Gly Gln Ala His Gln Pro Ser Val Tyr Val Leu Pro
        115                 120                 125

Pro Ser Arg Glu Glu Leu Ser Lys Asn Thr Val Ser Leu Thr Cys Leu
    130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
    210                 215                 220
```

<210> SEQ ID NO 16
<211> LENGTH: 225
<212> TYPE: PRT
<213> ORGANISM: Artificial Sequence
<220> FEATURE:
<223> OTHER INFORMATION: Fc Fragment dIgGC

<400> SEQUENCE: 16

```
Cys Asn Asn Cys Pro Cys Pro Gly Cys Gly Leu Leu Gly Gly Pro Ser
1               5                   10                  15

Val Phe Ile Phe Pro Pro Lys Pro Lys Asp Ile Leu Val Thr Ala Arg
            20                  25                  30

Thr Pro Thr Val Thr Cys Val Val Val Asp Leu Asp Pro Glu Asn Pro
        35                  40                  45

Glu Val Gln Ile Ser Trp Phe Val Asp Ser Lys Gln Val Gln Thr Ala
    50                  55                  60

Asn Thr Gln Pro Arg Glu Glu Gln Ser Asn Gly Thr Tyr Arg Val Val
65                  70                  75                  80

Ser Val Leu Pro Ile Gly His Gln Asp Trp Leu Ser Gly Lys Gln Phe
                85                  90                  95

Lys Cys Lys Val Asn Asn Lys Ala Leu Pro Ser Pro Ile Glu Glu Ile
            100                 105                 110
```

Ile Ser Lys Thr Pro Gly Gln Ala His Gln Pro Asn Val Tyr Val Leu
115 120 125

Pro Pro Ser Arg Asp Glu Met Ser Lys Asn Thr Val Thr Leu Thr Cys
130 135 140

Leu Val Lys Asp Phe Phe Pro Pro Glu Ile Asp Val Glu Trp Gln Ser
145 150 155 160

Asn Gly Gln Gln Glu Pro Glu Ser Lys Tyr Arg Met Thr Pro Pro Gln
165 170 175

Leu Asp Glu Asp Gly Ser Tyr Phe Leu Tyr Ser Lys Leu Ser Val Asp
180 185 190

Lys Ser Arg Trp Gln Arg Gly Asp Thr Phe Ile Cys Ala Val Met His
195 200 205

Glu Ala Leu His Asn His Tyr Thr Gln Ile Ser Leu Ser His Ser Pro
210 215 220

Gly
225

<210> SEQ ID NO 17
<211> LENGTH: 225
<212> TYPE: PRT
<213> ORGANISM: Artificial Sequence
<220> FEATURE:
<223> OTHER INFORMATION: Fc Fragment dIgGD

<400> SEQUENCE: 17

Cys Ile Ser Pro Cys Pro Val Pro Glu Ser Leu Gly Gly Pro Ser Val
1 5 10 15

Phe Ile Phe Pro Pro Lys Pro Lys Asp Ile Leu Arg Ile Thr Arg Thr
20 25 30

Pro Glu Ile Thr Cys Val Val Leu Asp Leu Gly Arg Glu Asp Pro Glu
35 40 45

Val Gln Ile Ser Trp Phe Val Asp Gly Lys Glu Val His Thr Ala Lys
50 55 60

Thr Gln Pro Arg Glu Gln Gln Phe Asn Ser Thr Tyr Arg Val Val Ser
65 70 75 80

Val Leu Pro Ile Glu His Gln Asp Trp Leu Thr Gly Lys Glu Phe Lys
85 90 95

Cys Arg Val Asn His Ile Gly Leu Pro Ser Pro Ile Glu Arg Thr Ile
100 105 110

Ser Lys Ala Arg Gly Gln Ala His Gln Pro Ser Val Tyr Val Leu Pro
115 120 125

Pro Ser Pro Lys Glu Leu Ser Ser Ser Asp Thr Val Thr Leu Thr Cys
130 135 140

Leu Ile Lys Asp Phe Phe Pro Pro Glu Ile Asp Val Glu Trp Gln Ser
145 150 155 160

Asn Gly Gln Pro Glu Pro Glu Ser Lys Tyr His Thr Thr Ala Pro Gln
165 170 175

Leu Asp Glu Asp Gly Ser Tyr Phe Leu Tyr Ser Lys Leu Ser Val Asp
180 185 190

Lys Ser Arg Trp Gln Gln Gly Asp Thr Phe Thr Cys Ala Val Met His
195 200 205

Glu Ala Leu Gln Asn His Tyr Thr Asp Leu Ser Leu Ser His Ser Pro
210 215 220

Gly
225

<210> SEQ ID NO 18
<211> LENGTH: 224
<212> TYPE: PRT
<213> ORGANISM: Artificial Sequence
<220> FEATURE:
<223> OTHER INFORMATION: Fc Fragment dIgGB-cNg-S

<400> SEQUENCE: 18

```
Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
            20                  25                  30

Pro Glu Val Thr Cys Val Val Val Asp Leu Asp Pro Glu Asp Pro Glu
        35                  40                  45

Val Gln Ile Ser Trp Phe Val Asp Gly Lys Gln Met Gln Thr Ala Lys
    50                  55                  60

Thr Gln Pro Arg Glu Glu Gln Phe Ser Gly Thr Tyr Arg Val Val Ser
65                  70                  75                  80

Val Leu Pro Ile Gly His Gln Asp Trp Leu Lys Gly Lys Gln Phe Thr
                85                  90                  95

Cys Lys Val Asn Asn Lys Ala Leu Pro Ser Pro Ile Glu Arg Thr Ile
            100                 105                 110

Ser Lys Ala Arg Gly Gln Ala His Gln Pro Ser Val Tyr Val Leu Pro
        115                 120                 125

Pro Ser Arg Glu Glu Leu Ser Lys Asn Thr Val Ser Leu Thr Cys Leu
    130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
    210                 215                 220
```

<210> SEQ ID NO 19
<211> LENGTH: 9
<212> TYPE: PRT
<213> ORGANISM: Artificial Sequence
<220> FEATURE:
<223> OTHER INFORMATION: Linker

<400> SEQUENCE: 19

```
Gly Gly Gly Gly Gln Gly Gly Gly Gly
1               5
```

<210> SEQ ID NO 20
<211> LENGTH: 303
<212> TYPE: PRT
<213> ORGANISM: Artificial Sequence
<220> FEATURE:
<223> OTHER INFORMATION: Insulin-Fc Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H
<220> FEATURE:
<221> NAME/KEY: Xaa
<222> LOCATION: (58)..(58)
<223> OTHER INFORMATION: Xaa is absent or N

<400> SEQUENCE: 20

```
Phe Val Asn Gln His Leu Cys Gly Ser Xaa Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys Xaa Gly Gly Gly Gly Gly Gln
    50                  55                  60

Gly Gly Gly Gly Gln Gly Gly Gly Gly Gln Gly Gly Gly Gly Gly Asp
65                  70                  75                  80

Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125

Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
            180                 185                 190

Lys Ala Arg Gly Gln Ala His Gln Pro Ser Val Tyr Val Leu Pro Pro
        195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
            260                 265                 270

Arg Trp Gln Arg Gly Asp Thr Phe Ile Cys Ala Val Met His Glu Ala
        275                 280                 285

Leu His Asn His Tyr Thr Gln Glu Ser Leu Ser His Ser Pro Gly
    290                 295                 300
```

<210> SEQ ID NO 21
<211> LENGTH: 303
<212> TYPE: PRT
<213> ORGANISM: Artificial Sequence
<220> FEATURE:
<223> OTHER INFORMATION: Insulin-Fc Fusion Protein
<220> FEATURE:
<221> NAME/KEY: Xaa
<222> LOCATION: (58)..(58)
<223> OTHER INFORMATION: Xaa is absent or N

<400> SEQUENCE: 21

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Xaa Gly Gly Gly Gly Gly Gln
50 55 60

Gly Gly Gly Gly Gln Gly Gly Gly Gly Gln Gly Gly Gly Gly Gly Asp
65 70 75 80

Cys Pro Lys Cys Pro Ala Pro Glu Met Leu Gly Gly Pro Ser Val Phe
85 90 95

Ile Phe Pro Pro Lys Pro Lys Asp Thr Leu Leu Ile Ala Arg Thr Pro
100 105 110

Glu Val Thr Cys Val Val Val Asp Leu Asp Pro Glu Asp Pro Glu Val
115 120 125

Gln Ile Ser Trp Phe Val Asp Gly Lys Gln Met Gln Thr Ala Lys Thr
130 135 140

Gln Pro Arg Glu Glu Gln Phe Asn Gly Thr Tyr Arg Val Val Ser Val
145 150 155 160

Leu Pro Ile Gly His Gln Asp Trp Leu Lys Gly Lys Gln Phe Thr Cys
165 170 175

Lys Val Asn Asn Lys Ala Leu Pro Ser Pro Ile Glu Arg Thr Ile Ser
180 185 190

Lys Ala Arg Gly Gln Ala His Gln Pro Ser Val Tyr Val Leu Pro Pro
195 200 205

Ser Arg Glu Glu Leu Ser Lys Asn Thr Val Ser Leu Thr Cys Leu Ile
210 215 220

Lys Asp Phe Phe Pro Pro Asp Ile Asp Val Glu Trp Gln Ser Asn Gly
225 230 235 240

Gln Gln Glu Pro Glu Ser Lys Tyr Arg Thr Thr Pro Pro Gln Leu Asp
245 250 255

Glu Asp Gly Ser Tyr Phe Leu Tyr Ser Lys Leu Ser Val Asp Lys Ser
260 265 270

Arg Trp Gln Arg Gly Asp Thr Phe Ile Cys Ala Val Met His Glu Ala
275 280 285

Leu His Asn His Tyr Thr Gln Glu Ser Leu Ser His Ser Pro Gly
290 295 300

<210> SEQ ID NO 22
<211> LENGTH: 302
<212> TYPE: PRT
<213> ORGANISM: Artificial Sequence
<220> FEATURE:
<223> OTHER INFORMATION: Insulin-Fc Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 22

Phe Val Asn Gln His Leu Cys Gly Ser Xaa Leu Val Glu Ala Leu Ala
1 5 10 15

-continued

```
Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300
```

<210> SEQ ID NO 23
<211> LENGTH: 57
<212> TYPE: DNA
<213> ORGANISM: Artificial Sequence
<220> FEATURE:
<223> OTHER INFORMATION: Leader sequence cDNA

<400> SEQUENCE: 23
atggaatgga gctgggtctt tctcttcttc ctgtcagtaa cgactggtgt ccactcc 57

<210> SEQ ID NO 24
<211> LENGTH: 19
<212> TYPE: PRT
<213> ORGANISM: Artificial Sequence
<220> FEATURE:
<223> OTHER INFORMATION: Leader sequence

<400> SEQUENCE: 24

```
Met Glu Trp Ser Trp Val Phe Leu Phe Phe Leu Ser Val Thr Thr Gly
1               5                   10                  15
```

Val His Ser

<210> SEQ ID NO 25
<211> LENGTH: 966
<212> TYPE: DNA
<213> ORGANISM: Artificial Sequence
<220> FEATURE:
<223> OTHER INFORMATION: cDNA for Insulin-Fc Fusion Protein

<400> SEQUENCE: 25
atggaatgga gctgggtctt tctcttcttc ctgtcagtaa cgactggtgt ccactccttc 60
gtgaaccagc acctgtgcgg ctcccacctg gtggaagctc tggaactcgt gtgcggcgag 120
cggggcttcc actacggggg tggcggagga ggttctggtg gcggcggagg catcgtggaa 180
cagtgctgca cctccacctg ctccctggac cagctggaaa actactgcgg tggcggaggt 240
ggtcaaggag gcggtggaca gggtggaggt gggcagggag gaggcggggg agactgcccc 300
aagtgccccg ctcccgagat gctgggcgga cccagcgtgt tcatcttccc tcccaagccc 360
aaggacacac tgctgatcgc caggaccccg gaggtgacct gcgtggtggt ggacctggat 420
cccgaagacc ccgaggtgca gatcagctgg ttcgtggatg gaaagcagat gcagaccgcc 480
aagacccaac cccgggaaga gcagttcaac ggcacctaca gggtggtgag tgtgttgccc 540
atcggccacc aggactggct gaaggggaag caattcacat gcaaggttaa taacaaggcc 600
ctgcccagcc ccatcgagag gaccatcagc aaggccaggg gccaggccca ccagccatct 660
gtgtacgtgc tgcccccatc tagggaggaa ctgagcaaga acacagtcag ccttacttgc 720
ctgatcaagg acttcttccc accggacata gacgtggagt ggcagagtaa cggccagcag 780
gagcccgaga gcaagtatag gaccacaccg ccccaactgg acgaggacgg aagctacttc 840
ctctacagca aattgagcgt tgacaaaagc aggtggcagc gaggcgacac cttcatctgc 900
gccgtgatgc acgaggcttt gcataaccac tacacccagg agagcctgtc ccacagcccc 960
ggatag 966

<210> SEQ ID NO 26
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 26

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Asp Cys
65 70 75 80

Pro Lys Cys Pro Ala Pro Glu Met Leu Gly Gly Pro Ser Val Phe Ile
85 90 95

Phe Pro Pro Lys Pro Lys Asp Thr Leu Leu Ile Ala Arg Thr Pro Glu
100 105 110

Val Thr Cys Val Val Val Asp Leu Asp Pro Glu Asp Pro Glu Val Gln
115 120 125

-continued

```
Ile Ser Trp Phe Val Asp Gly Lys Gln Met Gln Thr Ala Lys Thr Gln
    130                 135                 140

Pro Arg Glu Glu Gln Phe Asn Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300
```

<210> SEQ ID NO 27
<211> LENGTH: 969
<212> TYPE: DNA
<213> ORGANISM: Artificial Sequence
<220> FEATURE:
<223> OTHER INFORMATION: cDNA for Insulin-Fc Fusion Protein

<400> SEQUENCE: 27

```
atggaatgga gctgggtctt tctcttcttc ctgtcagtaa cgactggtgt ccactccttc      60

gtgaaccagc acctgtgcgg ctcccacctg gtggaagctc tggaactcgt gtgcggcgag     120

cggggcttcc actacggggg tggcggagga ggttctggtg gcggcggagg catcgtggaa     180

cagtgctgca cctccacctg ctccctggac cagctggaaa actactgcaa cggtggcgga     240

ggtggtcaag gaggcggtgg acagggtgga ggtgggcagg gaggaggcgg gggagactgc     300

cccaagtgcc ccgctcccga gatgctgggc ggacccagcg tgttcatctt ccctcccaag     360

cccaaggaca cactgctgat cgccaggacc ccggaggtga cctgcgtggt ggtggacctg     420

gatcccgaag accccgaggt gcagatcagc tggttcgtgg atggaaagca gatgcagacc     480

gccaagaccc aaccccggga agagcagttc aacggcacct acagggtggt gagtgtgttg     540

cccatcggcc accaggactg gctgaagggg aagcaattca catgcaaggt taataacaag     600

gccctgccca gccccatcga gaggaccatc agcaaggcca ggggccaggc ccaccagcca     660

tctgtgtacg tgctgccccc atctagggag gaactgagca agaacacagt cagccttact     720

tgcctgatca aggacttctt cccaccggac atagacgtgg agtggcagag taacggccag     780

caggagcccg agagcaagta taggaccaca ccgccccaac tggacgagga cggaagctac     840

ttcctctaca gcaaattgag cgttgacaaa agcaggtggc agcgaggcga caccttcatc     900

tgcgccgtga tgcacgaggc tttgcataac cactacaccc aggagagcct gtcccacagc     960

cccggatag                                                             969
```

<210> SEQ ID NO 28
<211> LENGTH: 303
<212> TYPE: PRT
<213> ORGANISM: Artificial Sequence
<220> FEATURE:
<223> OTHER INFORMATION: Insulin-Fc Fusion Protein

<400> SEQUENCE: 28

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Asn Gly Gly Gly Gly Gly Gln
    50                  55                  60

Gly Gly Gly Gly Gln Gly Gly Gly Gly Gln Gly Gly Gly Gly Gly Asp
65                  70                  75                  80

Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125

Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
            180                 185                 190

Lys Ala Arg Gly Gln Ala His Gln Pro Ser Val Tyr Val Leu Pro Pro
        195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
            260                 265                 270

Arg Trp Gln Arg Gly Asp Thr Phe Ile Cys Ala Val Met His Glu Ala
        275                 280                 285

Leu His Asn His Tyr Thr Gln Glu Ser Leu Ser His Ser Pro Gly
    290                 295                 300
```

<210> SEQ ID NO 29
<211> LENGTH: 966
<212> TYPE: DNA
<213> ORGANISM: Artificial Sequence
<220> FEATURE:
<223> OTHER INFORMATION: cDNA for Insulin-Fc Fusion Protein

<400> SEQUENCE: 29

```
atggaatgga gctgggtctt tctcttcttc ctgtcagtaa cgactggtgt ccactccttc      60

gtgaaccagc acctgtgcgg ctcccacctg gtggaagctc tggcactcgt gtgcggcgag     120
```

```
cggggcttcc actacggggg tggcggagga ggttctggtg gcggcggagg catcgtggaa    180

cagtgctgca cctccacctg ctccctggac cagctggaaa actactgcgg tggcggaggt    240

ggtcaaggag gcggtggaca gggtggaggt gggcagggag gaggcggggg agactgcccc    300

aagtgccccg ctcccgagat gctgggcgga cccagcgtgt tcatcttccc tcccaagccc    360

aaggacacac tgctgatcgc caggaccccg gaggtgacct gcgtggtggt ggacctggat    420

cccgaagacc ccgaggtgca gatcagctgg ttcgtggatg gaaagcagat gcagaccgcc    480

aagacccaac cccgggaaga gcagttctca ggcacctaca gggtggtgag tgtgttgccc    540

atcggccacc aggactggct gaaggggaag caattcacat gcaaggttaa taacaaggcc    600

ctgcccagcc ccatcgagag gaccatcagc aaggccaggg gccaggccca ccagccatct    660

gtgtacgtgc tgccccccatc tagggaggaa ctgagcaaga acacagtcag ccttacttgc    720

ctgatcaagg acttcttccc accggacata gacgtggagt ggcagagtaa cggccagcag    780

gagcccgaga gcaagtatag gaccacaccg ccccaactgg acgaggacgg aagctacttc    840

ctctacagca aattgagcgt tgacaaaagc aggtggcagc gaggcgacac cttcatctgc    900

gccgtgatgc acgaggcttt gcataaccac tacacccagg agagcctgtc ccacagcccc    960

ggatag                                                                966
```

<210> SEQ ID NO 30
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 30

```
Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205
```

-continued

```
Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300


<210> SEQ ID NO 31
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 31

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270
```

```
Cys Ala Val Met His Glu Thr Leu Gln Asn His Tyr Thr Asp Leu Ser
        275                 280                 285

Leu Ser His Ser Pro Gly
    290


<210> SEQ ID NO 32
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 32

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Leu His Glu Ala Leu His Ser His Tyr Thr Gln Lys Ser
        275                 280                 285

Leu Ser Leu Ser Pro Gly
    290


<210> SEQ ID NO 33
<211> LENGTH: 294
<212> TYPE: PRT
<213> ORGANISM: Artificial Sequence
```

<220> FEATURE:
<223> OTHER INFORMATION: Insulin-Fc Fusion Protein

<400> SEQUENCE: 33

Phe Val Asn Gln His Leu Cys Gly Ser Asp Leu Val Glu Ala Leu Ala
1 5 10 15

Leu Val Cys Gly Glu Arg Gly Phe Phe Tyr Thr Asp Pro Thr Gly Gly
20 25 30

Gly Pro Arg Arg Gly Ile Val Glu Gln Cys Cys His Ser Ile Cys Ser
35 40 45

Leu Tyr Gln Leu Glu Asn Tyr Cys Asn Gly Gly Gly Gly Ala Gly Gly
50 55 60

Gly Gly Arg Cys Thr Asp Thr Pro Pro Cys Pro Val Pro Glu Pro Leu
65 70 75 80

Gly Gly Pro Ser Val Leu Ile Phe Pro Pro Lys Pro Lys Asp Ile Leu
85 90 95

Arg Ile Thr Arg Thr Pro Glu Val Thr Cys Val Val Leu Asp Leu Gly
100 105 110

Arg Glu Asp Pro Glu Val Gln Ile Ser Trp Phe Val Asp Gly Lys Glu
115 120 125

Val His Thr Ala Lys Thr Gln Ser Arg Glu Gln Gln Phe Asn Gly Thr
130 135 140

Tyr Arg Val Val Ser Val Leu Pro Ile Glu His Gln Asp Trp Leu Thr
145 150 155 160

Gly Lys Glu Phe Lys Cys Arg Val Asn His Ile Asp Leu Pro Ser Pro
165 170 175

Ile Glu Arg Thr Ile Ser Lys Ala Arg Gly Arg Ala His Lys Pro Ser
180 185 190

Val Tyr Val Leu Pro Pro Ser Pro Lys Glu Leu Ser Ser Ser Asp Thr
195 200 205

Val Ser Ile Thr Cys Leu Ile Lys Asp Phe Tyr Pro Pro Asp Ile Asp
210 215 220

Val Glu Trp Gln Ser Asn Gly Gln Gln Glu Pro Glu Arg Lys His Arg
225 230 235 240

Met Thr Pro Pro Gln Leu Asp Glu Asp Gly Ser Tyr Phe Leu Tyr Ser
245 250 255

Lys Leu Ser Val Asp Lys Ser Arg Trp Gln Gln Gly Asp Pro Phe Thr
260 265 270

Cys Ala Val Leu His Glu Thr Leu Gln Ser His Tyr Thr Asp Leu Ser
275 280 285

Leu Ser His Ser Pro Gly
290

<210> SEQ ID NO 34
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 34

Phe Val Asn Gln His Leu Cys Gly Ser Asp Leu Val Glu Ala Leu Ala
1 5 10 15

Leu Val Cys Gly Glu Arg Gly Phe Phe Tyr Thr Asp Pro Thr Gly Gly
20 25 30

Gly Pro Arg Arg Gly Ile Val Glu Gln Cys Cys His Ser Ile Cys Ser

```
        35                  40                  45

Leu Tyr Gln Leu Glu Asn Tyr Cys Asn Gly Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Met His Glu Thr Leu Gln Ser His Tyr Thr Asp Leu Ser
        275                 280                 285

Leu Ser His Ser Pro Gly
    290


<210> SEQ ID NO 35
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 35

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
```

```
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Leu His Glu Thr Leu Gln Asn His Tyr Thr Asp Leu Ser
        275                 280                 285

Leu Ser His Ser Pro Gly
    290


<210> SEQ ID NO 36
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 36

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Asn Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
```

```
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290


<210> SEQ ID NO 37
<211> LENGTH: 291
<212> TYPE: PRT
<213> ORGANISM: Artificial Sequence
<220> FEATURE:
<223> OTHER INFORMATION: Insulin-Fc Fusion Protein

<400> SEQUENCE: 37

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Cys Asn Asn Cys Pro Cys Pro Gly Cys Gly Leu Leu Gly Gly
65                  70                  75                  80

Pro Ser Val Phe Ile Phe Pro Pro Lys Pro Lys Asp Ile Leu Val Thr
                85                  90                  95

Ala Arg Thr Pro Thr Val Thr Cys Val Val Val Asp Leu Asp Pro Glu
            100                 105                 110

Asn Pro Glu Val Gln Ile Ser Trp Phe Val Asp Ser Lys Gln Val Gln
        115                 120                 125

Thr Ala Asn Thr Gln Pro Arg Glu Glu Gln Ser Asn Gly Thr Tyr Arg
    130                 135                 140

Val Val Ser Val Leu Pro Ile Gly His Gln Asp Trp Leu Ser Gly Lys
145                 150                 155                 160

Gln Phe Lys Cys Lys Val Asn Asn Lys Ala Leu Pro Ser Pro Ile Glu
                165                 170                 175

Glu Ile Ile Ser Lys Thr Pro Gly Gln Ala His Gln Pro Asn Val Tyr
            180                 185                 190

Val Leu Pro Pro Ser Arg Asp Glu Met Ser Lys Asn Thr Val Thr Leu
        195                 200                 205

Thr Cys Leu Val Lys Asp Phe Phe Pro Pro Glu Ile Asp Val Glu Trp
    210                 215                 220

Gln Ser Asn Gly Gln Gln Glu Pro Glu Ser Lys Tyr Arg Met Thr Pro
```

```
225                 230                 235                 240

Pro Gln Leu Asp Glu Asp Gly Ser Tyr Phe Leu Tyr Ser Lys Leu Ser
                245                 250                 255

Val Asp Lys Ser Arg Trp Gln Arg Gly Asp Thr Phe Ile Cys Ala Val
            260                 265                 270

Met His Glu Ala Leu His Asn His Tyr Thr Gln Ile Ser Leu Ser His
        275                 280                 285

Ser Pro Gly
    290


<210> SEQ ID NO 38
<211> LENGTH: 291
<212> TYPE: PRT
<213> ORGANISM: Artificial Sequence
<220> FEATURE:
<223> OTHER INFORMATION: Insulin-Fc Fusion Protein

<400> SEQUENCE: 38

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Cys Ile Ser Pro Cys Pro Val Pro Glu Ser Leu Gly Gly Pro
65                  70                  75                  80

Ser Val Phe Ile Phe Pro Pro Lys Pro Lys Asp Ile Leu Arg Ile Thr
                85                  90                  95

Arg Thr Pro Glu Ile Thr Cys Val Val Leu Asp Leu Gly Arg Glu Asp
            100                 105                 110

Pro Glu Val Gln Ile Ser Trp Phe Val Asp Gly Lys Glu Val His Thr
        115                 120                 125

Ala Lys Thr Gln Pro Arg Glu Gln Gln Phe Asn Ser Thr Tyr Arg Val
    130                 135                 140

Val Ser Val Leu Pro Ile Glu His Gln Asp Trp Leu Thr Gly Lys Glu
145                 150                 155                 160

Phe Lys Cys Arg Val Asn His Ile Gly Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Pro Lys Glu Leu Ser Ser Ser Asp Thr Val Thr Leu
        195                 200                 205

Thr Cys Leu Ile Lys Asp Phe Phe Pro Pro Glu Ile Asp Val Glu Trp
    210                 215                 220

Gln Ser Asn Gly Gln Pro Glu Pro Glu Ser Lys Tyr His Thr Thr Ala
225                 230                 235                 240

Pro Gln Leu Asp Glu Asp Gly Ser Tyr Phe Leu Tyr Ser Lys Leu Ser
                245                 250                 255

Val Asp Lys Ser Arg Trp Gln Gln Gly Asp Thr Phe Thr Cys Ala Val
            260                 265                 270

Met His Glu Ala Leu Gln Asn His Tyr Thr Asp Leu Ser Leu Ser His
        275                 280                 285

Ser Pro Gly
```

290

<210> SEQ ID NO 39
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 39

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Gln Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 40
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 40

-continued

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Ser Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290


<210> SEQ ID NO 41
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 41

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60
```

Gly Gly Asp Cys Pro Lys Cys Pro Ala Pro Glu Met Leu Gly Gly Pro
65 70 75 80

Ser Val Phe Ile Phe Pro Pro Lys Pro Lys Asp Thr Leu Leu Ile Ala
85 90 95

Arg Thr Pro Glu Val Thr Cys Val Val Val Asp Leu Asp Pro Glu Asp
100 105 110

Pro Glu Val Gln Ile Ser Trp Phe Val Asp Gly Lys Gln Met Gln Thr
115 120 125

Ala Lys Thr Gln Pro Arg Glu Glu Gln Phe Asp Gly Thr Tyr Arg Val
130 135 140

Val Ser Val Leu Pro Ile Gly His Gln Asp Trp Leu Lys Gly Lys Gln
145 150 155 160

Phe Thr Cys Lys Val Asn Asn Lys Ala Leu Pro Ser Pro Ile Glu Arg
165 170 175

Thr Ile Ser Lys Ala Arg Gly Gln Ala His Gln Pro Ser Val Tyr Val
180 185 190

Leu Pro Pro Ser Arg Glu Glu Leu Ser Lys Asn Thr Val Ser Leu Thr
195 200 205

Cys Leu Ile Lys Asp Phe Phe Pro Pro Asp Ile Asp Val Glu Trp Gln
210 215 220

Ser Asn Gly Gln Gln Glu Pro Glu Ser Lys Tyr Arg Thr Thr Pro Pro
225 230 235 240

Gln Leu Asp Glu Asp Gly Ser Tyr Phe Leu Tyr Ser Lys Leu Ser Val
245 250 255

Asp Lys Ser Arg Trp Gln Arg Gly Asp Thr Phe Ile Cys Ala Val Met
260 265 270

His Glu Ala Leu His Asn His Tyr Thr Gln Glu Ser Leu Ser His Ser
275 280 285

Pro Gly
290

<210> SEQ ID NO 42
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 42

Phe Val Asn Gln His Leu Cys Gly Ser Asp Leu Val Glu Ala Leu Ala
1 5 10 15

Leu Val Cys Gly Glu Arg Gly Phe Phe Tyr Thr Asp Pro Thr Gly Gly
20 25 30

Gly Pro Arg Arg Gly Ile Val Glu Gln Cys Cys His Ser Ile Cys Ser
35 40 45

Leu Tyr Gln Leu Glu Asn Tyr Cys Asn Gly Gly Gly Gly Ala Gly Gly
50 55 60

Gly Gly Asp Cys Pro Lys Cys Pro Ala Pro Glu Met Leu Gly Gly Pro
65 70 75 80

Ser Val Phe Ile Phe Pro Pro Lys Pro Lys Asp Thr Leu Leu Ile Ala
85 90 95

Arg Thr Pro Glu Val Thr Cys Val Val Val Asp Leu Asp Pro Glu Asp
100 105 110

Pro Glu Val Gln Ile Ser Trp Phe Val Asp Gly Lys Gln Met Gln Thr
115 120 125

-continued

```
Ala Lys Thr Gln Pro Arg Glu Glu Gln Phe Lys Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290


<210> SEQ ID NO 43
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 43

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Gln Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190
```

```
Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290


<210> SEQ ID NO 44
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 44

Phe Val Asn Gln His Leu Cys Gly Ser His Leu Val Gln Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Gly Gly Gly Gly Ala Gly Gly Gly
    50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255
```

Lys Ser Arg Trp Gln Arg Gly Asp Thr Phe Ile Cys Ala Val Met His
260 265 270

Glu Ala Leu His Asn His Tyr Thr Gln Glu Ser Leu Ser His Ser Pro
275 280 285

Gly

<210> SEQ ID NO 45
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 45

Phe Val Asn Gln His Leu Cys Gly Ser Glu Leu Val Glu Ala Leu Ala
1 5 10 15

Leu Val Cys Gly Glu Arg Gly Phe Phe Tyr Thr Asp Pro Thr Gly Gly
20 25 30

Gly Pro Arg Arg Gly Ile Val Glu Gln Cys Cys Thr Ser Ile Cys Ser
35 40 45

Leu Tyr Gln Leu Glu Asn Tyr Cys Gly Gly Gly Gly Ala Gly Gly Gly
50 55 60

Gly Asp Cys Pro Lys Cys Pro Ala Pro Glu Met Leu Gly Gly Pro Ser
65 70 75 80

Val Phe Ile Phe Pro Pro Lys Pro Lys Asp Thr Leu Leu Ile Ala Arg
85 90 95

Thr Pro Glu Val Thr Cys Val Val Val Asp Leu Asp Pro Glu Asp Pro
100 105 110

Glu Val Gln Ile Ser Trp Phe Val Asp Gly Lys Gln Met Gln Thr Ala
115 120 125

Lys Thr Gln Pro Arg Glu Glu Gln Phe Ser Gly Thr Tyr Arg Val Val
130 135 140

Ser Val Leu Pro Ile Gly His Gln Asp Trp Leu Lys Gly Lys Gln Phe
145 150 155 160

Thr Cys Lys Val Asn Asn Lys Ala Leu Pro Ser Pro Ile Glu Arg Thr
165 170 175

Ile Ser Lys Ala Arg Gly Gln Ala His Gln Pro Ser Val Tyr Val Leu
180 185 190

Pro Pro Ser Arg Glu Glu Leu Ser Lys Asn Thr Val Ser Leu Thr Cys
195 200 205

Leu Ile Lys Asp Phe Phe Pro Pro Asp Ile Asp Val Glu Trp Gln Ser
210 215 220

Asn Gly Gln Gln Glu Pro Glu Ser Lys Tyr Arg Thr Thr Pro Pro Gln
225 230 235 240

Leu Asp Glu Asp Gly Ser Tyr Phe Leu Tyr Ser Lys Leu Ser Val Asp
245 250 255

Lys Ser Arg Trp Gln Arg Gly Asp Thr Phe Ile Cys Ala Val Met His
260 265 270

Glu Ala Leu His Asn His Tyr Thr Gln Glu Ser Leu Ser His Ser Pro
275 280 285

Gly

<210> SEQ ID NO 46
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 46

Phe Val Asn Gln His Leu Cys Gly Ser His Leu Val Glu Ala Leu Ala
1 5 10 15

Leu Val Cys Gly Glu Ala Gly Phe Phe Tyr Thr Asp Pro Thr Gly Gly
20 25 30

Gly Pro Arg Arg Gly Ile Val Glu Gln Cys Cys Thr Ser Ile Cys Ser
35 40 45

Leu Tyr Gln Leu Glu Asn Tyr Cys Gly Gly Gly Gly Ala Gly Gly Gly
50 55 60

Gly Asp Cys Pro Lys Cys Pro Ala Pro Glu Met Leu Gly Gly Pro Ser
65 70 75 80

Val Phe Ile Phe Pro Pro Lys Pro Lys Asp Thr Leu Leu Ile Ala Arg
85 90 95

Thr Pro Glu Val Thr Cys Val Val Val Asp Leu Asp Pro Glu Asp Pro
100 105 110

Glu Val Gln Ile Ser Trp Phe Val Asp Gly Lys Gln Met Gln Thr Ala
115 120 125

Lys Thr Gln Pro Arg Glu Glu Gln Phe Ser Gly Thr Tyr Arg Val Val
130 135 140

Ser Val Leu Pro Ile Gly His Gln Asp Trp Leu Lys Gly Lys Gln Phe
145 150 155 160

Thr Cys Lys Val Asn Asn Lys Ala Leu Pro Ser Pro Ile Glu Arg Thr
165 170 175

Ile Ser Lys Ala Arg Gly Gln Ala His Gln Pro Ser Val Tyr Val Leu
180 185 190

Pro Pro Ser Arg Glu Glu Leu Ser Lys Asn Thr Val Ser Leu Thr Cys
195 200 205

Leu Ile Lys Asp Phe Phe Pro Pro Asp Ile Asp Val Glu Trp Gln Ser
210 215 220

Asn Gly Gln Gln Glu Pro Glu Ser Lys Tyr Arg Thr Thr Pro Pro Gln
225 230 235 240

Leu Asp Glu Asp Gly Ser Tyr Phe Leu Tyr Ser Lys Leu Ser Val Asp
245 250 255

Lys Ser Arg Trp Gln Arg Gly Asp Thr Phe Ile Cys Ala Val Met His
260 265 270

Glu Ala Leu His Asn His Tyr Thr Gln Glu Ser Leu Ser His Ser Pro
275 280 285

Gly

<210> SEQ ID NO 47
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 47

Phe Val Asn Gln His Leu Cys Gly Ser His Leu Val Glu Ala Leu Ala
1 5 10 15

Leu Val Cys Gly Glu Arg Gly Phe Tyr Tyr Thr Asp Pro Thr Gly Gly
20 25 30

Gly Pro Arg Arg Gly Ile Val Glu Gln Cys Cys Thr Ser Ile Cys Ser
35 40 45

Leu Tyr Gln Leu Glu Asn Tyr Cys Gly Gly Gly Gly Ala Gly Gly Gly
50 55 60

Gly Asp Cys Pro Lys Cys Pro Ala Pro Glu Met Leu Gly Gly Pro Ser
65 70 75 80

Val Phe Ile Phe Pro Pro Lys Pro Lys Asp Thr Leu Leu Ile Ala Arg
85 90 95

Thr Pro Glu Val Thr Cys Val Val Val Asp Leu Asp Pro Glu Asp Pro
100 105 110

Glu Val Gln Ile Ser Trp Phe Val Asp Gly Lys Gln Met Gln Thr Ala
115 120 125

Lys Thr Gln Pro Arg Glu Glu Gln Phe Ser Gly Thr Tyr Arg Val Val
130 135 140

Ser Val Leu Pro Ile Gly His Gln Asp Trp Leu Lys Gly Lys Gln Phe
145 150 155 160

Thr Cys Lys Val Asn Asn Lys Ala Leu Pro Ser Pro Ile Glu Arg Thr
165 170 175

Ile Ser Lys Ala Arg Gly Gln Ala His Gln Pro Ser Val Tyr Val Leu
180 185 190

Pro Pro Ser Arg Glu Glu Leu Ser Lys Asn Thr Val Ser Leu Thr Cys
195 200 205

Leu Ile Lys Asp Phe Phe Pro Pro Asp Ile Asp Val Glu Trp Gln Ser
210 215 220

Asn Gly Gln Gln Glu Pro Glu Ser Lys Tyr Arg Thr Thr Pro Pro Gln
225 230 235 240

Leu Asp Glu Asp Gly Ser Tyr Phe Leu Tyr Ser Lys Leu Ser Val Asp
245 250 255

Lys Ser Arg Trp Gln Arg Gly Asp Thr Phe Ile Cys Ala Val Met His
260 265 270

Glu Ala Leu His Asn His Tyr Thr Gln Glu Ser Leu Ser His Ser Pro
275 280 285

Gly

<210> SEQ ID NO 48
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 48

Phe Val Asn Gln His Leu Cys Gly Ser His Leu Val Glu Ala Leu Ala
1 5 10 15

Leu Val Cys Gly Glu Arg Gly Phe Phe Tyr Thr Asp Pro Thr Gly Gly
20 25 30

Gly Pro Arg Arg Gly Ile Val Glu Gln Cys Cys Thr Ser Ile Cys Ser
35 40 45

Leu Tyr Gln Leu Glu Asn Tyr Cys Gly Gly Gly Gly Ala Gly Gly Gly
50 55 60

Gly Asp Cys Pro Lys Cys Pro Ala Pro Glu Met Leu Gly Gly Pro Ser
65 70 75 80

Val Phe Ile Phe Pro Pro Lys Pro Lys Asp Thr Leu Leu Ile Ala Arg
85 90 95

Thr Pro Glu Val Thr Cys Val Val Val Asp Leu Asp Pro Glu Asp Pro
100 105 110

```
Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly


<210> SEQ ID NO 49
<211> LENGTH: 292
<212> TYPE: PRT
<213> ORGANISM: Artificial Sequence
<220> FEATURE:
<223> OTHER INFORMATION: Insulin-Fc Fusion Protein

<400> SEQUENCE: 49

Phe Val Asn Gln His Leu Cys Gly Ser His Leu Val Gln Ala Leu Tyr
1               5                   10                  15

Leu Val Cys Gly Glu Arg Gly Phe Phe Tyr Thr Asp Pro Thr Gln Arg
            20                  25                  30

Gly Gly Gly Gly Gly Gln Arg Gly Ile Val Glu Gln Cys Cys Thr Ser
        35                  40                  45

Ile Cys Ser Leu Tyr Gln Leu Glu Asn Tyr Cys Gly Gly Gly Gly Ala
    50                  55                  60

Gly Gly Gly Gly Asp Cys Pro Lys Cys Pro Ala Pro Glu Met Leu Gly
65                  70                  75                  80

Gly Pro Ser Val Phe Ile Phe Pro Pro Lys Pro Lys Asp Thr Leu Leu
                85                  90                  95

Ile Ala Arg Thr Pro Glu Val Thr Cys Val Val Val Asp Leu Asp Pro
            100                 105                 110

Glu Asp Pro Glu Val Gln Ile Ser Trp Phe Val Asp Gly Lys Gln Met
        115                 120                 125

Gln Thr Ala Lys Thr Gln Pro Arg Glu Glu Gln Phe Ser Gly Thr Tyr
    130                 135                 140

Arg Val Val Ser Val Leu Pro Ile Gly His Gln Asp Trp Leu Lys Gly
145                 150                 155                 160

Lys Gln Phe Thr Cys Lys Val Asn Asn Lys Ala Leu Pro Ser Pro Ile
                165                 170                 175

Glu Arg Thr Ile Ser Lys Ala Arg Gly Gln Ala His Gln Pro Ser Val
```

```
            180                 185                 190

Tyr Val Leu Pro Pro Ser Arg Glu Glu Leu Ser Lys Asn Thr Val Ser
        195                 200                 205

Leu Thr Cys Leu Ile Lys Asp Phe Phe Pro Pro Asp Ile Asp Val Glu
    210                 215                 220

Trp Gln Ser Asn Gly Gln Gln Glu Pro Glu Ser Lys Tyr Arg Thr Thr
225                 230                 235                 240

Pro Pro Gln Leu Asp Glu Asp Gly Ser Tyr Phe Leu Tyr Ser Lys Leu
                245                 250                 255

Ser Val Asp Lys Ser Arg Trp Gln Arg Gly Asp Thr Phe Ile Cys Ala
            260                 265                 270

Val Met His Glu Ala Leu His Asn His Tyr Thr Gln Glu Ser Leu Ser
        275                 280                 285

His Ser Pro Gly
    290


<210> SEQ ID NO 50
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 50

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Gly Gly Gly Ser Gly Gly Gly Gly Gly Ile Val Glu Gln Cys Cys
        35                  40                  45

Thr Ser Ile Cys Ser Leu Tyr Gln Leu Glu Asn Tyr Cys Gly Gly Gly
    50                  55                  60

Gly Ala Gly Gly Gly Gly Asp Cys Pro Lys Cys Pro Ala Pro Glu Met
65                  70                  75                  80

Leu Gly Gly Pro Ser Val Phe Ile Phe Pro Pro Lys Pro Lys Asp Thr
                85                  90                  95

Leu Leu Ile Ala Arg Thr Pro Glu Val Thr Cys Val Val Val Asp Leu
            100                 105                 110

Asp Pro Glu Asp Pro Glu Val Gln Ile Ser Trp Phe Val Asp Gly Lys
        115                 120                 125

Gln Met Gln Thr Ala Lys Thr Gln Pro Arg Glu Glu Gln Phe Ser Gly
    130                 135                 140

Thr Tyr Arg Val Val Ser Val Leu Pro Ile Gly His Gln Asp Trp Leu
145                 150                 155                 160

Lys Gly Lys Gln Phe Thr Cys Lys Val Asn Asn Lys Ala Leu Pro Ser
                165                 170                 175

Pro Ile Glu Arg Thr Ile Ser Lys Ala Arg Gly Gln Ala His Gln Pro
            180                 185                 190

Ser Val Tyr Val Leu Pro Pro Ser Arg Glu Glu Leu Ser Lys Asn Thr
        195                 200                 205

Val Ser Leu Thr Cys Leu Ile Lys Asp Phe Phe Pro Pro Asp Ile Asp
    210                 215                 220

Val Glu Trp Gln Ser Asn Gly Gln Gln Glu Pro Glu Ser Lys Tyr Arg
225                 230                 235                 240

Thr Thr Pro Pro Gln Leu Asp Glu Asp Gly Ser Tyr Phe Leu Tyr Ser
```

```
                245                 250                 255

Lys Leu Ser Val Asp Lys Ser Arg Trp Gln Arg Gly Asp Thr Phe Ile
            260                 265                 270

Cys Ala Val Met His Glu Ala Leu His Asn His Tyr Thr Gln Glu Ser
        275                 280                 285

Leu Ser His Ser Pro Gly
    290


<210> SEQ ID NO 51
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 51

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Gly Gly Gly
            20                  25                  30

Gly Gly Gly Gly Gly Gly Ile Val Glu Gln Cys Cys Thr Ser Ile Cys
        35                  40                  45

Ser Leu Tyr Gln Leu Glu Asn Tyr Cys Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Ser Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290
```

<210> SEQ ID NO 52
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 52

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Gly Gly Gly Gly
            20                  25                  30

Gly Gly Gly Gly Gly Ile Val Glu Gln Cys Cys Thr Ser Ile Cys Ser
        35                  40                  45

Leu Tyr Gln Leu Glu Asn Tyr Cys Gly Gly Gly Gly Ala Gly Gly Gly
    50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly
```

<210> SEQ ID NO 53
<211> LENGTH: 301
<212> TYPE: PRT
<213> ORGANISM: Artificial Sequence
<220> FEATURE:
<223> OTHER INFORMATION: Insulin-Fc Fusion Protein

<400> SEQUENCE: 53

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
```

20 25 30

Gly Pro Arg Arg Gly Ile Val Glu Gln Cys Cys Thr Ser Ile Cys Ser
35 40 45

Leu Tyr Gln Leu Glu Asn Tyr Cys Gly Gly Gly Gly Gly Gln Gly Gly
50 55 60

Gly Gly Gln Gly Gly Gly Gly Gln Gly Gly Gly Gly Gly Asp Cys Pro
65 70 75 80

Lys Cys Pro Ala Pro Glu Met Leu Gly Gly Pro Ser Val Phe Ile Phe
85 90 95

Pro Pro Lys Pro Lys Asp Thr Leu Leu Ile Ala Arg Thr Pro Glu Val
100 105 110

Thr Cys Val Val Val Asp Leu Asp Pro Glu Asp Pro Glu Val Gln Ile
115 120 125

Ser Trp Phe Val Asp Gly Lys Gln Met Gln Thr Ala Lys Thr Gln Pro
130 135 140

Arg Glu Glu Gln Phe Ser Gly Thr Tyr Arg Val Val Ser Val Leu Pro
145 150 155 160

Ile Gly His Gln Asp Trp Leu Lys Gly Lys Gln Phe Thr Cys Lys Val
165 170 175

Asn Asn Lys Ala Leu Pro Ser Pro Ile Glu Arg Thr Ile Ser Lys Ala
180 185 190

Arg Gly Gln Ala His Gln Pro Ser Val Tyr Val Leu Pro Pro Ser Arg
195 200 205

Glu Glu Leu Ser Lys Asn Thr Val Ser Leu Thr Cys Leu Ile Lys Asp
210 215 220

Phe Phe Pro Pro Asp Ile Asp Val Glu Trp Gln Ser Asn Gly Gln Gln
225 230 235 240

Glu Pro Glu Ser Lys Tyr Arg Thr Thr Pro Pro Gln Leu Asp Glu Asp
245 250 255

Gly Ser Tyr Phe Leu Tyr Ser Lys Leu Ser Val Asp Lys Ser Arg Trp
260 265 270

Gln Arg Gly Asp Thr Phe Ile Cys Ala Val Met His Glu Ala Leu His
275 280 285

Asn His Tyr Thr Gln Glu Ser Leu Ser His Ser Pro Gly
290 295 300

<210> SEQ ID NO 54
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 54

Phe Val Asn Gln His Leu Cys Gly Ser His Leu Val Glu Ala Leu Ala
1 5 10 15

Leu Val Cys Gly Glu Arg Gly Phe Phe Tyr Thr Gln Gly Gly Gly Gly
20 25 30

Gly Gly Gly Gly Gly Ile Val Glu Gln Cys Cys Thr Ser Ile Cys Ser
35 40 45

Leu Tyr Gln Leu Glu Asn Tyr Cys Gly Gly Gly Gly Ala Gly Gly Gly
50 55 60

Gly Asp Cys Pro Lys Cys Pro Ala Pro Glu Met Leu Gly Gly Pro Ser
65 70 75 80

Val Phe Ile Phe Pro Pro Lys Pro Lys Asp Thr Leu Leu Ile Ala Arg

```
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly


<210> SEQ ID NO 55
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 55

Phe Val Asn Gln His Leu Cys Gly Ser His Leu Val Glu Ala Leu Glu
1               5                   10                  15

Leu Val Cys Gly Glu Arg Gly Phe Phe Tyr Thr Pro Lys Thr Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Asn Gly Thr Tyr Arg Val Val Ser Val Leu
145                 150                 155                 160
```

```
Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300


<210> SEQ ID NO 56
<211> LENGTH: 303
<212> TYPE: PRT
<213> ORGANISM: Artificial Sequence
<220> FEATURE:
<223> OTHER INFORMATION: Insulin-Fc Fusion Protein

<400> SEQUENCE: 56

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Asn His Gly Gly Gly Gly Gln
    50                  55                  60

Gly Gly Gly Gly Gln Gly Gly Gly Gly Gln Gly Gly Gly Gly Gly Asp
65                  70                  75                  80

Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125

Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
            180                 185                 190

Lys Ala Arg Gly Gln Ala His Gln Pro Ser Val Tyr Val Leu Pro Pro
        195                 200                 205

Ser Arg Glu Glu Leu Ser Lys Asn Thr Val Ser Leu Thr Cys Leu Ile
    210                 215                 220
```

Lys Asp Phe Phe Pro Pro Asp Ile Asp Val Glu Trp Gln Ser Asn Gly
225 230 235 240

Gln Gln Glu Pro Glu Ser Lys Tyr Arg Thr Thr Pro Pro Gln Leu Asp
245 250 255

Glu Asp Gly Ser Tyr Phe Leu Tyr Ser Lys Leu Ser Val Asp Lys Ser
260 265 270

Arg Trp Gln Arg Gly Asp Thr Phe Ile Cys Ala Val Met His Glu Ala
275 280 285

Leu His Asn His Tyr Thr Gln Glu Ser Leu Ser His Ser Pro Gly
290 295 300

<210> SEQ ID NO 57
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 57

Phe Val Asn Gln His Leu Cys Gly Ser His Leu Val Glu Ala Leu Glu
1 5 10 15

Leu Val Cys Gly Glu Arg Gly Phe Phe Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Asp Cys
65 70 75 80

Pro Lys Cys Pro Ala Pro Glu Met Leu Gly Gly Pro Ser Val Phe Ile
85 90 95

Phe Pro Pro Lys Pro Lys Asp Thr Leu Leu Ile Ala Arg Thr Pro Glu
100 105 110

Val Thr Cys Val Val Val Asp Leu Asp Pro Glu Asp Pro Glu Val Gln
115 120 125

Ile Ser Trp Phe Val Asp Gly Lys Gln Met Gln Thr Ala Lys Thr Gln
130 135 140

Pro Arg Glu Glu Gln Phe Asn Gly Thr Tyr Arg Val Val Ser Val Leu
145 150 155 160

Pro Ile Gly His Gln Asp Trp Leu Lys Gly Lys Gln Phe Thr Cys Lys
165 170 175

Val Asn Asn Lys Ala Leu Pro Ser Pro Ile Glu Arg Thr Ile Ser Lys
180 185 190

Ala Arg Gly Gln Ala His Gln Pro Ser Val Tyr Val Leu Pro Pro Ser
195 200 205

Arg Glu Glu Leu Ser Lys Asn Thr Val Ser Leu Thr Cys Leu Ile Lys
210 215 220

Asp Phe Phe Pro Pro Asp Ile Asp Val Glu Trp Gln Ser Asn Gly Gln
225 230 235 240

Gln Glu Pro Glu Ser Lys Tyr Arg Thr Thr Pro Pro Gln Leu Asp Glu
245 250 255

Asp Gly Ser Tyr Phe Leu Tyr Ser Lys Leu Ser Val Asp Lys Ser Arg
260 265 270

Trp Gln Arg Gly Asp Thr Phe Ile Cys Ala Val Met His Glu Ala Leu
275 280 285

His Asn His Tyr Thr Gln Glu Ser Leu Ser His Ser Pro Gly
290 295 300

<210> SEQ ID NO 58
<211> LENGTH: 306
<212> TYPE: PRT
<213> ORGANISM: Artificial Sequence
<220> FEATURE:
<223> OTHER INFORMATION: Insulin-Fc Fusion Protein

<400> SEQUENCE: 58

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Arg Cys
65 70 75 80

Thr Asp Thr Pro Pro Cys Pro Val Pro Glu Pro Leu Gly Gly Pro Ser
85 90 95

Val Leu Ile Phe Pro Pro Lys Pro Lys Asp Ile Leu Arg Ile Thr Arg
100 105 110

Thr Pro Glu Val Thr Cys Val Val Leu Asp Leu Gly Arg Glu Asp Pro
115 120 125

Glu Val Gln Ile Ser Trp Phe Val Asp Gly Lys Glu Val His Thr Ala
130 135 140

Lys Thr Gln Ser Arg Glu Gln Gln Phe Asn Gly Thr Tyr Arg Val Val
145 150 155 160

Ser Val Leu Pro Ile Glu His Gln Asp Trp Leu Thr Gly Lys Glu Phe
165 170 175

Lys Cys Arg Val Asn His Ile Asp Leu Pro Ser Pro Ile Glu Arg Thr
180 185 190

Ile Ser Lys Ala Arg Gly Arg Ala His Lys Pro Ser Val Tyr Val Leu
195 200 205

Pro Pro Ser Pro Lys Glu Leu Ser Ser Ser Asp Thr Val Ser Ile Thr
210 215 220

Cys Leu Ile Lys Asp Phe Tyr Pro Pro Asp Ile Asp Val Glu Trp Gln
225 230 235 240

Ser Asn Gly Gln Gln Glu Pro Glu Arg Lys His Arg Met Thr Pro Pro
245 250 255

Gln Leu Asp Glu Asp Gly Ser Tyr Phe Leu Tyr Ser Lys Leu Ser Val
260 265 270

Asp Lys Ser Arg Trp Gln Gln Gly Asp Pro Phe Thr Cys Ala Val Met
275 280 285

His Glu Thr Leu Gln Asn His Tyr Thr Asp Leu Ser Leu Ser His Ser
290 295 300

Pro Gly
305

<210> SEQ ID NO 59
<211> LENGTH: 303
<212> TYPE: PRT
<213> ORGANISM: Artificial Sequence
<220> FEATURE:
<223> OTHER INFORMATION: Insulin-Fc Fusion Protein

<400> SEQUENCE: 59

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Cys Asn
65 70 75 80

Asn Cys Pro Cys Pro Gly Cys Gly Leu Leu Gly Gly Pro Ser Val Phe
85 90 95

Ile Phe Pro Pro Lys Pro Lys Asp Ile Leu Val Thr Ala Arg Thr Pro
100 105 110

Thr Val Thr Cys Val Val Val Asp Leu Asp Pro Glu Asn Pro Glu Val
115 120 125

Gln Ile Ser Trp Phe Val Asp Ser Lys Gln Val Gln Thr Ala Asn Thr
130 135 140

Gln Pro Arg Glu Glu Gln Ser Asn Gly Thr Tyr Arg Val Val Ser Val
145 150 155 160

Leu Pro Ile Gly His Gln Asp Trp Leu Ser Gly Lys Gln Phe Lys Cys
165 170 175

Lys Val Asn Asn Lys Ala Leu Pro Ser Pro Ile Glu Glu Ile Ile Ser
180 185 190

Lys Thr Pro Gly Gln Ala His Gln Pro Asn Val Tyr Val Leu Pro Pro
195 200 205

Ser Arg Asp Glu Met Ser Lys Asn Thr Val Thr Leu Thr Cys Leu Val
210 215 220

Lys Asp Phe Phe Pro Pro Glu Ile Asp Val Glu Trp Gln Ser Asn Gly
225 230 235 240

Gln Gln Glu Pro Glu Ser Lys Tyr Arg Met Thr Pro Pro Gln Leu Asp
245 250 255

Glu Asp Gly Ser Tyr Phe Leu Tyr Ser Lys Leu Ser Val Asp Lys Ser
260 265 270

Arg Trp Gln Arg Gly Asp Thr Phe Ile Cys Ala Val Met His Glu Ala
275 280 285

Leu His Asn His Tyr Thr Gln Ile Ser Leu Ser His Ser Pro Gly
290 295 300

<210> SEQ ID NO 60
<211> LENGTH: 303
<212> TYPE: PRT
<213> ORGANISM: Artificial Sequence
<220> FEATURE:
<223> OTHER INFORMATION: Insulin-Fc Fusion Protein

<400> SEQUENCE: 60

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys

-continued

```
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Cys Ile
65                  70                  75                  80

Ser Pro Cys Pro Val Pro Glu Ser Leu Gly Gly Pro Ser Val Phe Ile
                85                  90                  95

Phe Pro Pro Lys Pro Lys Asp Ile Leu Arg Ile Thr Arg Thr Pro Glu
            100                 105                 110

Ile Thr Cys Val Val Leu Asp Leu Gly Arg Glu Asp Pro Glu Val Gln
        115                 120                 125

Ile Ser Trp Phe Val Asp Gly Lys Glu Val His Thr Ala Lys Thr Gln
    130                 135                 140

Pro Arg Glu Gln Gln Phe Asn Ser Thr Tyr Arg Val Val Ser Val Leu
145                 150                 155                 160

Pro Ile Glu His Gln Asp Trp Leu Thr Gly Lys Glu Phe Lys Cys Arg
                165                 170                 175

Val Asn His Ile Gly Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Pro Lys Glu Leu Ser Ser Ser Asp Thr Val Thr Leu Thr Cys Leu Ile
    210                 215                 220

Lys Asp Phe Phe Pro Pro Glu Ile Asp Val Glu Trp Gln Ser Asn Gly
225                 230                 235                 240

Gln Pro Glu Pro Glu Ser Lys Tyr His Thr Thr Ala Pro Gln Leu Asp
                245                 250                 255

Glu Asp Gly Ser Tyr Phe Leu Tyr Ser Lys Leu Ser Val Asp Lys Ser
            260                 265                 270

Arg Trp Gln Gln Gly Asp Thr Phe Thr Cys Ala Val Met His Glu Ala
        275                 280                 285

Leu Gln Asn His Tyr Thr Asp Leu Ser Leu Ser His Ser Pro Gly
    290                 295                 300


<210> SEQ ID NO 61
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 61

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
```

```
            100                 105                 110

Val Thr Cys Val Val Val Ala Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300


<210> SEQ ID NO 62
<211> LENGTH: 302
<212> TYPE: PRT
<213> ORGANISM: Artificial Sequence
<220> FEATURE:
<223> OTHER INFORMATION: Insulin-Fc Fusion Protein

<400> SEQUENCE: 62

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
```

-continued

```
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300


<210> SEQ ID NO 63
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 63

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn
    50                  55


<210> SEQ ID NO 64
<211> LENGTH: 10
<212> TYPE: PRT
<213> ORGANISM: Artificial Sequence
<220> FEATURE:
<223> OTHER INFORMATION: Linker

<400> SEQUENCE: 64

Gly Gly Gly Gly Gly Ala Gly Gly Gly Gly
1               5                   10


<210> SEQ ID NO 65
<211> LENGTH: 19
<212> TYPE: PRT
<213> ORGANISM: Artificial Sequence
<220> FEATURE:
<223> OTHER INFORMATION: Linker

<400> SEQUENCE: 65

Gly Gly Gly Gly Ser Gly Gly Gly Gly Ser Gly Gly Gly Gly Ser Gly
1               5                   10                  15

Gly Gly Gly


<210> SEQ ID NO 66
<211> LENGTH: 19
```

<212> TYPE: PRT
<213> ORGANISM: Artificial Sequence
<220> FEATURE:
<223> OTHER INFORMATION: Linker

<400> SEQUENCE: 66

Gly Gly Gly Gly Lys Gly Gly Gly Gly Lys Gly Gly Gly Gly Lys Gly
1               5                   10                  15

Gly Gly Gly

<210> SEQ ID NO 67
<211> LENGTH: 21
<212> TYPE: PRT
<213> ORGANISM: Artificial Sequence
<220> FEATURE:
<223> OTHER INFORMATION: Linker

<400> SEQUENCE: 67

Gly Gly Gly Gly Gly Ala Gly Gly Gly Gly Ala Gly Gly Gly Gly Ala
1               5                   10                  15

Gly Gly Gly Gly Gly
            20

<210> SEQ ID NO 68
<211> LENGTH: 21
<212> TYPE: PRT
<213> ORGANISM: Artificial Sequence
<220> FEATURE:
<223> OTHER INFORMATION: Linker

<400> SEQUENCE: 68

Ser Gly Gly Gly Gly Gln Gly Gly Gly Gly Gln Gly Gly Gly Gly Gln
1               5                   10                  15

Gly Gly Gly Gly Gly
            20

<210> SEQ ID NO 69
<211> LENGTH: 21
<212> TYPE: PRT
<213> ORGANISM: Artificial Sequence
<220> FEATURE:
<223> OTHER INFORMATION: Linker

<400> SEQUENCE: 69

His Gly Gly Gly Gly Gln Gly Gly Gly Gly Gln Gly Gly Gly Gly Gln
1               5                   10                  15

Gly Gly Gly Gly Gly
            20

<210> SEQ ID NO 70
<211> LENGTH: 22
<212> TYPE: PRT
<213> ORGANISM: Artificial Sequence
<220> FEATURE:
<223> OTHER INFORMATION: Linker

<400> SEQUENCE: 70

Pro Gly Gly Gly Gly Gly Gln Gly Gly Gly Gly Gln Gly Gly Gly Gly
1               5                   10                  15

Gln Gly Gly Gly Gly Gly
            20

<210> SEQ ID NO 71
<211> LENGTH: 11

<212> TYPE: PRT
<213> ORGANISM: Artificial Sequence
<220> FEATURE:
<223> OTHER INFORMATION: C-Chain

<400> SEQUENCE: 71

Gly Gly Gly Gly Gly Gly Ser Gly Gly Gly Gly
1               5                   10

<210> SEQ ID NO 72
<211> LENGTH: 7
<212> TYPE: PRT
<213> ORGANISM: Artificial Sequence
<220> FEATURE:
<223> OTHER INFORMATION: C-Chain

<400> SEQUENCE: 72

Gly Gly Ser Gly Gly Gly Gly
1               5

<210> SEQ ID NO 73
<211> LENGTH: 226
<212> TYPE: PRT
<213> ORGANISM: Artificial Sequence
<220> FEATURE:
<223> OTHER INFORMATION: Fc Fragment hIgG1

<400> SEQUENCE: 73

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 74
<211> LENGTH: 221
<212> TYPE: PRT
<213> ORGANISM: Artificial Sequence
<220> FEATURE:
<223> OTHER INFORMATION: Fc Fragment hIgG2

<400> SEQUENCE: 74

```
Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220
```

<210> SEQ ID NO 75
<211> LENGTH: 299
<212> TYPE: PRT
<213> ORGANISM: Artificial Sequence
<220> FEATURE:
<223> OTHER INFORMATION: Insulin-Fc Fusion Protein

<400> SEQUENCE: 75

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Glu Cys
65                  70                  75                  80

Pro Pro Cys Pro Ala Pro Pro Val Ala Gly Pro Ser Val Phe Leu Phe
                85                  90                  95
```

Pro Pro Lys Pro Lys Asp Thr Leu Met Ile Ser Arg Thr Pro Glu Val
100 105 110

Thr Cys Val Val Val Asp Val Ser His Glu Asp Pro Glu Val Gln Phe
115 120 125

Asn Trp Tyr Val Asp Gly Val Glu Val His Asn Ala Lys Thr Lys Pro
130 135 140

Arg Glu Glu Gln Phe Asn Ser Thr Phe Arg Val Val Ser Val Leu Thr
145 150 155 160

Val Val His Gln Asp Trp Leu Asn Gly Lys Glu Tyr Lys Cys Lys Val
165 170 175

Ser Asn Lys Gly Leu Pro Ala Pro Ile Glu Lys Thr Ile Ser Lys Thr
180 185 190

Lys Gly Gln Pro Arg Glu Pro Gln Val Tyr Thr Leu Pro Pro Ser Arg
195 200 205

Glu Glu Met Thr Lys Asn Gln Val Ser Leu Thr Cys Leu Val Lys Gly
210 215 220

Phe Tyr Pro Ser Asp Ile Ala Val Glu Trp Glu Ser Asn Gly Gln Pro
225 230 235 240

Glu Asn Asn Tyr Lys Thr Thr Pro Pro Met Leu Asp Ser Asp Gly Ser
245 250 255

Phe Phe Leu Tyr Ser Lys Leu Thr Val Asp Lys Ser Arg Trp Gln Gln
260 265 270

Gly Asn Val Phe Ser Cys Ser Val Met His Glu Ala Leu His Asn His
275 280 285

Tyr Thr Gln Lys Ser Leu Ser Leu Ser Pro Gly
290 295

<210> SEQ ID NO 76
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 76

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Asp Lys
65 70 75 80

Thr His Thr Cys Pro Pro Cys Pro Ala Pro Glu Leu Leu Gly Gly Pro
85 90 95

Ser Val Phe Leu Phe Pro Pro Lys Pro Lys Asp Thr Leu Met Ile Ser
100 105 110

Arg Thr Pro Glu Val Thr Cys Val Val Val Asp Val Ser His Glu Asp
115 120 125

Pro Glu Val Lys Phe Asn Trp Tyr Val Asp Gly Val Glu Val His Asn
130 135 140

Ala Lys Thr Lys Pro Arg Glu Glu Gln Tyr Asn Ser Thr Tyr Arg Val
145 150 155 160

```
Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 77
<211> LENGTH: 226
<212> TYPE: PRT
<213> ORGANISM: Artificial Sequence
<220> FEATURE:
<223> OTHER INFORMATION: Fc Fragment hIgG1 Consensus
<220> FEATURE:
<221> NAME/KEY: Xaa
<222> LOCATION: (77)..(77)
<223> OTHER INFORMATION: Xaa is S,D,A,R or Q

<400> SEQUENCE: 77

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Xaa Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly
225


<210> SEQ ID NO 78
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 78

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Ser Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 79
<211> LENGTH: 972
<212> TYPE: DNA
<213> ORGANISM: Artificial Sequence
```

<220> FEATURE:
<223> OTHER INFORMATION: cDNA for Insulin-Fc Fusion Protein

<400> SEQUENCE: 79

```
atggaatgga gctgggtctt tctcttcttc ctgtcagtaa cgactggtgt ccactccttc     60

gtgaaccagc acctgtgcgg ctcccacctg gtggaagctc tggcactcgt gtgcggcgag    120

cggggcttcc actacggggg tggcggagga ggttctggtg gcggcggagg catcgtggaa    180

cagtgctgca cctccacctg ctccctggac cagctggaaa actactgcgg tggcggaggt    240

ggtcaaggag gcggtggaca gggtggaggt gggcagggag gaggcggggg agacaaaact    300

cacacatgcc caccgtgccc agcacctgaa ctcctggggg gaccgtcagt cttcctcttc    360

cccccaaaac ccaaggacac cctcatgatc tcccggaccc ctgaggtcac atgcgtggtg    420

gtggacgtga gccacgaaga ccctgaggtc aagttcaact ggtacgtgga cggcgtggag    480

gtgcataatg ccaagacaaa gccgcgggag gagcagtaca gcagcacgta ccgtgtggtc    540

agcgtcctca ccgtcctgca ccaggactgg ctgaatggca aggagtacaa gtgcaaggtc    600

tccaacaaag ccctcccagc ccccatcgag aaaaccatct ccaaagccaa agggcagccc    660

cgagaaccac aggtgtacac cctgccccca tcccgggatg agctgaccaa gaaccaggtc    720

agcctgacct gcctggtcaa aggcttctat cccagcgaca tcgccgtgga gtgggagagc    780

aatgggcagc cggagaacaa ctacaagacc acgcctcccg tgctggactc cgacggctcc    840

ttcttcctct acagcaagct caccgtggac aagagcaggt ggcagcaggg gaacgtcttc    900

tcatgctccg tgatgcatga ggctctgcac aaccactaca cgcagaagag cctctccctg    960

tctccgggtt ag                                                        972
```

<210> SEQ ID NO 80
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 80

```
Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Asp Ser Thr Tyr Arg Val
145                 150                 155                 160
```

-continued

```
Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300
```

<210> SEQ ID NO 81
<211> LENGTH: 972
<212> TYPE: DNA
<213> ORGANISM: Artificial Sequence
<220> FEATURE:
<223> OTHER INFORMATION: cDNA for Insulin-Fc Fusion Protein

<400> SEQUENCE: 81

```
atggaatgga gctgggtctt tctcttcttc ctgtcagtaa cgactggtgt ccactccttc     60

gtgaaccagc acctgtgcgg ctcccacctg gtggaagctc tggcactcgt gtgcggcgag    120

cggggcttcc actacggggg tggcggagga ggttctggtg gcggcggagg catcgtggaa    180

cagtgctgca cctccacctg ctccctggac cagctggaaa actactgcgg tggcggaggt    240

ggtcaaggag gcggtggaca gggtggaggt gggcagggag gaggcggggg agacaaaact    300

cacacatgcc caccgtgccc agcacctgaa ctcctggggg gaccgtcagt cttcctcttc    360

cccccaaaac ccaaggacac cctcatgatc tcccggaccc ctgaggtcac atgcgtggtg    420

gtggacgtga gccacgaaga ccctgaggtc aagttcaact ggtacgtgga cggcgtggag    480

gtgcataatg ccaagacaaa gccgcgggag gagcagtacg acagcacgta ccgtgtggtc    540

agcgtcctca ccgtcctgca ccaggactgg ctgaatggca aggagtacaa gtgcaaggtc    600

tccaacaaag ccctcccagc ccccatcgag aaaaccatct ccaaagccaa agggcagccc    660

cgagaaccac aggtgtacac cctgccccca tcccgggatg agctgaccaa gaaccaggtc    720

agcctgacct gcctggtcaa aggcttctat cccagcgaca tcgccgtgga gtgggagagc    780

aatgggcagc cggagaacaa ctacaagacc acgcctcccg tgctggactc cgacggctcc    840

ttcttcctct acagcaagct caccgtggac aagagcaggt ggcagcaggg gaacgtcttc    900

tcatgctccg tgatgcatga ggctctgcac aaccactaca cgcagaagag cctctccctg    960

tctccgggtt ag                                                        972
```

<210> SEQ ID NO 82
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 82

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Ala Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300

<210> SEQ ID NO 83
<211> LENGTH: 972
<212> TYPE: DNA
<213> ORGANISM: Artificial Sequence
<220> FEATURE:
<223> OTHER INFORMATION: cDNA for Insulin-Fc Fusion Protein

<400> SEQUENCE: 83
atggaatgga gctgggtctt tctcttcttc ctgtcagtaa cgactggtgt ccactccttc      60
gtgaaccagc acctgtgcgg ctcccacctg gtggaagctc tggcactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcagggag gaggcggggg agacaaaact     300

```
cacacatgcc caccgtgccc agcacctgaa ctcctggggg gaccgtcagt cttcctcttc    360

cccccaaaac ccaaggacac cctcatgatc tcccggaccc ctgaggtcac atgcgtggtg    420

gtggacgtga gccacgaaga ccctgaggtc aagttcaact ggtacgtgga cggcgtggag    480

gtgcataatg ccaagacaaa gccgcgggag gagcagtacg ccagcacgta ccgtgtggtc    540

agcgtcctca ccgtcctgca ccaggactgg ctgaatggca aggagtacaa gtgcaaggtc    600

tccaacaaag ccctcccagc ccccatcgag aaaaccatct ccaaagccaa agggcagccc    660

cgagaaccac aggtgtacac cctgccccca tcccgggatg agctgaccaa gaaccaggtc    720

agcctgacct gcctggtcaa aggcttctat cccagcgaca tcgccgtgga gtgggagagc    780

aatgggcagc cggagaacaa ctacaagacc acgcctcccg tgctggactc cgacggctcc    840

ttcttcctct acagcaagct caccgtggac aagagcaggt ggcagcaggg gaacgtcttc    900

tcatgctccg tgatgcatga ggctctgcac aaccactaca cgcagaagag cctctccctg    960

tctccgggtt ag                                                        972
```

```
<210> SEQ ID NO 84
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 84

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Arg Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240
```

```
Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300
```

<210> SEQ ID NO 85
<211> LENGTH: 972
<212> TYPE: DNA
<213> ORGANISM: Artificial Sequence
<220> FEATURE:
<223> OTHER INFORMATION: cDNA for Insulin-Fc Fusion Protein

<400> SEQUENCE: 85

```
atggaatgga gctgggtctt tctcttcttc ctgtcagtaa cgactggtgt ccactccttc      60

gtgaaccagc acctgtgcgg ctcccacctg gtggaagctc tggcactcgt gtgcggcgag     120

cggggcttcc actacggggg tggcggagga ggttctggtg gcggcggagg catcgtggaa     180

cagtgctgca cctccacctg ctccctggac cagctggaaa actactgcgg tggcggaggt     240

ggtcaaggag gcggtggaca gggtggaggt gggcagggag gaggcggggg agacaaaact     300

cacacatgcc caccgtgccc agcacctgaa ctcctggggg gaccgtcagt cttcctcttc     360

cccccaaaac ccaaggacac cctcatgatc tcccggaccc ctgaggtcac atgcgtggtg     420

gtggacgtga gccacgaaga ccctgaggtc aagttcaact ggtacgtgga cggcgtggag     480

gtgcataatg ccaagacaaa gccgcgggag gagcagtaca gaagcacgta ccgtgtggtc     540

agcgtcctca ccgtcctgca ccaggactgg ctgaatggca aggagtacaa gtgcaaggtc     600

tccaacaaag ccctcccagc ccccatcgag aaaaccatct ccaaagccaa agggcagccc     660

cgagaaccac aggtgtacac cctgccccca tcccgggatg agctgaccaa gaaccaggtc     720

agcctgacct gcctggtcaa aggcttctat cccagcgaca tcgccgtgga gtgggagagc     780

aatgggcagc cggagaacaa ctacaagacc acgcctcccg tgctggactc cgacggctcc     840

ttcttcctct acagcaagct caccgtggac aagagcaggt ggcagcaggg gaacgtcttc     900

tcatgctccg tgatgcatga ggctctgcac aaccactaca cgcagaagag cctctccctg     960

tctccgggtt ag                                                         972
```

<210> SEQ ID NO 86
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 86

```
Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
```

```
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Gln Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 87
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 87

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Ala Gly
    50                  55                  60

Gly Gly Gly Ala Gly Gly Gly Gly Ala Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
```

```
    130                 135                 140

Ala Lys Thr Lys Pro Arg Glu Glu Gln Tyr Ser Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 88
<211> LENGTH: 972
<212> TYPE: DNA
<213> ORGANISM: Artificial Sequence
<220> FEATURE:
<223> OTHER INFORMATION: cDNA for Insulin-Fc Fusion Protein

<400> SEQUENCE: 88

atggaatgga gctgggtctt tctcttcttc ctgtcagtaa cgactggtgt ccactccttc      60

gtgaaccagc acctgtgcgg ctcccacctg gtggaagctc tggcactcgt gtgcggcgag     120

cggggcttcc actacggggg tggcggagga ggttctggtg gcggcggagg catcgtggaa     180

cagtgctgca cctccacctg ctccctggac cagctggaaa actactgcgg tggcggaggt     240

ggtgcaggag gcggtggagc cggtggaggt ggggctggag gaggcggggg agacaaaact     300

cacacatgcc caccgtgccc agcacctgaa ctcctggggg gaccgtcagt cttcctcttc     360

cccccaaaac ccaaggacac cctcatgatc tcccggaccc ctgaggtcac atgcgtggtg     420

gtggacgtga gccacgaaga ccctgaggtc aagttcaact ggtacgtgga cggcgtggag     480

gtgcataatg ccaagacaaa gccgcgggag gagcagtaca gcagcacgta ccgtgtggtc     540

agcgtcctca ccgtcctgca ccaggactgg ctgaatggca aggagtacaa gtgcaaggtc     600

tccaacaaag ccctcccagc ccccatcgag aaaaccatct ccaaagccaa agggcagccc     660

cgagaaccac aggtgtacac cctgccccca tcccgggatg agctgaccaa gaaccaggtc     720

agcctgacct gcctggtcaa aggcttctat cccagcgaca tcgccgtgga gtgggagagc     780

aatgggcagc cggagaacaa ctacaagacc acgcctcccg tgctggactc cgacggctcc     840

ttcttcctct acagcaagct caccgtggac aagagcaggt ggcagcaggg gaacgtcttc     900

tcatgctccg tgatgcatga ggctctgcac aaccactaca cgcagaagag cctctccctg     960

tctccgggtt ag                                                         972


<210> SEQ ID NO 89
<211> LENGTH: 292
```

<212> TYPE: PRT
<213> ORGANISM: Artificial Sequence
<220> FEATURE:
<223> OTHER INFORMATION: Insulin-Fc Fusion Protein

<400> SEQUENCE: 89

```
Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Ala Gly Gly
    50                  55                  60

Gly Gly Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Ser Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly
    290
```

<210> SEQ ID NO 90
<211> LENGTH: 936
<212> TYPE: DNA
<213> ORGANISM: Artificial Sequence
<220> FEATURE:
<223> OTHER INFORMATION: cDNA for Insulin-Fc Fusion Protein

<400> SEQUENCE: 90

```
atggaatgga gctgggtctt tctcttcttc ctgtcagtaa cgactggtgt ccactccttc     60

gtgaaccagc acctgtgcgg ctcccacctg gtggaagctc tggcactcgt gtgcggcgag    120

cggggcttcc actacggggg tggcggagga ggttctggtg gcggcggagg catcgtggaa    180
```

-continued

```
cagtgctgca cctccacctg ctccctggac cagctggaaa actactgcgg tggcggaggt    240

gccggaggcg ggggagacaa aactcacaca tgcccaccgt gcccagcacc tgaactcctg    300

gggggaccgt cagtcttcct cttcccccca aaacccaagg acaccctcat gatctcccgg    360

acccctgagg tcacatgcgt ggtggtggac gtgagccacg aagaccctga ggtcaagttc    420

aactggtacg tggacggcgt ggaggtgcat aatgccaaga caaagccgcg ggaggagcag    480

tacagcagca cgtaccgtgt ggtcagcgtc ctcaccgtcc tgcaccagga ctggctgaat    540

ggcaaggagt acaagtgcaa ggtctccaac aaagccctcc cagcccccat cgagaaaacc    600

atctccaaag ccaaagggca gccccgagaa ccacaggtgt acaccctgcc cccatcccgg    660

gatgagctga ccaagaacca ggtcagcctg acctgcctgg tcaaaggctt ctatcccagc    720

gacatcgccg tggagtggga gagcaatggg cagccggaga acaactacaa gaccacgcct    780

cccgtgctgg actccgacgg ctccttcttc ctctacagca agctcaccgt ggacaagagc    840

aggtggcagc aggggaacgt cttctcatgc tccgtgatgc atgaggctct gcacaaccac    900

tacacgcaga agagcctctc cctgtctccg ggttag                              936
```

<210> SEQ ID NO 91
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 91

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Ser Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220
```

```
Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 92
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 92

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Asp Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285
```

```
Ala Leu His Asn His Tyr Thr Gln Lys Ser Leu Ser Leu Ser Pro Gly
    290                 295                 300


<210> SEQ ID NO 93
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 93

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gly Gln Gly Gly Gly Gly Gly Asp Lys
65                  70                  75                  80

Thr His Thr Cys Pro Pro Cys Pro Ala Pro Glu Leu Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Ala Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Asp Glu Leu Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300


<210> SEQ ID NO 94
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 94
```

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Asp Lys
65 70 75 80

Thr His Thr Cys Pro Pro Cys Pro Ala Pro Glu Leu Leu Gly Gly Pro
85 90 95

Ser Val Phe Leu Phe Pro Pro Lys Pro Lys Asp Thr Leu Met Ile Ser
100 105 110

Arg Thr Pro Glu Val Thr Cys Val Val Val Asp Val Ser His Glu Asp
115 120 125

Pro Glu Val Lys Phe Asn Trp Tyr Val Asp Gly Val Glu Val His Asn
130 135 140

Ala Lys Thr Lys Pro Arg Glu Glu Gln Tyr Arg Ser Thr Tyr Arg Val
145 150 155 160

Val Ser Val Leu Thr Val Leu His Gln Asp Trp Leu Asn Gly Lys Glu
165 170 175

Tyr Lys Cys Lys Val Ser Asn Lys Ala Leu Pro Ala Pro Ile Glu Lys
180 185 190

Thr Ile Ser Lys Ala Lys Gly Gln Pro Arg Glu Pro Gln Val Tyr Thr
195 200 205

Leu Pro Pro Ser Arg Asp Glu Leu Thr Lys Asn Gln Val Ser Leu Thr
210 215 220

Cys Leu Val Lys Gly Phe Tyr Pro Ser Asp Ile Ala Val Glu Trp Glu
225 230 235 240

Ser Asn Gly Gln Pro Glu Asn Asn Tyr Lys Thr Thr Pro Pro Val Leu
245 250 255

Asp Ser Asp Gly Ser Phe Phe Leu Tyr Ser Lys Leu Thr Val Asp Lys
260 265 270

Ser Arg Trp Gln Gln Gly Asn Val Phe Ser Cys Ser Val Met His Glu
275 280 285

Ala Leu His Asn His Tyr Thr Gln Lys Ser Leu Ser Leu Ser Pro Gly
290 295 300

<210> SEQ ID NO 95
<211> LENGTH: 304
<212> TYPE: PRT
<213> ORGANISM: Artificial Sequence
<220> FEATURE:
<223> OTHER INFORMATION: Insulin-Fc Fusion Protein

<400> SEQUENCE: 95

Phe Val Asn Gln His Leu Cys Gly Ser His Leu Val Glu Ala Leu Glu
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Asp Lys
65 70 75 80

Thr His Thr Cys Pro Pro Cys Pro Ala Pro Glu Leu Leu Gly Gly Pro
85 90 95

Ser Val Phe Leu Phe Pro Pro Lys Pro Lys Asp Thr Leu Met Ile Ser
100 105 110

Arg Thr Pro Glu Val Thr Cys Val Val Val Asp Val Ser His Glu Asp
115 120 125

Pro Glu Val Lys Phe Asn Trp Tyr Val Asp Gly Val Glu Val His Asn
130 135 140

Ala Lys Thr Lys Pro Arg Glu Glu Gln Tyr Gln Ser Thr Tyr Arg Val
145 150 155 160

Val Ser Val Leu Thr Val Leu His Gln Asp Trp Leu Asn Gly Lys Glu
165 170 175

Tyr Lys Cys Lys Val Ser Asn Lys Ala Leu Pro Ala Pro Ile Glu Lys
180 185 190

Thr Ile Ser Lys Ala Lys Gly Gln Pro Arg Glu Pro Gln Val Tyr Thr
195 200 205

Leu Pro Pro Ser Arg Asp Glu Leu Thr Lys Asn Gln Val Ser Leu Thr
210 215 220

Cys Leu Val Lys Gly Phe Tyr Pro Ser Asp Ile Ala Val Glu Trp Glu
225 230 235 240

Ser Asn Gly Gln Pro Glu Asn Asn Tyr Lys Thr Thr Pro Pro Val Leu
245 250 255

Asp Ser Asp Gly Ser Phe Phe Leu Tyr Ser Lys Leu Thr Val Asp Lys
260 265 270

Ser Arg Trp Gln Gln Gly Asn Val Phe Ser Cys Ser Val Met His Glu
275 280 285

Ala Leu His Asn His Tyr Thr Gln Lys Ser Leu Ser Leu Ser Pro Gly
290 295 300

<210> SEQ ID NO 96
<211> LENGTH: 309
<212> TYPE: PRT
<213> ORGANISM: Artificial Sequence
<220> FEATURE:
<223> OTHER INFORMATION: Insulin-Fc Fusion Protein

<400> SEQUENCE: 96

Phe Val Asn Gln His Leu Cys Gly Ser His Leu Val Glu Ala Leu Ala
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gly Gln Gly
50 55 60

Gly Gly Gly Gln Gly Gly Gly Gly Gln Gly Gly Gly Gly Gly Gln Gly
65 70 75 80

Gly Gly Gly Asp Lys Thr His Thr Cys Pro Pro Cys Pro Ala Pro Glu
85 90 95

Leu Leu Gly Gly Pro Ser Val Phe Leu Phe Pro Pro Lys Pro Lys Asp
100 105 110

Thr Leu Met Ile Ser Arg Thr Pro Glu Val Thr Cys Val Val Val Asp
115 120 125

Val Ser His Glu Asp Pro Glu Val Lys Phe Asn Trp Tyr Val Asp Gly
130 135 140

Val Glu Val His Asn Ala Lys Thr Lys Pro Arg Glu Glu Gln Tyr Ser
145 150 155 160

Ser Thr Tyr Arg Val Val Ser Val Leu Thr Val Leu His Gln Asp Trp
165 170 175

Leu Asn Gly Lys Glu Tyr Lys Cys Lys Val Ser Asn Lys Ala Leu Pro
180 185 190

Ala Pro Ile Glu Lys Thr Ile Ser Lys Ala Lys Gly Gln Pro Arg Glu
195 200 205

Pro Gln Val Tyr Thr Leu Pro Pro Ser Arg Asp Glu Leu Thr Lys Asn
210 215 220

Gln Val Ser Leu Thr Cys Leu Val Lys Gly Phe Tyr Pro Ser Asp Ile
225 230 235 240

Ala Val Glu Trp Glu Ser Asn Gly Gln Pro Glu Asn Asn Tyr Lys Thr
245 250 255

Thr Pro Pro Val Leu Asp Ser Asp Gly Ser Phe Phe Leu Tyr Ser Lys
260 265 270

Leu Thr Val Asp Lys Ser Arg Trp Gln Gln Gly Asn Val Phe Ser Cys
275 280 285

Ser Val Met His Glu Ala Leu His Asn His Tyr Thr Gln Lys Ser Leu
290 295 300

Ser Leu Ser Pro Gly
305

<210> SEQ ID NO 97
<211> LENGTH: 292
<212> TYPE: PRT
<213> ORGANISM: Artificial Sequence
<220> FEATURE:
<223> OTHER INFORMATION: Insulin-Fc Fusion Protein

<400> SEQUENCE: 97

Phe Val Asn Gln His Leu Cys Gly Ser His Leu Val Glu Ala Leu Ala
1 5 10 15

Leu Val Cys Gly Glu Arg Gly Phe His Tyr Gly Gly Gly Gly Gly Gly
20 25 30

Ser Gly Gly Gly Gly Gly Ile Val Glu Gln Cys Cys Thr Ser Thr Cys
35 40 45

Ser Leu Asp Gln Leu Glu Asn Tyr Cys Gly Gly Gly Gly Gln Gly Gly
50 55 60

Gly Gly Asp Lys Thr His Thr Cys Pro Pro Cys Pro Ala Pro Glu Leu
65 70 75 80

Leu Gly Gly Pro Ser Val Phe Leu Phe Pro Pro Lys Pro Lys Asp Thr
85 90 95

Leu Met Ile Ser Arg Thr Pro Glu Val Thr Cys Val Val Val Asp Val
100 105 110

Ser His Glu Asp Pro Glu Val Lys Phe Asn Trp Tyr Val Asp Gly Val
115 120 125

Glu Val His Asn Ala Lys Thr Lys Pro Arg Glu Glu Gln Tyr Ser Ser
130 135 140

Thr Tyr Arg Val Val Ser Val Leu Thr Val Leu His Gln Asp Trp Leu
145 150 155 160

Asn Gly Lys Glu Tyr Lys Cys Lys Val Ser Asn Lys Ala Leu Pro Ala
165 170 175

```
Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly
    290


<210> SEQ ID NO 98
<211> LENGTH: 283
<212> TYPE: PRT
<213> ORGANISM: Artificial Sequence
<220> FEATURE:
<223> OTHER INFORMATION: Insulin-Fc Fusion Protein

<400> SEQUENCE: 98

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Asp Lys Thr His Thr Cys Pro
    50                  55                  60

Pro Cys Pro Ala Pro Glu Leu Leu Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser His Glu Asp Pro Glu Val Lys Phe
            100                 105                 110

Asn Trp Tyr Val Asp Gly Val Glu Val His Asn Ala Lys Thr Lys Pro
        115                 120                 125

Arg Glu Glu Gln Tyr Ser Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Ala Leu Pro Ala Pro Ile Glu Lys Thr Ile Ser Lys Ala
                165                 170                 175

Lys Gly Gln Pro Arg Glu Pro Gln Val Tyr Thr Leu Pro Pro Ser Arg
            180                 185                 190

Asp Glu Leu Thr Lys Asn Gln Val Ser Leu Thr Cys Leu Val Lys Gly
        195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240
```

-continued

Phe Phe Leu Tyr Ser Lys Leu Thr Val Asp Lys Ser Arg Trp Gln Gln
245 250 255

Gly Asn Val Phe Ser Cys Ser Val Met His Glu Ala Leu His Asn His
260 265 270

Tyr Thr Gln Lys Ser Leu Ser Leu Ser Pro Gly
275 280

<210> SEQ ID NO 99
<211> LENGTH: 26
<212> TYPE: PRT
<213> ORGANISM: Artificial Sequence
<220> FEATURE:
<223> OTHER INFORMATION: Linker

<400> SEQUENCE: 99

Gly Gly Gly Gly Gly Gln Gly Gly Gly Gly Gln Gly Gly Gly Gly Gln
1 5 10 15

Gly Gly Gly Gly Gly Gln Gly Gly Gly Gly
20 25

<210> SEQ ID NO 100
<211> LENGTH: 972
<212> TYPE: DNA
<213> ORGANISM: Artificial Sequence
<220> FEATURE:
<223> OTHER INFORMATION: cDNA for Insulin-Fc Fusion Protein

<400> SEQUENCE: 100
atggaatgga gctgggtctt tctcttcttc ctgtcagtaa cgactggtgt ccactccttc 60
gtgaaccagc acctgtgcgg ctcccacctg gtggaagctc tggcactcgt gtgcggcgag 120
cggggcttcc actacggggg tggcggagga ggttctggtg gcggcggagg catcgtggaa 180
cagtgctgca cctccacctg ctccctggac cagctggaaa actactgcgg tggcggaggt 240
ggtcaaggag gcggtggaca gggtggaggt gggcagggag gaggcggggg agacaaaact 300
cacacatgcc caccgtgccc agcacctgaa ctcctggggg gaccgtcagt cttcctcttc 360
cccccaaaac ccaaggacac cctcatgatc tcccggaccc ctgaggtcac atgcgtggtg 420
gtggacgtga gccacgaaga ccctgaggtc aagttcaact ggtacgtgga cggcgtggag 480
gtgcataatg ccaagacaaa gccgcgggag gagcagtacc aaagcacgta ccgtgtggtc 540
agcgtcctca ccgtcctgca ccaggactgg ctgaatggca aggagtacaa gtgcaaggtc 600
tccaacaaag ccctcccagc ccccatcgag aaaaccatct ccaaagccaa agggcagccc 660
cgagaaccac aggtgtacac cctgccccca tcccgggatg agctgaccaa gaaccaggtc 720
agcctgacct gcctggtcaa aggcttctat cccagcgaca tcgccgtgga gtgggagagc 780
aatgggcagc cggagaacaa ctacaagacc acgcctcccg tgctggactc cgacggctcc 840
ttcttcctct acagcaagct caccgtggac aagagcaggt ggcagcaggg gaacgtcttc 900
tcatgctccg tgatgcatga ggctctgcac aaccactaca cgcagaagag cctctccctg 960
tctccgggtt ag 972

The invention claimed is:

1. A cell engineered to express a fusion protein, said cell comprising a nucleic acid encoding said fusion protein, said fusion protein comprising an insulin polypeptide and an Fc fragment, wherein the insulin polypeptide and the Fc fragment are connected by a linker, wherein the Fc fragment is of human origin and comprises the following sequence:

(SEQ ID NO: 77)
DKTHTCPPCPAPELLGGPSVFLFPPKPKDTLMISRTPEVTCVVVDVSHE
DPEVKFNWYVDGVEVHNAKTKPREEQYX$_1$STYRVVSVLTVLHQDWLNGK
EYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKS
RWQQGNVFSCSVMHEALHNHYTQKSLSLSPG, wherein $X_1$ is S, D, A, or R, and wherein the insulin polypeptide consists of an insulin B-chain analog linked to an insulin A-chain analog via a C-chain, said insulin polypeptide comprising an alanine substitution at B16.

2. The cell of claim 1, wherein the insulin polypeptide comprises the following sequence: FVNQHLCGSX$_1$ LVEALALVCGERGFHYGGGGGGSGGGGGIVEQCCX$_2$ STCSLDQLENYC (SEQ ID NO: 9), wherein $X_1$ is not D, and $X_2$ is not H.

3. The cell of claim 1, wherein the insulin polypeptide comprises the following sequence:

(SEQ ID NO: 10)
FVNQHLCGSHLVEALALVCGERGFHYGGGGGGSGGGGGIVEQCCTSTCS
LDQLENYC.

4. The cell of claim 1, said fusion protein comprising domains in the following orientation from N- to C-terminus: (N-terminus)—insulin polypeptide—linker—Fc fragment—(C-terminus).

5. The cell of claim 1, wherein the cell is a HEK293 cell or a CHO cell.

6. The cell of claim 1, wherein the linker comprises the following sequence:

(SEQ ID NO: 11)
GGGGAGGGG

7. The cell of claim 1, wherein the linker comprises the following sequence:

(SEQ ID NO: 67)
GGGGGAGGGGAGGGGAGGGGG.

8. The cell of claim 1, wherein the linker comprises the following sequence:

(SEQ ID NO: 13)
GGGGGQGGGGQGGGGQGGGGG.

9. The cell of claim 1, wherein said nucleic acid comprises cDNA encoding said fusion protein, said fusion protein comprising the following sequence:

(SEQ ID NO: 78)
FVNQHLCGSHLVEALALVCGERGFHYGGGGGGSGGGGGIVEQCCTSTCS
LDQLENYCGGGGGQGGGGQGGGGQGGGGGDKTHTCPPCPAPELLGGPSV
FLFPPKPKDTLMISRTPEVTCVVVDVSHEDPEVKFNWYVDGVEVHNAKT
KPREEQYSSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFScSVMHEALHNHY
TQKSLSLSPG.

10. The cell of claim 9, wherein the cDNA comprises the following nucleic acid sequence:

(SEQ ID NO: 79)
atggaatggagctgggtctttctcttcttcctgtcagtaacgactggtg
tccactccttcgtgaaccagcacctgtgcggctcccacctggtggaagc
tctggcactcgtgtgcggcgagcggggcttccactacgggggtggcgga
ggaggttctggtggcggcggaggcatcgtggaacagtgctgcacctcca
cctgctccctggaccagctggaaaactactgcggtggcggaggtggtca
aggaggcggtggacagggtggaggtgggcagggaggaggcgggggagac
aaaactcacacatgcccaccgtgcccagcacctgaactcctgggggac
cgtcagtcttcctcttccccccaaaacccaaggacaccctcatgatctc
ccggacccctgaggtcacatgcgtggtggtggacgtgagccacgaagac
cctgaggtcaagttcaactggtacgtggacggcgtggaggtgcataatg
ccaagacaaagccgcgggaggagcagtacagcagcacgtaccgtgtggt
cagcgtcctcaccgtcctgcaccaggactggctgaatggcaaggagtac
aagtgcaaggtctccaacaaagccctcccagcccccatcgagaaaacca
tctccaaagccaaagggcagccccgagaaccacaggtgtacaccctgcc
cccatcccgggatgagctgaccaagaaccaggtcagcctgacctgcctg
gtcaaaggcttctatcccagcgacatcgccgtggagtgggagagcaatg
ggcagccggagaacaactacaagaccacgcctcccgtgctggactccga
cggctccttcttcctctacagcaagctcaccgtggacaagagcaggtgg
cagcaggggaacgtcttctcatgctccgtgatgcatgaggctctgcaca
accactacacgcagaagagcctctccctgtctccgggttag.

11. The cell of claim 1, wherein said nucleic acid comprises cDNA encoding said fusion protein, said fusion protein comprising the following sequence:

(SEQ ID NO: 80)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYDSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

12. The cell of claim 11, wherein the cDNA comprises the following nucleic acid sequence:

(SEQ ID NO: 81)
atggaatggagctgggtctttctcttcttcctgtcagtaacgactggtgt
ccactccttcgtgaaccagcacctgtgcggctcccacctggtggaagctc
tggcactcgtgtgcggcgagcggggcttccactacgggggtggcggagga
ggttctggtggcggcggaggcatcgtggaacagtgctgcacctccacctg
ctccctggaccagctggaaaactactgcggtggcggaggtggtcaaggag
gcggtggacagggtggaggtgggcagggaggaggcgggggagacaaaact
cacacatgcccaccgtgcccagcacctgaactcctggggggaccgtcagt
cttcctcttccccccaaaacccaaggacaccctcatgatctcccggaccc
ctgaggtcacatgcgtggtggtggacgtgagccacgaagaccctgaggtc
aagttcaactggtacgtggacggcgtggaggtgcataatgccaagacaaa
gccgcgggaggagcagtacgacagcacgtaccgtgtggtcagcgtcctca
ccgtcctgcaccaggactggctgaatggcaaggagtacaagtgcaaggtc
tccaacaaagccctcccagcccccatcgagaaaaccatctccaaagccaa
agggcagccccgagaaccacaggtgtacaccctgcccccatcccgggatg
agctgaccaagaaccaggtcagcctgacctgcctggtcaaaggcttctat
cccagcgacatcgccgtggagtgggagagcaatgggcagccggagaacaa
ctacaagaccacgcctcccgtgctggactccgacggctccttcttcctct
acagcaagctcaccgtggacaagagcaggtggcagcaggggaacgtcttc
tcatgctccgtgatgcatgaggctctgcacaaccactacacgcagaagag
cctctccctgtctccgggttag.

13. The cell of claim 1, wherein said nucleic acid comprises cDNA encoding said fusion protein, said fusion protein comprising the following sequence:

(SEQ ID NO: 82)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYASTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

14. The cell of claim 13, wherein the cDNA comprises the following nucleic acid sequence:

(SEQ ID NO: 83)
atggaatggagctgggtctttctcttcttcctgtcagtaacgactggtgt
ccactccttcgtgaaccagcacctgtgcggctcccacctggtggaagctc
tggcactcgtgtgcggcgagcggggcttccactacgggggtggcggagga
ggttctggtggcggcggaggcatcgtggaacagtgctgcacctccacctg
ctccctggaccagctggaaaactactgcggtggcggaggtggtcaaggag -continued gcggtggacagggtggaggtgggcagggaggaggcgggggagacaaaact
cacacatgcccaccgtgcccagcacctgaactcctggggggaccgtcagt
cttcctcttccccccaaaacccaaggacaccctcatgatctcccggaccc
ctgaggtcacatgcgtggtggtggacgtgagccacgaagaccctgaggtc
aagttcaactggtacgtggacggcgtggaggtgcataatgccaagacaaa
gccgcgggaggagcagtacgccagcacgtaccgtgtggtcagcgtcctca
ccgtcctgcaccaggactggctgaatggcaaggagtacaagtgcaaggtc
tccaacaaagccctcccagcccccatcgagaaaaccatctccaaagccaa
agggcagccccgagaaccacaggtgtacaccctgcccccatcccgggatg
agctgaccaagaaccaggtcagcctgacctgcctggtcaaaggcttctat
cccagcgacatcgccgtggagtgggagagcaatgggcagccggagaacaa
ctacaagaccacgcctcccgtgctggactccgacggctccttcttcctct
acagcaagctcaccgtggacaagagcaggtggcagcaggggaacgtcttc
tcatgctccgtgatgcatgaggctctgcacaaccactacacgcagaagag
cctctccctgtctccgggttag.

15. The cell of claim 1, wherein said nucleic acid comprises cDNA encoding said fusion protein, said fusion protein comprising the following sequence:

(SEQ ID NO: 84)
FVNQHLCGSHLVEALALVCGERGFHYGGGGGGSGGGGGIVEQCCTSTCSL
DQLENYCGGGGGQGGGGQGGGGQGGGGGDKTHTCPPCPAPELLGGPSVFL
FPPKPKDTLMISRTPEVTCVVVDVSHEDPEVKFNWYVDGVEVHNAKTKPR
EEQYRSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG.

16. The cell of claim 15, wherein the cDNA comprises the following nucleic acid sequence:

(SEQ ID NO: 85)
atggaatggagctgggtctttctcttcttcctgtcagtaacgactggtgt
ccactccttcgtgaaccagcacctgtgcggctcccacctggtggaagctc
tggcactcgtgtgcggcgagcggggcttccactacgggggtggcggagga
ggttctggtggcggcggaggcatcgtggaacagtgctgcacctccacctg
ctccctggaccagctggaaaactactgcggtggcggaggtggtcaaggag
gcggtggacagggtggaggtgggcagggaggaggcgggggagacaaaact
cacacatgcccaccgtgcccagcacctgaactcctggggggaccgtcagt
cttcctcttccccccaaaacccaaggacaccctcatgatctcccggaccc
ctgaggtcacatgcgtggtggtggacgtgagccacgaagaccctgaggtc
aagttcaactggtacgtggacggcgtggaggtgcataatgccaagacaaa
gccgcgggaggagcagtacagaagcacgtaccgtgtggtcagcgtcctca
ccgtcctgcaccaggactggctgaatggcaaggagtacaagtgcaaggtc -continued tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggttag.

17. The cell of claim 1, wherein said nucleic acid comprises cDNA encoding said fusion protein, said fusion protein comprising the following sequence:

(SEQ ID NO: 87)

FVNQHLCGSHLVEALALVCGERGFHYGGGGGGSGGGGGIVEQCCTSTCSL

DQLENYCGGGGGAGGGGAGGGGAGGGGGDKTHTCPPCPAPELLGGPSVFL

FPPKPKDTLMISRTPEVTCVVVDVSHEDPEVKFNWYVDGVEVHNAKTKPR

EEQYSSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPG.

18. The cell of claim 17, wherein the cDNA comprises the following nucleic acid sequence:

(SEQ ID NO: 88)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtggtgcaggag gcggtggagccggtggaggtggggctggaggaggcggggagacaaaact cacacatgcccaccgtgcccagcacctgaactcctggggggaccgtcagt cttcctcttccccccaaaacccaaggacaccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacagcagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggatg agctgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc -continued tcatgctccgtgatgcatgaggctctgcacaaccactacacgcagaagag cctctccctgtctccgggttag.

19. The cell of claim 1, wherein said nucleic acid comprises cDNA encoding said fusion protein, said fusion protein comprising the following sequence:

(SEQ ID NO: 89)

FVNQHLCGSHLVEALALVCGERGFHYGGGGGGSGGGGGIVEQCCTSTCSL

DQLENYCGGGGAGGGGDKTHTCPPCPAPELLGGPSVFLFPPKPKDTLMIS

RTPEVTCVVVDVSHEDPEVKFNWYVDGVEVHNAKTKPREEQYSSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPG.

20. The cell of claim 19, wherein the cDNA comprises the following nucleic acid sequence:

(SEQ ID NO: 90)

atggaatggagctgggtctttctcttcttcctgtcagtaacgactggtgt ccactccttcgtgaaccagcacctgtgcggctcccacctggtggaagctc tggcactcgtgtgcggcgagcggggcttccactacgggggtggcggagga ggttctggtggcggcggaggcatcgtggaacagtgctgcacctccacctg ctccctggaccagctggaaaactactgcggtggcggaggtgccggaggcg gggagacaaaactcacacatgcccaccgtgcccagcacctgaactcctg gggggaccgtcagtcttcctcttccccccaaaacccaaggacaccctcat gatctcccggacccctgaggtcacatgcgtggtggtggacgtgagccacg aagaccctgaggtcaagttcaactggtacgtggacggcgtggaggtgcat aatgccaagacaaagccgcgggaggagcagtacagcagcacgtaccgtgt ggtcagcgtcctcaccgtcctgcaccaggactggctgaatggcaaggagt acaagtgcaaggtctccaacaaagccctcccagcccccatcgagaaaacc atctccaaagccaaagggcagccccgagaaccacaggtgtacaccctgcc cccatcccgggatgagctgaccaagaaccaggtcagcctgacctgcctgg tcaaaggcttctatcccagcgacatcgccgtggagtgggagagcaatggg cagccggagaacaactacaagaccacgcctcccgtgctggactccgacgg ctccttcttcctctacagcaagctcaccgtggacaagagcaggtggcagc aggggaacgtcttctcatgctccgtgatgcatgaggctctgcacaaccac tacacgcagaagagcctctccctgtctccgggttag.

21. The cell of claim 1, wherein said nucleic acid comprises cDNA encoding said fusion protein, said fusion protein comprising the following sequence:

(SEQ ID NO: 96)

FVNQHLCGSHLVEALALVCGERGFHYGGGGGGSGGGGGIVEQCCTSTCSL

DQLENYCGGGGGQGGGGQGGGGQGGGGGQGGGGDKTHTCPPCPAPELLGG

PSVFLFPPKPKDTLMISRTPEVTCVVVDVSHEDPEVKFNWYVDGVEVHNA

-continued

```
KTKPREEQYSSTYRVVSVLTVLHQDWLNGKEYKCKVSNKALPAPIEKTIS

KAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYT

QKSLSLSPG.
```

22. The cell of claim 1, wherein said nucleic acid comprises cDNA encoding said fusion protein, said fusion protein comprising the following sequence:

```
                                           (SEQ ID NO: 97)
FVNQHLCGSHLVEALALVCGERGFHYGGGGGGSGGGGGIVEQCCTSTCSL

DQLENYCGGGGQGGGGDKTHTCPPCPAPELLGGPSVFLFPPKPKDTLMIS

RTPEVTCVVVDVSHEDPEVKFNWYVDGVEVHNAKTKPREEQYSSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPG.
```

23. A method of preparing a cell according to claim 1, said method comprising:

transfecting a host cell with a nucleic acid encoding for said fusion protein comprising said insulin polypeptide and said Fc fragment connected by said linker, wherein said fusion protein is expressed in said cell after said transfecting step.

* * * * *